US009808528B2

(12) United States Patent
Bodyak et al.

(10) Patent No.: US 9,808,528 B2
(45) **Date of Patent: *Nov. 7, 2017**

(54) PROTEIN-POLYMER-DRUG CONJUGATES AND METHODS OF USING SAME

(71) Applicant: Mersana Therapeutics, Inc., Cambridge, MA (US)

(72) Inventors: Natalya D. Bodyak, Brookline, MA (US); Timothy B. Lowinger, Carlisle, MA (US); Peter U. Park, Somerville, MA (US); Aleksandr V. Yurkovetskiy, Littleton, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,936

(22) Filed: Jun. 18, 2015

(65) Prior Publication Data

US 2015/0366982 A1 Dec. 24, 2015

Related U.S. Application Data

(60) Provisional application No. 62/013,851, filed on Jun. 18, 2014, provisional application No. 62/034,518, filed on Aug. 7, 2014, provisional application No. 62/147,964, filed on Apr. 15, 2015.

(51) Int. Cl.

| | |
|---|---|
| ***A61K 38/08*** | (2006.01) |
| ***A61P 35/00*** | (2006.01) |
| ***A61K 39/395*** | (2006.01) |
| ***A61K 45/06*** | (2006.01) |
| ***A61K 47/48*** | (2006.01) |

(52) U.S. Cl.

CPC .............. *A61K 45/06* (2013.01); *A61K 38/08* (2013.01); *A61K 39/39558* (2013.01); *A61K 47/48192* (2013.01)

(58) Field of Classification Search

None

See application file for complete search history.

(56) References Cited

U.S. PATENT DOCUMENTS

| | | | |
|---|---|---|---|
| 8,685,383 | B2 | 4/2014 | Yurkovetskiy et al. |
| 8,808,679 | B2 | 8/2014 | Yurkovetskiy et al. |
| 8,815,226 | B2 | 8/2014 | Yurkovetskiy et al. |
| 8,821,850 | B2 | 9/2014 | Yurkovetskiy et al. |
| 9,144,615 | B2 | 9/2015 | Yurkovetskiy et al. |
| 2012/0321583 | A1 | 12/2012 | Yurkovetskiy et al. |
| 2013/0101546 | A1 | 4/2013 | Yurkovetskiy et al. |
| 2014/0044704 | A1 | 2/2014 | Paton et al. |
| 2014/0086940 | A1 | 3/2014 | Bryant |
| 2014/0134127 | A1 | 5/2014 | Yurkovetskiy et al. |
| 2015/0064130 | A1 | 3/2015 | Yurkovetskiy et al. |
| 2015/0104407 | A1 | 4/2015 | Yurkovetskiy et al. |
| 2015/0125474 | A1 | 5/2015 | Smith et al. |
| 2015/0306240 | A1 | 10/2015 | Yurkovetskiy et al. |
| 2015/0314008 | A1 | 11/2015 | Yurkovetskiy et al. |
| 2015/0366987 | A1 | 12/2015 | Bodyak et al. |

FOREIGN PATENT DOCUMENTS

| | | | |
|---|---|---|---|
| WO | WO 2015104373 | A2 | 7/2015 |
| WO | WO 2015104385 | A2 | 7/2015 |
| WO | WO 2015115091 | A1 | 8/2015 |
| WO | WO 2015155976 | A1 | 10/2015 |
| WO | WO 2015162293 | A1 | 10/2015 |
| WO | WO 2015164665 | A1 | 10/2015 |

OTHER PUBLICATIONS

Hiorns et al., rsc.org, 2012, obtained online at: http://www.rsc.org/globalassets/05-journals-books-databases/our-journals/polymer-chemistry/brief-guide-to-polymer-nomenclature.pdf, downloaded on Nov. 30, 2016.*

Helwick, The ASCO Post, Nov. 1, 2013, obtained online at: http://www.ascopost.com/issues/november-1-2013/optimizing-anti-her2-treatment-for-metastatic-breast-cancer-in-2013/, downloaded on Nov. 30, 2016.*

Zsebik et al., Immunology Letters, 2006, 104, 146-155.*

Lewis Phillips et al., "Targeting HER2-Positive Breast Cancer with Trastuzumab-DM1,an Antibody-Cytotoxic Drug Conjugate." Cancer Research, Nov 15, 2008, 68:9280-9290.

LoRusso et al., Trastuzumab Emtansine: A Unique Antibody-Drug Conjugate in Development for Human Epidermal Growth Factor Receptor 2-Positive Cancer. *Clin Cancer Res* 2011;17:6437-6447. Published online Oct. 14, 2011.

Gianolio et al., Targeting HER2-positive cancer with dolastatin 15 derivatives conjugated to trastuzumab, novel antibody-drug conjugates. Cancer Chemother Pharmacol (2012) 70:439-449.

Yurkovetskiy et al., Advantages of polyacetal polymer-based ADCs: Application to low expression targets. Annual Meeting of the American Association of Cancer Research, San Diego, CA Apr. 5 to Apr. 9, 2014. Abstract #2645.

Smith, et al., ASN004, a Novel 5T4-Targeted Dolaflexin® ADC for the Treatment of Various Cancers. 5th World ADC, San Diego, CA, Oct. 27-29, 2014.

Bergstrom et al., Potent Promise. Innovations in Pharmaceutical Technology (2014) 49: 16-20.

Bodyak et al., Trastuzumab-Dolaflexin, a Highly Potent Fleximer-Based Antibody-Drug Conjugate, Demonstrates a Favorable Therapeutic Index in Exploratory Toxicology Studies in Multiple Species. Annual Meeting of the American Association of Cancer Research, Philadephia, PA Apr. 18 to Apr. 22, 2015. Abstract #641.

Aviles et al., MI130004, a New Antibody-Drug Conjugate, Induces Strong, Long-Lasting Antitumor Effect in HER2 Expressing Breast Tumor Models. Annual Meeting of the American Association of Cancer Research, Philadephia, PA Apr. 18 to Apr. 22, 2015. Abstract 2480.

(Continued)

*Primary Examiner* — Abigail VanHorn

(74) *Attorney, Agent, or Firm* — Cooley LLP; Heidi A. Ehrlacher

(57) ABSTRACT

A polymeric scaffold useful for conjugating with a protein based recognition-molecule (PBRM) to form a PBRM-polymer-drug conjugate is described herein. The scaffold includes one or more terminal maleimido groups. Also disclosed is a PBRM-polymer-drug conjugate prepared from the scaffold. Compositions comprising the conjugates, methods of their preparation, and methods of treating various disorders, such as cancer in a subject having low HER2 expression with the conjugates or their compositions are also described.

20 Claims, 5 Drawing Sheets

(56) References Cited

OTHER PUBLICATIONS

Humphreys et al., Site-specific conjugation of ARX788, an Antibody Drug Conjugate (ADC) targeting HER2, generates a potent and stable targeted therapeutic for multiple cancers. Annual Meeting of the American Association of Cancer Research, Philadephia, PA Apr. 18 to Apr. 22, 2015.

Bergstrom et al., A novel, highly potent HER2-targeted antibody-drug conjugate (ADC) for the treatment of low HER2-expressing tumors and combination with trastuzumab-based regimens in HER2-driven tumors. Annual Meeting of the American Association of Cancer Research, Philadephia, PA Apr. 18 to Apr. 22, 2015. Abstract #LBA-231.

Van Der Lee et al., The preclinical profile of the duocarmycin-based HER2-targeting ADC SYD985 predicts for clinical benefit in low HER2-expressing breast cancers. Annual Meeting of the American Association of Cancer Research, Philadephia, PA Apr. 18 to Apr. 22, 2015. Abstract #5360.

Smith, et al., ASN004, a Novel 5T4-Targeted Dolaflexin™ Antibody Drug Conjugate, Causes Complete Regression in Multiple Solid Tumor Models. Annual Meeting of the American Association of Cancer Research, Philadephia, PA Apr. 18 to Apr. 22, 2015. Abstract #1693.

Yurkovetskiy et al., A Polymer-based Antibody-Vinca Drug Conjugate Platform: Characterization and Preclinical Efficacy. Cancer Research, 75(16) OF1-OF8, 2015 (published on-line on Jun. 25, 2015).

Bergstrom et al., XMT-1522 induces tumor regressions in preclinical models representing HER2-positive and HER2 low-expressing breast cancer. The San Antonio Breast Cancer Symposium, San Antonio, TX, Dec. 8-12, 2015. Abstract # P4-14-28.

Yurkovetskiy et al.; "Fully Degradable Hydrophilic Polyals for Protein Modification", *Biomacromolecules*, vol. 6, No. 5, 2005, pp. 2648-2658.

Palanki et al.; "Development of novel linkers to conjugate pharmacophores to a carrier antibody", *Bioorganic & Medicinal Chemistry Letters*, vol. 22, No. 13, 2012, pp. 4249-4253.

* cited by examiner

PROTEIN-POLYMER-DRUG CONJUGATES AND METHODS OF USING SAME

RELATED APPLICATIONS

This application claims priority to, and the benefit of, U.S. provisional application Nos. 62/013,851, filed Jun. 18, 2014; 62/034,518, filed Aug. 7, 2014; and 62/147,964, filed Apr. 15, 2015, under 35 USC §119(e). The contents of each of these applications are hereby incorporated by reference in their entireties.

BACKGROUND OF THE INVENTION

Traditionally, pharmaceuticals have primarily consisted of small molecules that are dispensed orally (as solid pills and liquids) or as injectables. Over the past three decades, formulations (i.e., compositions that control the route and/or rate of drug delivery and allow delivery of the therapeutic agent at the site where it is needed) have become increasingly common and complex. Nevertheless, many questions and challenges regarding the development of new treatments as well as the mechanisms with which to administer them remain to be addressed. For example, many drugs exhibit limited or otherwise reduced potencies and therapeutic effects because they are either generally subject to partial degradation before they reach a desired target in the body, or accumulate in tissues other than the target, or both.

One objective in the field of drug delivery systems, therefore, is to deliver medications intact to specifically targeted areas of the body through a system that can stabilize the drug and control the in vivo transfer of the therapeutic agent utilizing either physiological or chemical mechanisms, or both.

Antibody-drug conjugates have been developed as target-specific therapeutic agents. Antibodies against various cancer cell-surface antigens have been conjugated with different cytotoxic agents that inhibit various essential cellular targets such as microtubules (maytansinoids, auristatins, taxanes: U.S. Pat. Nos. 5,208,020; 5,416,064; 6,333,410; 6,441,163; 6,340,701; 6,372,738; 6,436,931; 6,596,757; and 7,276,497); DNA (calicheamicin, doxorubicin, CC-1065 analogs; U.S. Pat. Nos. 5,475,092; 5,585,499; 5,846,545; 6,534,660; 6,756,397; and 6,630,579). Antibody conjugates with some of these cytotoxic drugs are actively being investigated in the clinic for cancer therapy (Ricart, A. D., and Tolcher, A. W., 2007, *Nature Clinical Practice*, 4, 245-255; Krop et al., 2010, *J. Clin. Oncol.*, 28, 2698-2704). However, existing antibody-drug conjugates have exhibited a few limitations. A major limitation is their inability to deliver a sufficient concentration of drug to the target site because of the limited number of targeted antigens and the relatively moderate cytotoxicity of cancer drugs like methotrexate, daunorubicin, maytansinoids, taxanes, and vincristine. One approach to achieving significant cytotoxicity is by linkage of a large number of drug molecules either directly or indirectly to the antibody. However such heavily modified antibodies often display impaired binding to the target antigen and fast in vivo clearance from the blood stream. Therefore, there is a need to improve the ability to deliver a sufficient concentration of a drug to the target such that maximum cytotoxicity for the drug is achieved.

SUMMARY OF THE INVENTION

The present invention relates to a protein-polymer-drug conjugate that is biodegradable, biocompatible and exhibits high drug load as well as strong binding to target antigen. The present invention also relates to a polymeric scaffold useful to conjugate with a protein based recognition-molecule (PBRM) so as to obtain the protein-polymer-drug conjugate.

In one aspect, the invention relates to a polymeric scaffold of Formula (Ia) useful to conjugate with a protein based recognition-molecule (PBRM) that has a molecular weight of 40 kDa or greater:

(Ia)

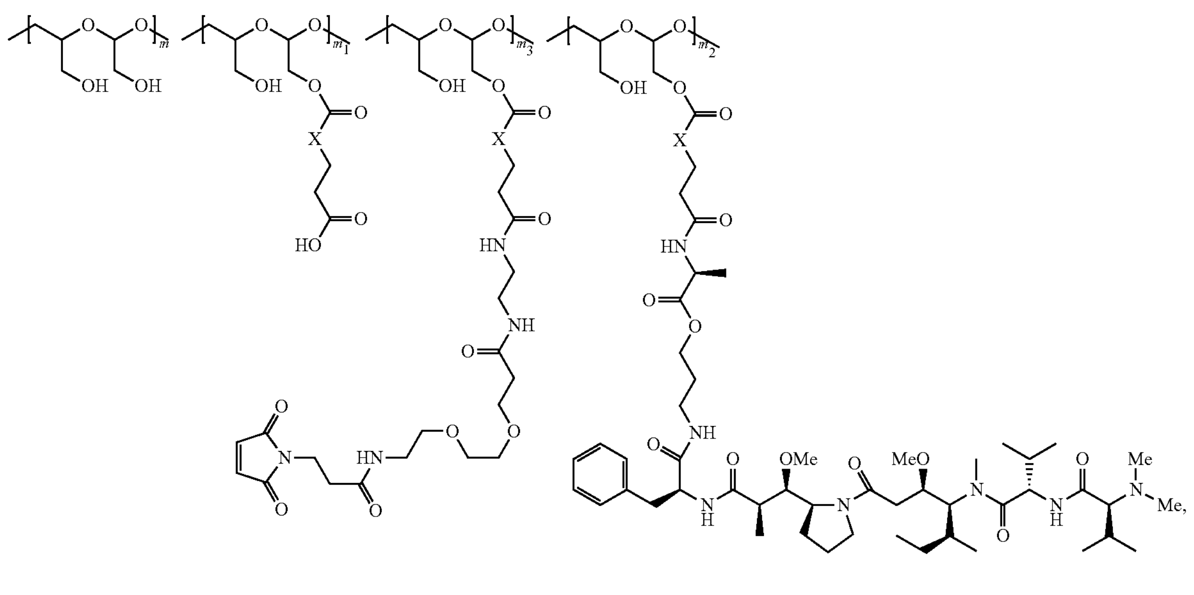

wherein:

the scaffold comprises poly(l-hydroxymethylethylene hydroxymethyl-formal) (PHF) having a molecular weight ranging from about 2 kDa to about 40 kDa;

X is $CH_2$, O, or NH;

m is an integer from 1 to about 300, $m_1$ is an integer from 1 to about 140, $m_2$ is an integer from 1 to about 40, $m_3$ is an integer from 1 to about 18, and the sum of m, $m_1$, $m_2$ and $m_3$ ranges from about 15 to about 300.

The scaffold of Formula (Ia) can include one or more of the following features:

When the PHF in Formula (Ia) has a molecular weight ranging from about 2 kDa to about 20 kDa, $m_2$ is an integer from 1 to about 20, $m_3$ is an integer from 1 to about 10, $m_1$ is an integer from 1 to about 70 and the sum of m, $m_1$, $m_2$ and $m_3$ ranges from about 15 to about 150.

When the PHF in Formula (Ia) has a molecular weight ranging from about 3 kDa to about 15 kDa, $m_2$ is an integer from 2 to about 15, $m_3$ is an integer from 1 to about 8, $m_1$ is an integer from 2 to about 50 and the sum of m, $m_1$, $m_2$ and $m_3$ ranges from about 20 to about 110.

When the PHF in Formula (Ia) has a molecular weight ranging from about 5 kDa to about 10 kDa, $m_2$ is an integer from about 2 to about 10, $m_3$ is an integer from 1 to about 5, $m_1$ is an integer from about 2 to about 35 and the sum of m, $m_1$, $m_2$ and $m_3$ ranges from about 40 to about 75.

In one embodiment, the scaffold of Formula (Ia) is of Formula (A) or (A1):

(A)

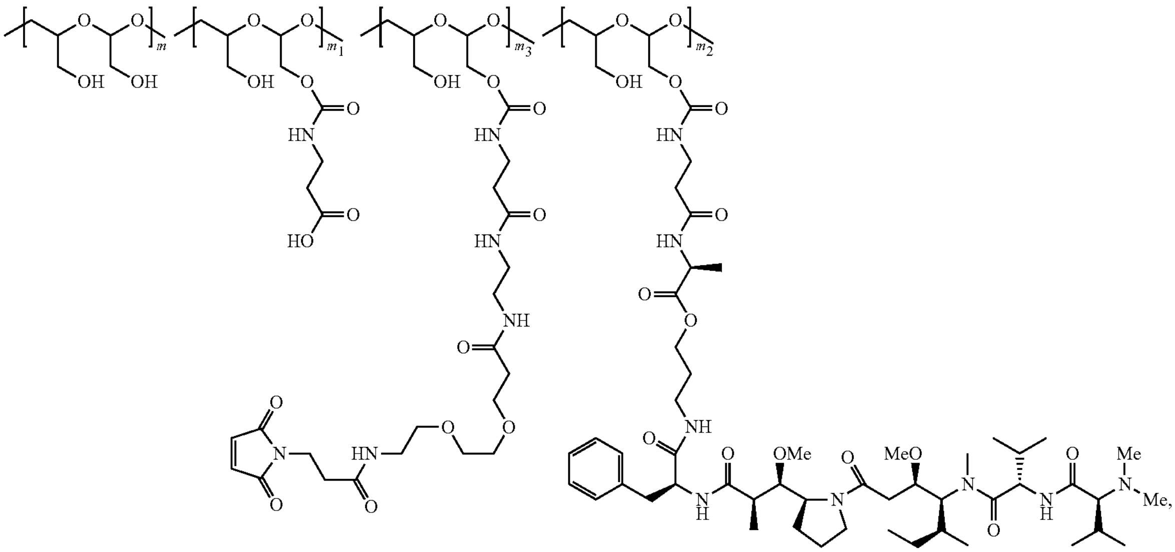

or (A1)

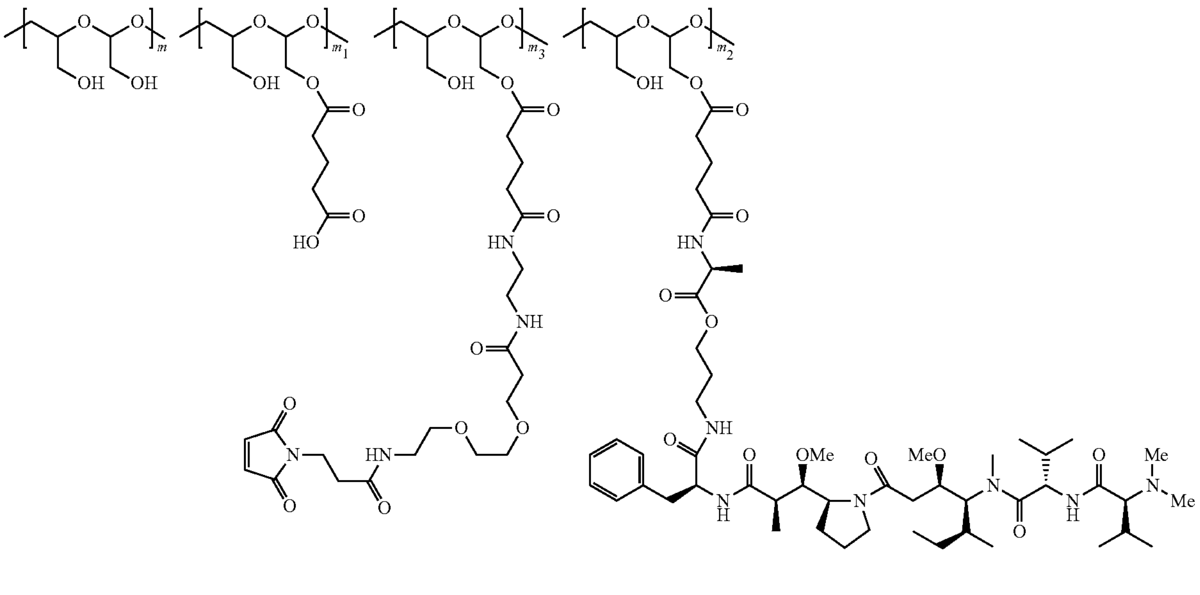

wherein:

the PHF has a molecular weight ranging from about 5 kDa to about 10 kDa;

m is an integer from 1 to about 75, $m_1$ is an integer from about 2 to about 35, $m_2$ is an integer from about 2 to about 10, $m_3$ is an integer from 1 to about 5, and the sum of m, $m_1$, $m_2$ and $m_3$ ranges from 40 to about 75.

The scaffold of Formula (Ia) further comprises a PBRM conjugated to the scaffold via one or more maleimido groups of the polymer scaffold. For example, the scaffold of Formula (Ia) further comprises one PBRM conjugated to the scaffold via two or more maleimido groups (e.g., up to five) of the scaffold.

The PBRM is of molecular weight 40 kDa or greater (e.g., 60 kDa or greater; 80 kDa or greater; 100 kDa or greater; 120 kDa or greater; 140 kDa or greater; 160 kDa or greater; 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa, or 140-150 kDa) and has a sulfhydryl (i.e., —SH or thiol) group.

The PBRM is conjugated to the drug carrying polymeric conjugate via the sulfhydryl group of the PBRM connected to the maleimido group of the drug carrying polymeric conjugate.

One PBRM is connected to one or more drug-carrying polymeric scaffold of Formula (Ia).

The scaffold comprising the PBRM is of Formula (Ib):

(Ib)

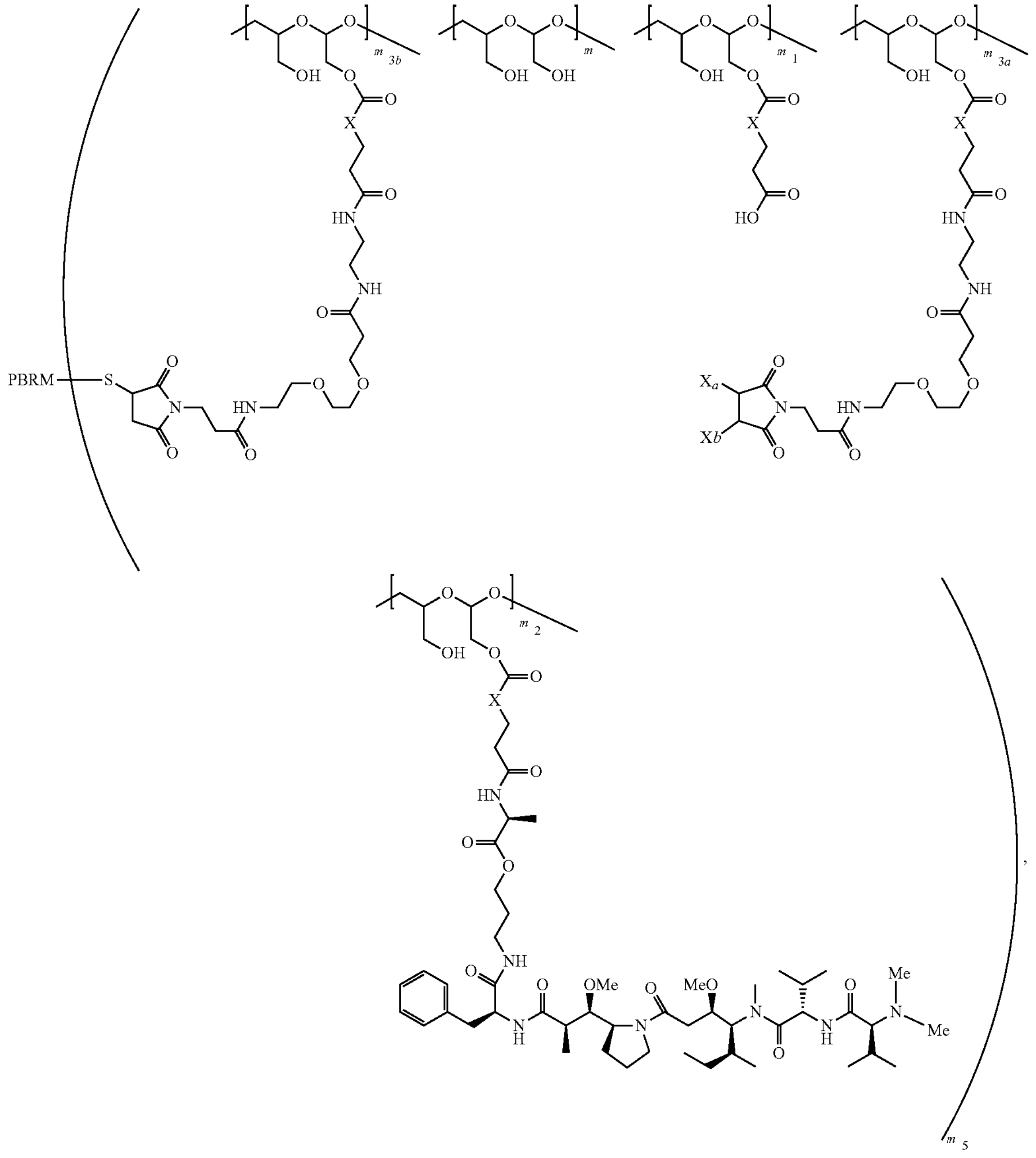

wherein:

the PBRM has a molecular weight of 40 kDa or greater, one of $X_a$ and $X_b$ is H and the other is a water-soluble maleimido blocking moiety, or $X_a$ and $X_b$, together with the carbon atoms to which they are attached for a carbon-carbon double bond;

$m_{3a}$ is an integer from 0 to about 17, $m_{3b}$ is an integer from 1 to about 8, wherein the sum of $m_{3a}$ and $m_{3b}$ is $m_3$ (e.g., an integer from 1 to about 18), the sum of m, $m_1$, $m_2$, $m_{3a}$, and $m_{3b}$ ranges from about 15 to about 300, and $m_5$ is an integer from 1 to about 10.

The scaffold of Formula (Ib) can include one or more of the following features:

The total number of the covalent bonds (e.g., sulfide bond) formed between the PHF and the PBRM (or total number of attachment points) is 10 or less.

The sum of $m_{3a}$ and $m_{3b}$ is between 1 and 18.

When the PHF in Formula (Ib) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and $m_5$ is an integer from 2 to about 8.

When the PHF in Formula (Ib) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8, and $m_5$ is an integer from 2 to about 8 (e.g., from about 2 to about 6 or from about 2 to about 4).

When the PHF in Formula (Ib) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5 and $m_5$ is an integer from 2 to about 8 (e.g., from about 2 to about 6 or from about 2 to about 4).

In certain embodiments, the ratio between auristatin F hydroxylpropyl amide ("AF HPA") and PBRM can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and PBRM can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and PBRM can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and PBRM can be about 16:1, 15:1, 14:1, 13:1, 12:1, 11:1 or 10:1.

In some embodiments, the ratio between AF and PBRM can be about 15:1, 14:1, 13:1, 12:1 or 11:1.

In some embodiments, the ratio between AF HPA and PBRM can be about 15:1, 14:1, 13:1 or 12:1.

In certain embodiments, the ratio between PHF and PBRM can be about 10:1, 9:1, 8:1, 7:1, 6:1, 5:1, 4:1, 3:1, 2:1 or 1:1.

In certain embodiments, the ratio between PHF and PBRM can be about 8:1, 7:1, 6:1, 5:1, 4:1, 3:1 or 2:1. In other embodiments, the ratio between PHF and PBRM can be about 6:1, 5:1, 4:1, 3:1, 2:1 or 1:1.

In other embodiments, the ratio between PHF and PBRM can be about 6:1, 5:1, 4:1, 3:1 or 2:1.

In other embodiments, the ratio between PHF and PBRM can be about 6:1, 5:1, 4:1 or 3:1.

In some embodiments, the ratio between PHF and PBRM can be about 5:1, 4:1 or 3:1.

In certain embodiments, the ratio between the PHF and PBRM can be about 4:1, 3:1 or 2:1.

The water-soluble maleimido blocking moieties (e.g., $X_a$ or $X_b$) are moieties that can be covalently attached to one of the two olefin carbon atoms upon reaction of the maleimido group with a thiol-containing compound of Formula (II):

$$R_{90}—(CH_2)_d—SH \quad (II)$$

wherein:

$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

In one embodiment, the water-soluble maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

In another aspect, the water-soluble maleimido blocking group is $—S—(CH_2)_d—R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

In another embodiment, the water-soluble maleimido blocking group is $—S—CH_2—CH(NH_2)COOH$.

The scaffold of Formula (Ib) is of Formula (B) or (B1):
(B)
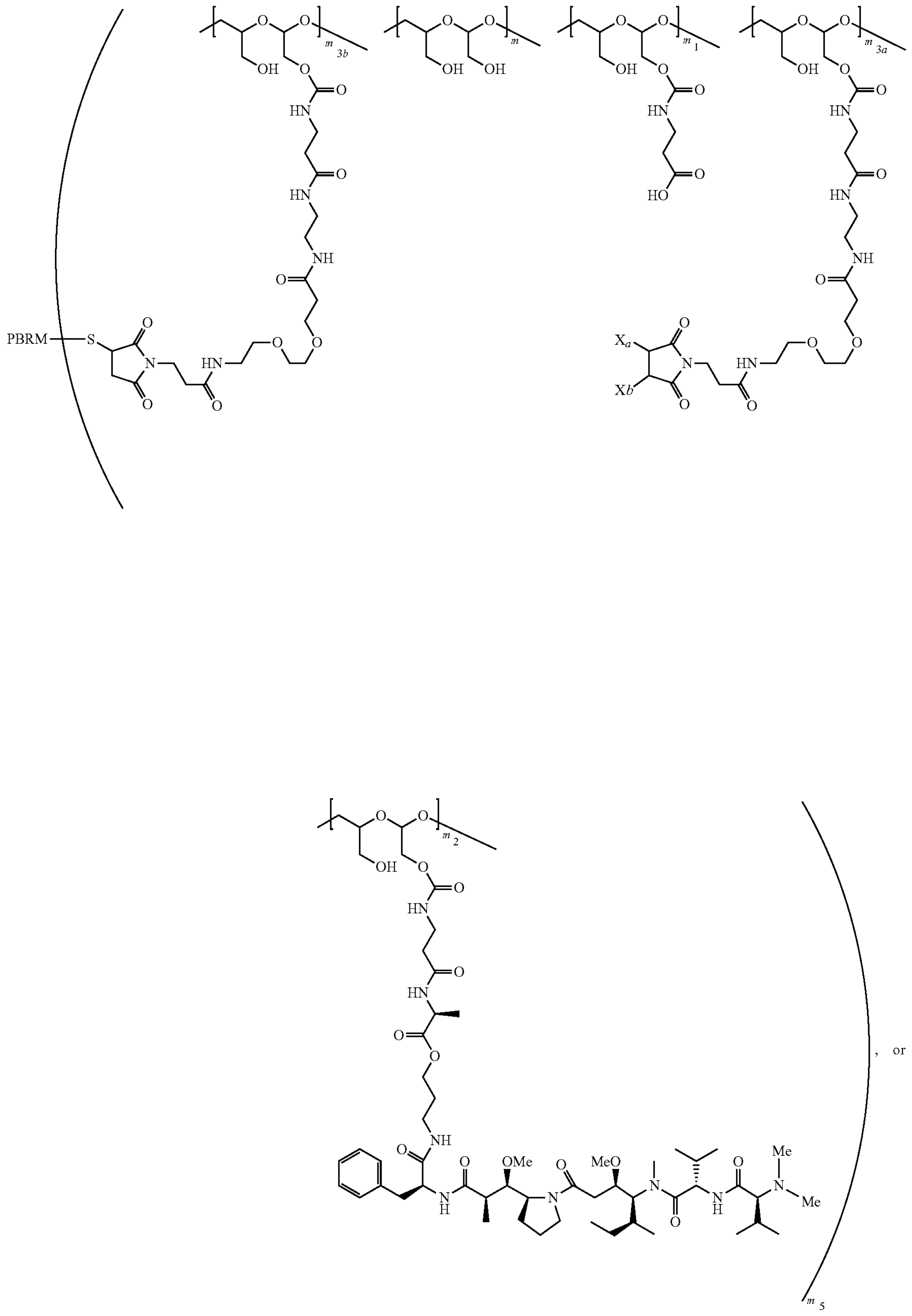
, or

-continued (B1)

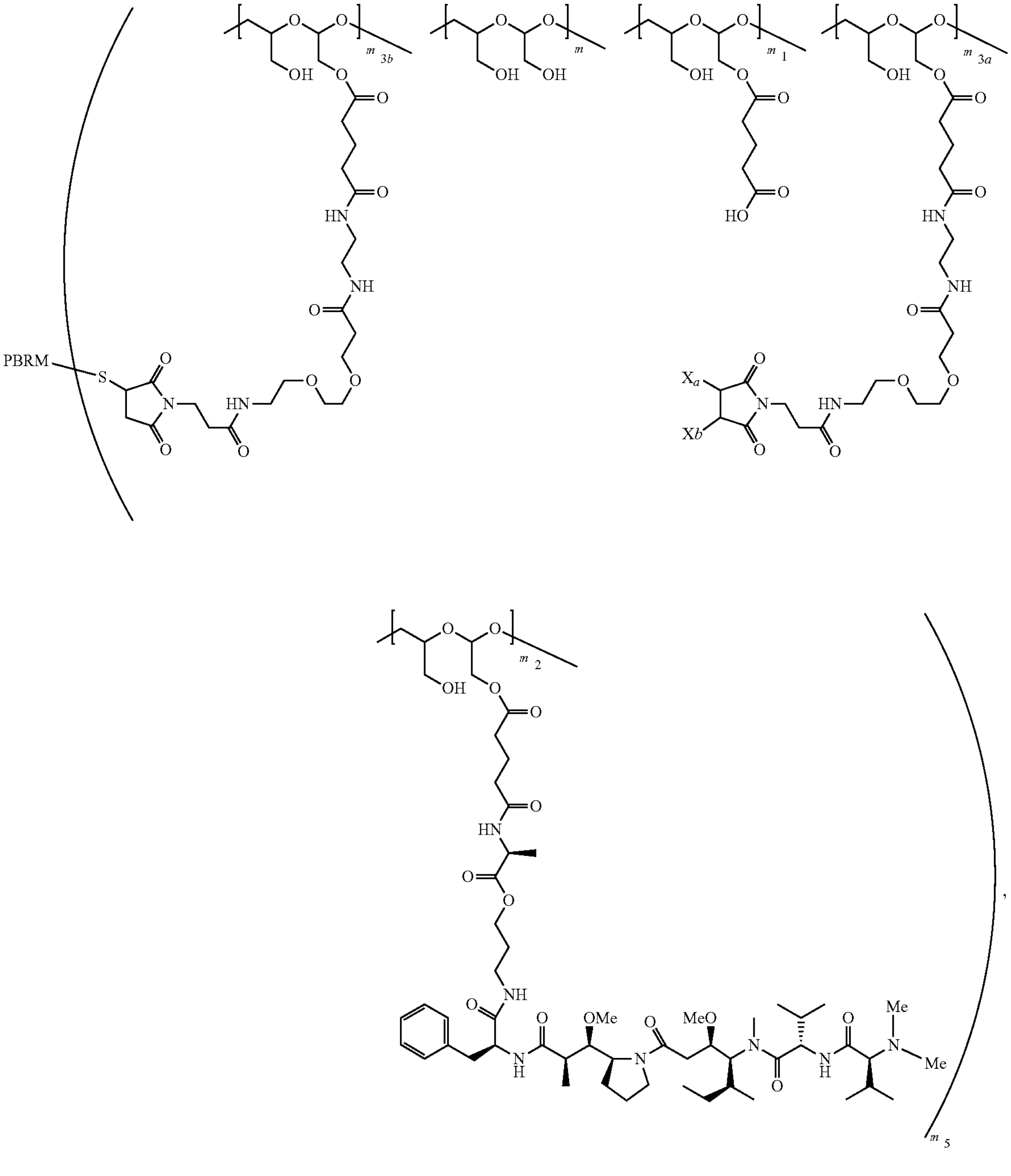

wherein:

the PHF has a molecular weight ranging from about 5 kDa to about 10 kDa;

m is an integer from 1 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of m, $m_1$, $m_2$, $m_{3a}$, and $m_{3b}$ ranges from about 40 to about 75, and $m_5$ is an integer from 2 to about 8. In certain embodiments, in Formula (B) or (B1), $m_5$ is an integer from about 2 to about 6 or from about 2 to about 4.

In certain embodiments, in Formula (B) or (B1), the total number of the covalent bonds (e.g., sulfide bond) formed between the PHF and the PBRM (or the total number of attachment points) is 10 or less (e.g., 8 or less, 6 or less, or 4 or less).

In certain embodiments, in any one of Formulae (Ib), (B) and (B1), the PBRM is trastuzumab or a biosimilar of trastuzumab.

The invention also provides for polymeric scaffolds of Formula (Ic):

(Ic)

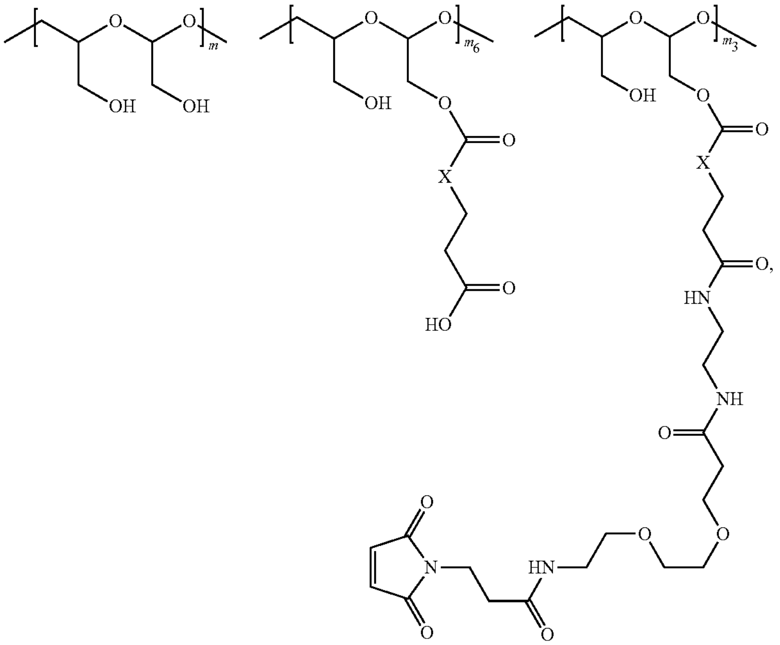

wherein:

the scaffold comprises PHF having a molecular weight ranging from about 2 kDa to about 40 kDa;

X is $CH_2$, O, or NH;

m is an integer from 1 to about 300, $m_6$ is an integer from 2 to about 180, $m_3$ is an integer from 1 to about 18, and the sum of m, $m_6$, and $m_3$ ranges from about 15 to about 300.

The scaffold of Formula (Ic) can include one or more of the following features:

When the PHF in Formula (Ic) has a molecular weight ranging from about 2 kDa to about 20 kDa, the sum of m, $m_6$ and $m_3$ ranges from about 15 to about 150, $m_6$ is an integer from 2 to about 90, and $m_3$ is an integer from 1 to about 10.

When the PHF in Formula (Ic) has a molecular weight ranging from about 3 kDa to about 15 kDa, the sum of m, $m_6$, and $m_3$ ranges from about 20 to about 110, $m_6$ is an integer from about 4 to about 65, and $m_3$ is an integer from 1 to about 8.

When the PHF in Formula (Ic) has a molecular weight ranging from about 5 kDa to about 10 kDa, the sum of m, $m_6$ and $m_3$ ranges from about 40 to about 75, $m_6$ is an integer from about 8 to about 45, and $m_3$ is an integer from 1 to about 5.

The scaffold of Formula (Ic) is of Formula (C) or (C1):

(C)

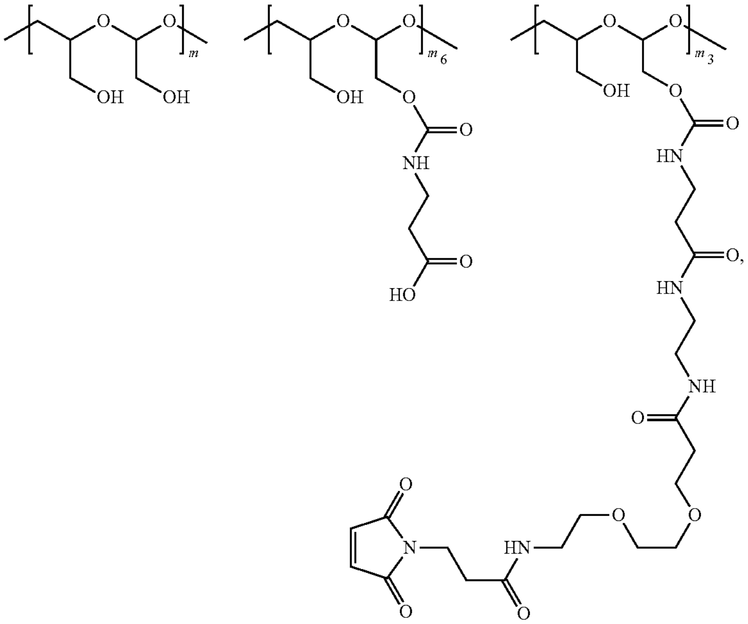

or

-continued (C1)

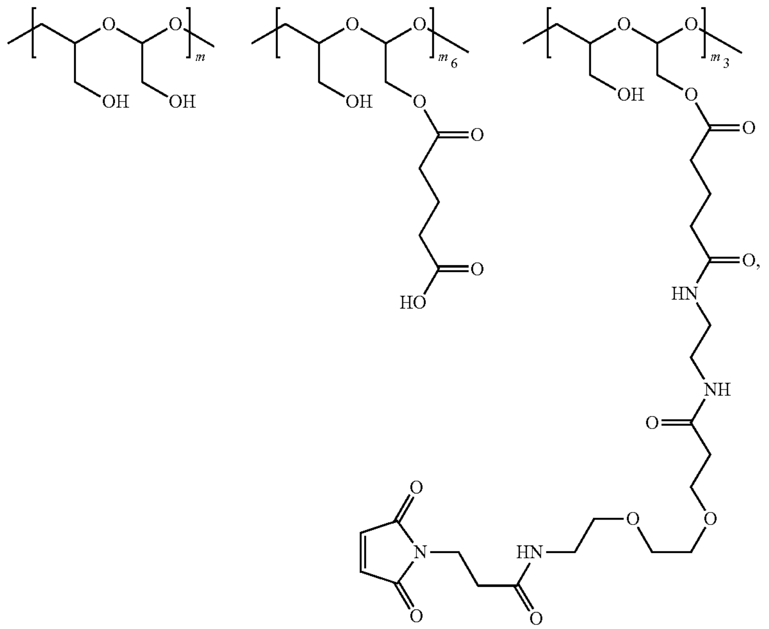

wherein:

the PHF has a molecular weight ranging from about 5 kDa to about 10 kDa;

m is an integer from 1 to about 75, $m_6$ is an integer from about 8 to about 45, $m_3$ is an integer from 1 to about 5, and the sum of m, $m_6$, and $m_3$ ranges from about 40 to about 75.

The scaffold of Formula (Ic) can further comprise one or more drug molecules ("D") connected to the PHF.

The D-containing scaffold of Formula (Ic) is of Formula (Id):

(Id)

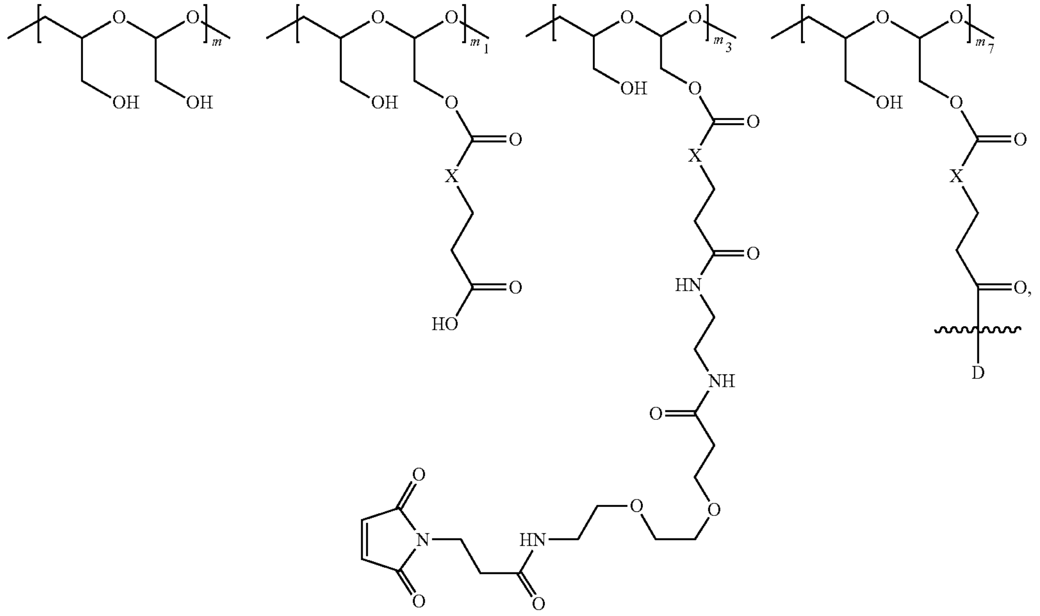

wherein:

each occurrence of D independently is a therapeutic agent having a molecular weight of ≤5 kDa, and the

between D and the carbonyl group denotes direct or indirect attachment of D to the carbonyl group, $m_1$ is an integer from 1 to about 140, and $m_7$ is an integer from 1 to about 40, wherein the sum of $m_1$ and $m_7$ is $m_6$ (i.e., from 2 to about 180).

The scaffold of Formula (Id) can further comprise a PBRM conjugated to the D-containing scaffold via one or more maleimido group of the D-containing scaffold forming a protein-polymer-drug conjugate. For example, the scaffold of Formula (Id) further comprises one PBRM conjugated to the D-containing scaffold via two or more maleimido groups (e.g., up to five) of the scaffold. For example, one PBRM is connected to one or more D-containing polymeric scaffold of Formula (Id).

In the protein-polymer-drug conjugate of Formula (Id), each D can be the same or different moiety and each PBRM can be the same or different moiety.

In certain embodiments the ratio between D and PBRM can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1 or 1:1.

In certain embodiments, the ratio between D and PBRM can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between D and PBRM can be about 20:1, 19:1, 18:1, 17:1, 16:1, 15:1, 14:1, 13:1, 12:1, 11:1, 10:1, 9:1, 8:1, 7:1 or 6:1.

In some embodiments, between D and PBRM can be about 16:1, 15:1, 14:1, 13:1, 12:1, 11:1 or 10:1.

In some embodiments, the ratio between D and PBRM can be about 15:1, 14:1, 13:1, 12:1 or 11:1.

In some embodiments, the ratio between D and PBRM can be about 15:1, 14:1, 13:1 or 12:1.

In some embodiments, between D and PBRM can be about 6:1, 5:1, 4:1, 3:1, 2:1 or 1:1.

In certain embodiments the ratio between PHF and PBRM can be about 10:1, 9:1, 8:1, 7:1, 6:1, 5:1, 4:1, 3:1, 2:1 or 1:1.

In certain embodiments, the ratio between PHF and PBRM can be about 8:1, 7:1, 6:1, 5:1, 4:1, 3:1 or 2:1.

In other embodiments, the ratio between PHF and PBRM can be about 6:1, 5:1, 4:1, 3:1, 2:1 or 1:1.

In other embodiments, the ratio between PHF and PBRM can be about 6:1, 5:1, 4:1, 3:1 or 2:1

In other embodiments, the ratio between PHF and PBRM can be about 6:1, 5:1, 4:1 or 3:1.

In some embodiments, the ratio between PHF and PBRM can be about 5:1, 4:1 or 3:1.

In some embodiments, the ratio between PHF and PBRM can be about 4:1, 3:1 or 2:1.

In certain embodiment, D is (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j) a DNA binding drug; (k) a kinase inhibitor; (1) a MEK inhibitor; (m) a KSP inhibitor; (n) a PI3 kinase inhibitor; (o) a topoisomerase inhibitor; or analogues thereof.

In one embodiment, the auristatin compound is auristatin, Dolastatin, monomethylauristatin E (MMAE), monomethylauristatin F (MMAF), auristatin F hydroxypropyl amide (AF HPA), or auristatin F phenylenediamine (AFP).

In one embodiment, the duocarmycin or analogs thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

Other examples of D include those described in, for example, U.S. Pat. No. 8,815,226; and co-pending applications with U.S. Ser. No. 14/512,316 filed Oct. 10, 2014, published as US20150104407; 61/988,011 filed May 2, 2014 and 62/010,972 filed Jun. 11, 2014; the disclosure of each of which is incorporated herein in its entirety.

In some embodiments, the number of D-carrying polymeric scaffolds that can be conjugated to PBRM is limited by the number of free cysteine residues. In some embodiments, free cysteine residues are introduced into the PBRM amino acid sequence by the methods described herein. Exemplary conjugates disclosed herein can include PBMRs that have 1, 2, 3, or 4 engineered cysteine amino acids (Lyon, R. et al (2012) Methods in Enzym. 502:123-138). In some embodiments, one or more free cysteine residues are already present in an antibody, without the use of engineering, in which case the existing free cysteine residues may be used to conjugate the PBRM to a D-carrying polymeric scaffold. In some embodiments, a PBRM is exposed to reducing conditions prior to conjugation of the PBRM in order to generate one or more free cysteine residues.

In one embodiment, D is AF HPA and the ratio between AF HPA and PBRM can be about 30:1, 29:1, 28:1, 27:1, 26:1, 25:1, 24:1, 23:1, 22:1, 21:1, 25:1, 20:1, 19:1, 18:1, 17:1, 16:1, 15:1, 14:1, 13:1, 12:1, 11:1, 10:1, 9:1, 8:1, 7:1 or 6:1.

In some embodiments, D is AF HPA and the ratio between AF HPA PBRM can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In another embodiment, D is AF HPA and the ratio between AF HPA and PBRM can be about 20:1, 15:1, 10:1, 5:1, 2:1 or 1:1.

In other embodiments, D is AF HPA and the ratio between AF HPA and PBRM can be about 20:1, 19:1, 18:1, 17:1, 16:1, 15:1, 14:1, 13:1, 12:1, 11:1, 10:1, 9:1, 8:1, 7:1 or 6:1.

In yet another embodiment, D is AF HPA and the ratio between AF HPA and PBRM can be about 16:1, 15:1, 13:1, 14:1, 12:1, 11:1 or 10:1.

In some embodiments, D is AF HPA and the ratio between AF HPA and PBRM can be about 15:1, 14:1, 13:1, 12:1 or 11:1.

In some embodiments, D is AF HPA and the ratio between AF HPA and PBRM can be about 15:1, 14:1, 13:1 or 12:1.

In some embodiments, D is AF HPA and the ratio between D-carrying PHF and PBRM can be about 6:1, 5:1, 4:1, 3:1, 2:1 or 1:1.

In Formulae disclosed herein, such as Formula (Ia), (Ib) (Ic), (Id), (Ie), (IIc), (IId), (A), (A1), (B), (B1), (C), or (C1), the disconnection or gap between the polyacetal units indicates that the units can be connected to each other in any order. Further, in certain Formulae (e.g., those in Table D) disclosed herein, the bracketed structures, i.e., polyacetal monomer units, are not accompanied with the number of repeating units (e.g., $m_1$, $m_2$, $m_3$, etc.) for the purpose of simplifying illustration and should not be construed as having only one repeating unit each.

Examples of PBRM include but are not limited to, full length antibodies such as IgG and IgM, single chain antibodies (scAb), domain antibodies (dAb), single domain heavy chain antibodies, single domain light chain antibodies or antibody fragments such as Fabs, $F(ab')_2$, single chain variable fragment (scFv), scFvFc, camelids, Fab2, and the like, small proteins, and peptides.

In one embodiment, the PBRM is trastuzumab or a biosimilar of trastuzumab.

In another aspect, the invention provides compositions comprising the conjugates, methods for their preparation, and methods of use thereof in the treatment of various disorders, including, but not limited to cancer. The target cancer can be anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterus cancer, ovarian cancer, prostate cancer, lung, non-small cell lung cancer (NSCLC), colon cancer, pancreatic cancer, renal cancer, or gastric cancer. The invention further relates to a pharmaceutical composition comprising a polymeric scaffold or conjugate described herein and a pharmaceutically acceptable carrier.

In yet another aspect, the invention relates to a method of diagnosing a disorder in a subject suspected of having the disorder. The method comprises administering an effective amount of the conjugate described herein to the subject suspected of having the disorder or performing an assay to detect a target antigen/receptor in a sample from the subject so as to determine whether the subject expresses target antigen or receptor.

The present invention also provides methods of treating, preventing, delaying the progression of or otherwise ameliorating a symptom of one or more pathologies associated with aberrant HER2 expression, function and/or activation or alleviating a symptom associated with such pathologies, by administering a PBRM-polymer-drug conjugate (e.g., a trastuzumab-polymer-drug conjugate) described herein to a subject in which such treatment or prevention is desired. The subject to be treated is, e.g., human. The PBRM-polymer-drug conjugate (e.g., a trastuzumab-polymer-drug conjugate) is administered in an amount sufficient to treat, prevent or alleviate a symptom associated with the pathology.

In embodiments, the trastuzumab-polymer-drug conjugate suitable for the methods disclosed herein includes trastuzumab or a biosimilar thereof connected to one or more D-carrying polymeric scaffolds wherein one or more D each is independently connected to the trastuzumab or a biosimilar thereof via the one or more polymeric scaffolds.

In some embodiments, each of the one or more polymeric scaffolds independently comprises poly(l-hydroxymethylethylene hydroxymethyl-formal) (PHF) having a molecular weight ranging from about 2 kDa to about 40 kDa.

In some embodiments, each of the one or more polymeric scaffolds independently is of Formula (IIc):

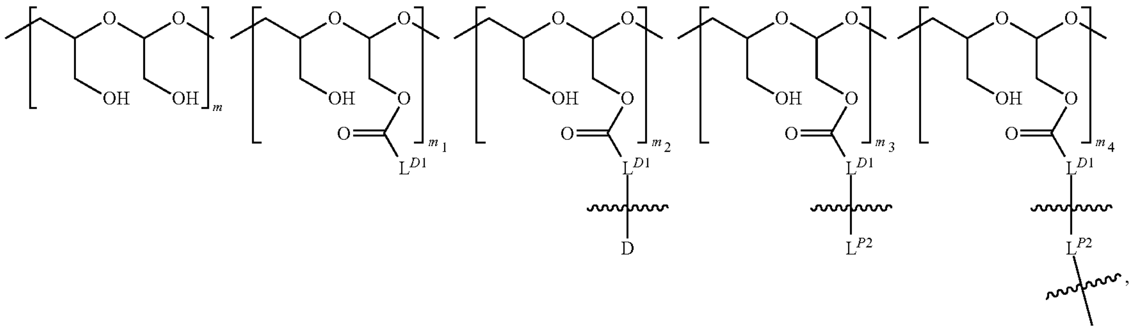

(IIc)

wherein:

$L^{D1}$ is a carbonyl-containing moiety;

each occurrence of

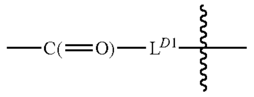

in

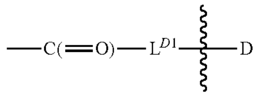

is independently a first linker that contains a biodegradable bond so that when the bond is broken, D is released in an active form for its intended therapeutic effect; and the

in

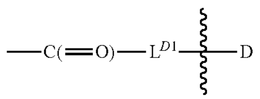

between $L^{D1}$ and D denotes direct or indirect attachment of D to $L^{D1}$;

each occurrence of

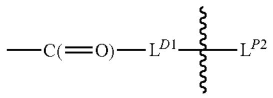

is independently a second linker not yet connected to the trastuzumab or a biosimilar thereof, in which $L^{P2}$ is a moiety containing a functional group that is yet to form a covalent bond with a functional group of the trastuzumab or a biosimilar thereof, and the

between $L^{D1}$ and $L^{P2}$ denotes direct or indirect attachment of $L^{P2}$ to $L^{D1}$, and each occurrence of the second linker is distinct from each occurrence of the first linker;

each occurrence of

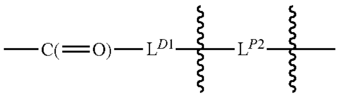

is independently a third linker that connects each D-carrying polymeric scaffold to the trastuzumab or a biosimilar thereof, in which the terminal

attached to $L^{P2}$ denotes direct or indirect attachment of $L^{P2}$ to the trastuzumab or a biosimilar thereof upon formation of a covalent bond between a functional group of $L^{P2}$ and a functional group of the trastuzumab or a biosimilar thereof; and each occurrence of the third linker is distinct from each occurrence of the first linker;

m is an integer from 1 to about 300, $m_1$ is an integer from 1 to about 140, $m_2$ is an integer from 1 to about 40, $m_3$ is an integer from 0 to about 18, $m_4$ is an integer from 1 to about 10; and the sum of m, $m_1$, $m_2$, $m_3$, and $m_4$ ranges from about 15 to about 300;

wherein the total number of $L^{P2}$ connected to the trastuzumab or a biosimilar thereof is 10 or less.

The conjugates described herein can include one or more of the following features:

For example, in Formula (IIc), $m_1$ is an integer from 1 to about 120 (e.g., about 1-90) and/or $m_3$ is an integer from 0 to about 10 (e.g., about 1-8).

For example, when the PHF in Formula (IIc) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 0 to about 9, $m_4$ is an integer from 1 to about 10, and/or $m_1$ is an integer from 1 to about 75 (e.g., $m_1$ being about 4-45).

For example, when the PHF in Formula (IIc) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 0 to about 7, $m_4$ is an integer from 1 to about 10, and/or $m_1$ is an integer from 1 to about 55 (e.g., $m_1$ being about 4-30).

For example, when the PHF in Formula (IIc) has a molecular weight ranging from about 2 kDa to about 20 kDa (i.e., the sum of m, $m_1$, $m_2$, $m_3$, and $m_4$ ranging from about 15 to about 150), $m_2$ is an integer from 1 to about 20, $m_3$ is an integer from 0 to about 10 (e.g., $m_3$ is from 0 to about 9), $m_4$ is an integer from 1 to about 8, and/or $m_1$ is an integer from 1 to about 70, and the total number of $L^{P2}$ connected to trastuzumab or a biosimilar thereof ranges from about 2 to about 8 (e.g., about 2, 3, 4, 5, 6, 7, or 8).

For example, when the PHF in Formula (IIc) has a molecular weight ranging from about 3 kDa to about 15 kDa (i.e., the sum of m, $m_1$, $m_2$, $m_3$, and $m_4$ ranging from about 20 to about 110), $m_2$ is an integer from 2 to about 15, $m_3$ is an integer from 0 to about 8 (e.g., $m_3$ is from 0 to about 7), $m_4$ is an integer from 1 to about 8, and/or $m_1$ is an integer from 2 to about 50, and the total number of $L^{P2}$ connected to trastuzumab or a biosimilar thereof ranges from about 2 to about 8 (e.g., about 2, 3, 4, 5, 6, 7, or 8).

For example, when the PHF in Formula (IIc) has a molecular weight ranging from about 5 kDa to about 10 kDa, (i.e. the sum of m, $m_1$, $m_2$, $m_{3a}$ and $m_{3b}$ ranges from about 40 to about 75), $m_2$ is an integer from about 2 to about 10 (e.g., $m_2$ being 3-10), $m_3$ is an integer from 0 to about 5 (e.g., $m_3$ ranging from 0 to about 4) $m_4$ is an integer from 1 to about 8, and/or $m_1$ is an integer from about 2 to about 35 (e.g., $m_1$ being about 5-35), and the total number of $L^{P2}$ connected to trastuzumab or a biosimilar thereof ranges from about 2 to about 8 (e.g., about 2, 3, 4, 5, 6, 7, or 8).

For example, each occurrence of D independently is a therapeutic agent having a molecular weight of ≤5 kDa.

For example, each occurrence of D independently is an anti-cancer drug, for example, selected from vinca alkaloids, auristatins, tubulysins, duocarmycins, non-natural camptothecin compounds, maytansinoids, calicheamicin compounds, pyrrolobenzodiazepines, DNA binding drugs, kinase inhibitors, PI3 kinase inhibitors, MEK inhibitors, KSP inhibitors, topoisomerase inhibitors, and analogs thereof.

For example, each

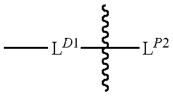

when not connected to trastuzumab or a biosimilar thereof, independently comprises a terminal group $W^P$, in which each $W^P$ independently is:

(1)

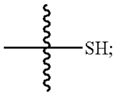

(2)

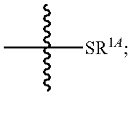

(3)

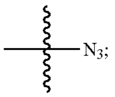

(4)

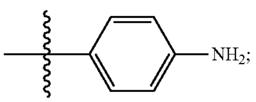

-continued (5)

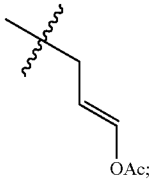

(6)

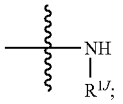

(7)

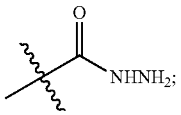

(8)

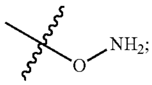

(9)

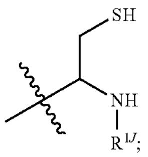

(10)

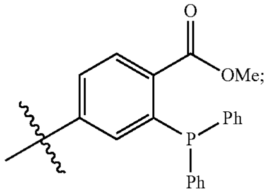

(11)

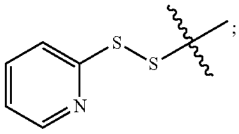

(12)

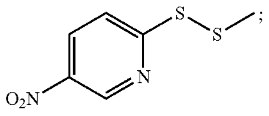

(13)

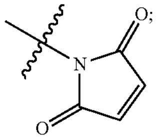

(14)

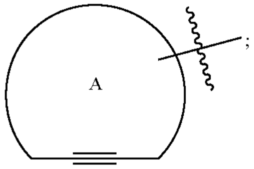

(15)

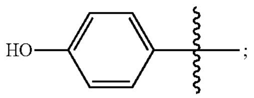

-continued (16)

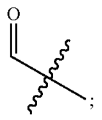

(17)

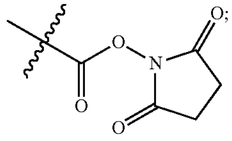

(18)

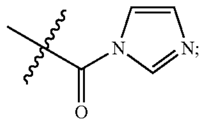

(19)

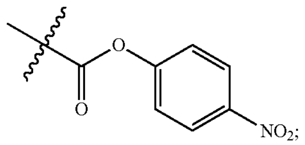

(20)

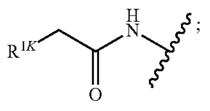

(21)

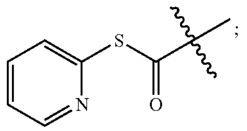

(22)

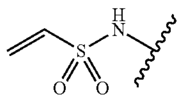

or;

(23)

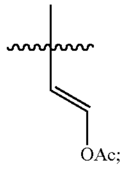

in which $R^{1K}$ is a leaving group (e.g., halide or RC(O)O— in which R is hydrogen, an aliphatic, heteroaliphatic, carbocyclic, or heterocycloalkyl moiety), $R^{1A}$ is a sulfur protecting group, and ring A is cycloalkyl or heterocycloalkyl, and $R^{1J}$ is hydrogen, an aliphatic, heteroaliphatic, carbocyclic, or heterocycloalkyl moiety.

For example, each $R^{1A}$ independently is

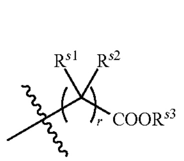

,

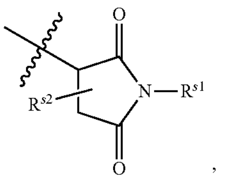

,

-continued

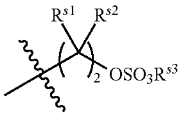

, or

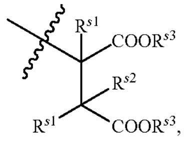

in which r is 1 or 2 and each of $R^{s1}$, $R^{s2}$, and $R^{s3}$ is hydrogen, an aliphatic, heteroaliphatic, carbocyclic, or heterocycloalkyl moiety.

For example, the functional group of $L^{P2}$ that is yet to form a covalent bond with a functional group of the trastuzumab or a biosimilar thereof is selected from —$SR^p$, —S—S-LG,

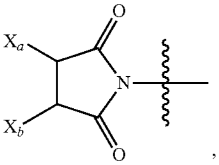

, and halo, in which LG is a leaving group, $R^p$ is H or a sulfur protecting group, and one of $X_a$ and $X_b$ is H and the other is a water-soluble maleimido blocking moiety, or $X_a$ and $X_b$, together with the carbon atoms to which they are attached for a carbon-carbon double bond. For example, the functional group of $L^{P2}$ that is yet to form a covalent bond is a functional group that is not reacted with a functional group of the trastuzumab or a biosimilar thereof, e.g.,

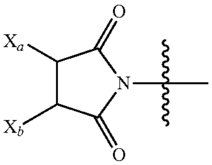

as the functional group of $L^{P2}$, in which one of $X_a$ and $X_b$ is H and the other is a water-soluble maleimido blocking moiety, or $X_a$ and $X_b$.

For example, $L^{D1}$ comprises —X—$(CH_2)_v$—C(═O)— with X directly connected to the carbonyl group of

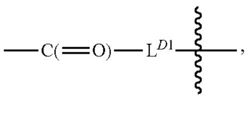

, in which X is $CH_2$, O, or NH, and v is an integer from 1 to 6.

For example, each occurrence of

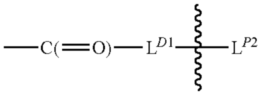

is independently —C(═O)—X—$(CH_2)_v$—C(═O)—NH—$(CH_2)_u$—NHC(═O)—$(CH_2)_w$—$(OCH_2)_x$—NHC(═O)—$(CH_2)_y$-M, in which X is $CH_2$, O, or NH, each of v, u, w, x and y independently is an integer from 1 to 6, and M is

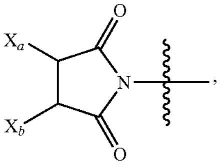

, wherein one of $X_a$ and $X_b$ is H and the other is a water-soluble maleimido blocking moiety, or $X_a$ and $X_b$, together with the carbon atoms to which they are attached for a carbon-carbon double bond.

For example, each of v, u, w, x and y is 2.

For example, the ratio between D and trastuzumab or a biosimilar thereof is about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1 or 1:1.

For example, the ratio between D and trastuzumab or a biosimilar thereof is about 20:1, 15:1, 10:1, 5:1, 2:1 or 1:1.

For example, the ratio between D and trastuzumab or a biosimilar thereof is about 16:1, 15:1, 14:1, 13:1, 12:1, 11:1 or 10:1.

For example, the ratio between D and trastuzumab or a biosimilar thereof is about 15:1, 14:1, 13:1, 12:1 or 11:1.

For example, the ratio between D and trastuzumab or a biosimilar thereof is about 15:1, 14:1, 13:1 or 12:1.

For example, the ratio between D and trastuzumab or a biosimilar thereof is about 6:1, 5:1, 4:1, 3:1, 2:1 or 1:1.

For example, each of the one or more D-carrying polymeric scaffolds independently is of Formula (IId):

(IId)

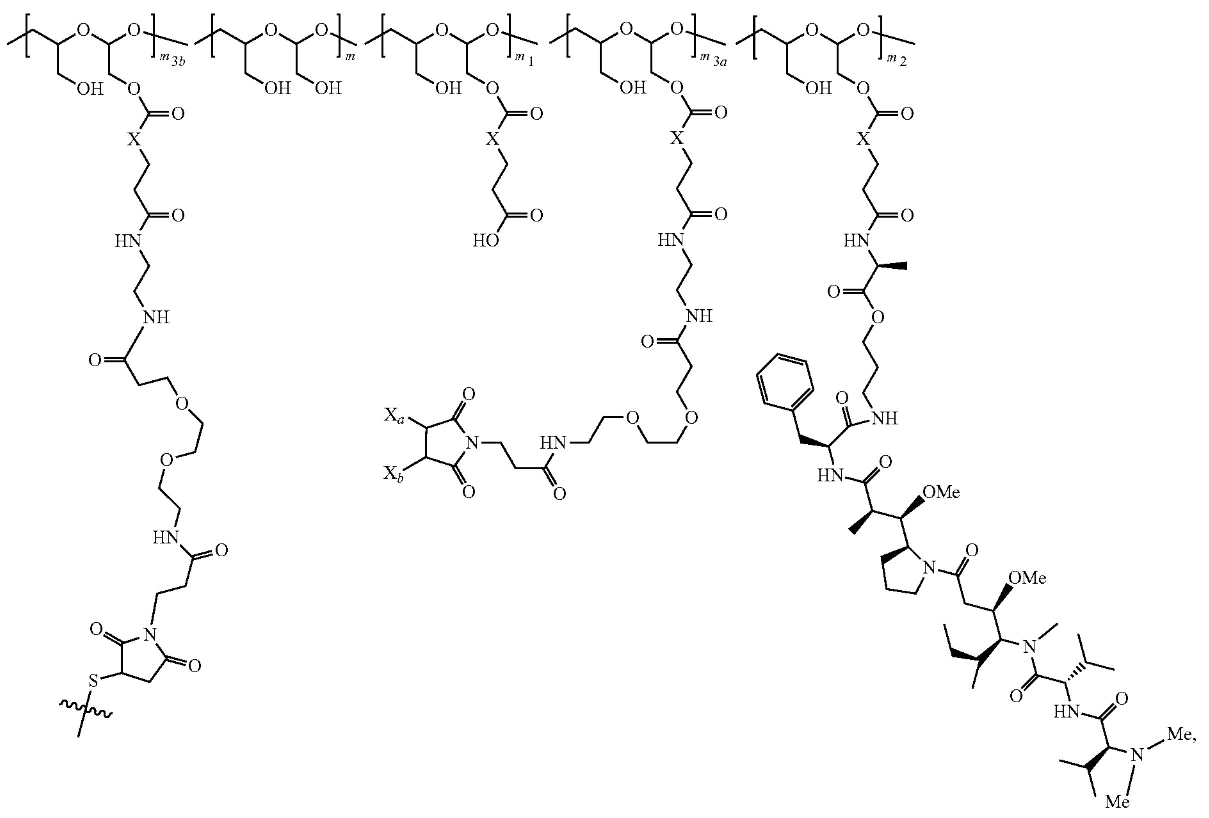

wherein:

$m_{3_a}$ is an integer from 0 to about 17, $m_{3_b}$ is an integer from 1 to about 8, and the terminal

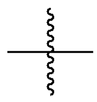

denotes the direct attachment of the one or more polymeric scaffolds to trastuzumab or a biosimilar thereof.

The scaffold of Formula (IId) can include one or more of the following features:

The sum of $m_{3_a}$ and $m_{3_b}$ is between 1 and 18.

When the PHF in Formula (IId) has a molecular weight ranging from about 2 kDa to about 40 kDa, the sum of m, $m_1$, $m_2$, $m_{3_a}$ and $m_{3_b}$ ranges from about 15 to about 300, $m_1$ is an integer from 1 to about 140, $m_2$ is an integer from 1 to about 40, $m_{3_a}$ is an integer from 0 to about 17, $m_{3_b}$ is an integer from 1 to about 8, the sum of $m_{3_a}$ and $m_{3_b}$ ranges from 1 and about 18, and the ratio between the PHF and the isolated HER2 antibody or antigen-binding fragment thereof is 10 or less.

When the PHF in Formula (IId) has a molecular weight ranging from about 2 kDa to about 20 kDa, the sum of m, $m_1$, $m_2$, $m_{3_a}$ and $m_{3_b}$ ranges from about 15 to about 150, $m_1$ is an integer from 1 to about 70, $m_2$ is an integer from 1 to about 20, $m_{3_a}$ is an integer from 0 to about 9, $m_{3_b}$ is an integer from 1 to about 8, the sum of $m_{3_a}$ and $m_{3_b}$ ranges from 1 and about 10, and the ratio between the PHF and trastuzumab or a biosimilar thereof is an integer from 2 to about 8.

When the PHF in Formula (IId) has a molecular weight ranging from about 3 kDa to about 15 kDa, the sum of m, $m_1$, $m_2$, $m_{3_a}$ and $m_{3_b}$ ranges from about 20 to about 110, $m_1$ is an integer from 2 to about 50, $m_2$ is an integer from 2 to about 15, $m_{3_a}$ is an integer from 0 to about 7, $m_{3_b}$ is an integer from 1 to about 8, the sum of $m_{3_a}$ and $m_{3_b}$ ranges from 1 and about 8, and the ratio between the PHF and trastuzumab or a biosimilar thereof is an integer from 2 to about 8 (e.g., from about 2 to about 6 or from about 2 to about 4).

When the PHF in Formula (IId) has a molecular weight ranging from about 5 kDa to about 10 kDa, the sum of m, $m_1$, $m_2$, $m_{3_a}$ and $m_{3_b}$ ranges from about 40 to about 75, $m_1$ is an integer from about 2 to about 35, $m_2$ is an integer from about 2 to about 10, $m_{3_a}$ is an integer from 0 to about 4, $m_{3_b}$ is an integer from 1 to about 5, the sum of $m_{3_a}$ and $m_{3_b}$ ranges from 1 and about 5, and the ratio between the PHF and trastuzumab or a biosimilar thereof is an integer from 2 to about 8 (e.g., from about 2 to about 6 or from about 2 to about 4).

In certain embodiments, the ratio between auristatin F hydroxylpropyl amide ("AF HPA") and trastuzumab or a biosimilar thereof can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and trastuzumab or a biosimilar thereof can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and trastuzumab or a biosimilar thereof can be about 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and trastuzumab or a biosimilar thereof can be about 20:1, 15:1, 10:1, 5:1, 2:1 or 1:1.

In other embodiments, the ratio between AF HPA and trastuzumab or a biosimilar thereof can be about 16:1, 15:1, 14:1, 13:1, 12:1, 11:1 or 10:1.

In some embodiments, the ratio between AF HPA and trastuzumab or a biosimilar thereof can be about 15:1, 14:1, 13:1, 12:1 or 11:1.

In some embodiments, the ratio between AF HPA and trastuzumab or a biosimilar thereof can be about 15:1, 14:1, 13:1 or 12:1.

In certain embodiments, the ratio between the AF HPA-carrying PHF and trastuzumab or a biosimilar thereof can be about 10:1, 9:1, 8:1, 7:1, 6:1, 5:1, 4:1, 3:1, 2:1 or 1:1.

In certain embodiments, the ratio between AF HPA-carrying PHF and trastuzumab or a biosimilar thereof can be about 8:1, 7:1, 6:1, 5:1, 4:1, 3:1 or 2:1.

In other embodiments, the ratio between the AF HPA-carrying PHF and trastuzumab or a biosimilar thereof can be about 6:1, 5:1, 4:1, 3:1, 2:1 or 1:1.

In other embodiments, the ratio between AF HPA-carrying PHF and trastuzumab or a biosimilar thereof can be about 6:1, 5:1, 4:1, 3:1 or 2:1.

In other embodiments, the ratio between AF HPA-carrying PHF and trastuzumab or a biosimilar thereof can be about 6:1, 5:1, 4:1 or 3:1.

In certain embodiments, the ratio between the AF HPA-carrying PHF and trastuzumab or a biosimilar thereof can be about 5:1, 4:1 or 3:1.

In certain embodiments, the ratio between the AF HPA-carrying PHF and trastuzumab or a biosimilar thereof can be about 4:1, 3:1 or 2:1.

In one embodiment, the trastuzumab-polymer-drug conjugate suitable for the methods disclosed herein is of Formula (Ie):

wherein:

the PHF has a molecular weight ranging from about 2 kDa to about 40 kDa;

PBRM is trastuzumab or a biosimilar thereof;

each occurrence of D independently is a therapeutic agent having a molecular weight of ≤5 kDa, and the

between D and the carbonyl group denotes direct or indirect attachment of D to the carbonyl group, X is $CH_2$, O, or NH;

one of $X_a$ and $X_b$ is H and the other is a water-soluble maleimido blocking moiety, or $X_a$ and $X_b$, together with the carbon atoms to which they are attached for a carbon-carbon double bond, $m_1$ is an integer from 1 to about 140, $m_7$ is an integer from 1 to about 40, wherein the sum of $m_1$ and $m_7$ is about 2 to about 180, m is an integer from 1 to about 300, $m_{3a}$ is an integer from 0 to about 17, $m_{3b}$ is an integer from 1 to about 8, wherein the sum of $m_{3a}$ and $m_{3b}$ is $m_3$, the sum of m, $m_1$, $m_7$, $m_{3a}$, and $m_{3b}$ ranges from about 15 to about 300, and $m_5$ is an integer from 1 to about 10.

In one embodiment, the trastuzumab-polymer-drug conjugate suitable for the methods disclosed herein is of Formula (B):

(Ie)

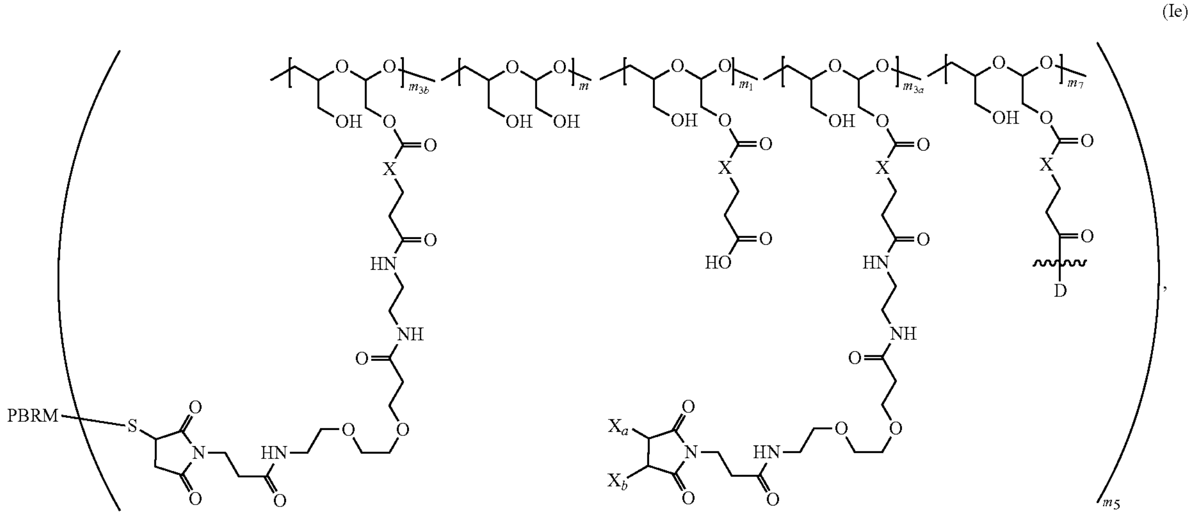

, (B)

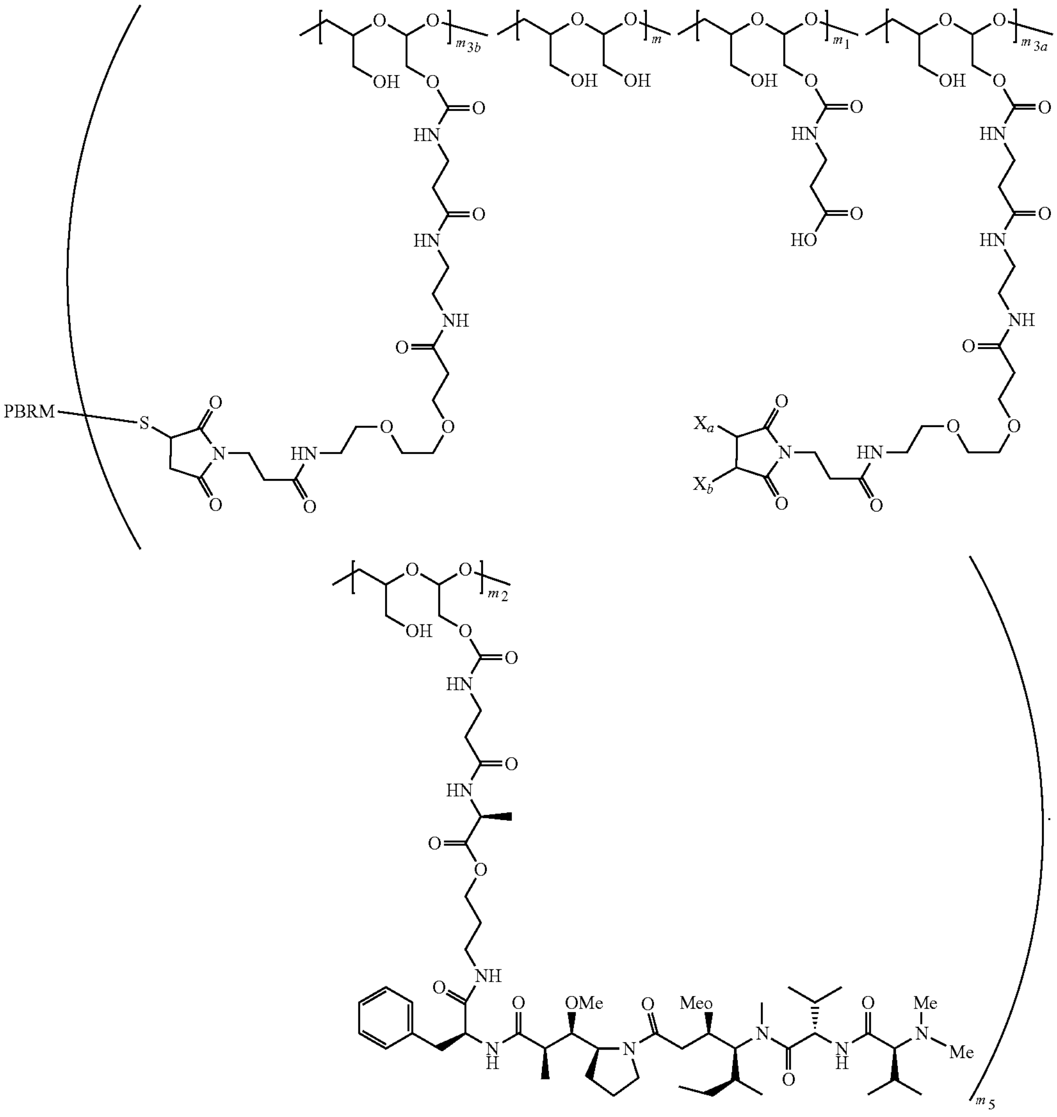

wherein:

the PHF has a molecular weight ranging from about 5 kDa to about 10 kDa;

PBRM is trastuzumab or a biosimilar thereof;

m is an integer from 1 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of m, $m_1$, $m_2$, $m_{3a}$, and $m_{3b}$ ranges from about 40 to about 75, and $m_5$ is an integer from 2 to about 8 (e.g., about 2, 3, 4, 5, 6, 7, or 8).

For example, the total number of sulfide bonds between trastuzumab or a biosimilar thereof and the PHF is 10 or less (e.g., 8 or less, 6 or less, or 4 or less).

The present disclosure also provides methods of treating, preventing, delaying the progression of or otherwise ameliorating a symptom of one or more pathologies associated with aberrant HER2 expression, function and/or activation or alleviating a symptom associated with such pathologies, by administering a PBRM-polymer-drug conjugate (e.g., a trastuzumab-polymer-drug conjugate) disclosed herein to a subject in which such treatment or prevention is desired. The subject to be treated is, e.g., human. The PBRM-polymer-drug conjugate is administered in an amount sufficient to treat, prevent or alleviate a symptom associated with the pathology.

The present disclosure also provides methods of treating, preventing, delaying the progression of or otherwise ameliorating a symptom of one or more pathologies associated with HER2 expression, function and/or activation or alleviating a symptom associated with such pathologies, by administering a PBRM-polymer-drug conjugate disclosed herein to a subject in which such treatment or prevention is desired. The subject to be treated is, e.g., human. The a PBRM-polymer-drug conjugate is administered in an amount sufficient to treat, prevent or alleviate a symptom associated with the pathology.

Pathologies treated and/or prevented using the PBRM-polymer-drug conjugate (e.g., a trastuzumab-polymer-drug conjugate) described herein include, for example, a cancer. For example, the PBRM-polymer-drug conjugate (e.g., a trastuzumab-polymer-drug conjugate) described herein are useful in treating, preventing, delaying the progression of or otherwise ameliorating a symptom of a cancer selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian cancer, prostate cancer, lung cancer, non-small cell lung cancer (NSCLC), colon cancer, pancreatic cancer, renal cancer, and gastric cancer.

In some embodiments, the PBRM-polymer-drug conjugate (e.g., a trastuzumab-polymer-drug conjugate) described herein are useful in treating, preventing, the delaying the progression of or otherwise ameliorating a symptom of breast cancer.

In some embodiments, the PBRM-polymer-drug conjugate (e.g., a trastuzumab-polymer-drug conjugate) described herein are useful in treating, preventing, the delaying the progression of or otherwise ameliorating a symptom of gastric cancer.

In some embodiments, the PBRM-polymer-drug conjugate (e.g., a trastuzumab-polymer-drug conjugate) described herein are useful in treating, preventing, the delaying the progression of or otherwise ameliorating a symptom of non-small cell lung cancer (NSCLC).

In some embodiments, the PBRM-polymer-drug conjugate (e.g., a trastuzumab-polymer-drug conjugate) described herein are useful in treating, preventing, the delaying the progression of or otherwise ameliorating a symptom of ovarian cancer.

The invention also provides kits and/or methods for identifying or otherwise refining, e.g., stratifying, a patient population suitable for therapeutic administration of a PBRM-polymer-drug conjugate (e.g., a trastuzumab-polymer-drug conjugate) described herein by identifying patients having low expression of HER2 prior to treatment with a PBRM-polymer-drug conjugate (e.g., a trastuzumab-polymer-drug conjugate). Low HER2 expression represents those patients having less than or equal to 100,000, less than or equal to 90,000, or less than or equal to 80,000 HER2 molecules per cell, for example, as measured per cell in a test cell population. The level of HER2 expression, i.e., number of HER2 molecules per cell, can be measured using any art-recognized method, including, but not limited to using the cell-based viability assays shown in the working examples provided herein The invention also provides kits and/or methods for identifying or otherwise refining, e.g., stratifying, a patient population suitable for therapeutic administration of a PBRM-polymer-drug conjugate (e.g., a trastuzumab-polymer-drug conjugate) described herein by identifying the HER2 score of subject prior to treatment with a trastuzumab-polymer-drug conjugate disclosed herein.

In some embodiments, the subject is identified as having a scoring of 1+ or 2+ for HER2 expression. In some embodiments, the subject is identified as having a scoring of 1+ or 2+ for HER2 expression as detected by immunohistochemistry (IHC) analysis performed on a test cell population, and wherein the HER2 gene is not amplified in the test cell population. In some embodiments, the test cell population is derived from fresh, unfrozen tissue from a biopsy sample. In some embodiments, the test cell population is derived from a frozen tissue from a biopsy sample.

The IHC test measures the amount of HER2 receptor protein on the surface of cells in a cancer tissue sample, e.g., a breast cancer tissue sample or a gastric cancer sample, and assigns the detected level of cell surface HER2 receptor a HER2 score of 0, 1+, 2+ or 3+. If the subject's HER2 score is in the range of 0 to 1+, the cancer is deemed to be "HER2 negative." If the score is 2+, the cancer is referred to as "borderline," and a score of 3+ signifies that the cancer is "HER2 positive."

In some embodiments, the subject is identified as having a scoring of 1+ or 2+ for HER2 expression and is refractory to chemotherapy, including standard, front-line chemotherapeutic agents. As used herein, the term subject includes humans and other mammals. In some embodiments, the subject is identified as having a scoring of 1+ or 2+ for HER2 expression and is suffering from breast cancer, gastric cancer, non-small cell lung cancer (NSCLC), or ovarian cancer.

In some embodiments, the antibodies and/or PBRM-polymer-drug conjugates disclosed herein are useful in treating, preventing, the delaying the progression of or otherwise ameliorating a symptom of breast cancer in patients who have HER2 IHC 1+ or HER2 IHC 2+ without gene amplification, e.g., FISH− (or fluorescence in situ hybridization negative).

In some embodiments, the antibodies and/or PBRM-polymer-drug conjugates disclosed herein are useful in treating, preventing, the delaying the progression of or otherwise ameliorating a symptom of breast cancer in patients who have advanced HER2 positive breast cancer and who have received prior treatment with Kadcyla.

In some embodiments, the antibodies and/or PBRM-polymer-drug conjugates disclosed herein are useful in treating, preventing, the delaying the progression of or otherwise ameliorating a symptom of breast cancer in patients who have advanced HER2 positive breast cancer and who have not received prior treatment with Kadcyla.

In some embodiments, the antibodies and/or PBRM-polymer-drug conjugates disclosed herein are useful in treating, preventing, the delaying the progression of or otherwise ameliorating a symptom of gastric cancer in patients who have HER2 IHC 1+ or HER2 IHC 2+ without gene amplification, e.g., FISH−.

In some embodiments, the antibodies and/or PBRM-polymer-drug conjugates disclosed herein are useful in treating, preventing, the delaying the progression of or otherwise ameliorating a symptom of non-small cell lung cancer (NSCLC) in patients who have HER2 IHC 2+, HER2 IHC 3+, any HER2 gene amplification or mutation status.

In some embodiments, the subject is refractory to chemotherapy, including standard, front-line chemotherapeutic agents. In some embodiments, the subject is resistant to treatment with Kadcyla.

A PBRM-polymer-drug conjugate (e.g., a trastuzumab-polymer-drug conjugate) used in any of the embodiments of the methods and uses provided herein can be administered at any stage of the disease. For example, such PBRM-polymer-drug conjugate (e.g., a trastuzumab-polymer-drug conjugate) can be administered to a patient suffering cancer of any stage, from early to metastatic.

A PBRM-polymer-drug conjugate (e.g., a trastuzumab-polymer-drug conjugate) used in any of the embodiments of these methods and uses can be administered either alone or in combination with one or more chemotherapeutic agents or other agents. In some embodiments, the agent is any of the toxins described herein. In some embodiments, the agent is (1) HER2 inhibitors, (2) EGFR inhibitors (e.g., tyrosine kinase inhibitors or targeted anti-EGFR antibodies), (3) BRAF inhibitors, (4) ALK inhibitors, (5) hormone receptor inhibitors, (6) mTOR inhibitors, (7) VEGF inhibitors, or (8) cancer vaccines. In some embodiments, the agent is a standard, first line chemotherapeutic agent, such as, for example trastuzumab, pertuzumab, ado-trastuzumab emtansine (Kadcyla), lapatinib, anastrozole, letrozole, exemestane, everolimus, fulvestrant, tamoxifen, toremifene, megestrol acetate, fluoxymesterone, ethinyl estradiol, paclitaxel, capecitabine, gemcitabine, eribulin, vinorelbine, cyclophosphamide, carboplatin, docetaxel, albumin-bound paclitaxel, cisplatin, epirubicin, ixabepilone, doxorubicin, fluorouracil, oxaliplatin, fluoropyrimidine, irinotecan, ramucirumab, mitomycin, leucovorin, cetuximab, bevacizumab, erlotinib, afatinib, crizotinib, permetrexed, ceritinib, etoposide, vinblastine, vincristine, ifosfamid, liposomal doxorubicin, topotecan, altretamine, melphalan or leuprolide acetate. In some embodiments, the second agent is Kadcyla.

In some embodiments, the agent is at least a second antibody or antigen binding fragment thereof that specifically binds HER2. In some embodiments, the PBRM-polymer-drug conjugate (e.g., a trastuzumab-polymer-drug conjugate) described herein is administered in combination with a HER2 antibody, a HER2 dimerization inhibitor antibody or a combination of a HER2 antibody and a HER2 dimerization inhibitor antibody, such as, for example, trastuzumab or pertuzumab or a combination thereof. In some embodiments, the PBRM-polymer-drug conjugate (e.g., a trastuzumab-polymer-drug conjugate) is administered in combination with a biosimilar of trastuzumab or a biosimilar of pertuzumab or a combination thereof.

These combinations of the PBRM-polymer-drug conjugate (e.g., a trastuzumab-polymer-drug conjugate) described herein and HER2 antibodies are useful in treating pathologies such as, for example, a cancer. For example, these combinations of PBRM-polymer-drug conjugates (e.g., trastuzumab-polymer-drug conjugates) and HER2 antibodies, e.g., a trastuzumab-polymer-drug conjugate in combination with a HER2 antibody, a HER2 dimerization inhibitor antibody or a combination of a HER2 antibody and a HER2 dimerization inhibitor antibody, such as, for example, trastuzumab, pertuzumab or both trastuzumab and pertuzumab or a biosimilar of trastuzumab, a biosimilar of pertuzumab or both biosimilars, are useful in treating, preventing, delaying the progression of or otherwise ameliorating a symptom of a cancer selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian cancer, prostate cancer, lung cancer, non-small cell lung cancer (NSCLC), colon cancer, pancreatic cancer, renal cancer, and gastric cancer.

These combinations are also useful for increasing the degradation of HER2 when a HER2-expressing cell is contacted with these combinations. The level of HER2 degradation is detected using any art-recognized method for detecting HER2 degradation, including, but not limited to detecting levels of HER2 degradation in the presence and absence of a combination of HER2 antibodies (or biosimilars thereof) as shown in the working examples provided herein. For example, the level of HER2 degradation is determined using western analysis of the lysates of HER2-expressing cells that have been treated with a combination of trastuzumab-polymer-drug conjugates and HER2 antibodies, as compared to the level of HER2 degradation in HER2-expressing cells that have not been treated with a combination of trastuzumab-polymer-drug conjugate and HER2 antibodies.

In some embodiments, the HER2 antibody and/or a PBRM-polymer-drug conjugate (e.g., a trastuzumab-polymer-drug conjugate) described herein and additional agent(s) are formulated into a single therapeutic composition, and the HER2 antibody and/or trastuzumab-polymer-drug conjugate and additional agent are administered simultaneously. Alternatively, the HER2 antibody and/or trastuzumab-polymer-drug conjugate and additional agent are separate from each other, e.g., each is formulated into a separate therapeutic composition, and HER2 antibody and/or trastuzumab-polymer-drug conjugate and the additional agent are administered simultaneously, or HER2 antibody and/or trastuzumab-polymer-drug conjugate and the additional agent are administered at different times during a treatment regimen. For example, the HER2 antibody and/or trastuzumab-polymer-drug conjugate is administered prior to the administration of the additional agent, the HER2 antibody and/or trastuzumab-polymer-drug conjugate is administered subsequent to the administration of the additional agent, or the HER2 antibody and/or trastuzumab-polymer-drug conjugate and the additional agent are administered in an alternating fashion. As described herein, the HER2 antibody and/or trastuzumab-polymer-drug conjugate and additional agent are administered in single doses or in multiple doses.

Pharmaceutical compositions according to the invention can include a PBRM-polymer-drug conjugate and a suitable carrier. These pharmaceutical compositions can be included in kits, such as, for example, diagnostic kits.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

One of the advantages of the present invention is that the protein-polymer-drug conjugates or the polymeric scaffolds described herein greatly enhances the bioavailability of the drugs to be delivered and/or enhances the bioavailability of the protein attached to the polymeric carrier. Another advantage of the present invention is that the efficacy of the protein-polymer-drug conjugates described herein increases or at least remains substantially the same with increases in the drug load of the conjugates. Yet another advantage of the present invention is that the protein-polymer conjugates via thiol conjugation to the cysteine moiety of the protein exhibits substantially improved stability. Other features and advantages of the invention will be apparent from the following detailed description and claims.

DETAILED DESCRIPTION OF CERTAIN PREFERRED EMBODIMENTS OF THE INVENTION

Figure 1:
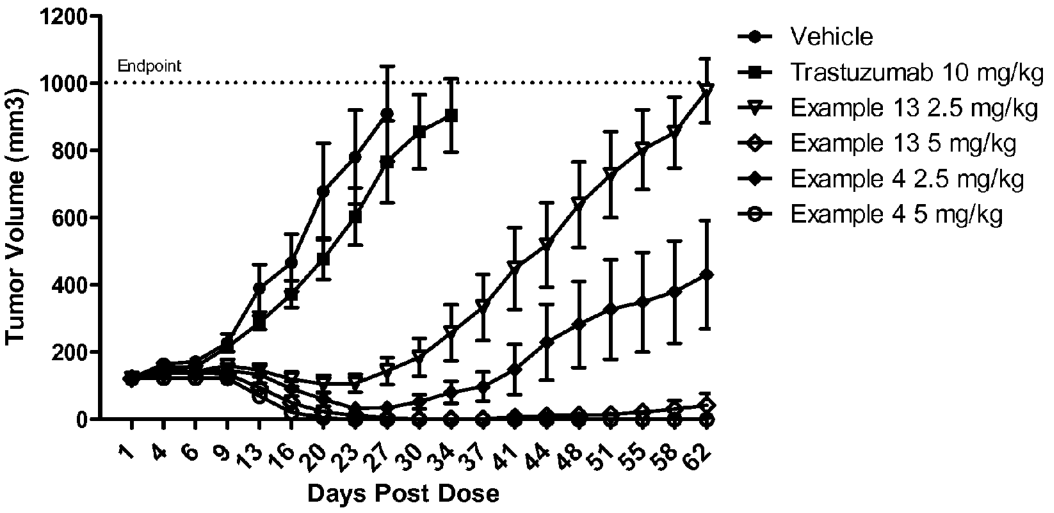
FIG. 1 shows the tumor response in mice inoculated subcutaneously with BT474 tumor fragments (n=10 for each group) after IV administration as a single dose on day 1 of vehicle; PBRM (trastuzumab) at 10 mg/kg; PBRM-polymer-drug conjugates described in Example 4 and Example 13, at 2.5 mg/kg and 5 mg/kg.

The present invention provides novel protein-polymer-drug conjugates, polymeric scaffolds for making the conjugates, synthetic methods for making the conjugates or polymeric scaffolds, pharmaceutical compositions containing them and various uses of the conjugates.

The present invention also provides novel polymer-drug conjugates, synthetic methods for making the conjugates, pharmaceutical compositions containing them and various uses of the conjugates.

The present invention further provides novel drug derivatives, synthetic methods for making the derivatives, pharmaceutical compositions containing them and various uses of the drug derivatives.

Definitions/Terminology

Certain compounds disclosed herein, and definitions of specific functional groups are also described in more detail herein. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. For example, a polymeric scaffold of a certain formula includes all the monomer units shown in the formula and may also include additional monomer units not shown in the formula. Additionally whenever "comprising" or another open-ended term is used in an embodiment, it is to be understood that the same embodiment can be more narrowly claimed using the intermediate term "consisting essentially of" or the closed term "consisting of"

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

"Antibody" refers to a full-length antibody or functional fragment of an antibody comprising an immunoglobulin. By a "functional fragment" it is meant a sufficient portion of the immunoglobulin or antibody is provided that the moiety effectively binds or complexes with the cell surface molecule for its target cell population. Antibody as used herein includes biosimilars thereof. An immunoglobulin may be purified, generated recombinantly, generated synthetically, or combinations thereof, using techniques known to those of skill in the art. While immunoglobulins within or derived from IgG antibodies are particularly well-suited for use in this invention, immunoglobulins from any of the classes or subclasses may be selected, e.g., IgG, IgA, IgM, IgD and IgE. Suitably, the immunoglobulin is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, intracellular antibodies ("intrabodies"), recombinant antibodies, anti-idiotypic antibodies, domain antibodies, linear antibody, multispecific antibody, antibody fragments, such as, Fv, Fab, $F(ab)_2$, $F(ab)_3$, Fab', Fab'-SH, $F(ab')_2$, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, dual-affinity antibodies such as, dual-affinity retargeting proteins (DART™), divalent (or bivalent) single-chain variable fragments (di-scFvs, bi-scFvs) including but not limited to minibodies, diabodies, triabodies or tribodies, tetrabodies, and the like, and multivalent antibodies. "Antibody fragment" refers to at least a portion of the variable region of the immunoglobulin molecule that binds to its target, i.e., the antigen-binding region. As used herein, the term "antibody" refers to both the full-length antibody and antibody fragments unless otherwise specified.

"Protein based recognition-molecule" or "PBRM" refers to a molecule that recognizes and binds to a cell surface marker or receptor such as, a transmembrane protein, surface immobilized protein, or protoglycan. Examples of PBRMs include but are not limited to, antibodies (e.g., Trastuzumab, Cetuximab, Rituximab, Bevacizumab, Epratuzumab, Veltuzumab, Labetuzumab, B7-H4, B7-H3, CAl25, CD33, CXCR2, EGFR, FGFR1, FGFR2, FGFR3, FGFR4, HER2, NaPi2b, c-Met, MUC-1, NOTCH1, NOTCH2, NOTCH3, NOTCH4, PD-L1 and anti-5T4) or peptides (LHRH receptor targeting peptides, EC-1 peptide), lipocalins, such as, for example, anticalins, proteins such as, for example, interferons, lymphokines, growth factors, colony stimulating factors, and the like, peptides or peptide mimics, and the like. The protein based recognition molecule, in addition to targeting the modified polymer conjugate to a specific cell, tissue or location, may also have certain therapeutic effect such as antiproliferative (cytostatic and/or cytotoxic) activity against a target cell or pathway. The protein based recognition molecule comprises or may be engineered to comprise at least one chemically reactive group such as, —COOH, primary amine, secondary amine —NHR, —SH, or a chemically reactive amino acid moiety or side chains such as, for example, tyrosine, histidine, cysteine, or lysine. In one embodiment, a PBRM may be a ligand (LG) or targeting moiety which specifically binds or complexes with a cell surface molecule, such as a cell surface receptor or antigen, for a given target cell population. Following specific binding or complexing of the ligand with its receptor, the cell is permissive for uptake of the ligand or ligand-drug-conjugate, which is then internalized into the cell. As used herein, a ligand that "specifically binds or complexes with" or "targets" a cell surface molecule preferentially associates with a cell surface molecule via intermolecular forces. For example, the ligand can preferentially associate with the cell surface molecule with a dissociation constant ($K_d$ or $K_D$) of less than about 50 nM, less than about 5 nM, or less than 500 pM. Techniques for measuring binding affinity of a ligand to a cell surface molecule are well-known; for example, one suitable technique, is termed surface plasmon resonance (SPR). In one embodiment, the ligand is used for targeting and has no detectable therapeutic effect as separate from the drug which it delivers. In another embodiment, the ligand functions both as a targeting moiety and as a therapeutic or immunomodulatory agent (e.g., to enhance the activity of the active drug or prodrug).

"Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. Preferably (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" polymers are polymers that are susceptible to biological processing in vivo. As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable protein-polymer-drug conjugates (or their components, e.g., the biodegradable polymeric carrier and the linkers between the carrier and the antibody or the drug molecule) described herein, for example, include exposure of the biodegradable conjugates to water at a temperature and a pH of lysosomal intracellular compartment. Biodegradation of some protein-polymer-drug conjugates (or their components, e.g., the biodegradable polymeric carrier and the linkers between the carrier and the antibody or the drug molecule), can also be enhanced extracellularly, e.g., in low pH regions of the animal body, e.g., an inflamed area, in the close vicinity of activated macrophages or other cells releasing degradation facilitating factors. In certain preferred embodiments, the effective size of the polymer carrier at pH~7.5 does not detectably change over 1 to 7 days, and remains within 50% of the original polymer size for at least several weeks. At pH~5, on the other hand, the polymer carrier preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Bioavailability": The term "bioavailability" refers to the systemic availability (i.e., blood/plasma levels) of a given amount of drug or compound administered to a subject. Bioavailability is an absolute term that indicates measurement of both the time (rate) and total amount (extent) of drug or compound that reaches the general circulation from an administered dosage form.

"Maleimido blocking compound": as used herein refers to a compound that can react with maleimide to convert it to succinimide and "maleimido blocking moiety" refers to the chemical moiety attached to the succinimide upon conversion. In certain embodiments, the maleimido blocking compound is a compound having a terminal thiol group for reacting with the maleimide. In one embodiment, the maleimido blocking compound is cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol.

"Hydrophilic": The term "hydrophilic" as it relates to substituents, e.g., on the polymer monomeric units or on a maleimido blocking moiety to render them hydrophilic or water soluble, does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, cycloalkyl, heteroaliphatic, heterocycloalkyl, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In certain embodiments, hydrophilic substituents comprise a carboxyl group (COOH), an aldehyde group (CHO), a ketone group ($COC_{1-4}$ alkyl), a methylol ($CH_2OH$) or a glycol (for example, $CHOH—CH_2OH$ or $CH—(CH_2OH)_2$), $NH_2$, F, cyano, $SO_3H$, $PO_3H$, and the like.

The term "hydrophilic" as it relates to the polymers disclosed herein generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Polymeric Carrier": The term polymeric carrier, as used herein, refers to a polymer or a modified polymer, which is suitable for covalently attaching to or can be covalently attached to one or more drug molecules with a designated linker and/or one or more PBRMs with a designated linker.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxyaldehydes or polyhydroxyketones, or change to such substances on simple chemical transformations, such as hydrolysis, oxidation or reduction. Typically, carbohydrates are present in the form of cyclic acetals or ketals (such as, glucose or fructose). These cyclic units (monosaccharides) may be connected to each other to form molecules with few (oligosaccharides) or several (polysaccharides) monosaccharide units. Often, carbohydrates with well defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or derivatives of naturally occurring sugars (e.g., 2'-fluororibose, 2'-deoxyribose, and hexose).

"Drug": As used herein, the term "drug" refers to a compound which is biologically active and provides a desired physiological effect following administration to a subject in need thereof (e.g., an active pharmaceutical ingredient).

"Prodrug": As used herein the term "prodrug" refers to a precursor of an active drug, that is, a compound that can be transformed to an active drug. Typically such a prodrug is subject to processing in vivo, which converts the drug to a physiologically active form. In some instances, a prodrug may itself have a desired physiologic effect. A desired physiologic effect may be, e.g., therapeutic, cytotoxic, immunomodulatory, or the like.

"Cytotoxic": As used herein the term "cytotoxic" means toxic to cells or a selected cell population (e.g., cancer cells). The toxic effect may result in cell death and/or lysis. In certain instances, the toxic effect may be a sublethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"Cytostatic": As used herein the term "cytostatic" refers to a drug or other compound which inhibits or stops cell growth and/or multiplication.

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". In certain embodiments, the drug molecule has MW less than or equal to about 5 kDa. In other embodiments, the drug molecule has MW less than or equal to about 1.5 kDa. In embodiments, the drug molecule is selected from vinca alkaloids, auristatins, duocarmycins, tubulysins, non-natural camptothecin compounds, DNA binding drugs, kinase inhibitors, MEK inhibitors, KSP inhibitors, maytansinoids, PI3 kinase inhibitors, calicheamicins, SN38, pyrrolobenodiazepines, topoisomerase inhibitors, and analogs thereof Preferably, though not necessarily, the drug is one that has already been deemed safe and effective for use by an appropriate governmental agency or body, e.g., the FDA. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered suitable for use with the present hydrophilic polymers.

Classes of drug molecules that can be used in the practice of the present invention include, but are not limited to, anti-cancer substances, radionuclides, vitamins, anti-AIDS substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs and such large molecules may be used in the conjugates and other constructs described herein. Examples of suitable large molecules include, e.g., amino acid based molecules. Amino acid based molecules may encompass, e.g., peptides, polypeptides, enzymes, antibodies, immunoglobulins, or functional fragments thereof, among others.

A more complete, although not exhaustive, listing of classes and specific drugs suitable for use in the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, each of which is incorporated herein by reference. In preferred embodiments, the drug used in this invention is a therapeutic agent that has antiproliferative (cytostatic and/or cytotoxic) activity against a target cell or pathway. The drug may have a chemically reactive group such as, for example, —COOH, primary amine, secondary amine —NHR, —OH, —SH, —C(O)H, —C(O)R, —C(O)NHR$^{2b}$, C(S)OH, —S(O)$_2$OR$^{2b}$, —P(O)$_2$OR$^{2b}$, —CN, —NC or —ONO, in which R is an aliphatic, heteroaliphatic, carbocyclic or heterocycloalkyl moiety and R$^{2b}$ is a hydrogen, an aliphatic, heteroaliphatic, carbocyclic, or heterocyclic moiety.

"Drug derivative" or "modified drug" or the like as used herein, refers to a compound that comprises the drug molecule intended to be delivered by the conjugate disclosed herein and a functional group capable of attaching the drug molecule to the polymeric carrier.

"Active form" as used herein refers to a form of a compound that exhibits intended pharmaceutical efficacy in vivo or in vitro. In particular, when a drug molecule intended to be delivered by the conjugate disclosed herein is released from the conjugate, the active form can be the drug itself or its derivatives, which exhibit the intended therapeutic properties. The release of the drug from the conjugate can be achieved by cleavage of a biodegradable bond of the linker which attaches the drug to the polymeric carrier. The active drug derivatives accordingly can comprise a portion of the linker.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a conjugate disclosed herein, such diagnostic labels permit the monitoring of the conjugate in vivo. Alternatively or additionally, constructs and compositions that include diagnostic labels can be used to monitor biological functions or structures. Examples of diagnostic labels include, without limitation, labels that can be used in medical diagnostic procedures, such as, radioactive isotopes (radionuclides) for gamma scintigraphy and Positron Emission Tomography (PET), contrast agents for Magnetic Resonance Imaging (MRI) (for example paramagnetic atoms and superparamagnetic nanocrystals), contrast agents for computed tomography and other X-ray-based imaging methods, agents for ultrasound-based diagnostic methods (sonography), agents for neutron activation (e.g., boron, gadolinium), fluorophores for various optical procedures, and, in general moieties which can emit, reflect, absorb, scatter or otherwise affect electromagnetic fields or waves (e.g., gamma-rays, X-rays, radiowaves, microwaves, light), particles (e.g., alpha particles, electrons, positrons, neutrons, protons) or other forms of radiation, e.g., ultrasound. The following are more general terms used throughout the present application:

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone. The term "subject" encompasses animals.

"Efficient amount": In general, as it refers to an active agent or drug delivery device, the term "efficient amount" refers to the amount necessary to elicit the desired biological response. As will be appreciated by those of ordinary skill in this art, the efficient amount of an agent or device may vary depending on such factors as the desired biological endpoint, the agent to be delivered, the composition of the encapsulating matrix, the target tissue, etc. For example, the efficient amount of microparticles containing an antigen to be delivered to immunize an individual is the amount that results in an immune response sufficient to prevent infection with an organism having the administered antigen.

"Natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

"Unnatural amino acid" as used herein refers to any amino acid which is not a natural amino acid. This includes, for example, amino acids that comprise α-, β-, ω-, D-, L-amino acyl residues. More generally, the unnatural amino acid comprises a residue of the general formula

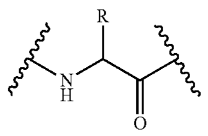

wherein the side chain R is other than the amino acid side chains occurring in nature. Exemplary unnatural amino acids, include, but are not limited to, sarcosine (N-methylglycine), citrulline (cit), homocitrulline, β-ureidoalanine, thiocitrulline, hydroxyproline, allothreonine, pipecolic acid (homoproline), α-aminoisobutyric acid, tert-butylglycine, tert-butylalanine, allo-isoleucine, norleucine, α-methylleucine, cyclohexylglycine, β-cyclohexylalanine, β-cyclopentylalanine, α-methylproline, phenylglycine, α-methylphenylalanine and homophenylalanine "Amino acyl": More generally, the term amino acyl, as used herein, encompasses natural amino acid and unnatural amino acids.

"Polyamide": refers to homo- or hetero-polymers of natural amino acid and unnatural amino acids. Illustrative homopolymers include, but are not limited to, poly-lysine, poly-arginine, poly-γ-glutaric acid, and the like. Illustrative hetero-polymers include, but are not limited to, polymers comprising peptides fragments selected from peptidases, lysozymes, metalloproteinases, and the like.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

As used herein an antibody which "inhibits HER dimerization" shall mean an antibody which inhibits, or interferes with, formation of a HER dimer. Preferably, such an antibody binds to HER2 at the heterodimeric binding site thereof. In one embodiment the dimerization inhibiting antibody herein is pertuzumab or MAb 2C4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., J. Biol. Chem. 279(29):30375-30384 (2004)); antibodies which bind to HER3 and inhibit dimerization thereof with one or more other HER receptors; and antibodies which bind to HER4 and inhibit dimerization thereof with one or more other HER receptors.

The term "HER2 dimerization inhibitor" as used herein shall mean an agent that inhibits formation of a dimer or heterodimer comprising HER2.

As used herein, "molecular weight" or "MW" of a polymer or polymeric carrier/scaffold or polymer conjugates refers to the weight average molecular weight unless otherwise specified.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is intended to include all isomers of the compound, which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

Polymeric Carriers

In certain exemplary embodiments, the conjugates disclosed herein find use in biomedical applications, such as drug delivery and tissue engineering, and the carrier is biocompatible and biodegradable. In certain embodiments, the carrier is a soluble polymer, nanoparticle, gel, liposome, micelle, suture, implant, etc. In certain embodiments, the term "soluble polymer" encompasses biodegradable biocompatible polymer such as a polyal (e.g., hydrophilic polyacetal or polyketal). In certain other embodiments, the carrier is a fully synthetic, semi-synthetic or naturally-occurring polymer. In certain other embodiments, the carrier is hydrophilic.

In certain exemplary embodiments, the carriers used in the present invention are biodegradable biocompatible polyals comprising at least one hydrolysable bond in each monomer unit positioned within the main chain. This ensures that the degradation process (via hydrolysis/cleavage of the monomer units) will result in fragmentation of the polymer conjugate to the monomeric components (i.e., degradation), and confers to the polymer conjugates disclosed herein their biodegradable properties. The properties (e.g., solubility, bioadhesivity and hydrophilicity) of biodegradable biocompatible polymer conjugates can be modified by subsequent substitution of additional hydrophilic or hydrophobic groups. Examples of biodegradable biocompatible polymers suitable for practicing the invention can be found inter alia in U.S. Pat. Nos. 5,811,510; 5,863,990; 5,958,398; 7,838,619 and 7,790,150; and U.S. Publication No. 2006/0058512; each of the above listed patent documents is incorporated herein by reference in its entirety. Guidance on the significance, preparation, and applications of this type of polymers may be found in the above-cited documents. In certain embodiments, it is anticipated that the present invention will be particularly useful in combination with the above-referenced patent documents, as well as U.S. Pat. Nos. 5,582,172 and 6,822,086, each of the above listed patent documents is incorporated herein by reference in its entirety. The conjugates of this invention are hydrophilic, hydrolysable and comprise drug molecules (e.g., vinca alkaloids or derivatives, non-natural camptothecin compounds or derivatives, auristatins, tubulysins, duocarmycins, PI3 kinases, MEK inhibitors, KSP inhibitors, maytansinoids, DNA binding drugs, calicheamicins, SN38, non-natural camptothecin compounds, pyrrolobenodiazepines, topoisomerase inhibitors, and analogs thereof) and antibodies (e.g., Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, NaPi2b, c-Met, MUC-1, NOTCH1, NOTCH2, NOTCH3, NOTCH4, PD-L1 and anti-5T4) or peptides (LHRH receptor targeting peptides, EC-1 peptide) covalently attached to the polymer carrier via linkages that contain one or more biodegradable bonds. Thus, in certain exemplary embodiments, carriers suitable for practicing the present invention are polyals having at least one acetal/ketal oxygen atom in each monomer unit positioned within the main chain. As discussed above, this ensures that the degradation process (via hydrolysis/cleavage of the polymer acetal/ketal groups) will result in fragmentation of the polyal conjugate to low molecular weight components (i.e., degradation).

In certain embodiments, biodegradable biocompatible polymer carriers, used for preparation of polymer conjugates disclosed herein, are naturally occurring polysaccharides, glycopolysaccharides, and synthetic polymers of polyglycoside, polyacetal, polyamide, polyether, and polyester origin and products of their oxidation, fictionalization, modification, cross-linking, and conjugation.

In certain other embodiments, the carrier is a hydrophilic biodegradable polymer selected from the group consisting of carbohydrates, glycopolysaccharides, glycolipids, glycoconjugates, polyacetals, polyketals, and derivatives thereof In certain exemplary embodiments, the carrier is a naturally occurring linear and/or branched biodegradable biocompatible homopolysaccharide selected from the group consisting of cellulose, amylose, dextran, levan, fucoidan, carraginan, inulin, pectin, amylopectin, glycogen and lixenan.

In certain other exemplary embodiments, the carrier is a naturally occurring linear and branched biodegradable biocompatible heteropolysaccharide selected from the group consisting of agarose, hyluronan, chondroitinsulfate, dermatansulfate, keratansulfate, alginic acid and heparin.

In yet other exemplary embodiments, the polymeric carrier comprises a copolymer of a polyacetal/polyketal and a hydrophilic polymer selected from the group consisting of polyacrylates, polyvinyl polymers, polyesters, polyorthoesters, polyamides, polypeptides, and derivatives thereof In yet another embodiment, the polymeric carrier is dextrin that is produced by the hydrolysis of a starch obtained from various natural products such as, for example, wheat, rice, maize and tapioca. Depending on the structure of the starch starting material each dextrin comprises a unique distribution of α-1,4 linkages and α-1,6 linkages. Since the rate of biodegradability of α-1,6 linkages is typically less than that for α-1,4 linkages, preferably the percentage of α-1,6 linkages is less than 10% and more preferably less than 5%. In one embodiment the molecular weight of the dextrin is in the range of about 2 kDa to about 40 kDa, more preferably from about 2 kDa to about 20 kDa, or from about 3 kDa to about 15 kDa or from about 5 kDa to about 10 kDa.

In certain embodiments, the carrier comprises polysaccharides activated by selective oxidation of cyclic vicinal diols of 1,2-, 1,4-, 1,6-, and 2,6-pyranosides, and 1,2-, 1,5-, 1,6-furanosides, or by oxidation of lateral 6-hydroxy and 5,6-diol containing polysaccharides prior to conjugation with drug molecules or PBRMs.

In still other embodiments, the polymeric carrier comprises a biodegradable biocompatible polyacetal wherein at least a subset of the polyacetal repeat structural units have the following chemical structure:

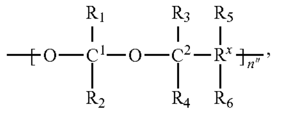

wherein for each occurrence of the n bracketed structure, one of $R_1$ and $R_2$ is hydrogen, and the other is a biocompatible group and includes a carbon atom covalently attached to $C^1$; $R^x$ is a carbon atom covalently attached to $C^2$; n" is an integer; each occurrence of $R_3$, $R_4$, $R_5$ and $R_6$ is a biocompatible group and is independently hydrogen or an organic moiety; and for each occurrence of the bracketed structure n, at least one of $R_1$, $R_2$, $R_3$, $R_4$, $R_5$ and $R_6$ comprises a functional group suitable for coupling. In certain embodiments, the functional group is a hydroxyl moiety.

In one embodiment, the polymeric carrier comprises activated hydrophilic biodegradable biocompatible polymers comprising from 0.1% to 100% polyacetal moieties whose backbone is represented by the following chemical structure:

$$(—CH_2—CHR_7—O—CHR_8—O—)_o,$$

wherein:

$R_7$ and $R_8$ are independently hydrogen, hydroxyl, hydroxy alkyl (e.g., $—CH_2OH$, —CH(OH)—CH(OH), —CHO, —CH(OH)—CHO or -carbonyl; and o is an integer from 20 to 2000.

In yet other embodiments, the polymeric carrier comprises a biodegradable biocompatible polyketal wherein at least a subset of the polyketal repeatable structural units have the following chemical structure:

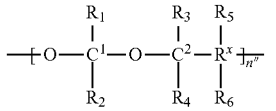

or

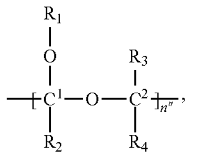

wherein each occurrence of $R_1$ and $R_2$ is a biocompatible group and $R^x$, $R_3$, $R_4$, $R_5$, $R_6$ and are as defined herein.

In certain embodiments, the ketal units are monomers of Formula (IIa) or (IIb):

(IIa)

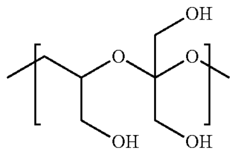

or

-continued (IIb)

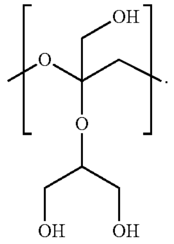

Biodegradable, biocompatible polyketal polymers and their methods of making have been described in U.S. Pat. Nos. 5,811,510, 7,790,150 and 7,838,619, which are hereby incorporated by reference in their entireties.

In one embodiment, the polymeric carrier can be obtained from partially oxidized dextran (β1→6)-D-glucose) followed by reduction. In this embodiment, the polymer comprises a random mixture of the unmodified dextran (A), partially oxidized dextran acetal units (B) and exhaustively dextran acetal units (C) of the following structures:

(A)

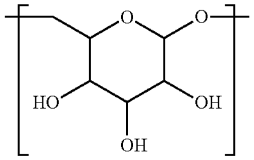

(B)

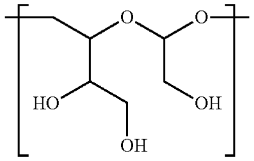

(B)

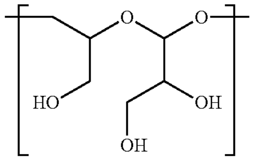

(C)

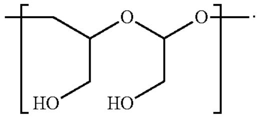

In another embodiment, the polymeric carrier comprises unmodified acetal units, i.e., polyacetal segments. In some embodiments, the polyacetals can be derived from exhaustively oxidized dextran followed by reduction. These polymers have been described in references, see, e.g., U.S. Pat. No. 5,811,510, which is hereby incorporated by reference for its description of polyacetals at column 2, line 65 to column 8, line 55 and their synthesis at column 10, line 45 to column 11, line 14. In one embodiment, the unmodified polyacetal polymer is a poly(hydroxymethylethylene hydroxymethyl formal) polymer (PHF).

In addition to poly(hydroxymethylethylene hydroxymethyl formal) polymers, the backbone of the polymeric carrier can also comprise co-polymers of poly(hydroxymethylethylene hydroxymethyl formal) blocks and other acetal or non-acetal monomers or polymers. For example, polyethylene glycol polymers are useful as a stealth agent in the polymer backbone because they can decrease interactions between polymer side chains of the appended functional groups. Such groups can also be useful in limiting interactions such as between serum factors and the modified polymer. Other stealth agent monomers for inclusion in the polymer backbone include, for example, ethyleneimine, methacrylic acid, acrylamide, glutamic acid, and combinations thereof The acetal or ketal units are present in the modified polymer in an amount effective to promote biocompatibility. The unmodified acetal or ketal unit can be described as a "stealth agent" that provides biocompatibility and solubility to the modified polymers. In addition, conjugation to a polyacetal or polyketal polymer can modify the susceptibility to metabolism and degradation of the moieties attached to it, and influence biodistribution, clearance and degradation.

The unmodified acetal units are monomers of Formula (III):

(III)

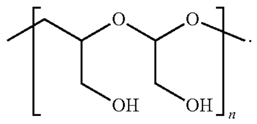

The molar fraction, n, of unmodified polyacetal units is the molar fraction available to promote biocompatibility, solubility and increase half-life, based on the total number of polymer units in the modified polymer. The molar fraction n may be the minimal fraction of unmodified monomer acetal units needed to provide biocompatibility, solubility, stability, or a particular half-life, or can be some larger fraction. The most desirable degree of cytotoxicity is substantially none, i.e., the modified polymer is substantially inert to the subject. However, as is understood by those of ordinary skill in the art, some degree of cytotoxicity can be tolerated depending on the severity of disease or symptom being treated, the efficacy of the treatment, the type and degree of immune response, and like considerations.

In one embodiment, the modified polymer backbone comprises units of Formula (IV):

(IV)

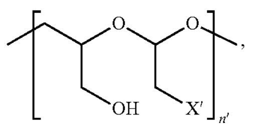

wherein X' indicates the substituent for the hydroxyl group of the polymer backbone. As shown in Formula (IV) and the other formulae described herein, each polyacetal unit has a single hydroxyl group attached to the glycerol moiety of the unit and an X' group (or another substituent such as $-L^D-D$ attached to the glycolaldehyde moiety of the unit. This is for convenience only and it should be construed that the polymer having units of Formula (IV) and other formulae described herein can contain a random distribution of units having a X' group (or another substituent such as a linker comprising a maleimide terminus) attached to the glycolaldehyde moiety of the units and those having a single X' group (or another substituent such as a linker comprising a maleimide terminus) attached to the glycerol moiety of the units as well as units having two X' groups (or other substituents such as a linker comprising a maleimide terminus) with one attached to the glycolaldehyde moiety and the other attached to the glycerol moiety of the units.

In one embodiment, biodegradable biocompatible polyals suitable for practicing the present invention have a molecular weight of between about 0.5 and about 300 kDa. For example, the biodegradable biocompatible polyals have a molecular weight of between about 1 and about 300 kDa (e.g., between about 1 and about 200 kDa, between about 2 and about 300 kDa, between about 2 and about 200 kDa, between about 5 and about 100 kDa, between about 10 and about 70 kDa, between about 20 and about 50 kDa, between about 20 and about 300 kDa, between about 40 and about 150 kDa, between about 50 and about 100 kDa, between about 2 and about 40 kDa, between about 6 and about 20 kDa, or between about 8 and about 15 kDa). For example, the biodegradable biocompatible polyal used for the polymer scaffold or conjugate disclosed herein is PHF having a molecular weight of between about 2 and about 40 kDa (e.g., about 2-20 kDa, 3-15 kDa, or 5-10 kDa)

In one embodiment, the biodegradable biocompatible polyals suitable for practicing the present invention are modified before conjugating with a drug or a PBRM. For example, the polyals contains —C(=O)—X—$(CH_2)_v$—C(=O)— with X being $CH_2$, O, or NH, and v being an integer from 1 to 6. Table A below provides some examples of the modified polyals suitable for conjugating with a drug or PBRM or derivatives thereof. Unless otherwise specified, reference numbers in Tables A through D below correspond to the Example numbers described herein; the term "ND" means not determined; and X is $CH_2$, O, or NH.

Therapeutic Agents

In certain embodiments, the therapeutic agent is a small molecule having a molecular weight preferably ≤about 5 kDa, more preferably ≤about 4 kDa, more preferably ≤about 3 kDa, most preferably ≤about 1.5 kDa or ≤about 1 kDa.

In certain embodiments, the therapeutic agent has an $IC_{50}$ of about less than 1 nM.

In another embodiment, the therapeutic agent has an $IC_{50}$ of about greater than 1 nM, for example, the therapeutic agent has an $IC_{50}$ of about 1 to 50 nM.

Some therapeutic agents having an $IC_{50}$ of greater than about 1 nM (e.g., "less potent drugs") are unsuitable for conjugation with a PBRM using art-recognized conjugation techniques. Without wishing to be bound by theory, such therapeutic agents have a potency that is insufficient for use in targeted PBRM-drug conjugates using conventional techniques as sufficient copies of the drug (i.e., more than 8) cannot be conjugated using art-recognized techniques without resulting in diminished pharmacokinetic and physiochemical properties of the conjugate. However sufficiently high loadings of these less potent drugs can be achieved using the conjugation strategies described herein thereby resulting in high loadings of the therapeutic agent while maintaining the desirable pharmacokinetic and physiochemical properties. Thus, the invention also relates to a PBRM-polymer-drug conjugate which includes a PBRM, PHF and at least eight therapeutic agent moieties, wherein the therapeutic agent has an $IC_{50}$ of greater than about 1 nM.

In certain embodiments, about 0.3 to about 15% monomers comprise a therapeutic agent, more preferably about 2 to about 12%, and even more preferably about 5 to about 10%.

The small molecule therapeutic agents used in this invention (e.g., antiproliferative (cytotoxic and cytostatic) agents capable of being linked to a polymer carrier) include, but are not limited to, cytotoxic compounds (e.g., broad spectrum),

TABLE A

| Ref # | Polymer Scaffold |
|---|---|
| X = NH<br>Ex 2<br>X = $CH_2$<br>Ex 11 | 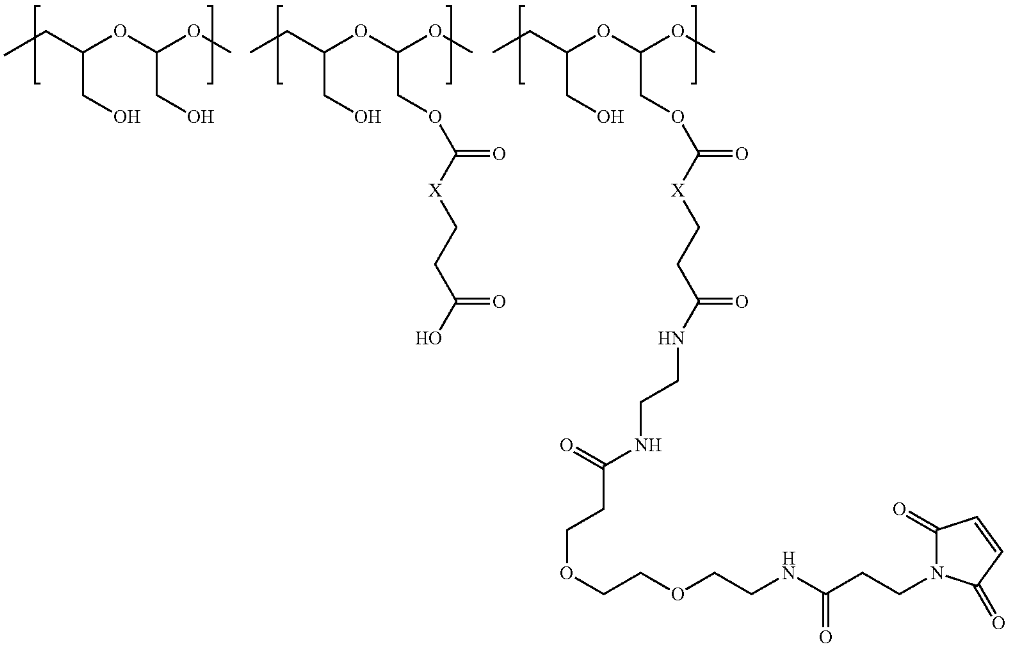 |

angiogenesis inhibitors, cell cycle progression inhibitors, PI3K/m-TOR/AKT pathway inhibitors, MAPK signaling pathway inhibitors, kinase inhibitors, protein chaperones inhibitors, HDAC inhibitors, PARP inhibitors, Wnt/Hedgehog signaling pathway inhibitors and RNA polymerase inhibitors.

Broad spectrum cytotoxins include, but are not limited to, DNA-binding or alkylating drugs, microtubule stabilizing and destabilizing agents, platinum compounds, and topoisomerase I inhibitors.

Exemplary DNA-binding or alkylating drugs include, CC-1065 and its analogs, anthracyclines (doxorubicin, epirubicin, idarubicin, daunorubicin) and its analogs, alkylating agents, such as calicheamicins, dactinomycines, mitromycines, pyrrolobenzodiazepines, and the like.

Exemplary CC-1065 analogs include duocarmycin SA, duocarmycin A, duocarmycin C1, duocarmycin C2, duocarmycin B1, duocarmycin B2, duocarmycin D, DU-86, KW-2189, adozelesin, bizelesin, carzelesin, seco-adozelesin, and related analogs and prodrug forms, examples of which are described in U.S. Pat. Nos. 5,475,092; 5,595,499; 5,846,545; 6,534,660; 6,586,618; 6,756,397 and 7,049,316. Doxorubicin and its analogs include those described in U.S. Pat. No. 6,630,579. Calicheamicins include, e.g., enediynes, e.g., esperamicin, and those described in U.S. Pat. Nos. 5,714,586 and 5,739,116. Duocarmycins include those described in U.S. Pat. Nos. 5,070,092; 5,101,038; 5,187,186; 6,548,530; 6,660,742; and 7,553,816 B2; and Li et al., Tet Letts., 50:2932-2935 (2009). Pyrrolobenzodiazepines (PBD) and analogs thereof include those described in Denny, *Exp. Opin. Ther. Patents,* 10(4):459-474 (2000).

Exemplary microtubule stabilizing and destabilizing agents include taxane compounds, such as paclitaxel, docetaxel, tesetaxel and carbazitaxel; maytansinoids, auristatins and analogs thereof, vinca alkaloid derivatives, epothilones and cryptophycins.

Exemplary maytansinoids or maytansinoid analogs include maytansinol and maytansinol analogs, maytansine or DM-1 and DM-4 are those described in U.S. Pat. Nos. 5,208,020; 5,416,064; 6,333,410; 6,441,163; 6,716,821; RE39,151 and 7,276,497. In certain embodiments, the cytotoxic agent is a maytansinoid, another group of anti-tubulin agents (ImmunoGen, Inc.; see also Chari et al., 1992, Cancer Res. 52:127-131), maytansinoids or maytansinoid analogs. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Exemplary auristatins include auristatin E (also known as a derivative of dolastatin-10), auristatin EB (AEB), auristatin EFP (AEFP), monomethyl auristatin E (MMAE), monomethyl auristatin F (MMAF), auristatin F, auristatin F phenylenediamine (AFP), auristatin F HPA and dolastatin. Suitable auristatins are also described in U.S. Publication Nos. 2003/0083263, 2011/0020343, and 2011/0070248; PCT Application Publication Nos. WO 09/117531, WO 2005/081711, WO 04/010957; WO 02/088172 and WO01/24763, and U.S. Pat. Nos. 7,498,298; 6,884,869; 6,323,315; 6,239,104; 6,124,431; 6,034,065; 5,780,588; 5,767,237; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, the disclosures of which are incorporated herein by reference in their entirety.

Exemplary vinca alkaloids include vincristine, vinblastine, vindesine, and navelbine (vinorelbine). Suitable Vinca alkaloids that can be used in the present invention are also disclosed in U.S. Publication Nos. 2002/0103136 and 2010/0305149, and in U.S. Pat. No. 7,303,749 B1, the disclosures of which are incorporated herein by reference in their entirety.

Exemplary epothilone compounds include epothilone A, B, C, D, E and F, and derivatives thereof. Suitable epothilone compounds and derivatives thereof are described, for example, in U.S. Pat. Nos. 6,956,036; 6,989,450; 6,121,029; 6,117,659; 6,096,757; 6,043,372; 5,969,145; and 5,886,026; and WO 97/19086; WO 98/08849; WO 98/22461; WO 98/25929; WO 98/38192; WO 99/01124; WO 99/02514; WO 99/03848; WO 99/07692; WO 99/27890; and WO 99/28324; the disclosures of which are incorporated herein by reference in their entirety.

Exemplary cryptophycin compounds are described in U.S. Pat. Nos. 6,680,311 and 6,747,021.

Exemplary platinum compounds include cisplatin (PLATINOL®), carboplatin (PARAPLATIN®), oxaliplatin (ELOXATINE®), iproplatin, ormaplatin, and tetraplatin.

Still other classes of compounds or compounds with these or other cytotoxic modes of action may be selected, including, e.g., mitomycin C, mitomycin A, daunorubicin, doxorubicin, morpholino-doxorubicin, cyanomorpholino-doxorubicin, aminopterin, bleomycin, 1-(chloromethyl)-2,3-dihydro-1H-benzo[e]indol-5-ol, pyrrolobenzodiazepine (PBD) polyamide and dimers thereof. Other suitable cytotoxic agents include, for example, puromycins, topotecan, rhizoxin, echinomycin, combretastatin, netropsin, estramustine, cryptophysins, cemadotin, discodermolide, eleutherobin, and mitoxantrone.

Exemplary topoisomerase inhibitors include camptothecin, camptothecin, derivatives, camptothecin analogs and non-natural camptothecins, such as, for example, CPT-11 (irinotecan), SN-38, topotecan, 9-aminocamptothecin, rubitecan, gimatecan, karenitecin, silatecan, lurtotecan, exatecan, diflomotecan, belotecan, lurtotecan and 539625. Other camptothecin compounds that can be used in the present invention include those described in, for example, J. Med. Chem., 29:2358-2363 (1986); J. Med. Chem., 23:554 (1980); J. Med. Chem., 30:1774 (1987).

Angiogenesis inhibitors include, but are not limited, MetAP2 inhibitors, VEGF inhibitors, PIGF inhibitors, VGFR inhibitors, PDGFR inhibitors, MetAP2 inhibitors. Exemplary VGFR and PDGFR inhibitors include sorafenib (Nexavar), sunitinib (Sutent) and vatalanib. Exemplary MetAP2 inhibitors include fumagillol analogs, meaning any compound that includes the fumagillin core structure, including fumagillamine, that inhibits the ability of MetAP-2 to remove $NH_2$-terminal methionines from proteins as described in Rodeschini et al., *J. Org. Chem.,* 69, 357-373, 2004 and Liu, et al., *Science* 282, 1324-1327, 1998. Non limiting examples of "fumagillol analogs" are disclosed in *J. Org. Chem.,* 69, 357, 2004; *J. Org. Chem.,* 70, 6870, 2005; European Patent Application 0 354 787; *J. Med. Chem.,* 49, 5645, 2006; *Bioorg. Med. Chem.,* 11, 5051, 2003; *Bioorg. Med. Chem.,* 14, 91, 2004; *Tet. Lett.* 40, 4797, 1999; WO99/61432; U.S. Pat. Nos. 6,603,812; 5,789,405; 5,767,293; 6,566,541; and 6,207,704.

Exemplary cell cycle progression inhibitors include CDK inhibitors such as, for example, BMS-387032 and PD0332991; Rho-kinase inhibitors such as, for example GSK429286; checkpoint kinase inhibitors such as, for example, AZD7762; aurora kinase inhibitors such as, for example, AZD1152, MLN8054 and MLN8237; PLK inhibitors such as, for example, BI 2536, BI6727 (Volasertib), GSK461364, ON-01910 (Estybon); and KSP inhibitors such as, for example, SB 743921, SB 715992 (ispinesib), MK-0731, AZD8477, AZ3146 and ARRY-520.

Exemplary PI3K/m-TOR/AKT signaling pathway inhibitors include phosphoinositide 3-kinase (PI3K) inhibitors, GSK-3 inhibitors, ATM inhibitors, DNA-PK inhibitors and PDK-1 inhibitors.

Exemplary PI3 kinases are disclosed in U.S. Pat. No. 6,608,053, and include BEZ235, BGT226, BKM120, CAL101, CAL263, demethoxyviridin, GDC-0941, GSK615, IC87114, LY294002, Palomid 529, perifosine, PF-04691502, PX-866, SAR245408, SAR245409, SF1126, Wortmannin, XL147 and XL765.

Exemplary AKT inhibitors include, but are not limited to AT7867.

Exemplary MAPK signaling pathway inhibitors include MEK, Ras, JNK, B-Raf and p38 MAPK inhibitors.

Exemplary MEK inhibitors are disclosed in U.S. Pat. No. 7,517,994 and include GDC-0973, GSK1120212, MSC1936369B, AS703026, R05126766 and R04987655, PD0325901, AZD6244, AZD 8330 and GDC-0973.

Exemplary B-raf inhibitors include CDC-0879, PLX-4032, and SB590885.

Exemplary B p38 MAPK inhibitors include BIRB 796, LY2228820 and SB 202190.

Receptor tyrosine kinases (RTK) are cell surface receptors which are often associated with signaling pathways stimulating uncontrolled proliferation of cancer cells and neoangiogenesis. Many RTKs, which over express or have mutations leading to constitutive activation of the receptor, have been identified, including, but not limited to, VEGFR, EGFR, FGFR, PDGFR, EphR and RET receptor family receptors. Exemplary specific RTK targets include ErbB2, FLT-3, c-Kit, and c-Met.

Exemplary inhibitors of ErbB2 receptor (EGFR family) include but not limited to AEE788 (NVP-AEE 788), BIBW2992, (Afatinib), Lapatinib, Erlotinib (Tarceva), and Gefitinib (Iressa).

Exemplary RTK inhibitors targeting more than one signaling pathway (multitargeted kinase inhibitors) include AP24534 (Ponatinib) that targets FGFR, FLT-3, VEGFR-PDGFR and Bcr-Abl receptors; ABT-869 (Linifanib) that targets FLT-3 and VEGFR-PDGFR receptors; AZD2171 that targets VEGFR-PDGFR, Flt-1 and VEGF receptors; CHR-258 (Dovitinib) that targets VEGFR-PDGFR, FGFR, Flt-3, and c-Kit receptors; Sunitinib (Sutent) that targets VEGFR, PDGFR, KIT, FLT-3 and CSF-IR; Sorafenib (Nexavar) and Vatalanib that target VEGFR, PDGFR as well as intracellular serine/threonine kinases in the Raf/Mek/Erk pathway.

Exemplary protein chaperon inhibitors include HSP90 inhibitors. Exemplary HSP90 inhibitors include 17AAG derivatives, BIIB021, BIIB028, SNX-5422, NVP-AUY-922 and KW-2478.

Exemplary HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCD0103 (Mocetinostat), MS-275 (Entinostat), PCI-24781, Pyroxamide (NSC 696085), SB939, Trichostatin A and Vorinostat (SAHA).

Exemplary PARP inhibitors include iniparib (BSI 201), olaparib (AZD-2281), ABT-888 (Veliparib), AG014699, CEP 9722, MK 4827, KU-0059436 (AZD2281), LT-673, 3-aminobenzamide, A-966492, and AZD2461.

Exemplary Wnt/Hedgehog signaling pathway inhibitors include vismodegib (RG3616/GDC-0449), cyclopamine (11-deoxojervine) (Hedgehog pathway inhibitors) and XAV-939 (Wnt pathway inhibitor)

Exemplary RNA polymerase inhibitors include amatoxins. Exemplary amatoxins include α-amanitins, β-amanitins, γ-amanitins, ε-amanitins, amanullin, amanullic acid, amaninamide, amanin, and proamanullin. In one embodiment the drug disclosed herein is a non-natural camptothecin compound, vinca alkaloid, kinase inhibitor (e.g., PI3 kinase inhibitor (GDC-0941 and PI-103)), MEK inhibitor, KSP inhibitor, RNA polymerse inhibitor, PARP inhibitor, docetaxel, paclitaxel, doxorubicin, duocarmycin, auristatin, dolastatin, calicheamicins, SN38, pyrrolobenodiazepines, DNA binding drugs, non-natural camptothecin compounds, maytansinoids or a platinum compound, and analogs thereof. In specific embodiments, the drug is a derivative of SN-38, vindesine, vinblastine, PI-103, AZD 8330, auristatin E, auristatin F, a duocarmycin compound, or ARRY-520.

In another embodiment, the drug used in the invention is a combination of two or more drugs, such as, for example, PI3 kinases and MEK inhibitors; broad spectrum cytotoxic compounds and platinum compounds; PARP inhibitors and platinum compounds; broad spectrum cytotoxic compounds and PARP inhibitors.

In yet another embodiment, the drug used in the invention is auristatin F-hydroxypropylamide-L-alanine In one embodiment, the Vinca alkaloid is a compound of Formula (V):

(V)

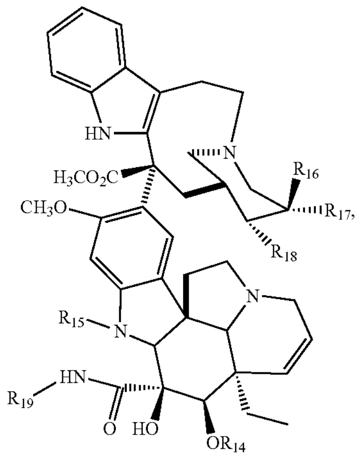

wherein:

$R_{14}$ is hydrogen, —C(O)—$C_{1-3}$ alkyl or —C(O)-chloro substituted $C_{1-3}$ alkyl;

$R_{15}$ is hydrogen, —$CH_3$ or —CHO;

when $R_{17}$ and $R_{18}$ are taken independently, $R_{18}$ is hydrogen, and either $R_{16}$ or $R_{17}$ is ethyl and the other is hydroxyl;

when $R_{17}$ and $R_{18}$ are taken together with the carbon to which they are attached to form an oxiran ring, $R_{16}$ is ethyl;

$R_{19}$ is hydrogen, OH, amino group, alkyl amino or —[C($R_{20}R_{21}$)]$_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NH_2$, —COOH, —$R_{82}$—C(O)$(CH_2)_c$—C(H)($R_{23}$)—N(H)($R_{23}$), —$R_{82}$—C(O)$(CH_2)_d$—($OCH_2$—$CH_2)_f$—N(H)($R_{23}$) or —$R_{82}$—(C(O)—CH($X^2$)—NH$)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing heterocyclic moiety;

$R_{82}$ is —NH or oxygen;

a is an integer from 1 to 6;

c is an integer from 0 to 3;

d is an integer from 1 to 3; and f is an integer from 1 to 12.

Further examples of Vinca alkaloids are described in US 2010/0305149 and US 2002/0103136.

In one embodiment the Vinca alkaloid of Formula (V) is a compound of Formula (VI):

(VI)

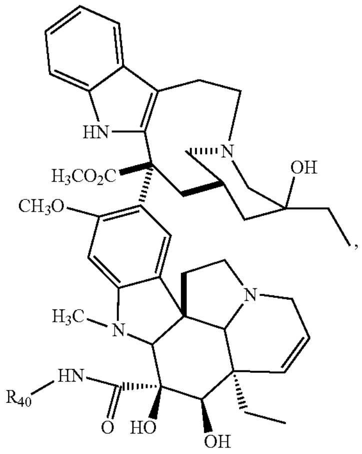

wherein:

$R_{40}$ is hydrogen, —OH, —$NH_2$, or any of the following structures:

(1)

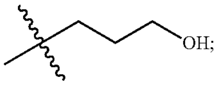

(2)

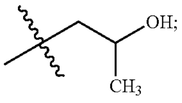

(3)

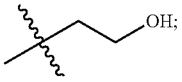

(4)

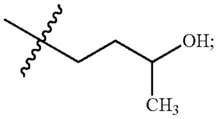

-continued (5)

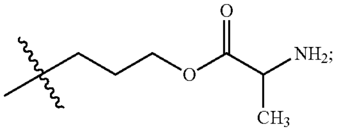

(6)

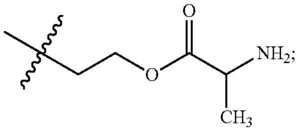

(7)

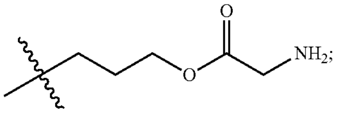

(8)

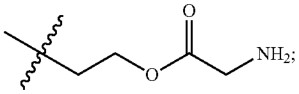

(9)

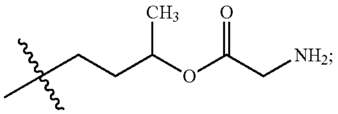

(10)

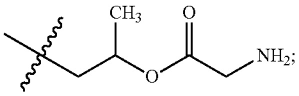

(11)

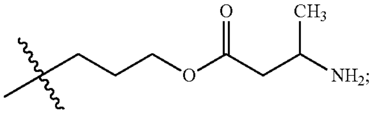

(12)

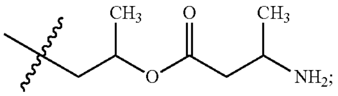

(13)

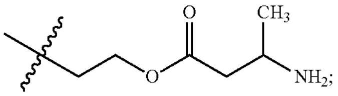

(14)

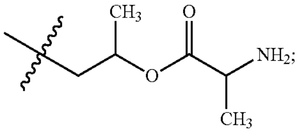

(15)

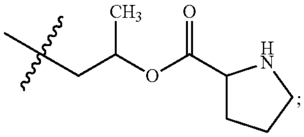

(16)

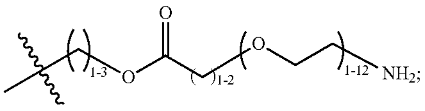

-continued (17)

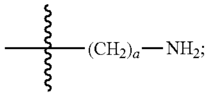

(18)

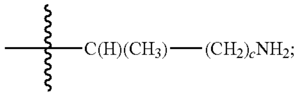

(19)

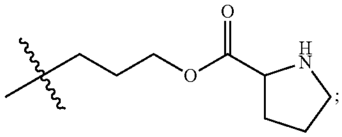

; and (20)

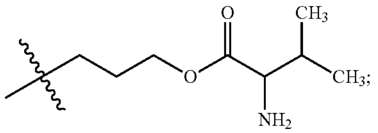

wherein:

a is an integer from 1 to 6; and c is an integer from 0 to 3.

In one embodiment, in Formula (VI), $R_{40}$ is

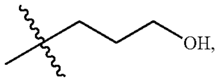 [SMILES: *CCCO]

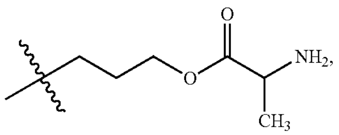

or.

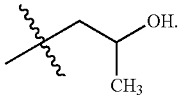

In another embodiment, $R_{40}$ is

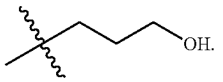

In another embodiment, the compound of Formula (VI) is a compound of Formula (VIa) or (VIb):

(VIa)

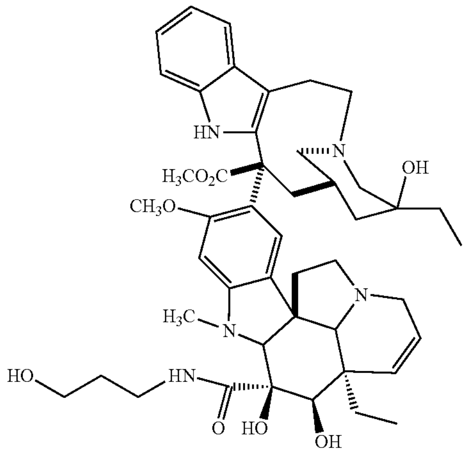

or (VIb)

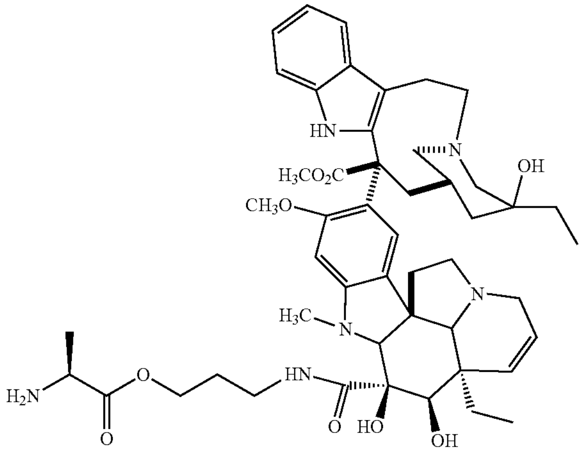

In another embodiment, non-natural camptothecin is a compound of Formula (VII):

(VII)

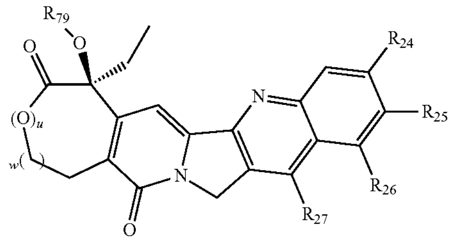

wherein:

$R_{24}$ is —H, —Cl, —F, —OH or alkyl; or $R_{24}$ and $R_{25}$, may be taken together to form an optionally substituted five- or six-membered ring;

$R_{25}$ is —H, —F, —OH, —$CH_3$, —CH═N—O-t-Butyl, —$CH_2CH_2Si(CH_3)_3$, —$Si((CH_3)_2)$-t-butyl, —O—C(O)—$R_{29}$;

$R_{29}$ is —$NH_2$, —$R_{28}$—$C_{1-6}$ alkyl-$R_{22}$, 5 to 12-membered heterocycloalkyl, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{26}$ is —H, —$CH_2$—$N(CH_3)_2$, $NH_2$, or $NO_2$;

$R_{27}$ is —H, ethyl, N-methyl piperidine, cycloalkyl, —$CH_2CH_2NHCH(CH_3)_2$, or —N-4-methylcyclohexylamine;

$R_{79}$ is —H or —C(O)—$R_{28}$—[C($R_{20}R_{21}$)]—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NH_2$, —COOH, —$R_{82}$—C(O)$(CH_2)_c$—C(H)($R_{23}$)—N(H)($R_{23}$), —$R_{82}$—C(O)$(CH_2)_d$—$(OCH_2—CH_2)_f$—N(H)($R_{23}$), or —$R_{82}$—(C(O)—CH($X^2$)—NH$)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

or $R_{26}$ and $R_{27}$ when taken together with the two carbon atoms to which they attach and the third carbon atom connecting the two carbon atoms form an optionally substituted six-membered ring;

$R_{28}$ is absent, NH or oxygen;

a is an integer from 1 to 6;

c is an integer from 0 to 3;

d is an integer from 1 to 3;

f is an integer from 1 to 12;

u is an integer 0 or 1;

w is an integer 0 or 1; and with the proviso that the compound of Formula (VII) must contain at least one of $R_{29}$ and $R_{79}$.

In one embodiment the non-natural camptothecin compound of Formula (VII) is a compound of Formula (VIII) or Formula (XXV):

(VIII)

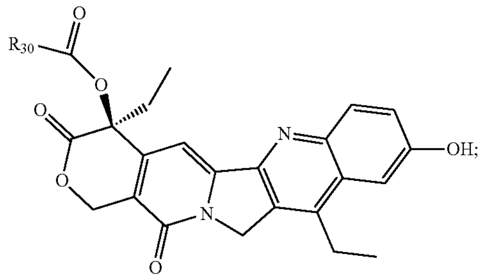

or (XXV)

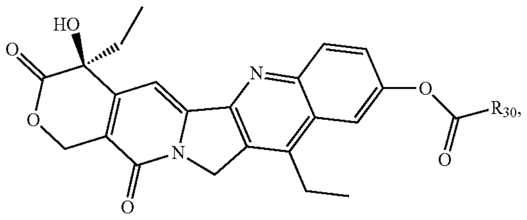

wherein $R_{30}$ is —$NH_2$, —$R_{28}$—$C_{1-6}$ alkyl-$R_{22}$, 5 to 12-membered heterocycloalkyl, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$;

$R_{28}$ is absent, NH or oxygen;

$R_{22}$ is —OH, —$NH_2$, —COOH, —$R_{82}$—C(O)$(CH_2)_c$—C(H)($R_{23}$)—N(H)($R_{23}$), —$R_{82}$—C(O)$(CH_2)_d$—$(OCH_2—CH_2)_f$—N(H)($R_{23}$) or —$R_{82}$—(C(O)—CH($X^2$)—NH$)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

c is an integer from 0 to 3;

d is an integer from 1 to 3; and f is an integer from 1 to 12.

In some embodiments $R_{30}$ is any one of the following structures:

(1)

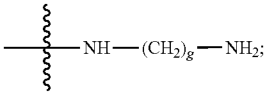

(2)

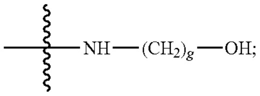

(3)

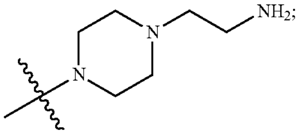

(4)

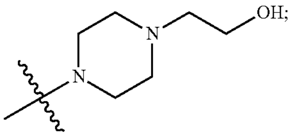

(5)

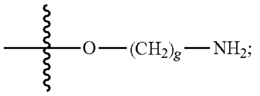

(6)

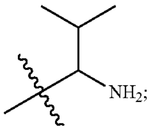

(7)

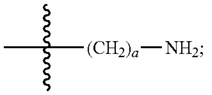

(8)

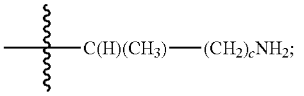

and (9)

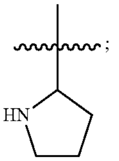

wherein:

a is an integer from 1 to 6;

c is an integer from 0 to 3; and g is an integer from 2 to 6.

In another embodiment the PI3 kinase is a compound of Formula (IX):

(IX)

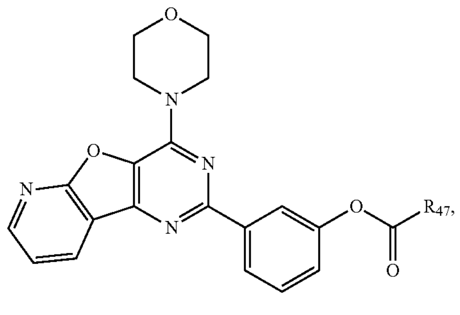

wherein $R_{47}$ is an amino group, $—R_9—[C(R_{20}R_{21})]_a—R_{10}$, $—R_9—C_{5-12}$ heterocycloalkyl-$C_{1-6}$ alkyl-$R_{10}$, 5 to 12-membered heterocycloalkyl, or $—R_9—C_{6-10}$ aryl;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{10}$ is —OH, $—NHR_{83}$, $—N—(R_{83})R_{11}$, —COOH, $—R_{82}—C(O)(CH_2)_c—C(H)(R_{23})—N(H)(R_{23})$, $—R_{82}—C(O)(CH_2)_d—(OCH_2—CH_2)_f—N(H)(R_{23})$, $—R_{82}—(C(O)—CH(X^2)—NH)_d—R_{77}$ or $—R_{82}—C(O)—[C(R_{20}R_{21})]_a—R_{82}—R_{83}$;

each $R_{23}$ independently is hydrogen, $C_{1-6}$ alkyl, $C_{6-10}$ aryl, $C_{3-8}$ cycloalkyl, —COOH, or $—COO—C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

$R_9$ is absent, $N—(R_{83})$ or oxygen;

$R_{83}$ is hydrogen or $CH_3$;

$R_{11}$ is:

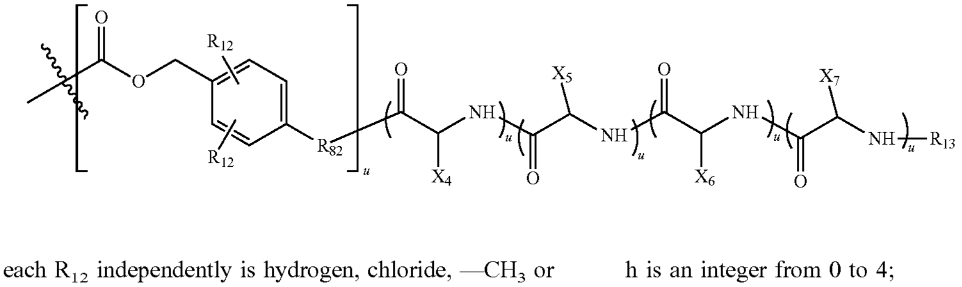

each $R_{12}$ independently is hydrogen, chloride, $—CH_3$ or $—OCH_3$;

$R_{13}$ is hydrogen or $—C(O)—(CH_2)_d—(0\text{-}CH_2—CH_2)_f—NH_2$;

$R_{82}$ is —NH or oxygen $X_4$ is the side chain of lysine, arginine, citrulline, alanine or glycine;

$X_5$ is the side chain of phenylalanine, valine, leucine, isoleucine or tryptophan;

each of $X_6$ and $X_7$ is independently the side chain of glycine, alanine, serine, valine or proline;

a is an integer from 1 to 6;

c is an integer from 0 to 3;

d is an integer from 1 to 3;

f is an integer from 1 to 12; and each u independently is an integer 0 or 1;

or $R_{11}$ is $—Y_u—W_q—R_{88}$, wherein:

Y is any one of the following structures:

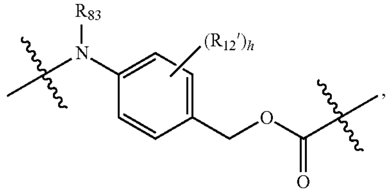

, and

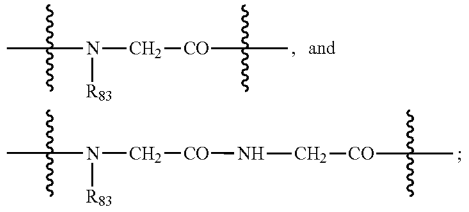

in each of which the terminal $NR_{83}$ group of Y is proximal to $R_{88}$;

$R_{83}$ is hydrogen or $CH_3$;

each W is an amino acid unit;

each $R_{12}'$ independently is halogen, $—C_{1-8}$ alkyl, $—O—C_{1-8}$ alkyl, nitro or cyano;

$R_{88}$ is hydrogen or $—C(O)—(CH_2)_{ff}—(NH—C(O))_{aa}\text{-}E_j\text{-}(CH_2)_{bb}—R_{85}$ $R_{85}$ is $NH_2$ or OH;

E is $—CH_2—$ or $—CH_2CH_2O—$;

u is an integer 0 or 1;

q is an integer from 0 to 12;

aa is an integer 0 or 1;

bb is an integer 0 or 2;

ff is an integer from 0 to 10;

h is an integer from 0 to 4;

j is an integer from 0 to 12; and when E is $—CH_2—$, bb is 0 and j is an integer from 0 to 10; and when E is $—CH_2CH_2—O—$, bb is 2 and j is an integer from 1 to 12;

or $R_{11}$ is

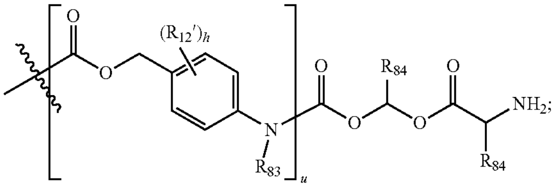

wherein:

$R_{83}$ is hydrogen or $CH_3$;

$R_{84}$ is $C_{1-6}$ alkyl or $C_{6-10}$ aryl;

each $R_{12}'$ independently is halogen, $—C_{1-8}$ alkyl, $—O—C_{1-8}$ alkyl, nitro or cyano;

h is an integer from 0 to 4; and u is an integer 0 or 1.

In some embodiments, $R_{11}$ is:

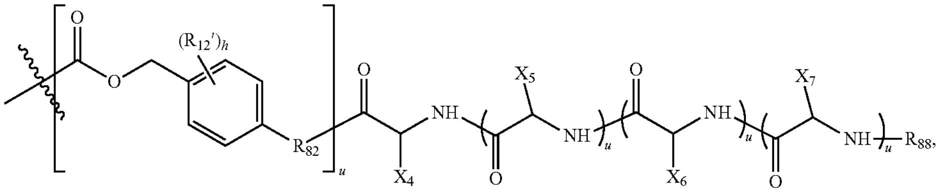

wherein:

each $R_{12}'$ independently is chloride, $—CH_3$ or $—OCH_3$;

$R_{88}$ is hydrogen or $—C(O)—(CH_2)_{ff}4$ $CH_2—CH_2OVCH_2—CH_2—NH_2$;

$R_{82}$ is —NH or oxygen $X_4$ is the side chain of lysine, arginine, citrulline, alanine or glycine;

$X_5$ is the side chain of phenylalanine, valine, leucine, isoleucine or tryptophan;

each of $X_6$ and $X_7$ is independently the side chain of glycine, alanine, serine, valine or proline;

ff is an integer from 1 to 3;

j is an integer from 1 to 12 h is an integer from 0 to 4; and each u independently is an integer 0 or 1.

In some embodiments,

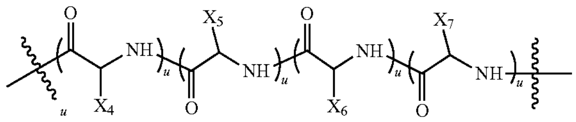

is citrulline-valine; lysine-phenylalanine; citrulline-phenylalanine; citrulline-leucine; citrulline-valine-glycine-glycine; glycine-phenylalanine-glycine-glycine; valine; proline; leucine or isoleucine.

In another embodiment, $R_{11}$ is any one of the following structures:

(1)

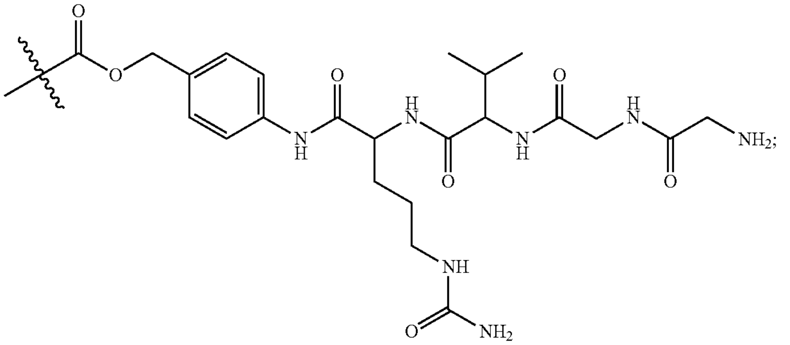

-continued
(2)
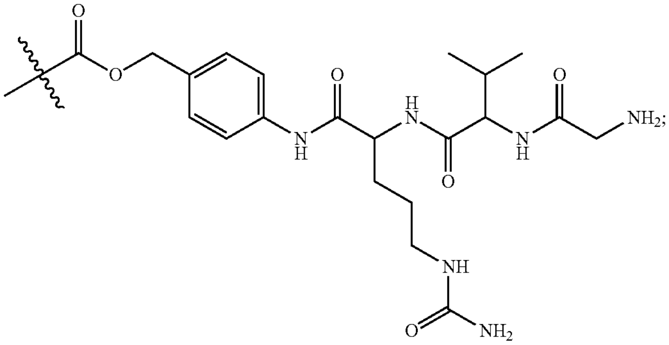
(3)
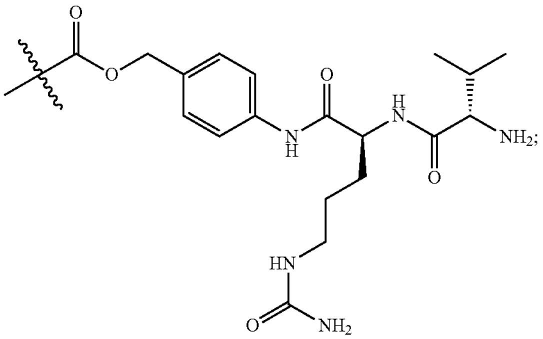
(4)
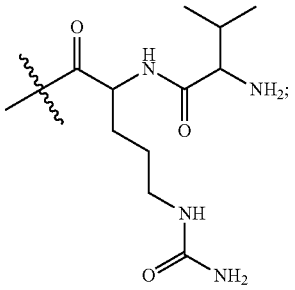
(5)
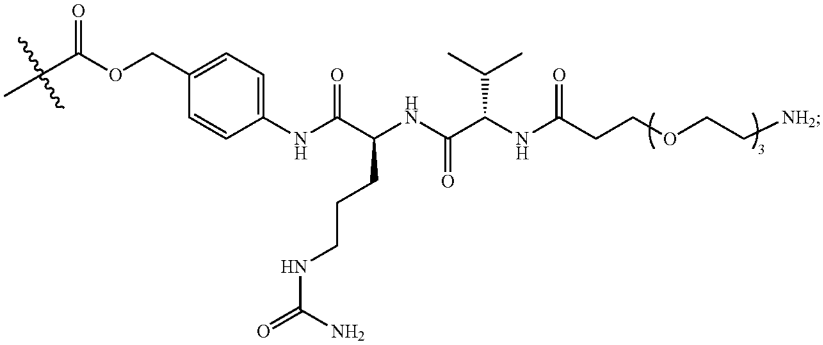
(6)
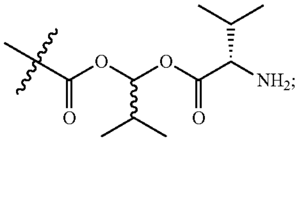
(7)
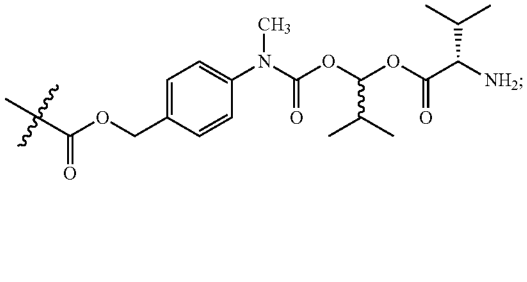
(8)
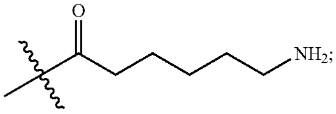
and -continued
(10)
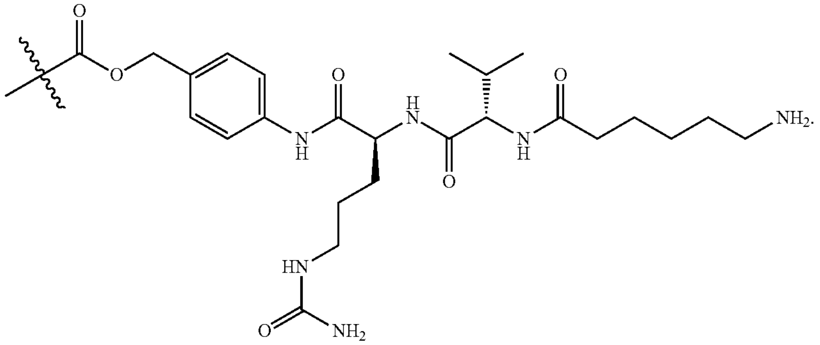
In some embodiments $R_{47}$ is any one of the following structures:
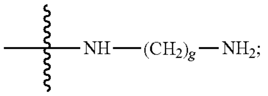
(1)
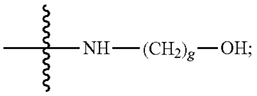
(2)
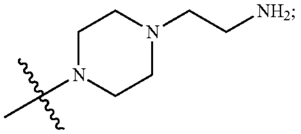
(3)
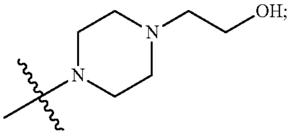
(4)
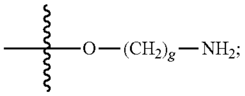
(5)
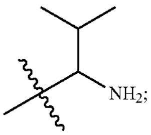
(6)
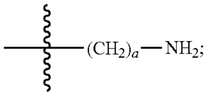
(7)
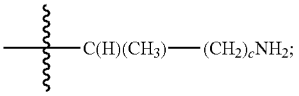
(8)
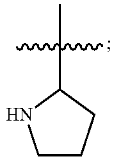
(9)
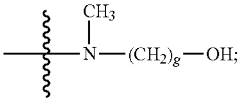
(10)
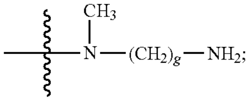
(11)
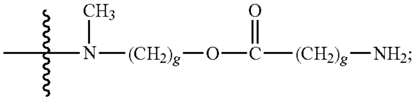
(12)
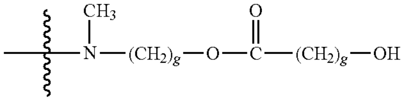
(13)
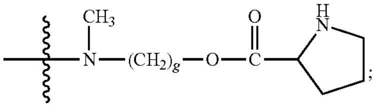
(14)

-continued
(15)
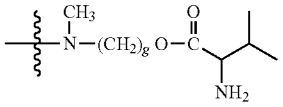
(16)
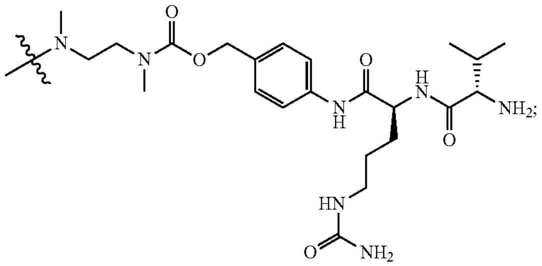
(17)
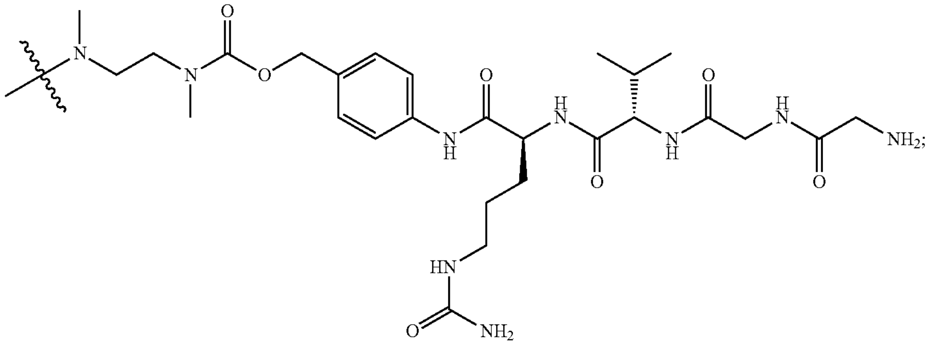
(18)
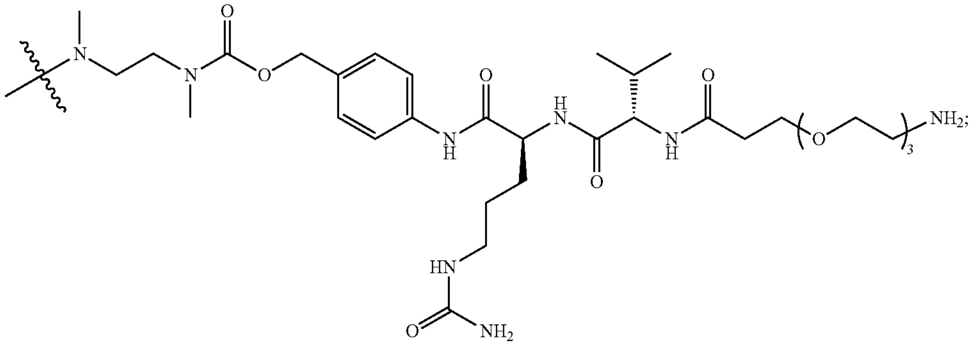
(19)
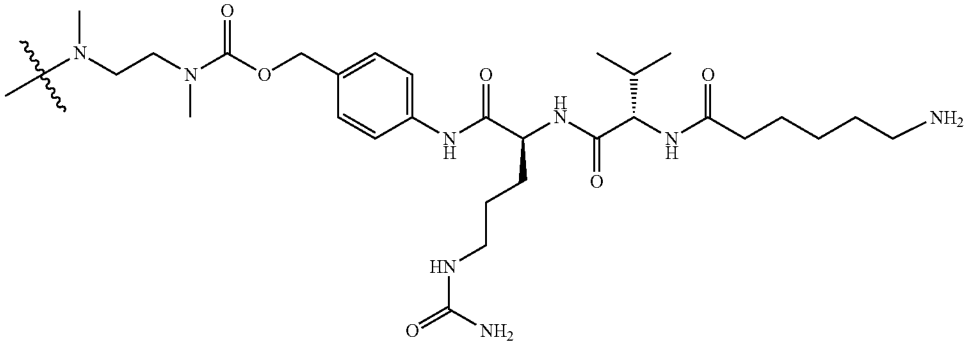
or
(20)
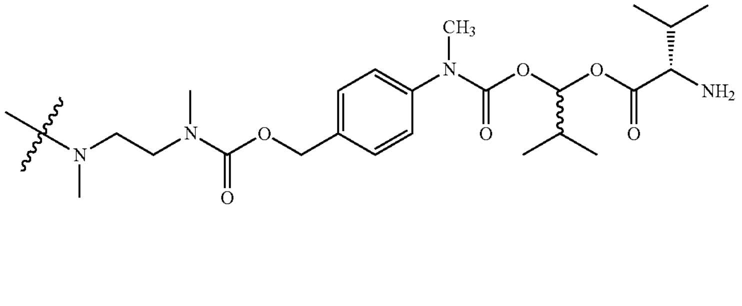

wherein:

a is an integer from 1 to 6;

c is an integer from 0 to 3; and g is an integer from 2 to 6.

In another embodiment the auristatin is a compound of Formula (X):

(X)

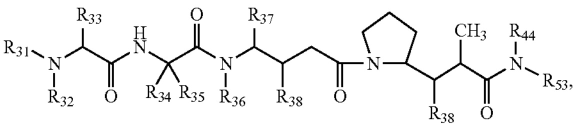

wherein:

each of $R_{31}$ and $R_{32}$ independently is hydrogen or C1-8 alkyl and at most one of $R_{31}$ and $R_{32}$ is hydrogen;

$R_{33}$ is hydrogen, $C_{1-8}$ alkyl, $C_{3-8}$ carbocycle, $C_{6-10}$ aryl, $C_{1-8}$ alkyl-$C_{6-10}$ aryl, $X^1$—($C_{3-8}$ carbocycle), $C_{3-8}$ heterocycle or $X^1$—($C_{3-8}$ heterocycle);

$R_{34}$ is hydrogen, $C_{1-8}$ alkyl, $C_{3-8}$ carbocycle, $C_{6-10}$ aryl, $X^1$—$C_{6-10}$ aryl, $X^1$—($C_{3-8}$ carbocycle), $C_{3-8}$ heterocycle or $X^1$—($C_{3-8}$ heterocycle);

$R_{35}$ is hydrogen or methyl;

or $R_{34}$ and $R_{35}$, together with the carbon atom to which they attach form a carbocyclic ring having the formula —$(CR_{55}R_{41})_b$— wherein each of $R_{55}$ and $R_{41}$ independently is hydrogen or $C_{1-8}$ alkyl and b is an integer from 3 to 7;

$R_{36}$ is hydrogen or $C_{1-8}$ alkyl;

$R_{37}$ is hydrogen, $C_{1-8}$ alkyl, $C_{3-8}$ carbocycle, $C_{6-10}$ aryl, —$X^1$—$C_{6-10}$ aryl, —$X^1$—($C_{3-8}$ carbocycle), $C_{3-8}$ heterocycle or —$X^1$—($C_{3-8}$ heterocycle);

each $R_{38}$ independently is hydrogen, OH, $C_{1-8}$ alkyl, $C_{3-8}$ carbocycle or O—($C_{1-8}$ alkyl);

$R_{53}$ is:

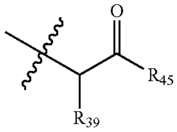

or $R_{54}$ $R_{39}$ is H, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-$NH_2$, or $(CH_2)_2SCH_3$ each $X^1$ independently is $C_{1-10}$ alkylene or $C_{3-10}$ cycloalkylene;

$R_{44}$ is hydrogen or $C_{1-8}$ alkyl;

$R_{45}$ is $X^3$—$R_{42}$ or NH—$R_{19}$;

$X^3$ is O or S;

$R_{19}$ is hydrogen, OH, amino group, alkyl amino or —$[C(R_{20}R_{21})]_a$—$R_{22}$;

$R_{42}$ is an amino group, $C_{1-6}$ alkyl amino or —$[C(R_{20}R_{21})]_a$ —$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NHR_{23}$, —COOH, —$R_{82}$—$C(O)(CH_2)_c$—$C(H)(R_{23})$—$N(H)(R_{23})$, —$R_{82}$—$C(O)(CH_2)_d$—$(OCH_2$—$CH_2)_f$—$N(H)(R_{23})$ or —$R_{82}$—$(C(O)$—$CH(X^2)$—$NH)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

$R_{54}$ is —$C(R_{56})_2$—$C(R_{56})_2$—$C_{6-10}$ aryl, —$C(R_{56})_2$—$C(R_{56})_2$—$C_{3-8}$ heterocycle or —$C(R_{56})_2$—$C(R_{56})_2$—$C_{3-8}$ carbocycle;

$R_{56}$ is independently selected from H, OH, $C_{1-8}$ alkyl, $C_{3-8}$ carbocycle, —O—$C_{1-8}$ alkyl, —O—C(O)—$R_{29}$ and —O—$R_{23}$—O—$C_{1-6}$ alkyl-$NH_2$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$[C(R_{20}R_{21})]_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, NH or oxygen;

a is an integer from 1 to 6;

c is an integer from 0 to 3;

d is an integer from 1 to 3; and f is an integer from 1 to 12.

In some embodiments, in the auristatin compound of Formula (X):

$R_{39}$ is benzyl or

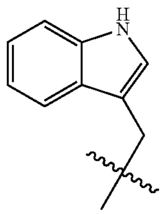 ;

and $R_{44}$ is hydrogen.

In another embodiment the auristatin is a compound of Formula (Xa):

(Xa)

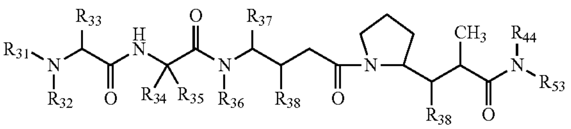

wherein:

$R_{33}$ through $R_{38}$, and $R_{44}$ are as defined herein, one of $R_{31}$ and $R_{32}$ is hydrogen or $C_{1-8}$ alkyl and the other is:

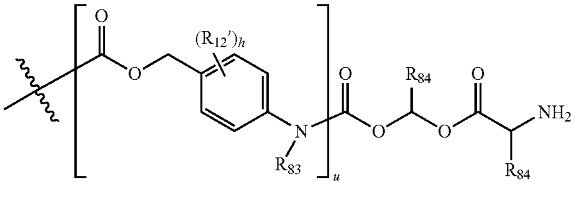

wherein:

$R_{83}$ is hydrogen or $CH_3$;

$R_{84}$ is $C_{1-6}$ alkyl or $C_{6-10}$ aryl;

each $R_{12}'$ independently is halogen, —$C_{1-8}$ alkyl, —O—$C_{1-8}$ alkyl, nitro or cyano;

h is an integer from 0 to 4; and u is an integer 0 or 1;

$R_{53}$ is:

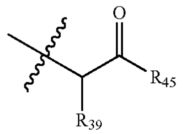

or $R_{54}$ $R_{54}$ is —$C(R_{56})_2$—$C(R_{56})_2$—$C_{6-10}$ aryl, —$C(R_{56})_2$—$C(R_{56})_2$—$C_{3-8}$ heterocycle or —$C(R_{56})_2$—$C(R_{56})_2$—$C_{3-8}$ carbocycle;

$R_{56}$ is independently selected from H, OH, $C_{1-8}$ alkyl, $C_{3-8}$ carbocycle, —O—$C_{1-8}$ alkyl, —O—C(O)—$R_{29}$ and —O—$R_{23}$—O—$C_{1-6}$ alkyl-$NH_2$;

$R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$[C(R_{20}R_{21})]_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, NH or oxygen;

a is an integer from 1 to 6;

c is an integer from 0 to 3;

d is an integer from 1 to 3; and f is an integer from 1 to 12.

In one embodiment, the auristatin compound of Formula (Xa) is a compound of Formula (XIa) or Formula (XIb):

(XIa)

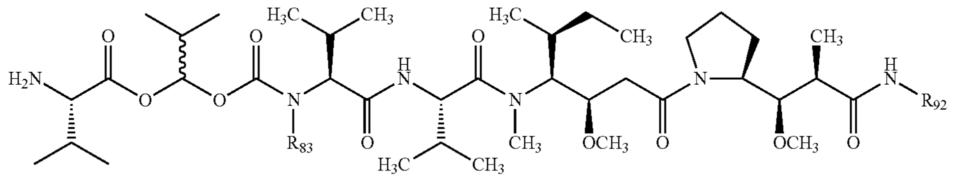

or (XIb)

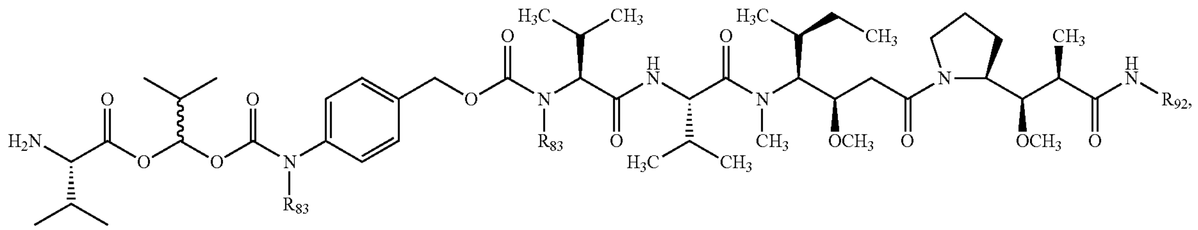

$R_{39}$ is H, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-$NH_2$, or $(CH_2)_2SCH_3$, each $X^1$ independently is $C_{1-10}$ alkylene or $C_{3-10}$ cycloalkylene;

$R_{45}$ is $X^3$—$R_{42}$ or NH—$R_{19}$;

$X^3$ is O or S;

$R_{19}$ is hydrogen, OH, amino group, alkyl amino or —$[C(R_{20}R_{21})]_a$—$R_{22}$;

$R_{42}$ is H, an amino group, $C_{1-6}$ alkyl amino or —$[C(R_{20}R_{21})]_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NHR_{23}$, —COOH, —$R_{82}$—$C(O)(CH_2)_c$—$C(H)(R_{23})$—$N(H)(R_{23})$, —$R_{82}$—$C(O)(CH_2)_d$—$(OCH_2$—$CH_2)_f$—$N(H)(R_{23})$ or —$R_{82}$—$(C(O)$—$CH(X^2)$—$NH)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

wherein:

$R_{92}$ is:

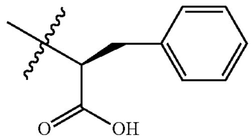

;

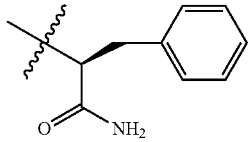

or

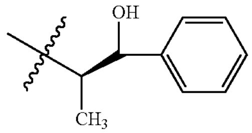

and $R_{83}$ is hydrogen or $CH_3$.

In one embodiment the auristatin of Formula (X) is a compound of Formula (XI), Formula (XII) or Formula (XIII):

wherein the compound of Formula (XI) is:
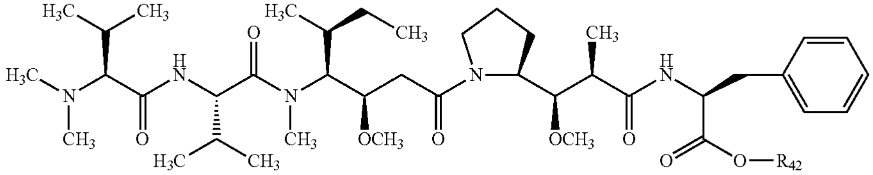
(XI)
wherein $R_{42}$ is —$CH_3$ or any one of the following structures:
(1)
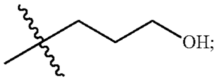
(2)
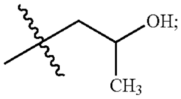
(3)
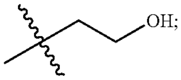
(4)
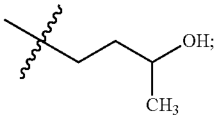
(5)
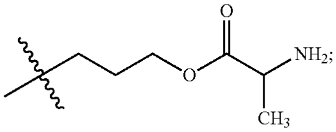
(6)
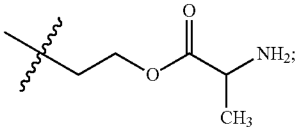
(7)
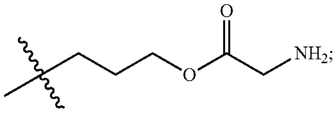
(8)
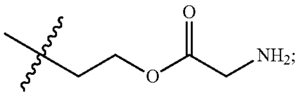
(9)
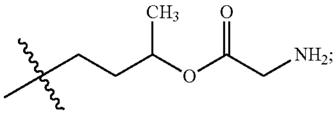
(10)
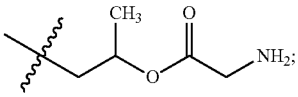
-continued
(11)
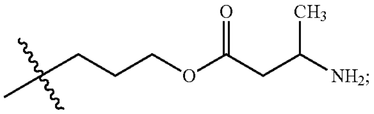
(12)
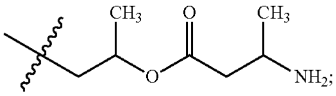
(13)
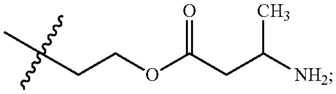
(14)
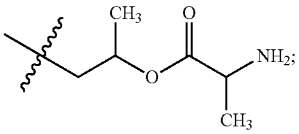
(15)
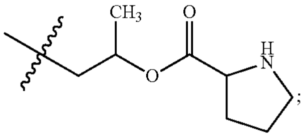
(16)
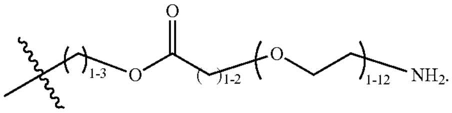
(17)
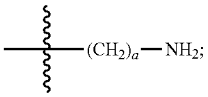
(18)
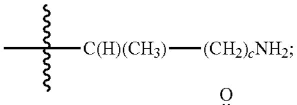
(19)
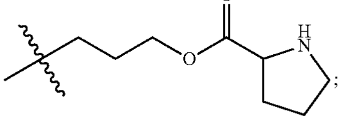
and
(20)
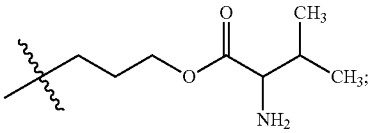
wherein:
a is an integer from 1 to 6; and
c is an integer from 0 to 3;

wherein the compound of Formula (XII) is:
(XII)
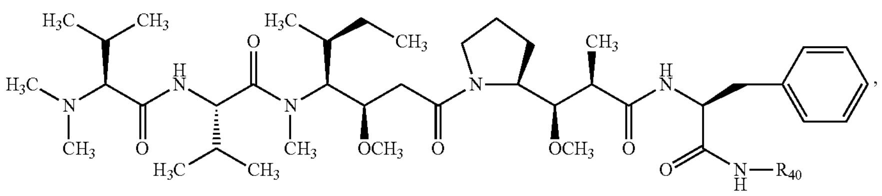
wherein $R_{40}$ is hydrogen, —OH, —$NH_2$, or any of the following structures:
(12)
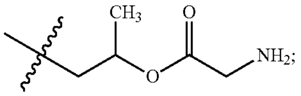
(1)
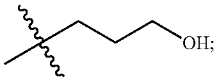
(2)
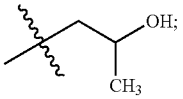
(3)
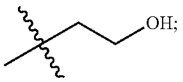
-continued
(4)
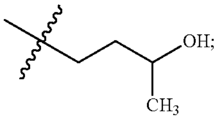
(5)
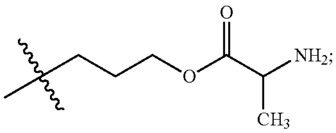
(6)
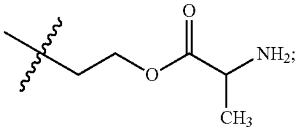
(7)
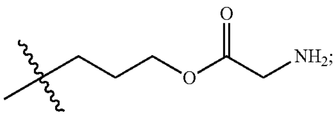

-continued
(8)
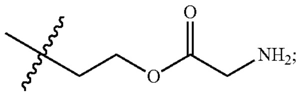
(9)
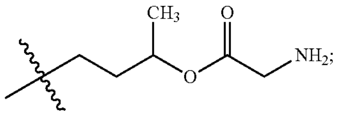
(10)
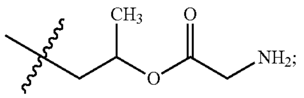
(11)
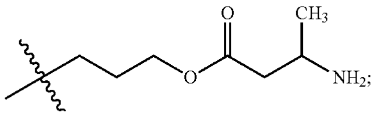
(12)
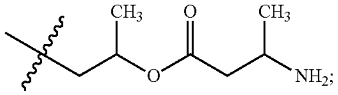
(13)
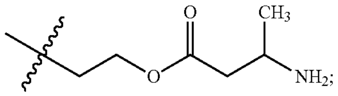
(14)
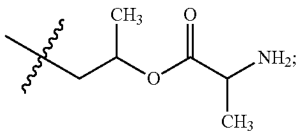
-continued
(15)
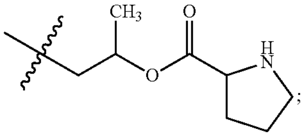
(16)
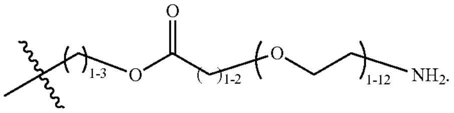
(17)
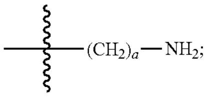
(18)
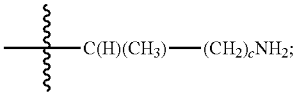
(19)
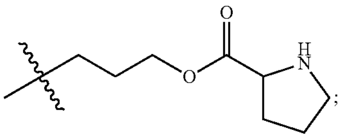
and
(20)
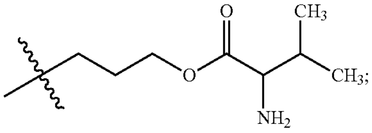
wherein:
a is an integer from 1 to 6; and
c is an integer from 0 to 3;
wherein the compound of Formula (XIII) is:
(XIII)
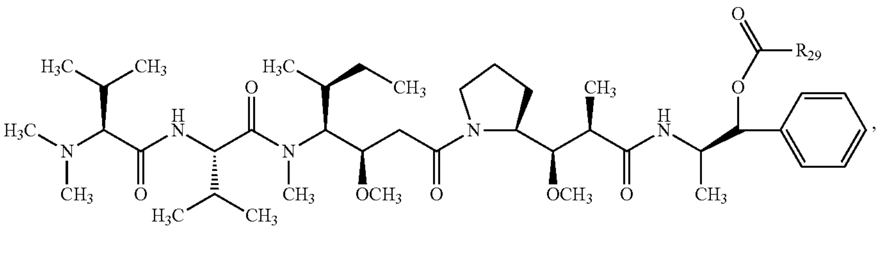

wherein $R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$R_{28}$—$[C(R_{20}R_{21})]_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NHR_{23}$, —COOH, —$R_{82}$—$C(O)(CH_2)_c$—$C(H)(R_{23})$—$N(H)(R_{23})$, —$R_{82}$—$C(O)(CH_2)_d$—$(OCH_2$—$CH_2)_f$—$N(H)(R_{23})$ or —$R_{82}$—$(C(O)$—$CH(X^2)$—$NH)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

$R_{28}$ is absent, NH or oxygen;

a is an integer from 1 to 6;

c is an integer from 0 to 3;

d is an integer from 1 to 3; and f is an integer from 1 to 12.

In one embodiment, in Formula (XII), $R_{40}$ is

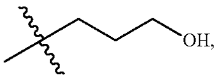

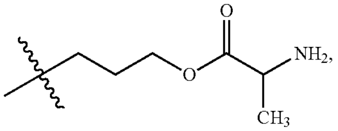

or

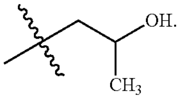

In another embodiment, the compound of Formula (XII) is a compound of Formula (XIIb) or (XIIc):

(XIIb)

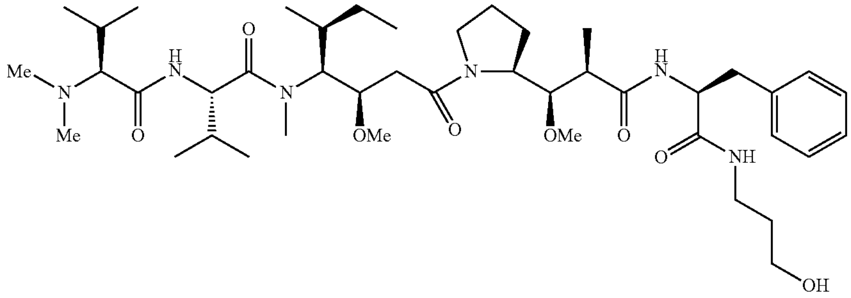

or (XIIc)

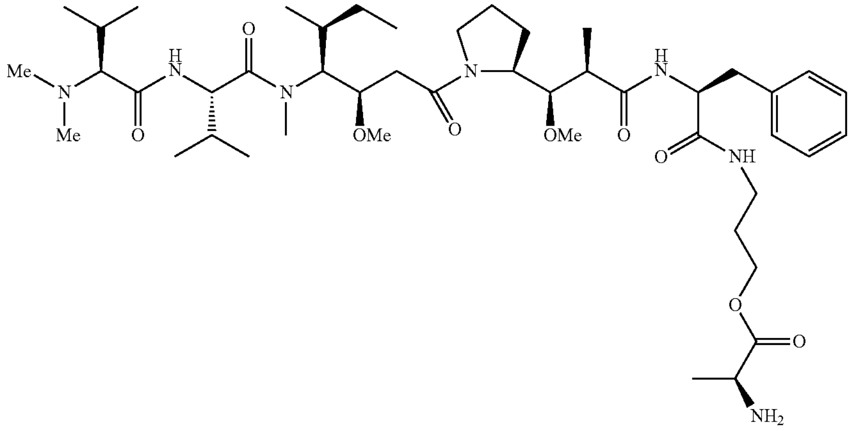

In one embodiment in the compound of Formula (XIII), $R_{29}$ is —$NH_2$, 5 membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, NH or oxygen;

$R_{22}$ is —OH, —$NHR_{23}$, —COOH, —$R_{82}$—C(O)$(CH_2)_c$—C(H)($R_{23}$)—N(H)($R_{23}$), —$R_{82}$—C(O)$(CH_2)_d$—$(OCH_2$—$CH_2)_f$—N(H)($R_{23}$) or —$R_{82}$—(C(O)—CH($X^2$)—NH$)_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

c is an integer from 0 to 3;

d is an integer from 1 to 3; and f is an integer from 1 to 12.

In yet another embodiment, $R_{29}$ is any one of the following structures:

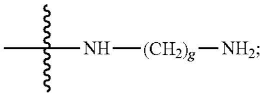

(1)

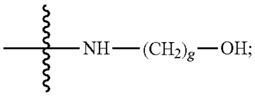

(2)

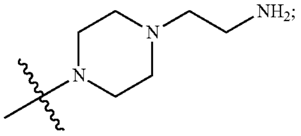

(3)

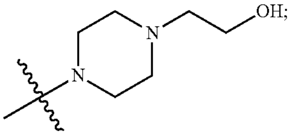

(4)

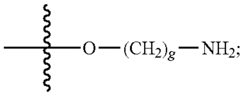

(5)

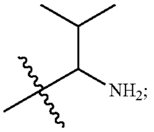

(6)

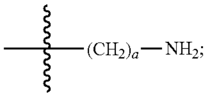

(7)

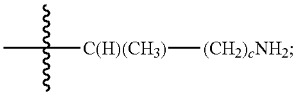

(8)

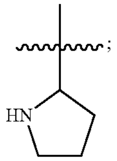

(9)

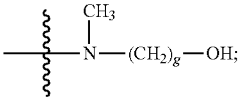

(10)

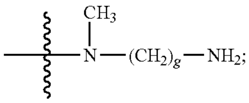

(11)

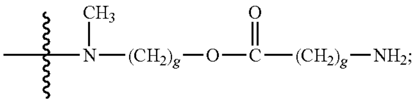

(12)

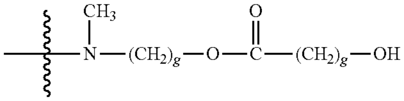

(13)

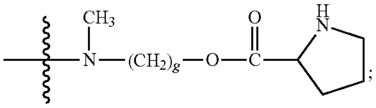

(14)

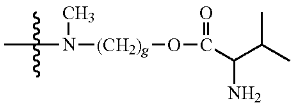

(15)

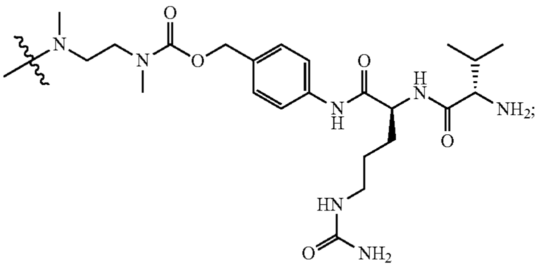

(16)

-continued
(17)
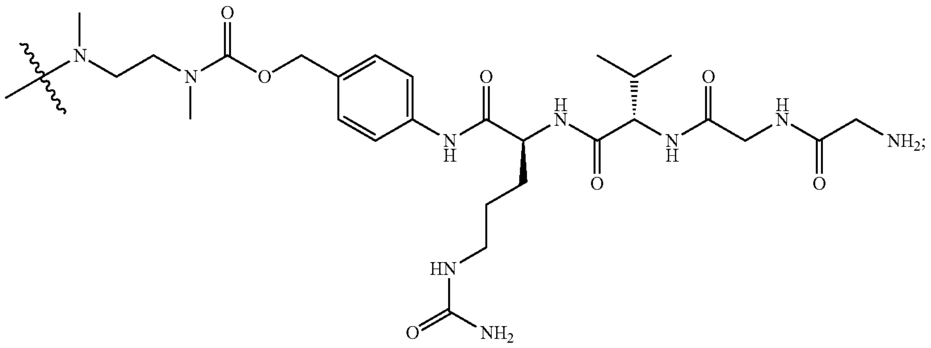
(18)
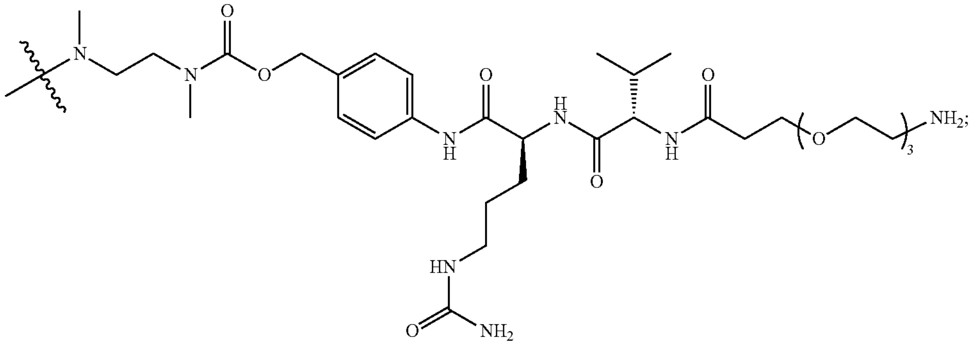
(19)
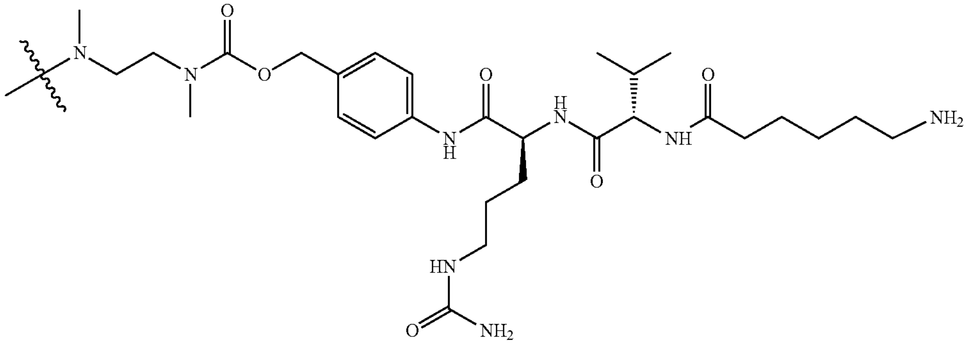
or
(20)
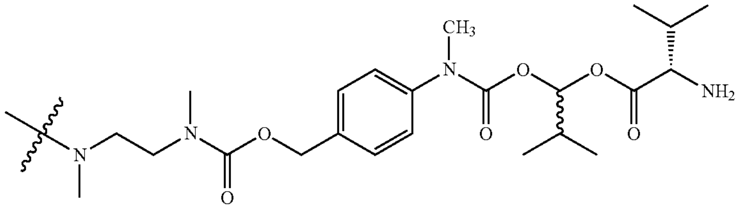

wherein:

a is an integer from 1 to 6;

c is an integer from 0 to 3; and g is an integer from 2 to 6.

In one embodiment, the MEK inhibitor is a compound of Formula (XIV):

(XIV)

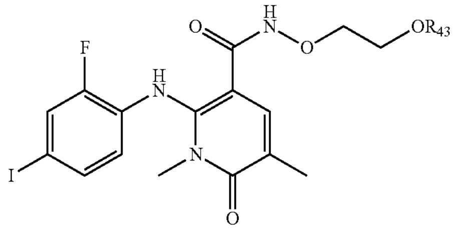

wherein $R_{43}$ is H or $—R_{46}—R_{47}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, $—NH_2$, —COOH, $—R_{82}—C(O)(CH_2)_c—C(H)(R_{23})—N(H)(R_{23})$, $—R_{82}—C(O)(CH_2)_d—(OCH_2—CH_2)_f—N(H)(R_{23})$ or $—R_{82}—(C(O)—CH(X^2)—NH)_d—R_{77}$;

each $R_{23}$ independently is hydrogen, $C_{1-6}$ alkyl, $C_{6-10}$ aryl, $C_{3-8}$ cycloalkyl, —COOH, or $—COO—C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

$R_{46}$ is —C(O)—; —C(O)—O—, —C(O)—NH—, or absent;

$R_{47}$ is as defined herein;

a is an integer from 1 to 6;

c is an integer from 0 to 3;

d is an integer from 1 to 3; and f is an integer from 1 to 12.

Further examples of the MEK inhibitor are disclosed in U.S. Pat. No. 7,517,994 B2.

In some embodiments $R_{43}$ is $—C(O)—(CH_2)_a—NH_2$, or $—C(O)—C(H)(CH_3)—(CH_2)_c—NH_2$; in which a is an integer from 1 to 6; and c is an integer from 0 to 3.

In another embodiment, the duocarmycin compound is a compound of Formula (XV):

(XV)

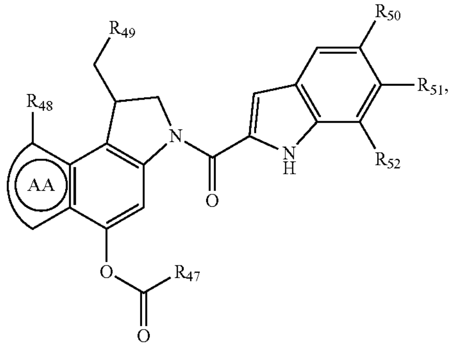

wherein:

$R_{47}$ is as defined herein;

$R_{48}$ is hydrogen, $—COOC_{1-6}$ alkyl, —COOH, $—NH_2$ or $—CH_3$;

$R_{49}$ is Cl, Br or —OH;

$R_{50}$ is hydrogen, $—OCH_3$,

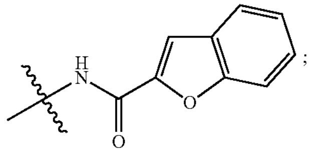

; or

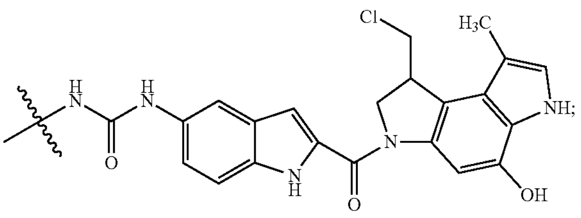

each of $R_{51}$ and $R_{52}$ independently is hydrogen or $—OCH_3$; and ring AA is either a phenyl or pyrrolyl ring.

Further examples of duocarmycin compounds are disclosed in U.S. Pat. No. 7,553,816.

In one embodiment the duocarmycin compound of Formula (XV) is a compound of Formula (XVI), (XVII), (XVIII) or (XIX):

(XVI)
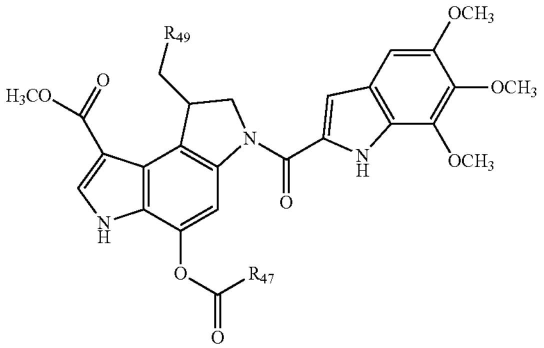
(XVII)
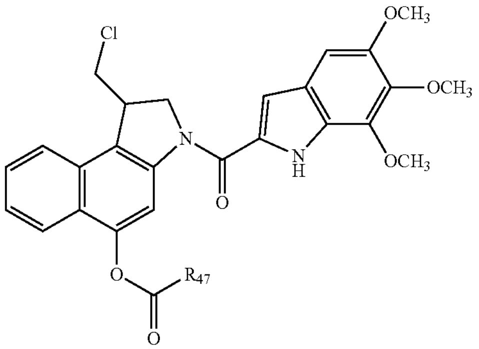
(XVIII)
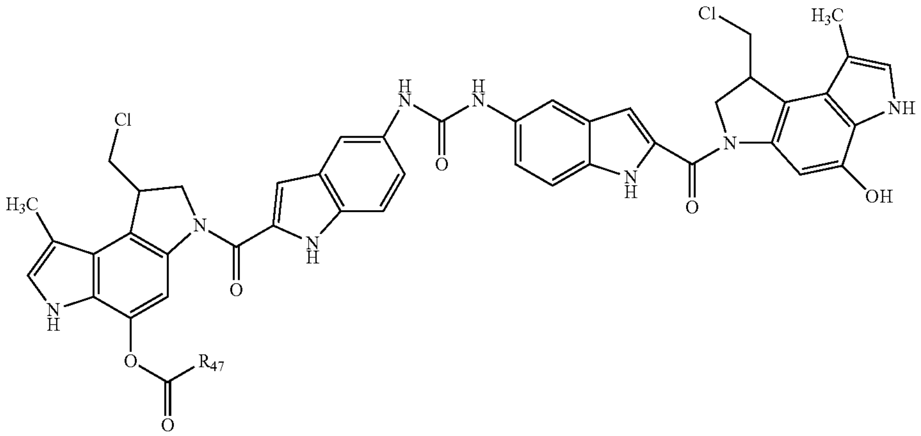
(XIX)
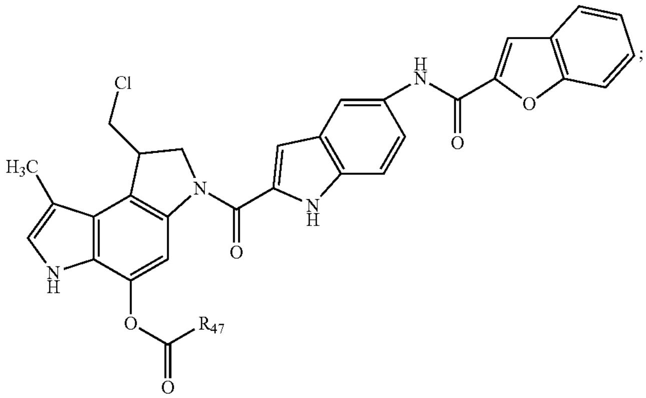
;

wherein:

$R_{49}$ is Cl, Br or —OH; and $R_{47}$ is as defined herein.

In another embodiment, the duocarmycin compound is a duocarmycin SA compound of Formula (XX): U.S. Pat. No. 5,101,038; or (XXI):

(XX)

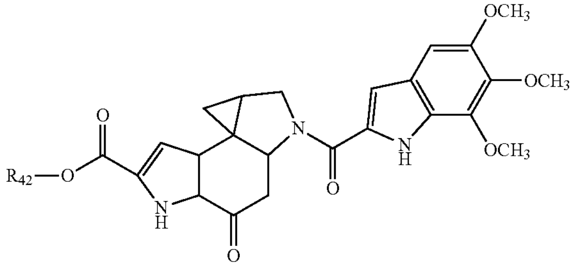

(XXI)

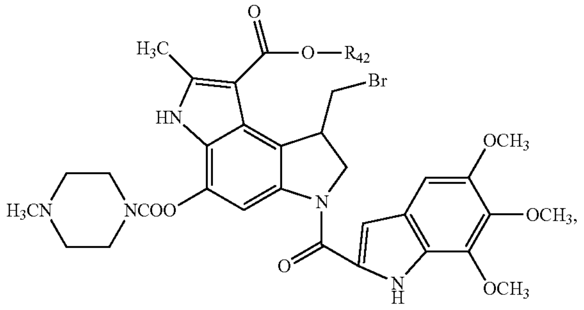

wherein:

$R_{42}$ is $C_{1-6}$ alkyl amino or $—[C(R_{20}R_{21})]_a—R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, $—NH_2$, —COOH, $—R_{82}—C(O)(CH_2)_c—C(H)(R_{23})—N(H)(R_{23})$, $—R_{82}—C(O)(CH_2)_d—(OCH_2—CH_2)_f—N(H)(R_{23})$, or $—R_{82}—(C(O)—CH(X^2)—NH)_d—R_{77}$;

each $R_{23}$ independently is hydrogen, $C_{1-6}$ alkyl, $C_{6-10}$ aryl, $C_{3-8}$ cycloalkyl, —COOH, or $—COO—C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

a is an integer from 1 to 6;

c is an integer from 0 to 3;

d is an integer from 1 to 3; and f is an integer from 1 to 12.

In some embodiments, $R_{42}$ is any one of the following structures:

(1)

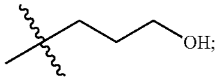

-continued (2)

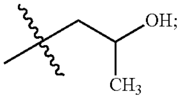

(3)

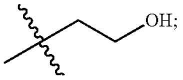

(4)

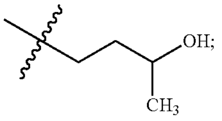

(5)

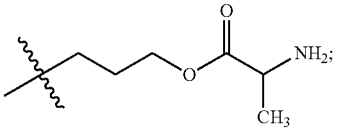

(6)

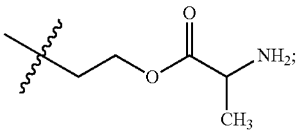

(7)

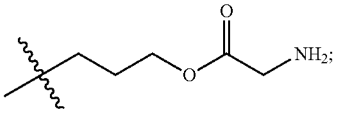

(8)

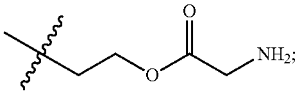

(9)

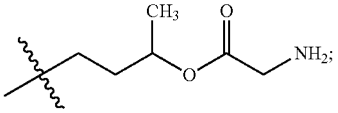

(10)

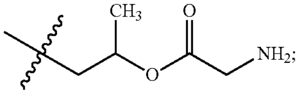

(11)

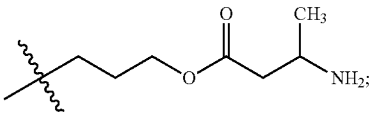

(12)

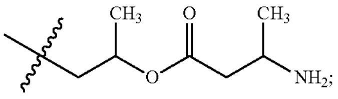

(13)

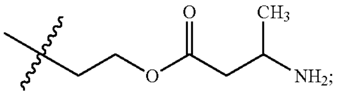

(14)

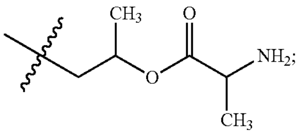

-continued (15)

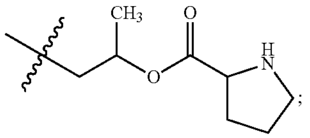

(16)

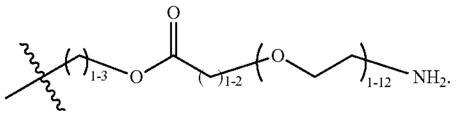

(17)

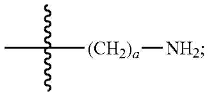

(18)

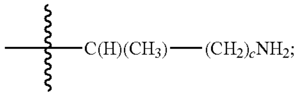

(19)

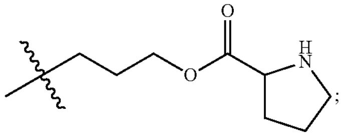

and (20)

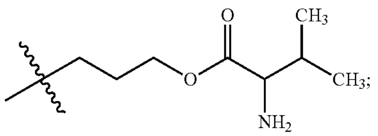

wherein:

a is an integer from 1 to 6; and c is an integer from 0 to 3.

In another embodiment, the KSP inhibitor compound is a compound of Formula (XXVI):

(XXVI)

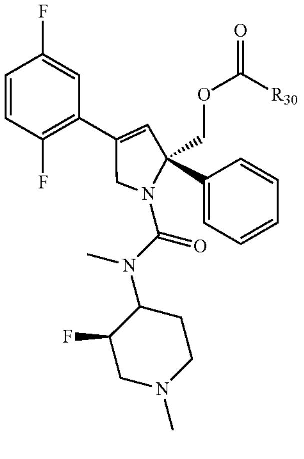

wherein $R_{30}$ is as defined herein.

In some embodiments $R_{30}$ is:

(1)

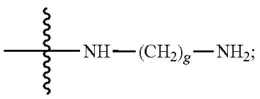

(2)

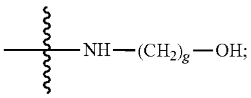

(3)

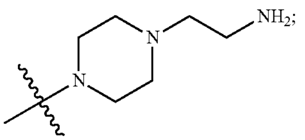

(4)

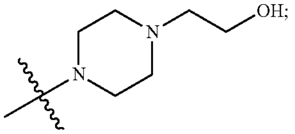

(5)

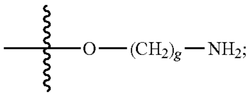

(6)

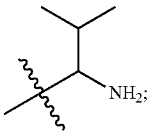

(7)

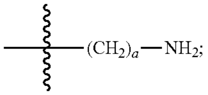

or (8)

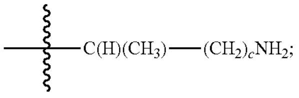

(9)

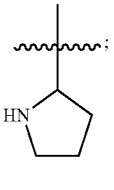

wherein:

a is an integer from 1 to 6;

c is an integer from 0 to 3; and g is an integer from 2 to 6.

In another embodiment, the duocarmycin compound is Duocarmycin A, Duocarmycin B1, Duocarmycin B2, Duocarmycin C1, Duocarmycin C2, Duocarmycin D, CC-1065, Adozelesin, Bizelesin or Carzelesin In another embodiment the KSP inhibitor compound is a compound of Formula (XXVII), (XXVIII) or (XXIX):

(XXVII)

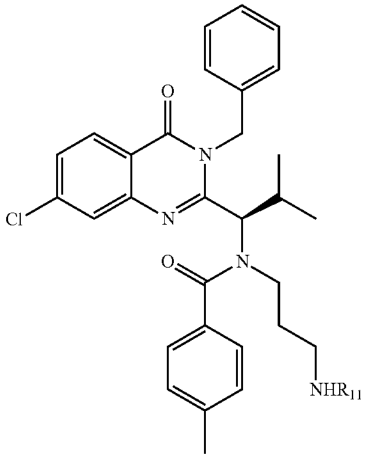

(XXVIII)

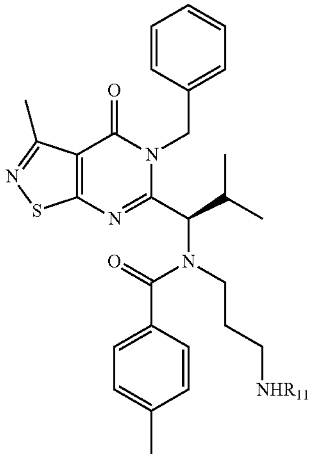

-continued (XXIX)

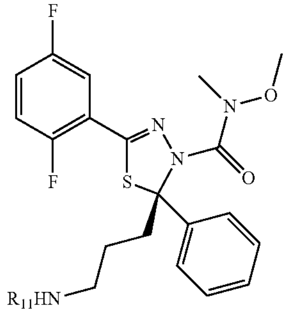

wherein:

$R_{11}$ is as defined herein.

One skilled in the art of therapeutic agents will readily understand that each of the therapeutic agents described herein can be modified in such a manner that the resulting compound still retains the specificity and/or activity of the original compound. The skilled artisan will also understand that many of these compounds can be used in place of the therapeutic agents described herein. Thus, the therapeutic agents disclosed herein include analogues and derivatives of the compounds described herein.

Table B below provides more examples of the therapeutic agents and derivatives thereof suitable for conjugation to form the polymer-drug-protein conjugates or polymer-drug scaffolds disclosed herein. Spectral data of certain compounds are also provided (ND in the table means "not determined"). These examples may also be the active form of the drug when it is released from the conjugates in vitro or in vivo.

TABLE B (VI)

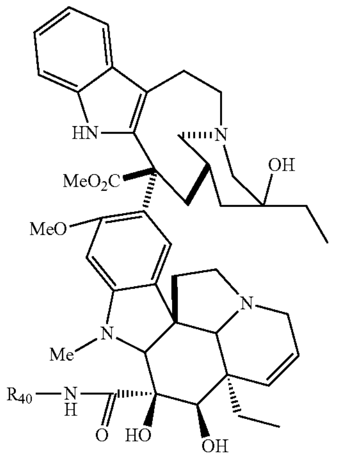

| $R_{40}$ | m/z |
|---|---|
| 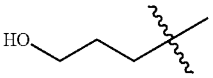 [SMILES: *CCCO] | ND |

TABLE B-continued
| | |
|---|---|
| 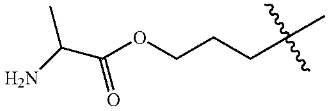 [SMILES: *CCCOC(=O)C(C)N] | ND |
| 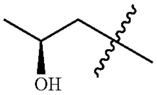 [SMILES: *C[C@H](C)O] | ND |
| 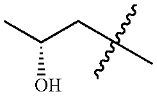 [SMILES: *C[C@@H](C)O] | ND |
(IX)
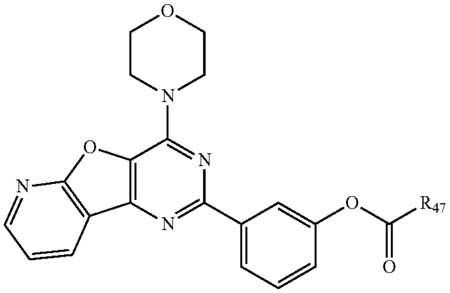
| $R_{47}$ | m/z |
|---|---|
| 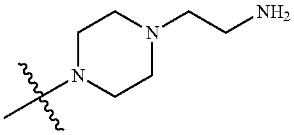 [SMILES: *N1CCN(CCN)CC1] | ND |
| 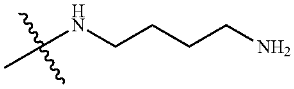 [SMILES: *NCCCCN] | ND |
| 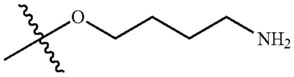 [SMILES: *OCCCCN] | ND |
| 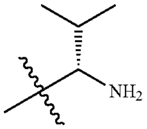 [SMILES: *[C@@H](N)C(C)C] | ND |

TABLE B-continued
(XI)
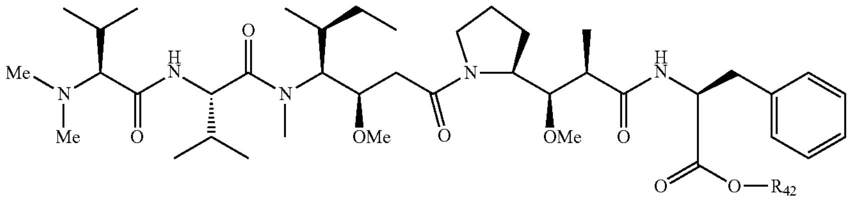
| $R_{42}$ | m/z |
|---|---|
| H | ND |
| —$CH_3$ | 760 |
| 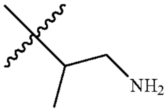 [SMILES: *C(C)CN] | 802.6 |
| 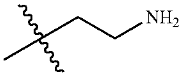 [SMILES: *CCN] | 790 |
| 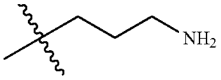 | 804 |
(XII)
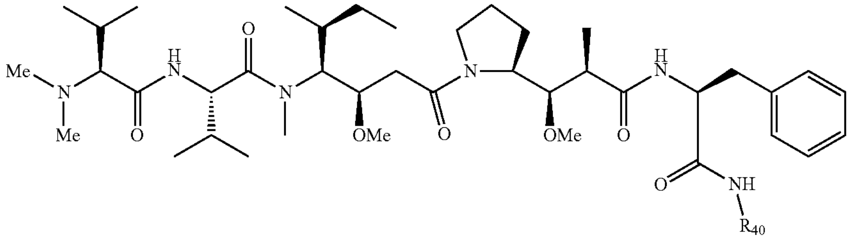
| $R_{40}$ | m/z |
|---|---|
| —H | ND |
| 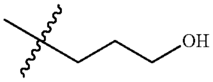 [SMILES: *CCCO] | 803.5 |
| 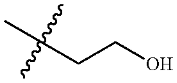 [SMILES: *CCO] | 789.1 |
| 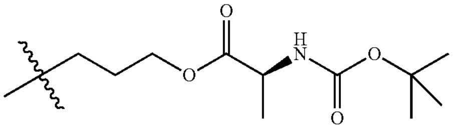 [SMILES: *CCCOC(=O)[C@H](C)NC(=O)OC(C)(C)C] | 974.2 |
| 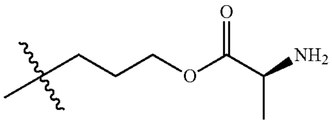 [SMILES: *CCCOC(=O)[C@H](C)N] | 874.5 |
| 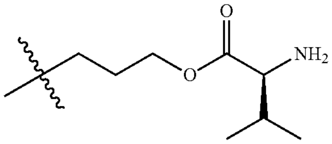 [SMILES: *CCCOC(=O)[C@@H](N)C(C)C] | 902.2 |

TABLE B-continued
| | |
|---|---|
| 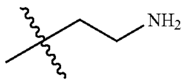 [SMILES: *CCN] | ND |
| 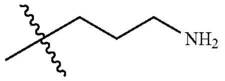 [SMILES: *CCCN] | ND |
| —OH | 788 |
| 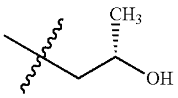 | 803.4 |
| 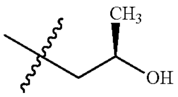 [SMILES: *C[C@@H](C)O] | 803.4 |
| 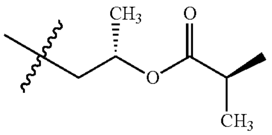 | 874.4 |
| 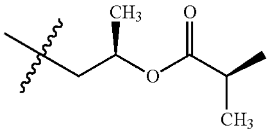 | 874.4 |
| 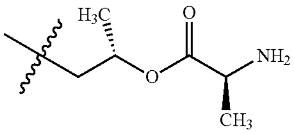 [SMILES: *C[C@H](C)OC(=O)[C@H](C)N] | 874.4 |
| 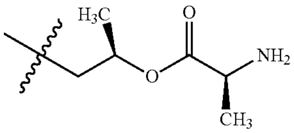 [SMILES: *C[C@@H](C)OC(=O)[C@H](C)N] | 874.4 |
| 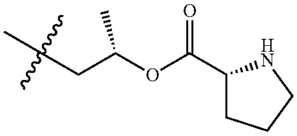 [SMILES: *C[C@H](C)OC(=O)[C@H]1CCCN1] | 900.2 |
| 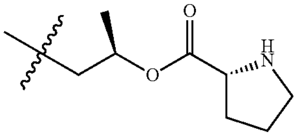 [SMILES: *C[C@@H](C)OC(=O)[C@H]1CCCN1] | 900.2 |
| 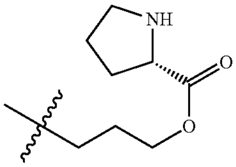 [SMILES: *CCCOC(=O)[C@@H]1CCCN1] | 900.5 |

TABLE B-continued
| | |
|---|---|
| 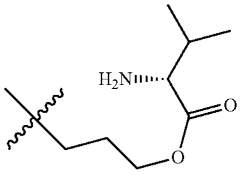 [SMILES: *CCCOC(=O)[C@H](N)C(C)C] | 900.5 |
(XIII)
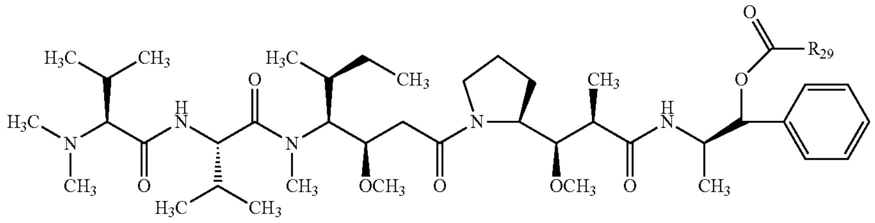
| —C(O)—$R_{29}$ | m/z |
|---|---|
| 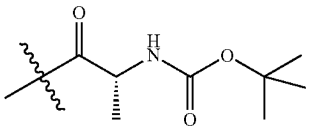 [SMILES: *C(=O)[C@@H](C)NC(=O)OC(C)(C)C] | 903.2 |
| 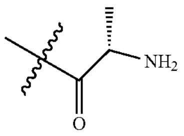 [SMILES: *C(=O)[C@H](C)N] | 803.1 |
| 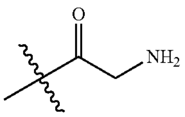 [SMILES: *C(=O)CN] | 790 |
| 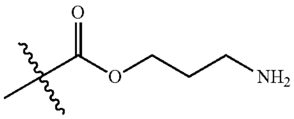 [SMILES: *C(=O)OCCCN] | 832.6 |
| 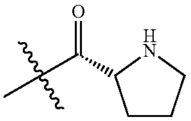 | 829.1 |
| 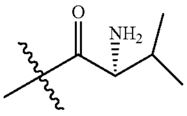 [SMILES: *C(=O)[C@@H](N)C(C)C] | 802 |

TABLE B-continued
| | |
|---|---|
| 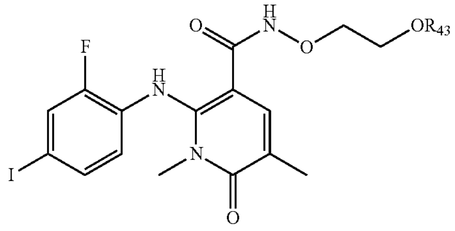 | (XIV) |
| $R_{43}$ | m/z |
| 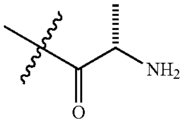 [SMILES: *C(=O)[C@H](C)N] | ND |
| 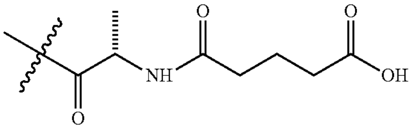 [SMILES: *C(=O)[C@H](C)NC(=O)CCCC(=O)O] | 644.9 |
| 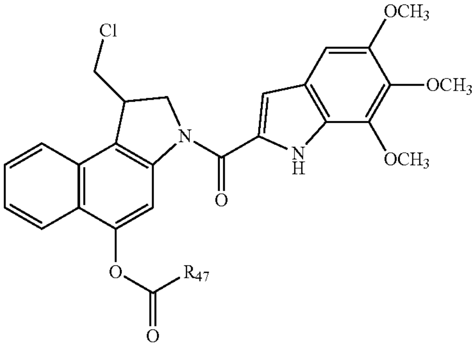 | (XVII) |
| $R_{47}$ | m/z |
| 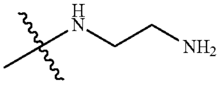 [SMILES: *NCCN] | 553.1 |
| 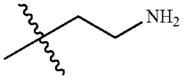 [SMILES: *CCN] | 538.1 |
| 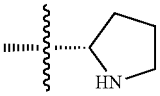 | 564.1 |
| 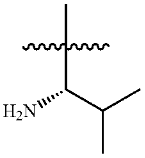 | 566.1 |

TABLE B-continued
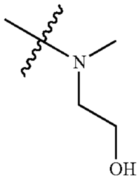 [SMILES: *N(C)CCO]
568.1
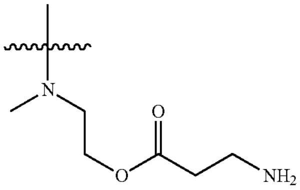 [SMILES: *N(C)CCOC(=O)CCN]
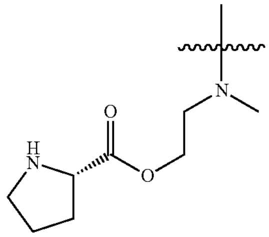 [SMILES: *N(C)CCOC(=O)[C@@H]1CCCN1]
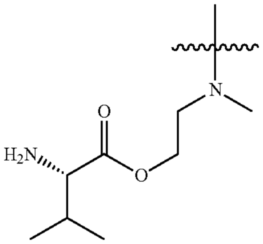 [SMILES: *N(C)CCOC(=O)[C@@H](N)C(C)C]
667.2
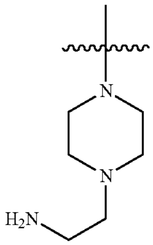
622.2
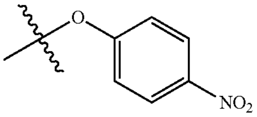 [SMILES: *Oc1ccc([N+](=O)[O-])cc1]
632.02

TABLE B-continued
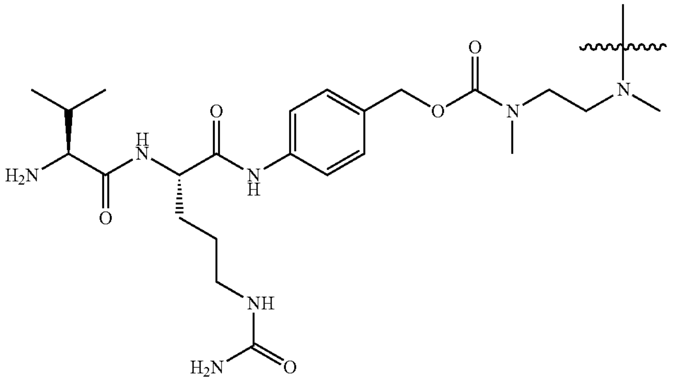 [SMILES: *N(C)CCN(C)C(=O)OCc1ccc(NC(=O)[C@H](CCCNC(N)=O)NC(=O)[C@@H](N)C(C)C)cc1]
986.2
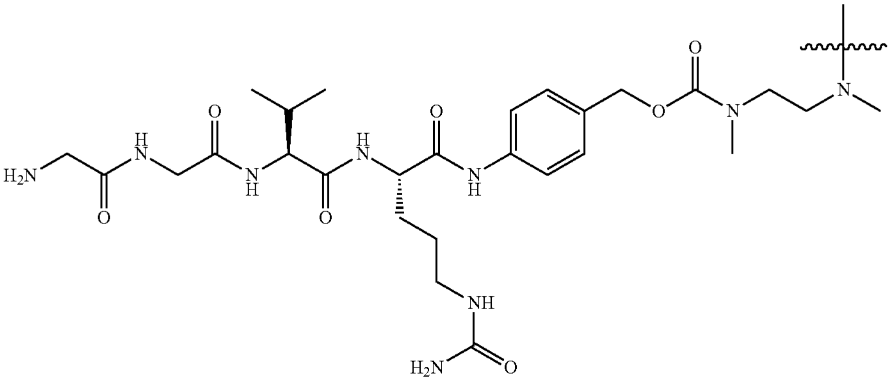 [SMILES: *N(C)CCN(C)C(=O)OCc1ccc(NC(=O)[C@H](CCCNC(N)=O)NC(=O)[C@@H](NC(=O)CNC(=O)CN)C(C)C)cc1]
ND
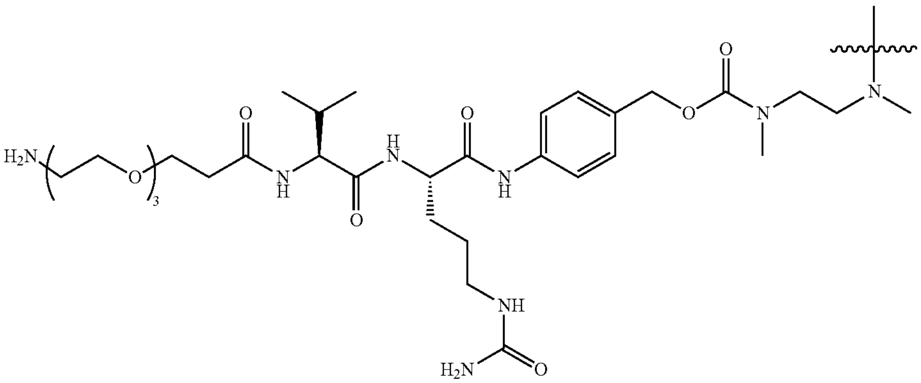
ND

TABLE B-continued
(XXVII)
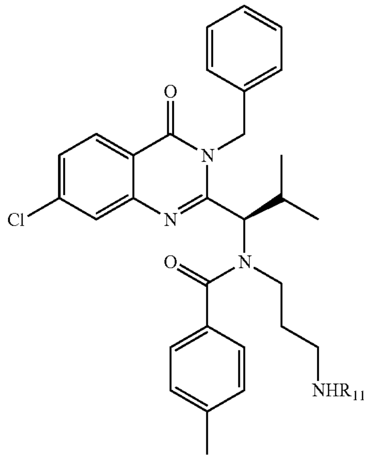
(XXVIII)
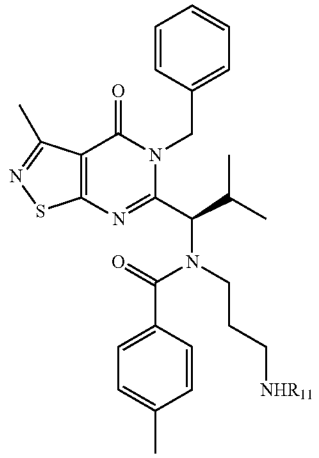
(XXIX)
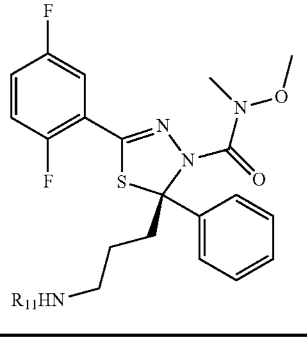

TABLE B-continued
| $R_{11}$ | m/z (XXVII) |
|---|---|
| 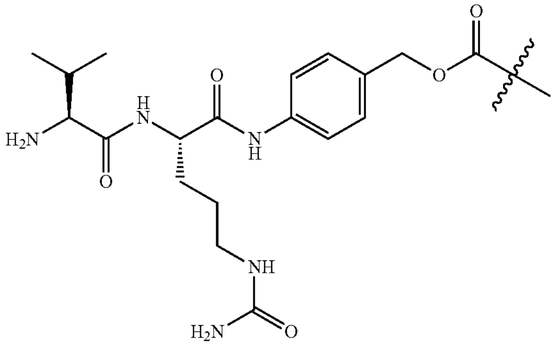 [SMILES: *C(=O)OCc1ccc(NC(=O)[C@H](CCCNC(N)=O)NC(=O)[C@@H](N)C(C)C)cc1] | 922.3 |
| 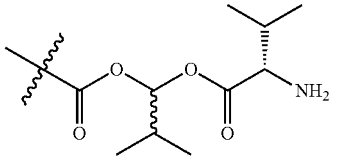 [SMILES: *C(=O)OC(OC(=O)[C@@H](N)C(C)C)C(C)C] | 732.2 |
| 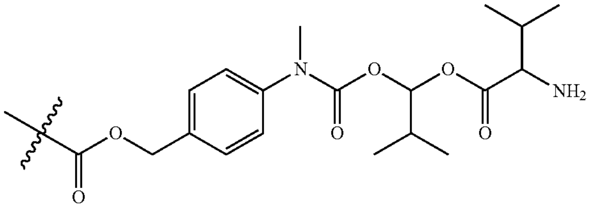 [SMILES: *C(=O)OCc1ccc(N(C)C(=O)OC(OC(=O)C(N)C(C)C)C(C)C)cc1] | ND |
| 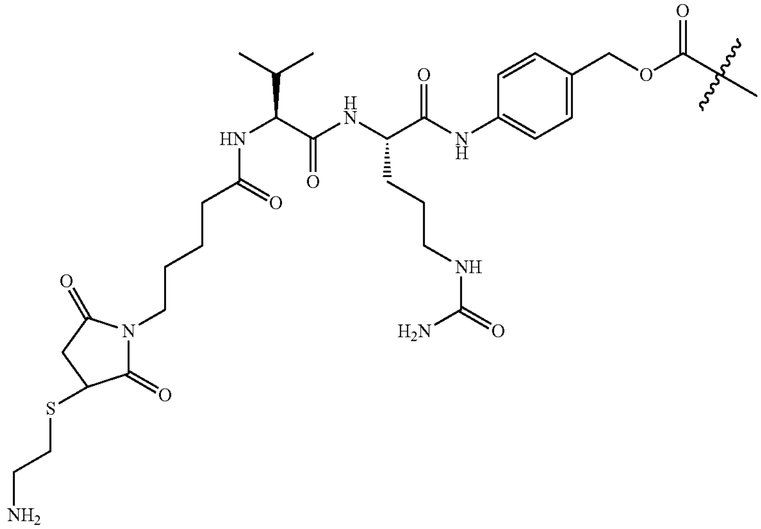 [SMILES: *C(=O)OCc1ccc(NC(=O)[C@H](CCCNC(N)=O)NC(=O)[C@@H](NC(=O)CCCCN2C(=O)CC(SCCN)C2=O)C(C)C)cc1] | ND |
| 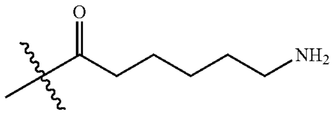 [SMILES: *C(=O)CCCCCN] | ND |

TABLE B-continued

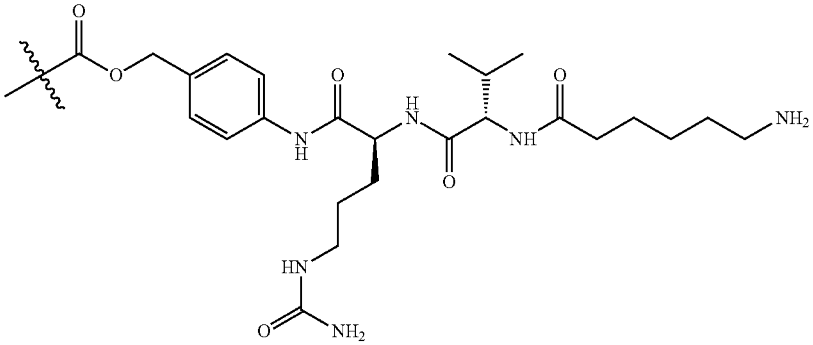 [SMILES: *C(=O)OCc1ccc(NC(=O)[C@H](CCCNC(N)=O)NC(=O)[C@@H](NC(=O)CCCCCN)C(C)C)cc1]

ND

Protein-Based Recognition Molecules (PBRMs)

The protein-based recognition molecule directs the drug-polymer carrier conjugates to specific tissues, cells, or locations in a cell. The protein-based recognition molecule can direct the modified polymer in culture or in a whole organism, or both. In each case, the protein-based recognition molecule has a ligand that is present on the cell surface of the targeted cell(s) to which it binds with an effective specificity, affinity and avidity. In some embodiments, the protein-based recognition molecule targets the modified polymer to tissues other than the liver. In other embodiments the protein-based recognition molecule targets the modified polymer to a specific tissue such as the liver, kidney, lung or pancreas. The protein-based recognition molecule can target the modified polymer to a target cell such as a cancer cell, such as a receptor expressed on a cell such as a cancer cell, a matrix tissue, or a protein associated with cancer such as tumor antigen. Alternatively, cells comprising the tumor vasculature may be targeted. Protein-based recognition molecules can direct the polymer to specific types of cells such as specific targeting to hepatocytes in the liver as opposed to Kupffer cells. In other cases, protein-based recognition molecules can direct the polymer to cells of the reticular endothelial or lymphatic system, or to professional phagocytic cells such as macrophages or eosinophils. (In such cases the polymer itself might also be an effective delivery system, without the need for specific targeting).

In still other embodiments, the protein based recognition molecule can target the modified polymer to a location within the cell, such as the nucleus, the cytoplasm, or the endosome, for example. In specific embodiments, the protein based recognition molecule can enhance cellular binding to receptors, or cytoplasmic transport to the nucleus and nuclear entry or release from endosomes or other intracellular vesicles.

In specific embodiments the protein based recognition molecules include antibodies, proteins and peptides or peptide mimics.

In a preferred embodiment, the protein based recognition molecule comprises a sulfhydryl group and the protein based recognition molecule is conjugated to the polymer-drug conjugate by forming a covalent bond via the sulfhydryl group and a functional group of the polymer.

Exemplary antibodies or antibodies derived from Fab, Fab2, scFv or camel antibody heavy-chain fragments specific to the cell surface markers, include, but are not limited to, 5T4, AOC3, ALK, AXL, C242, CA-125, CCL11, CCR 5, CD2, CD3, CD4, CD5, CD15, CA15-3, CD18, CD19, CA19-9, CD20, CD22, CD23, CD25, CD28, CD30, CD31, CD33, CD37, CD38, CD40, CD41, CD44, CD44 v6, CD51, CD52, CD54, CD56, CD62E, CD62P, CD62L, CD70, CD74, CD79-B, CD80, CD125, CD138, CD141, CD147, CD152, CD154, CD326, CEA, clumping factor, CTLA-4, CXCR2, EGFR (HER1), ErbB2, ErbB3, EpCAM, EPHA2, EPHB2, EPHB4, FGFR (i.e. FGFR1, FGFR2, FGFR3, FGFR4), FLT3, folate receptor, FAP, GD2, GD3, GPNMB, HGF, HER2, HER3, HMI.24, ICAM, ICOS-L, IGF-1 receptor, VEGFR1, EphA2, TRPV1, CFTR, gpNMB, CA9, Cripto, c-KIT, c-MET, ACE, APP, adrenergic receptor-beta2, Claudine 3, Mesothelin, MUC1, NaPi2b, NOTCH1, NOTCH2, NOTCH3, NOTCH4, RON, ROR1, PD-L1, PD-L2, B7-H3, B7-H4, IL-2 receptor, IL-4 receptor, IL-13 receptor, integrins (including $\alpha_4$, $\alpha_v\beta_3$, $\alpha_v\beta_5$, $\alpha_v\beta_6$, $\alpha_1\beta_4$, $\alpha_4\beta_1$, $\alpha_4\beta_7$, $\alpha_5\beta_1$, $\alpha_6\beta_4$, $\alpha_{IIb}\beta_3$ intergins), IFN-α, IFN-γ, IgE, IgE, IGF-1 receptor, IL-1, IL-12, IL-23, IL-13, IL-22, IL-4, IL-5, IL-6, interferon receptor, ITGB2 (CD18), LFA-1 (CD11a), L-selectin (CD62L), mucin, MUC1, myostatin, NCA-90, NGF, PDGFRα, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGF-β2, TGF-β, TNF-α, TRAIL-R1, TRAIL-R2, tumor antigen CTAA16.88, VEGF-A, VEGFR2, vimentin, and the like.

In one embodiment the antibodies or antibody derived from Fab, Fab2, scFv or camel antibody heavy-chain fragments specific to the cell surface markers include CA-125, C242, CD3, CD19, CD22, CD25, CD30, CD31, CD33, CD37, CD40, CD44, CD51, CD54, CD56, CD62E, CD62P, CD62L, CD70, CD138, CD141, CD326, CEA, CTLA-4, EGFR (HER1), ErbB2, ErbB3, FAP, folate receptor, IGF-1 receptor, GD3, GPNMB, HGF, HER2, VEGF-A, VEGFR2, VEGFR1, EphA2, EpCAM, 5T4, TAG-72, tenascin C, TRPV1, CFTR, gpNMB, CA9, Cripto, ACE, APP, PDGFR a, phosphatidylserine, prostatic carcinoma cells, adrenergic receptor-beta2, Claudine 3, mucin, MUC1, Mesothelin, IL-2 receptor, IL-4 receptor, IL-13 receptor and integrins (including $\alpha_v\beta_3$, $\alpha_v\beta_5$, $\alpha_v\beta_6$, $\alpha_1\beta_4$, $\alpha_4\beta_1$, $\alpha_5\beta_1$, $\alpha_6\beta_4$ intergins), tenascin C, TRAIL-R2 and vimentin.

Exemplary antibodies include 3F8, abagovomab, abciximab (REOPRO), adalimumab (HUMIRA), adecatumumab, afelimomab, afutuzumab, alacizumab, ALD518, alemtuzumab (CAMPATH), altumomab, amatuximab, anatumomab, anrukinzumab, apolizumab, arcitumomab (CEA-SCAN), aselizumab, atlizumab (tocilizumab, Actemra, RoActemra), atorolimumab, bapineuzumab, basiliximab (Simulect), bavituximab, bectumomab (LYMPHOSCAN), belimumab (BENLYSTA), benralizumab, bertilimumab, besilesomab (SCINITIMUN), bevacizumab (AVASTIN), biciromab (FIBRISCINT), bivatuzumab, blinatumomab, brentuximab, briakinumab, canakinumab (ILARIS), cantuzumab, capromab, catumaxomab (REMOVAB), CC49, cedelizumab, certolizumab, cetuximab (ERBITUX), citatuzumab, cixutumumab, clenoliximab, clivatuzumab, conatumumab, CR6261, dacetuzumab, daclizumab (ZENAPAX), daratumumab, denosumab (PROLIA), detumomab, dorlimomab, dorlixizumab, ecromeximab, eculizumab (SOLIRIS), edobacomab, edrecolomab (PANOREX), efalizumab (RAPTIVA), efungumab (MYCOGRAB), elotuzumab, elsilimomab, enlimomab, epitumomab, epratuzumab, erlizumab, ertumaxomab (REXOMUN), etaracizumab (ABEGRIN), exbivirumab, fanolesomab (NEUTROSPEC), faralimomab, farletuzumab, felvizumab, fezakinumab, figitumumab, fontolizumab (HuZAF), foravirumab, fresolimumab, galiximab, gantenerumab, gavilimomab, gemtuzumab girentuximab, glembatumumab, golimumab (SIMPONI), gomiliximab, ibalizumab, ibritumomab, igovomab (INDIMACIS-125), imciromab (MYOSCINT), infliximab (REMICADE), intetumumab, inolimomab, inotuzumab, ipilimumab, iratumumab, kelixkimab, labetuzumab (CEA-CIDE), lebrikizumab, lemalesomab, lerdelimumab, lexatumumab, libivirumab, lintuzumab, lucatumumab, lumiliximab, mapatumumab, maslimomab, matuzumab, mepolizumab (BOSATRIA), metelimumab, milatuzumab, minretumomab, mitumomab, morolimumab, motavizumab (NUMAX), muromonab-CD3 (ORTHOCLONE OKT3), nacolomab, naptumomab, natalizumab (TYSABRI), nebacumab, necitumumab, nerelimomab, nimotuzumab (THERACIM), nofetumomab, ocrelizumab, odulimomab, ofatumumab (ARZERRA), olaratumab, omalizumab (XOLAIR), ontecizumab, oportuzumab, oregovomab (OVAREX), otelixizumab, pagibaximab, palivizumab (SYNAGIS), panitumumab (VECTIBIX), panobacumab, pascolizumab, pemtumomab (THERAGYN), pertuzumab (OMNITARG), pexelizumab, pintumomab, priliximab, pritumumab, PRO 140, rafivirumab, ramucirumab, ranibizumab (LUCENTIS), raxibacumab, regavirumab, reslizumab, rilotumumab, rituximab (RITUXAN), robatumumab, rontalizumab, rovelizumab (LEUKARREST), ruplizumab (ANTOVA), satumomab pendetide, sevirumab, sibrotuzumab, sifalimumab, siltuximab, siplizumab, solanezumab, sonepcizumab, sontuzumab, stamulumab, sulesomab (LEUKOSCAN), tacatuzumab (AFP-CIDE), tetraxetan, tadocizumab, talizumab, tanezumab, taplitumomab paptox, tefibazumab (AUREXIS), telimomab, tenatumomab, teneliximab, teplizumab, TGN1412, ticilimumab (tremelimumab), tigatuzumab, TNX-650, tocilizumab (atlizumab, ACTEMRA), toralizumab, tositumomab (BEXXAR), trastuzumab (HERCEPTIN), tremelimumab, tucotuzumab, tuvirumab, urtoxazumab, ustekinumab (STELERA), vapaliximab, vedolizumab, veltuzumab, vepalimomab, visilizumab (NUVION), volociximab (HUMASPECT), votumumab, zalutumumab (HuMEX-EGFr), zanolimumab (HuMAX-CD4), ziralimumab and zolimomab.

In some embodiments the antibodies are directed to cell surface markers for 5T4, CA-125, CEA, CD3, CD19, CD20, CD22, CD30, CD33, CD40, CD44, CD51, CTLA-4, EpCAM, HER2, EGFR (HER1), FAP, folate receptor, HGF, integrin $\alpha_v\beta_3$, integrin $\alpha_5\beta_1$, IGF-1 receptor, GD3, GPNMB, mucin, MUC1, phosphatidylserine, prostatic carcinoma cells, PDGFR α, TAG-72, tenascin C, TRAIL-R2, VEGF-A and VEGFR2. In this embodiment the antibodies are abagovomab, adecatumumab, alacizumab, altumomab, anatumomab, arcitumomab, bavituximab, bevacizumab (AVASTIN), bivatuzumab, blinatumomab, brentuximab, cantuzumab, catumaxomab, capromab, cetuximab, citatuzumab, clivatuzumab, conatumumab, dacetuzumab, edrecolomab, epratuzumab, ertumaxomab, etaracizumab, farletuzumab, figitumumab, gemtuzumab, glembatumumab, ibritumomab, igovomab, intetumumab, inotuzumab, labetuzumab, lexatumumab, lintuzumab, lucatumumab, matuzumab, mitumomab, naptumomab estafenatox, necitumumab, oportuzumab, oregovomab, panitumumab, pemtumomab, pertuzumab, pritumumab, rituximab (RITUXAN), rilotumumab, robatumumab, satumomab, sibrotuzumab, taplitumomab, tenatumomab, tenatumomab, ticilimumab (tremelimumab), tigatuzumab, trastuzumab (HERCEPTIN), tositumomab, tremelimumab, tucotuzumab celmoleukin, volociximab and zalutumumab.

In specific embodiments the antibodies directed to cell surface markers for HER2 are pertuzumab or trastuzumab and for EGFR (HER1) the antibody is cetuximab or panitumumab; and for CD20 the antibody is arituximab and for VEGF-A is bevacizumab and for CD-22 the antibody is epratuzumab or veltuzumab and for CEA the antibody is labetuzumab.

Exemplary peptides or peptide mimics include integrin targeting peptides (RGD peptides), LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides, ApoA protein peptides, somatostatin receptor targeting peptides, chlorotoxin derived peptides, and bombesin.

In specific embodiments the peptides or peptide mimics are LHRH receptor targeting peptides and ErbB2 (HER2) receptor targeting peptides Exemplary proteins comprise insulin, transferrin, fibrinogen-gamma fragment, thrombospondin, claudin, apolipoprotein E, Affibody molecules such as, for example, ABY-025, Ankyrin repeat proteins, ankyrin-like repeats proteins and synthetic peptides.

In some embodiments of the invention the protein-polymer-drug conjugates comprise broad spectrum cytotoxins in combination with cell surface markers for HER2 such as pertuzumab or trastuzumab; for EGFR such as cetuximab and panitumumab; for CEA such as labetuzumab; for CD20 such as rituximab; for VEGF-A such as bevacizumab; or for CD-22 such as epratuzumab or veltuzumab.

In other embodiments of the invention the protein-drug-polymer conjugates or protein-polymer conjugates used in the invention comprise combinations of two or more protein based recognition molecules, such as, for example, combination of bispecific antibodies directed to the EGF receptor (EGFR) on tumor cells and to CD3 and CD28 on T cells; combination of antibodies or antibody derived from Fab, Fab2, scFv or camel antibody heavy-chain fragments and peptides or peptide mimetics; combination of antibodies or antibody derived from Fab, Fab2, scFv or camel antibody heavy-chain fragments and proteins; combination of two bispecific antibodies such as CD3×CD19 plus CD28×CD22 bispecific antibodies.

In other embodiments of the invention the protein-drug-polymer conjugates or protein-polymer conjugates used in the invention comprise protein based recognition molecules are antibodies against antigens, such as, for example, B7-H4, B7-H3, CA125, CD33, CXCR2, EGFR, FGFR1, FGFR2, FGFR3, FGFR4, HER2, NaPi2b, c-Met, MUC-1, NOTCH1, NOTCH2, NOTCH3, NOTCH4, and PD-L1 and 5T4.

Conjugates or Polymeric Scaffolds

Conjugates disclosed herein comprise one or more occurrences of D, where D is a therapeutic agent, e.g., a drug, wherein the one or more occurrences of D may be the same or different.

In certain other embodiments, one or more occurrences of PBRM is attached to the polymeric carrier, wherein the one or more occurrences of PBRM may be the same or different. In certain other embodiments, one or more polymer carriers that contains one or more occurrences of D are connected to a PBRM (e.g., an antibody).

As discussed more generally above, in certain embodiments, each polymeric carrier independently, has about 0.1% to about 25% monomers comprising a D, more preferably about 0.5% to about 20%, more preferably about 1% to about 15%, and even more preferably about 2% to about 10%. For example, the polymeric carrier is PHF having a molecular weight of about 2 kDa to about 40 kDa and has about 0.3% to about 15% monomers comprising auristatin F, more preferably about 2%-12%, more preferably about 5%-10%.

In certain embodiments, the conjugate of this invention is of Formula (Id):

between D and the carbonyl group denotes direct or indirect attachment of D to the carbonyl group, $m_1$ is an integer from 1 to about 140, and $m_7$ is an integer from 1 to about 40, wherein the sum of $m_1$ and $m_7$ is $m_6$ (i.e., 2 to about 180).

In certain embodiment, D is (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j)

(Id)

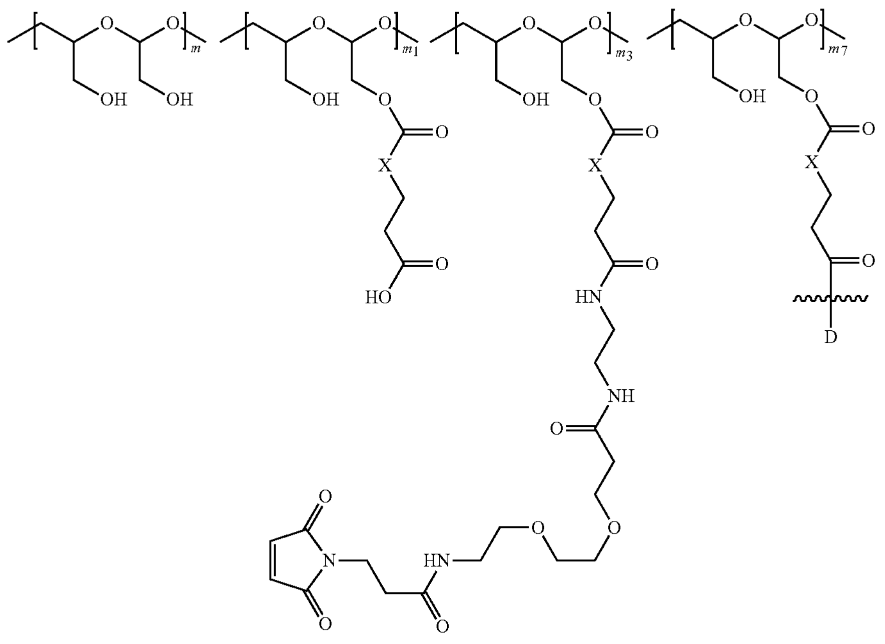

wherein:

the PHF has a molecular weight ranging from about 2 kDa to about 40 kDa;

X is $CH_2$, O, or NH;

each occurrence of D independently is a therapeutic agent having a molecular weight of ≤5 kDa, and the a DNA binding drug; (k) a kinase inhibitor; (1) a MEK inhibitor; (m) a KSP inhibitor; (n) a PI3 kinase inhibitor; (o) a topoisomerase inhibitor; or analogues thereof.

In certain embodiment, D is (a) an auristatin compound; (b) a calicheamicin compound; (c) a duocarmycin compound; (d) SN38, (e) pyrrolobenzodiazepine; (f) a vinca compound; or analogues thereof.

For example, the auristatin compound is auristatin, Dolastatin, monomethylauristatin E (MMAE), monomethylauristatin F (MMAF), auristatin F, AF HPA, phenylenediamine (AFP).

For example, the duocarmycin or analogs thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

The polymer-drug conjugate of Formula (Id) is useful for conjugation with a PBRM that has a molecular weight of 40 kDa or greater.

For example, for conjugating a PBRM having a molecular weight of 40 kDa or greater (e.g., 60 kDa or greater, 80 kDa or greater, 100 kDa or greater, 120 kDa or greater, 140 kDa or greater, 160 kDa or greater, or 180 kDa or greater, or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa or 140-150 kDa), the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example, for conjugating a PBRM having a molecular weight of 40 kDa to 200 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa).

For example, for conjugating a PBRM having a molecular weight of 40 kDa to 80 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

PBRMs in this molecular weight range include, but are not limited to, for example, antibody fragments, such as, for example, Fabs.

For example, for conjugating a PBRM having a molecular weight of 60 kDa to 120 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

PBRMs in this molecular weight range include, but are not limited to, for example, camelids, Fab2, scFvFc, and the like.

For example, for conjugating a PBRM having a molecular weight of 140 kDa to 180 kDa or of 140 kDa to 150 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

PBRMs in this molecular weight range include, but are not limited to, for example, full length antibodies, such as, IgG, IgM.

In certain embodiments, the polymer drug conjugate (Id) when conjugated to a PBRM is of Formula (Ie):

(Ie)

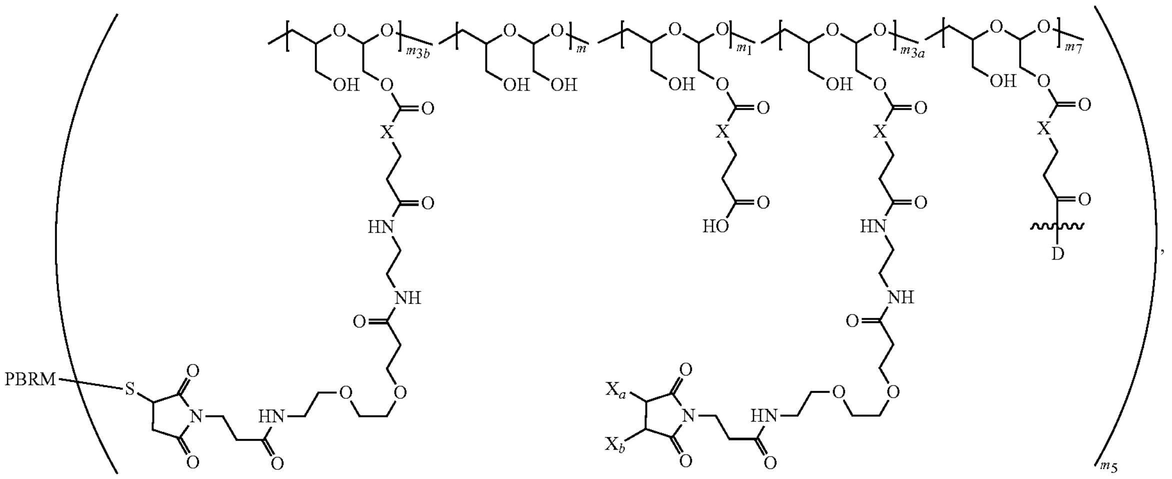

wherein, the PHF has a molecular weight ranging from about 2 kDa to about 40 kDa;

$m_1$ is an integer from 1 to about 140, $m_7$ is an integer from 1 to about 40, wherein the sum of $m_1$ and $m_7$ is about 2 to about 180, m is an integer from 1 to about 300, $m_{3a}$ is an integer from 0 to about 17, $m_{3b}$ is an integer from 1 to about 8, wherein the sum of $m_{3a}$ and $m_{3b}$ is between 1 and 18, the sum of m, $m_1$, $m_7$, $m_{3a}$, and $m_{3b}$ ranges from about 15 to about 300; and $m_5$ is an integer from 1 to about 10.

In certain embodiments, the protein-polymer drug conjugate of this invention is of Formula (Ib) as described herein:

(Ib)

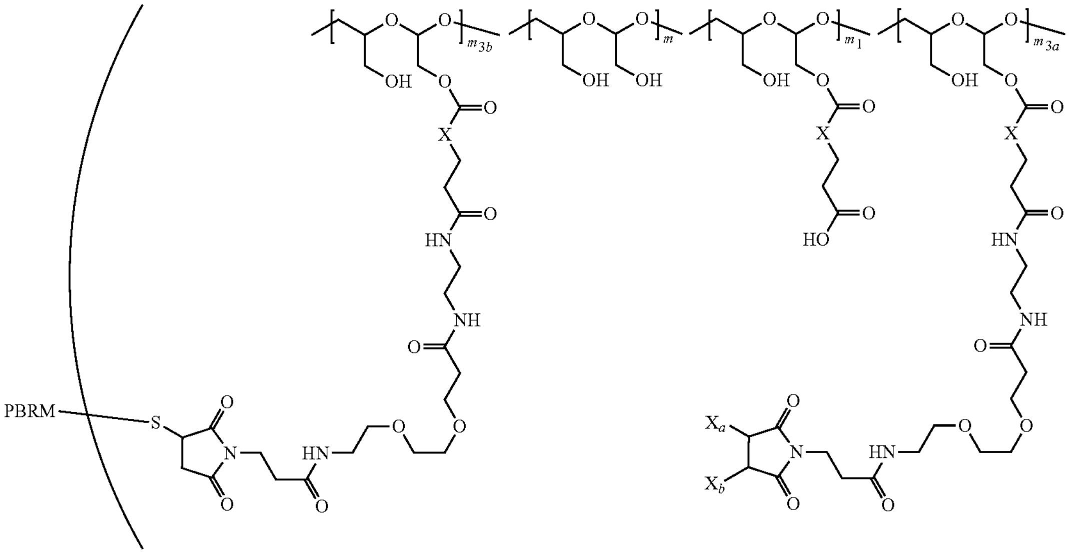

-continued

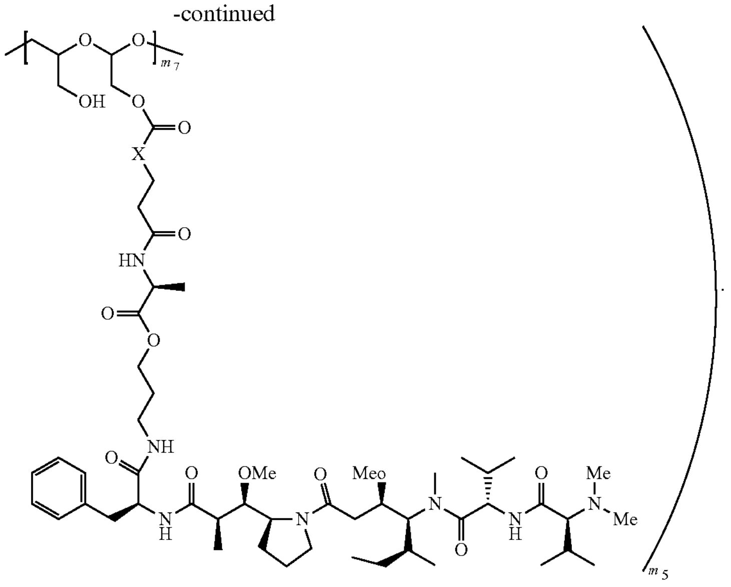

wherein:

the PBRM has a molecular weight of 40 kDa or greater, one of $X_a$ and $X_b$ is H and the other is a water-soluble maleimido blocking moiety, or $X_a$ and $X_b$, together with the carbon atoms to which they are attached for a carbon-carbon double bond, $m_{3a}$ is an integer from 0 to about 17, $m_{3b}$ is an integer from 1 to about 8, wherein the sum of $m_{3a}$ and $m_{3b}$ is $m_3$, the sum of m, $m_1$, $m_2$, $m_{3a}$, and $m_{3b}$ ranges from about 15 to about 300, and $m_5$ is an integer from 1 to about 10.

The conjugate of Formula (Ie) or (Ib), may have one or more of the following features.

For example, the PBRM is trastuzumab or a biosimilar of trastuzumab.

For example, the total number of sulfide bonds formed between the PHF and the PBRM (or total number of attachment points) is 10 or less.

For example, the ratio between $m_2$ and $m_{3b}$ is greater than 1:1 and less than or equal to 10:1.

For example, the ratio between $m_2$ and $m_{3b}$ is about 9:1, 8:1, 7:1, 6:1, 5:1, 4:1, 3:1, or 2:1.

For example, the ratio between $m_2$ and $m_{3b}$ is between 2:1 and 8:1.

For example, the ratio between $m_2$ and $m_{3b}$ is about 8:1, 7:1, 6:1, 5:1, 4:1, 3:1, or 2:1.

For example, the ratio between $m_2$ and $m_{3b}$ is between 2:1 and 4:1.

For example, the ratio between $m_2$ and $m_{3b}$ is about 4:1, 3:1, or 2:1.

For example, the ratio between $m_2$ and $m_{3b}$ is between 3:1 and 5:1.

For example, the ratio between $m_2$ and $m_{3b}$ is about 3:1, 4:1, or 5:1.

For example, when the PHF in Formula (Ib) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and $m_5$ is an integer from 2 to about 8.

For example, when the PHF in Formula (Ib) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 10, and $m_5$ is an integer from 2 to about 8 (e.g., an integer from 2 to about 6 or an integer from 2 to about 4).

For example, when the PHF in Formula (Ib) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5, and $m_5$ is an integer from 2 to about 8 (e.g., an integer from 2 to about 6 or an integer from 2 to about 4).

For example, the water-soluble maleimido blocking moieties are moieties that can be covalently attached to one of the two olefin carbon atoms upon reaction of the maleimido group with a thiol-containing compound of Formula (II):

$$R_{90}—(CH_2)_d—SH \quad (II)$$

wherein:

$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

For example, the water-soluble maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

For example, the water-soluble maleimido blocking group is —S—$(CH_2)_d$—$R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

For example, the water-soluble maleimido blocking group is $—S—CH_2—CH(NH_2)COOH$.

In certain embodiments, in the polymer drug conjugate of Formula (Ib), the PBRM is trastuzumab or a biosimilar of trastuzumab.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40, (e.g., about 1-20 or about 2-15 or about 3-10). This scaffold can be used, for example, for conjugating a PBRM having a molecular weight of 40 kDa or greater (e.g., 60 kDa or greater; 80 kDa or greater; or 100 kDa or greater; 120 kDa or greater; 140 kDa or greater; 160 kDa or greater 180 kDa or greater, or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa, or 140-150 kDa). In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4, between about 1:2 and about 1:3, between about 1:3 and about 1:4, or between about 1:3 and about 1:5.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40, (e.g., about 1-20 or about 2-15 or about 3-10). This scaffold can be used, for example, for conjugating a PBRM having a molecular weight of 140 kDa to 180 kDa or of 140 kDa to 150 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4, between about 1:2 and about 1:3, between about 1:3 and about 1:4, or between about 1:3 and about 1:5.

PBRMs in this molecular weight range include, but are not limited to, for example, full length antibodies, such as, IgG, IgM.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40, (e.g., about 1-20 or about 2-15 or about 3-10). This scaffold can be used, for example, for conjugating a PBRM having a molecular weight of 60 kDa to 120 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4, between about 1:2 and about 1:3, between about 1:3 and about 1:4, or between about 1:3 and about 1:5.

PBRMs in this molecular weight range include, but are not limited to, for example, antibody fragments such as, for example Fab2, scFcFv and camelids.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40, (e.g., about 1-20 or about 2-15 or about 3-10). This scaffold can be used, for example, for conjugating a PBRM having a molecular weight of 40 kDa to 80 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:6, between about 1:2 and about 1:5, between about 1:2 and about 1:4, between about 1:2 and about 1:3, between about 1:3 and about 1:4, or between about 1:3 and about 1:5.

PBRMs in this molecular weight range include, but are not limited to, for example, antibody fragments, such as, Fabs.

In another aspect, the invention features a polymeric scaffold useful to conjugate with both a protein based recognition-molecule (PBRM) and a therapeutic agent (D). The D-free scaffold comprises a polymeric carrier, one or more linkers connected to the polymeric carrier which is suitable for connecting a PBRM to the polymeric carrier, and one or more linkers suitable for connecting a drug (D) to the polymeric carrier.

In certain embodiments, the conjugates are formed in several steps. These steps include (1) modifying a polymer so that it contains a functional group that can react with a functional group of the drug or its derivative; (2) reacting the modified polymer with the drug or its derivative so that the drug is linked to the polymer; (3) modifying the polymer-drug conjugate so that the polymer contains a functional group that can react with a functional group of the PBRM or its derivative; and (4) reacting the modified polymer-drug conjugate with the PBRM or its derivative to form the conjugate of this invention. Step (3) may be omitted if the modified polymer produced by step (1) contains a functional group that can react with a functional group of the PBRM or its derivative.

In another embodiment the conjugates are formed in several steps: (1) modifying a polymer so that it contains a functional group that can react with a functional group of a first drug or its derivative; (2) reacting the modified polymer with the first drug or its derivative so that the first drug is linked to the polymer; (3) modifying the polymer-drug conjugate so that it contains a different functional group that can react with a functional group of a second drug or its derivative (4) reacting the modified polymer-drug conjugate with the second drug or its derivative so that the second drug is linked to the polymer-drug conjugate; (5) modifying the polymer-drug conjugate containing 2 different drugs so that the polymer contains a functional group that can react with a functional group of the PBRM or its derivative; and (6) reacting the modified polymer-drug conjugate of step (5) with the PBRM or its derivative to form the conjugate of this invention. Steps (5) and (6) may be repeated if 2 different PBRM or its derivatives are to be conjugated to form a polymer-drug conjugate comprising two different drugs and two different PBRMs.

In yet another embodiment, the conjugates are formed in several steps. These steps include (1) modifying a polymer so that it contains a functional group that can react with a functional group of the drug or its derivative; (2) further modifying the polymer so that it also contains a functional group that can react with a functional group of the PBRM or its derivative; (3) reacting the modified polymer with the drug or its derivative so that the drug is linked to the polymer; and (4) reacting the modified polymer-drug conjugate with the PBRM or its derivative to form the conjugate of this invention. The sequence of steps (1) and (2) or that of steps (3) and (4) can be reversed. Further either step (1) or (2) may be omitted if the modified polymer contains a functional group that can react with both a functional group of the drug or its derivatives and a functional group of the PBRM or its derivative.

In another embodiment the conjugates are formed in several steps: (1) modifying a polymer so that it contains a functional group that can react with a functional group of a first drug or its derivative; (2) further modifying a polymer so that it contains a functional group that can react with a functional group of the PBRM or its derivative; (3) reacting the modified polymer with the first drug or its derivative so that the first drug is linked to the polymer; (4) modifying the polymer-drug conjugate so that it contains a different functional group that can react with a functional group of a second drug or its derivative (5) reacting the modified polymer-drug conjugate with the second drug or its derivative so that the second drug is linked to the polymer-drug conjugate; (6) reacting the modified polymer-drug conjugate containing 2 different drugs so that the polymer with the PBRM or its derivative to form the conjugate of this invention. Step (6) may be repeated if 2 different PBRM or its derivatives are to be conjugated to form a polymer-drug conjugate comprising two different drugs and two different PBRMs. Step (4) may be carried out after step (1) so that the modified polymer contains two different functional groups that can react with two different drugs or their derivatives. In this embodiment, the modified polymer containing two different functional group that can react with two different drugs or their derivatives can be further modified so that it contains a functional group that can react with a functional group of the PBRM or its derivative; prior to the reaction of the modified polymer with either the two different drugs (step (3) and step (5) or PBRM (step (6).

The biodegradable biocompatible conjugates disclosed herein can be prepared to meet desired requirements of biodegradability and hydrophilicity. For example, under physiological conditions, a balance between biodegradability and stability can be reached. For instance, it is known that molecules with molecular weights beyond a certain threshold (generally, above 40-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. One skilled on the art can select other suitable methods for studying various fragments of the degraded conjugates of this invention.

In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells. Accordingly, in certain embodiments, the conjugates disclosed herein are expected to be biodegradable, in particular upon uptake by cells, and relatively "inert" in relation to biological systems. The products of carrier degradation are preferably uncharged and do not significantly shift the pH of the environment. It is proposed that the abundance of alcohol groups may provide low rate of polymer recognition by cell receptors, particularly of phagocytes. The polymer backbones disclosed herein generally contain few, if any, antigenic determinants (characteristic, for example, for some polysaccharides and polypeptides) and generally do not comprise rigid structures capable of engaging in "key-and-lock" type interactions in vivo unless the latter are desirable. Thus, the soluble, cross-linked and solid conjugates of this invention are predicted to have low toxicity and bioadhesivity, which makes them suitable for several biomedical applications.

In certain embodiments of the present invention, the biodegradable biocompatible conjugates can form linear or branched structures. For example, the biodegradable biocompatible polyal conjugates disclosed herein can be chiral (optically active). Optionally, the biodegradable biocompatible polyal conjugates disclosed herein can be scalemic.

In certain embodiments, the conjugates disclosed herein are water-soluble. In certain embodiments, the conjugates disclosed herein are water-insoluble. In certain embodiments, the inventive conjugate is in a solid form. In certain embodiments, the conjugates disclosed herein are colloids. In certain embodiments, the conjugates disclosed herein are in particle form. In certain embodiments, the conjugates disclosed herein are in gel form.

This invention also features a polymeric scaffold useful for conjugating with a PBRM to form a polymer-drug-PBRM conjugate described herein. The scaffold comprises a polymeric carrier of Formula (Ia) useful to conjugate with a protein based recognition-molecule (PBRM) that has a molecular weight of 40 kDa or greater:

(Ia)

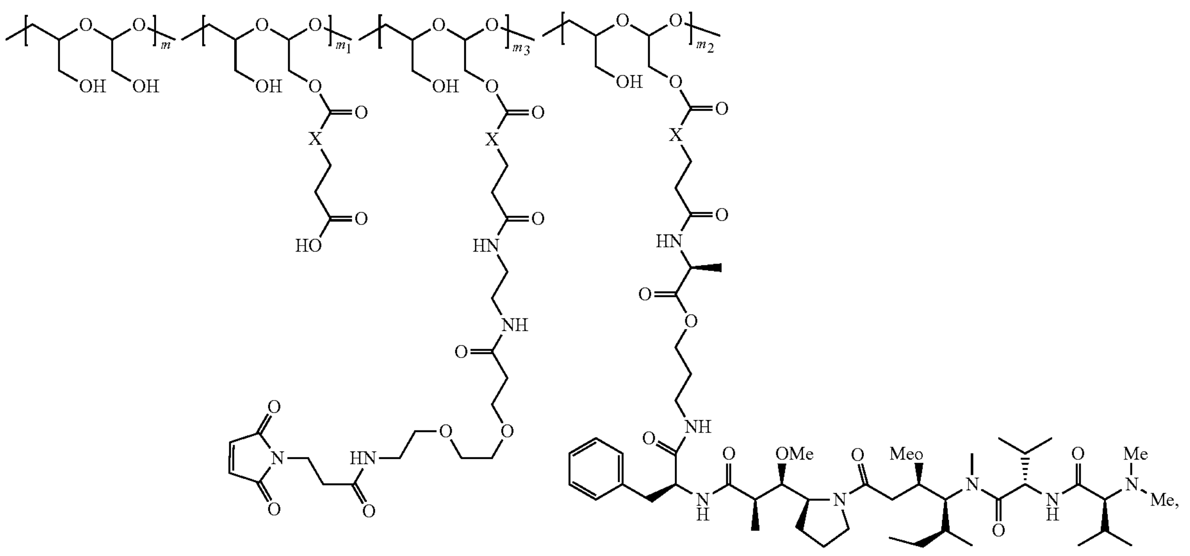

the scaffold comprises poly(1-hydroxymethylethylene hydroxymethyl-formal) (PHF) having a molecular weight ranging from about 2 kDa to about 40 kDa;

X is $CH_2$, O, or NH;

m is an integer from 1 to about 300, $m_1$ is an integer from 1 to about 140, $m_2$ is an integer from 1 to about 40, $m_3$ is an integer from 1 to about 18, and the sum of m, $m_1$, $m_2$ and $m_3$ ranges from about 15 to about 300.

For example, for conjugating a PBRM having a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa or 140-150 kDa), the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa).

For example, for conjugating a PBRM having a molecular weight of 40 kDa to 200 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa).

For example, for conjugating a PBRM having a molecular weight of 40 kDa to 80 kDa, the polymeric carrier of the scaffold disclosed herein is a polyacetal, e.g., a PHF having a molecular weight (i.e., MW of the unmodified PHF) (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

PBRMs in this molecular weight range include, but are not limited to, for example, antibody fragments, such as, for example, Fabs.

For example, for conjugating a PBRM having a molecular weight of 60 kDa to 120 kDa, the polymeric carrier of the scaffold disclosed herein is a polyacetal, e.g., a PHF having a molecular weight (i.e., MW of the unmodified PHF) ranging from about 5 kDa to about 40 kDa (e.g., about 5-30 kDa, about 5-20 kDa or about 5-15 kDa or about 5-10 kDa). For example the PHF has a molecular weight of about 10 kDa, 20 kDa, 30 kDa or 40 kDa.

PBRMs in this molecular weight range include, but are not limited to, for example, camelids, Fab2, scFcFv, and the like.

For example, for conjugating a PBRM having a molecular weight of 140 kDa to 180 kDa or of 140 kDa to 150 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

PBRMs in this molecular weight range include, but are not limited to, for example, full length antibodies, such as, IgG, IgM.

For example, when the PHF in Formula (Ia) has a molecular weight ranging from about 2 kDa to about 40 kDa (i.e., the sum of m, $m_1$, $m_2$, and $m_3$ ranging from about 1 to about 300), $m_2$ is an integer from 1 to about 40, $m_3$ is an integer from 1 to about 18, and/or $m_1$ is an integer from 1 to about 140 (e.g., $m_1$ being about 1-90).

For example, when the PHF in Formula (Ia) has a molecular weight ranging from about 2 kDa to about 20 kDa (i.e., the sum of m, $m_1$, $m_2$, and $m_3$ ranging from about 1 to about 150), $m_2$ is an integer from 1 to about 20, $m_3$ is an integer from 1 to about 10, and/or $m_1$ is an integer from 1 to about 70 (e.g., $m_1$ being about 4-45).

For example, when the PHF in Formula (Ia) has a molecular weight ranging from about 3 kDa to about 15 kDa (i.e., the sum of m, $m_1$, $m_2$, and $m_3$ ranging from about 1 to about 110), $m_2$ is an integer from 2 to about 15, $m_3$ is an integer from 1 to about 8, and/or $m_1$ is an integer from 2 to about 50 (e.g., $m_1$ being about 4-30).

For example, when the PHF in Formula (Ia) has a molecular weight ranging from about 5 kDa to about 10 kDa (i.e., the sum of m, $m_1$, $m_2$, and $m_3$ ranging from about 1 to about 75), $m_2$ is an integer from 2 to about 10, $m_3$ is an integer from 1 to about 5, and/or $m_1$ is an integer from 2 to about 35 (e.g., $m_1$ being about 10-25).

For example, one or more drug-carrying polymeric carriers are connected to one PBRM. For example, the scaffold (e.g., a PBRM-polymer-drug conjugate) comprises a PBRM with a molecular weight of 40 kDa or greater and one or more D-carrying polymeric carriers connected to the PBRM.

For example, the scaffold further comprises a PBRM connected to the polymeric carrier via the maleimido group.

The invention also provides for polymeric scaffolds of Formula (Ic) of molecular weight ranging from about 2 kDa to about 40 kDa;

(Ic)

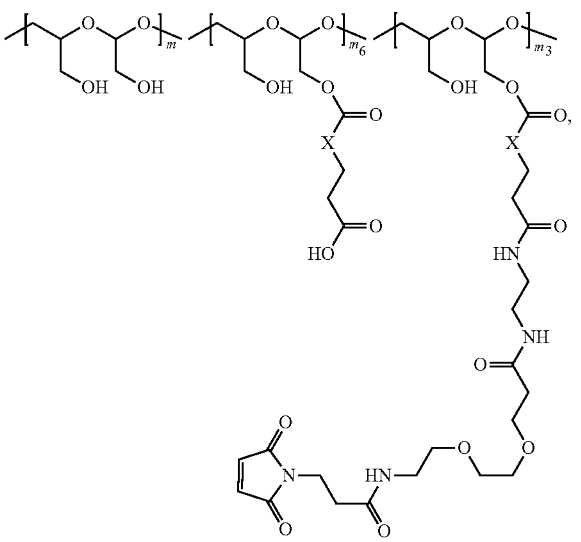

wherein:

X is $CH_2$, O, or NH;

m is an integer from 1 to about 300, $m_6$ is an integer from 2 to about 180, $m_3$ is an integer from 1 to about 18, and the sum of m, $m_6$, and $m_3$ ranges from about 15 to about 300.

For example, when the PHF in Formula (Ic) has a molecular weight ranging from about 2 kDa to about 20 kDa (i.e., the sum of m, $m_6$, and $m_3$ ranging from about 15 to about 150), $m_3$ is an integer from 1 to about 9, and/or $m_6$ is an integer from 2 to about 90 (e.g., $m_6$ being about 6-60).

For example, when the PHF in Formula (Ic) has a molecular weight ranging from about 3 kDa to about 15 kDa (i.e., the sum of m, $m_6$, and $m_3$ ranging from about 20 to about 110), $m_3$ is an integer from 1 to about 8, and/or $m_6$ is an integer from 4 to about 65 (e.g., $m_6$ being about 6-45).

For example, when the PHF in Formula (Ic) has a molecular weight ranging from about 5 kDa to about 10 kDa, the sum of m, $m_6$ and $m_3$ ranges from about 40 to about 75, $m_6$ is an integer from about 8 to about 45, and $m_3$ is an integer from 1 to about 5.

In some embodiments, the polymeric scaffold (e.g., a polyacetal polymer such as PHF) is conjugated with PBRMs by utilizing cysteine-based bioconjugation strategy. See, e.g., WO2010100430 and U.S. Pat. No. 7,595,292, the contents of which are hereby incorporated by reference in their entireties. In one embodiment, the polymeric scaffold (e.g., a polyacetal polymer such as PHF) conjugates with a PBRM (e.g., an antibody) via cysteines in the antibody hinge region. Without wishing to be bound by the theory, the resulting conjugate is stabilized through the formation of inter-chain bridge structures.

Accordingly, the invention also relates to a polymeric scaffold (e.g., a polyal polymer) comprising at least two moieties connected to the polymeric scaffold, in which each moiety is capable of conjugation to a thiol group from an amino acid (e.g., cysteine) in a PBRM so as to form a protein-polymer conjugate. In one embodiment, the at least two moieties connected to the polymeric scaffold are maleimide groups.

In embodiments, one or more free thiol groups of a PBRM are produced by reducing a protein. The one or more free thiol groups of the PBRM then react with the at least two moieties contained in the polymer scaffold that are capable of conjugation to a thiol group from an amino acid so as to conjugate the PBRM with the polymer scaffold. In one embodiment, the at least two moieties connected to the polymeric scaffold are maleimide groups.

In embodiments, the free thiol groups of the PBRM that are used for the conjugation are derived from a disulfide bridge of a native protein or a disulfide bridge of a protein complex consisting of two or more protein chains connected by the disulfide bridge. A disulfide bridge may be intrachain or interchain bridge. Alternatively, the free thiol groups of the PBRM are from cysteines or the unpaired thiol groups of the native protein that are not involved in inter or intra disulfide bridge formation.

Disulfide bonds can be reduced, for example, with dithiothreitol, mercaptoethanol, tris-carboxyethylphosphine, dehydroascorbic acid, copper sulfate, using conventional methods. A protein can contain one or more disulfide bridges. Reduction to give free thiol groups can be controlled to reduce one or more specific disulfide bridges in a protein. Depending on the extent of disulfide reduction and the stoichiometry of the moieties on the polymeric scaffold polymeric, it is possible to conjugate one or more polymer scaffolds to the protein. Immobilized reducing agents may be used if it is desired to reduce less than the total number of disulfides, as can partial reduction using different reaction conditions or the addition of denaturants.

Advantages of conjugating a polymer to a protein via a thiol include, but are not limited to optimized efficacy, improved dose to dose consistency and homogeneity (as the number of conjugated polymer molecules per protein is the substantially the same for each protein molecule), specific conjugation directed to a specific residue or residues on each protein, and easier purification. Also, the protein-polymer conjugates via the thiol conjugation exhibit substantially improved half-life, mean residence time, and/or clearance rate in circulation as compared to the unconjugated protein.

In some embodiments, the drug-polymer-PBRM conjugates, drug-polymer conjugates, drug carrying-polymeric scaffolds, or PBRM-carrying polymer scaffolds described herein each typically have a polydispersity index (PDI) of ≤1.5, e.g., <1.4, <1.3, <1.2 or <1.1.

PBRM-polymer-drug conjugates, drug carrying-polymeric scaffolds, or PBRM-carrying polymer scaffolds can be purified (i.e., removal of residual unreacted drug, PBRM, or polymeric starting materials) by extensive diafiltration. If necessary, additional purification by size exclusion chromatography can be conducted to remove any aggregated PBRM-polymer-drug conjugates. In general, the PBRMpolymer-drug conjugates as purified typically contain less than 5% (e.g., <2% w/w) aggregated PBRM-polymer-drug conjugates as determined by SEC; less than 0.5% (e.g., <0.1% w/w) free (unconjugated) drug as determined by RP-HPLC; less than 1% polymer-drug conjugate as determined by SEC and less than 2% (e.g., <1% w/w) unconjugated PBRM as determined by HIC-HPLC.

Tables C and D below provide examples of the drug-carrying polymeric scaffolds and the polymer-drug-protein conjugates disclosed herein respectively. In Table D, $m_5$ in the chemical structures is defined as in Formula (Ib) described herein.

TABLE C
| Ref # | Drug: Polymer Ratio | Structure |
|---|---|---|
| Ex 3 | 6:1 | 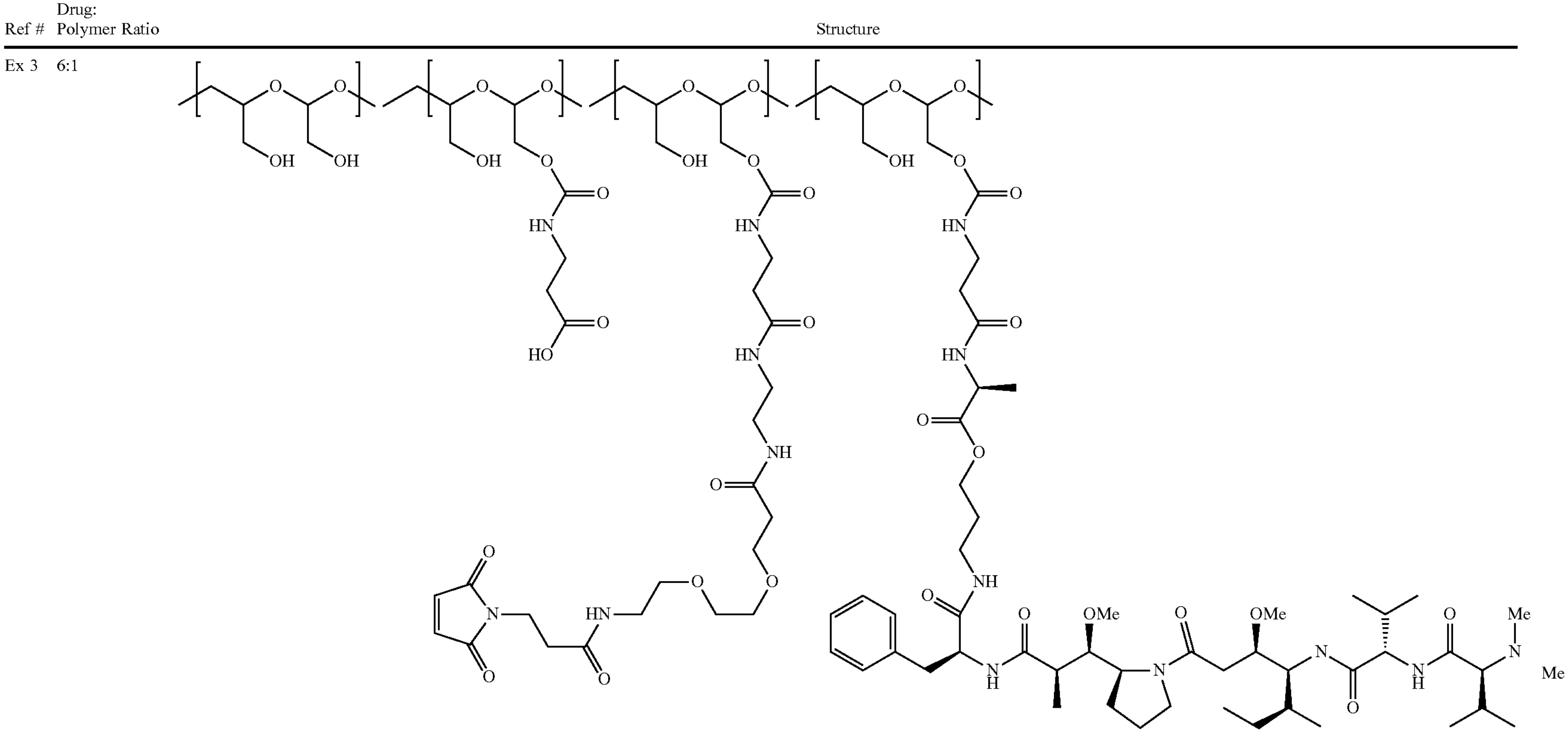 |

TABLE C-continued
| Ref # | Drug: Polymer Ratio | Structure |
|---|---|---|
| Ex 5 | 6:1 | 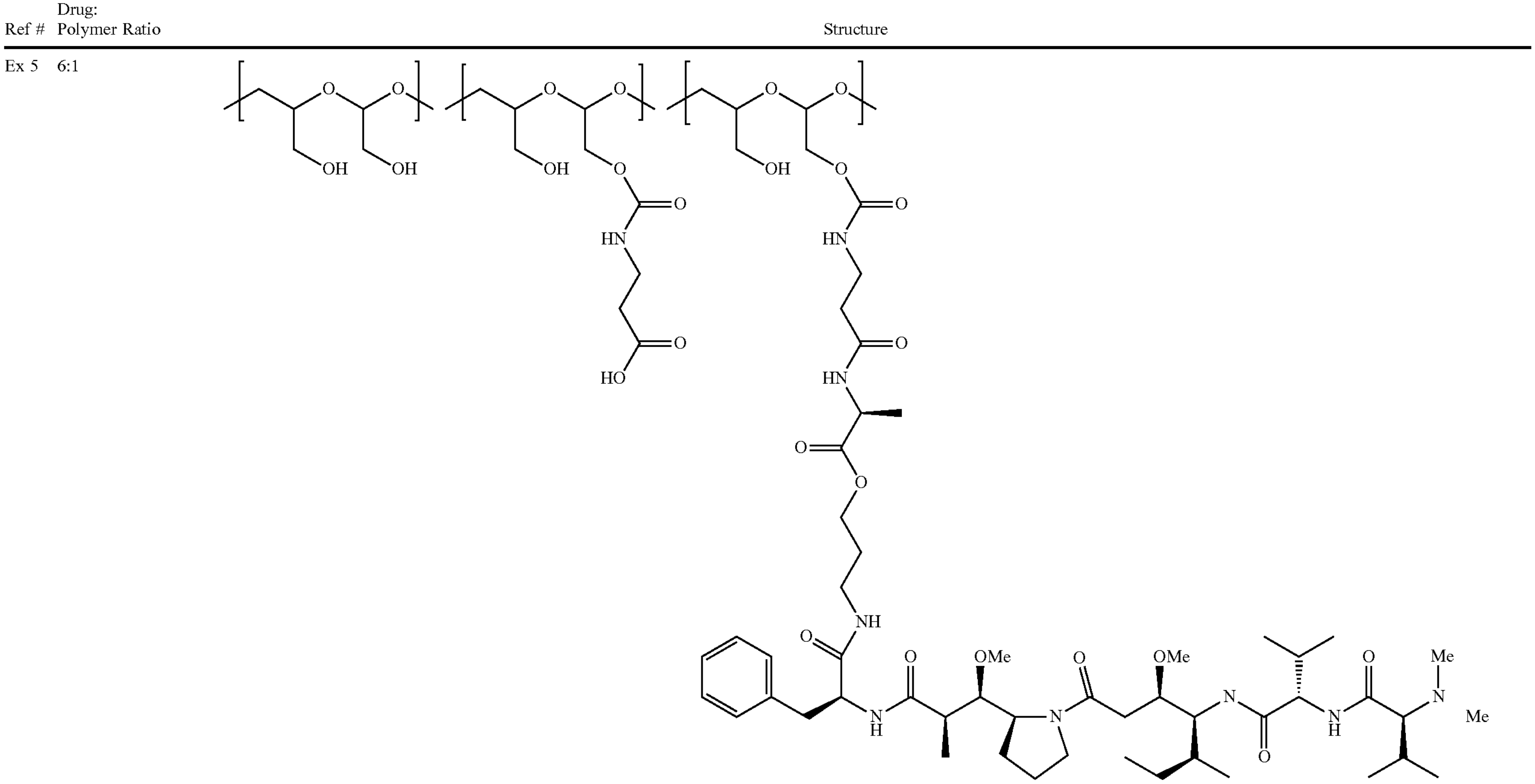 |

TABLE C-continued
| Ref # | Drug: Polymer Ratio | Structure |
|---|---|---|
| Ex 6 | 6:1 | 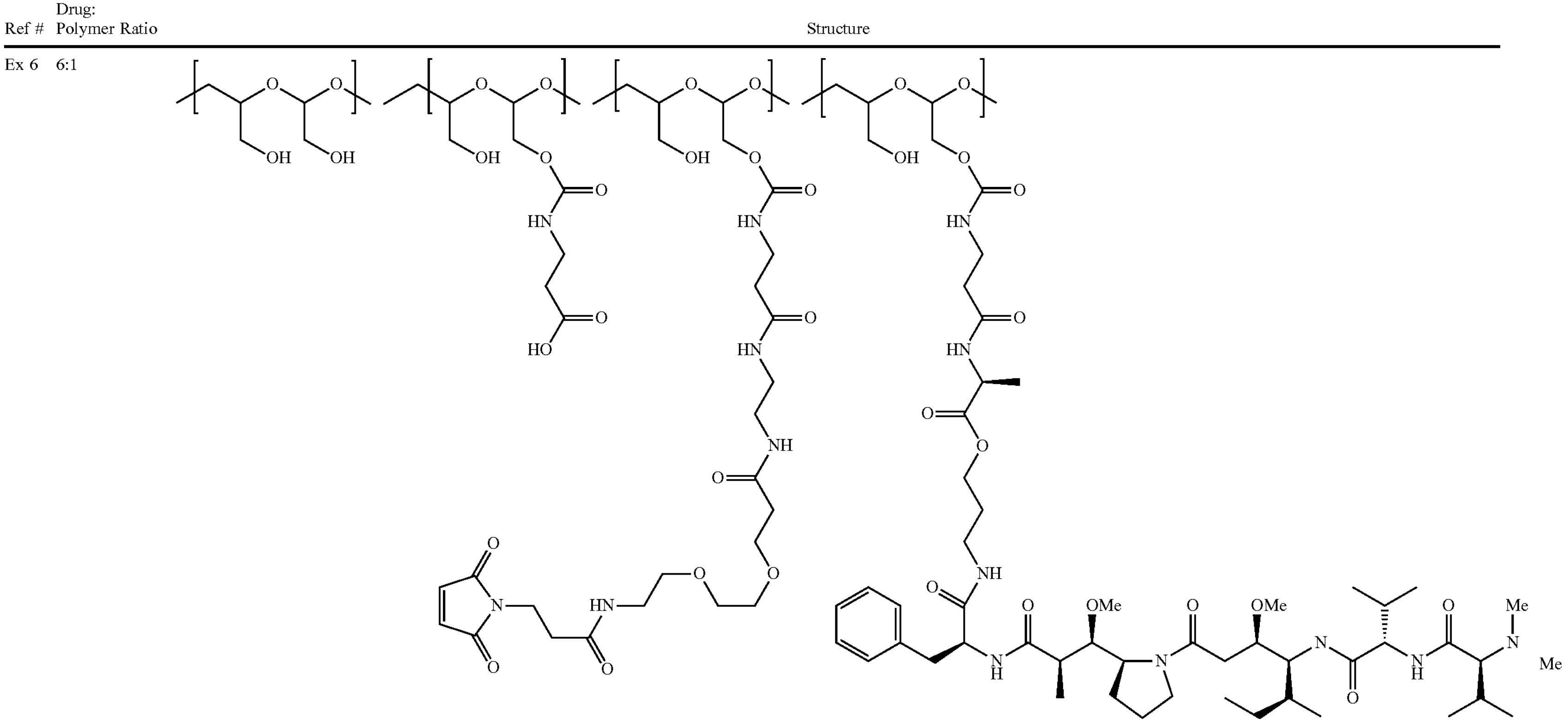 |

TABLE C-continued
| Ref # | Drug: Polymer Ratio | Structure |
| --- | --- | --- |
| Ex 12 | 4.5:1 | 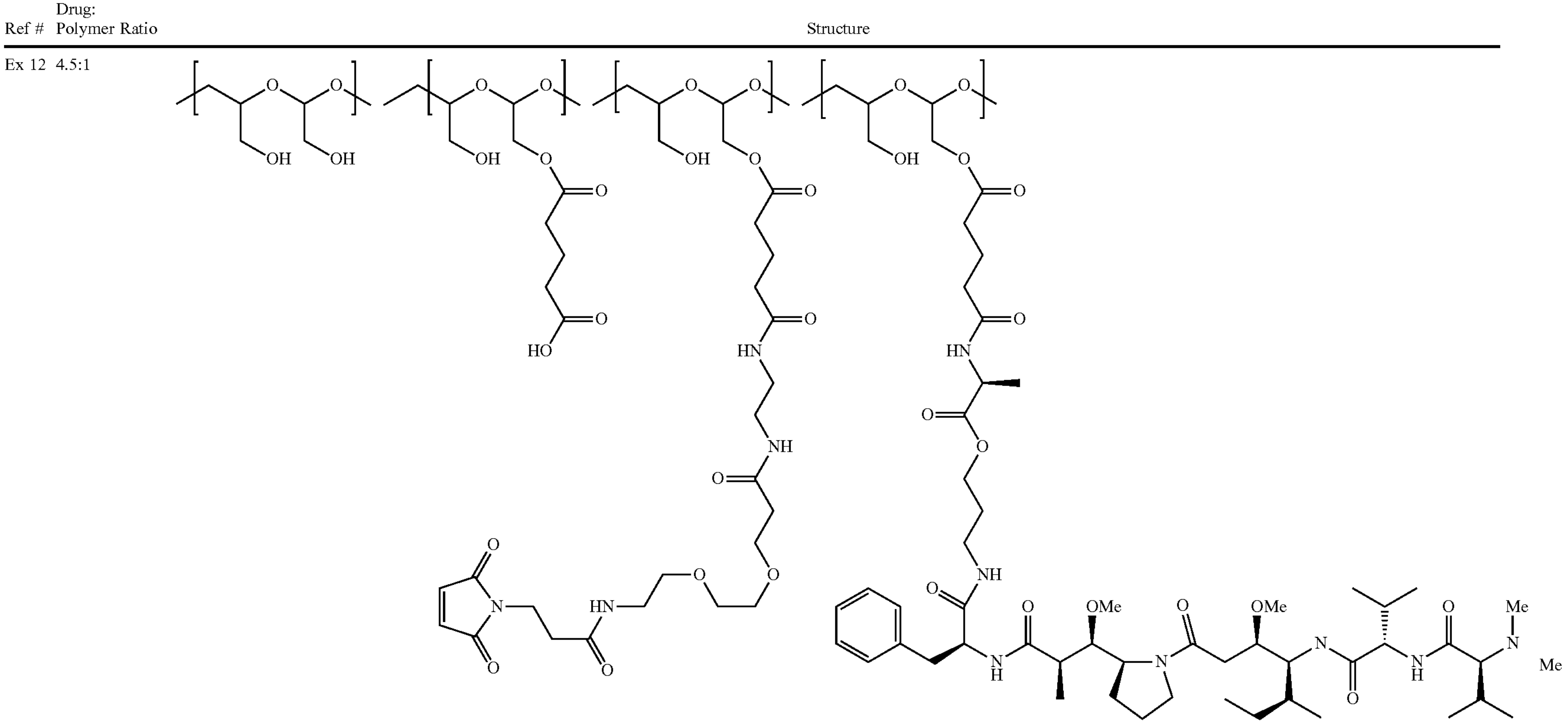 |

TABLE C-continued
| Ref # | Drug: Polymer Ratio | Structure |
|---|---|---|
| | | 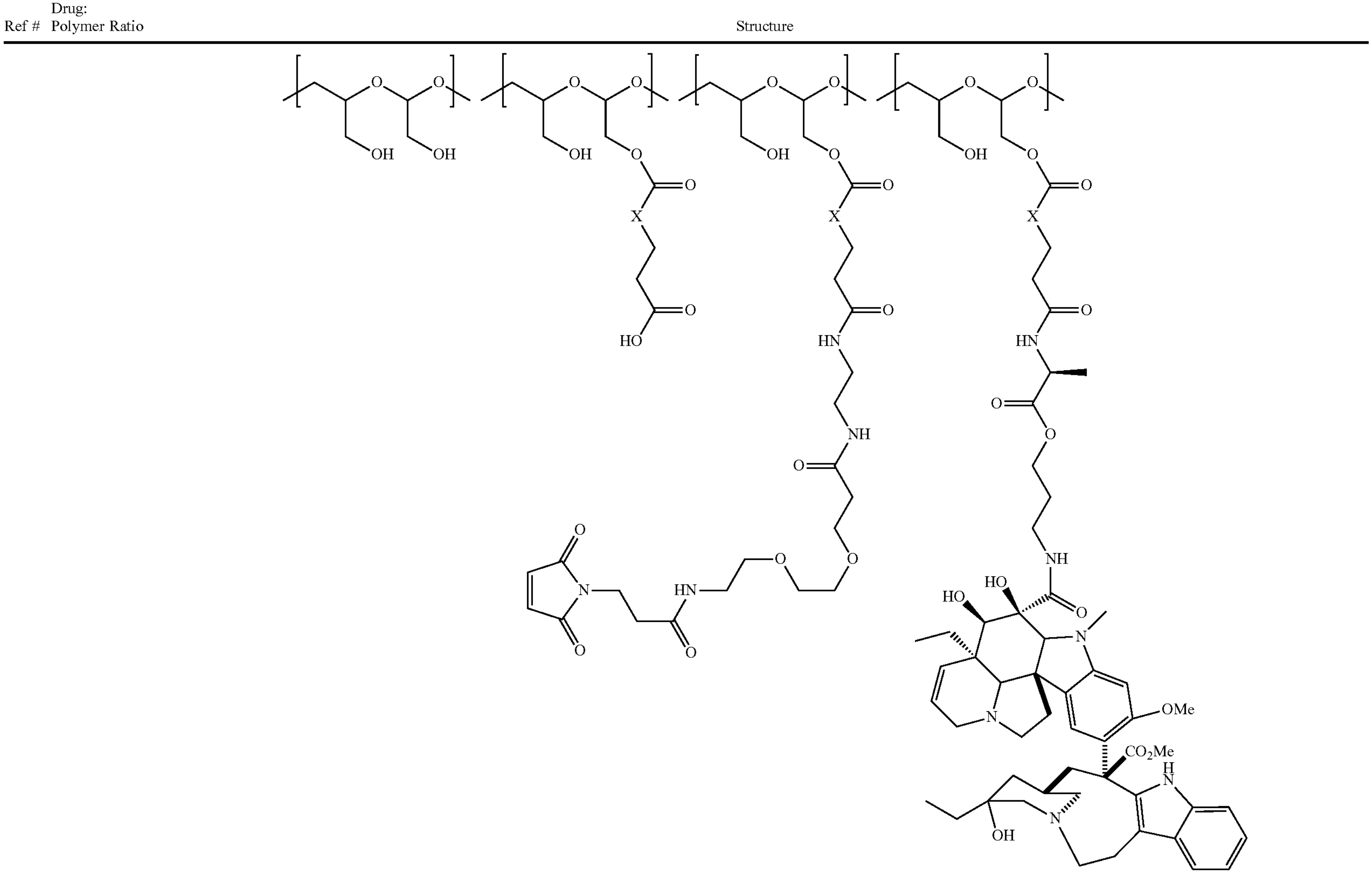 |

TABLE D
| Ref # | Drug: PBRM Ratio | Structure |
|---|---|---|
| Ex 4<br>Ex 7 | 12:1 to 17:1<br>16:1 to 21:1 | 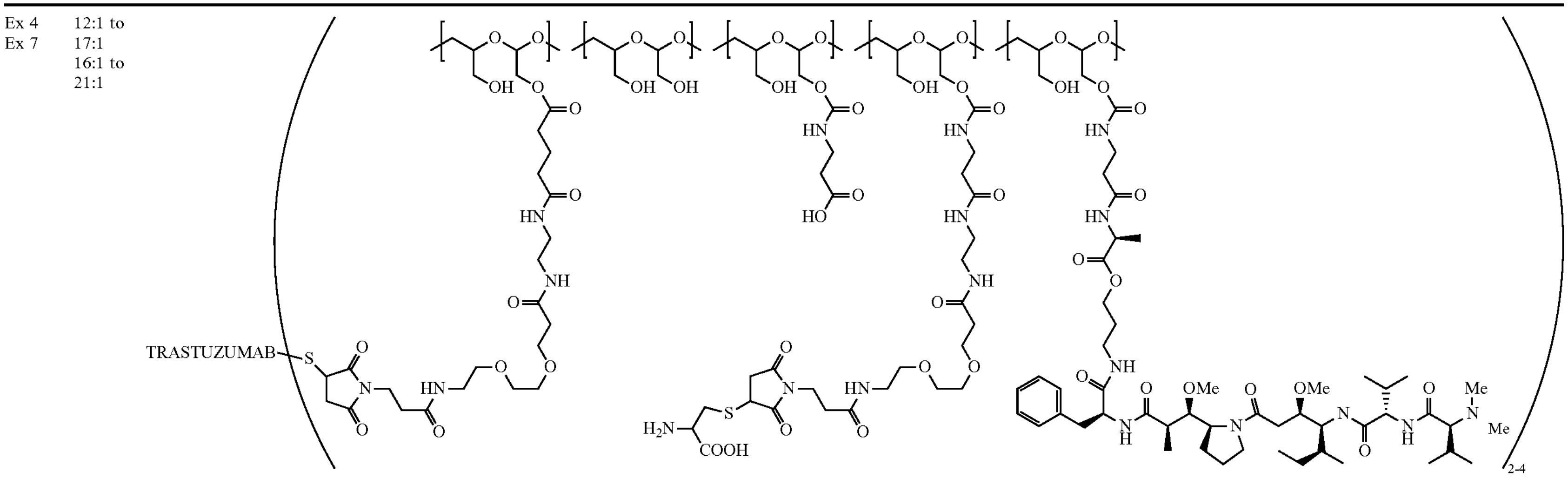 |

TABLE D-continued
| Ref # | Drug: PBRM Ratio | Structure |
|---|---|---|
| Ex 8 | 10:1 to 15:1 | 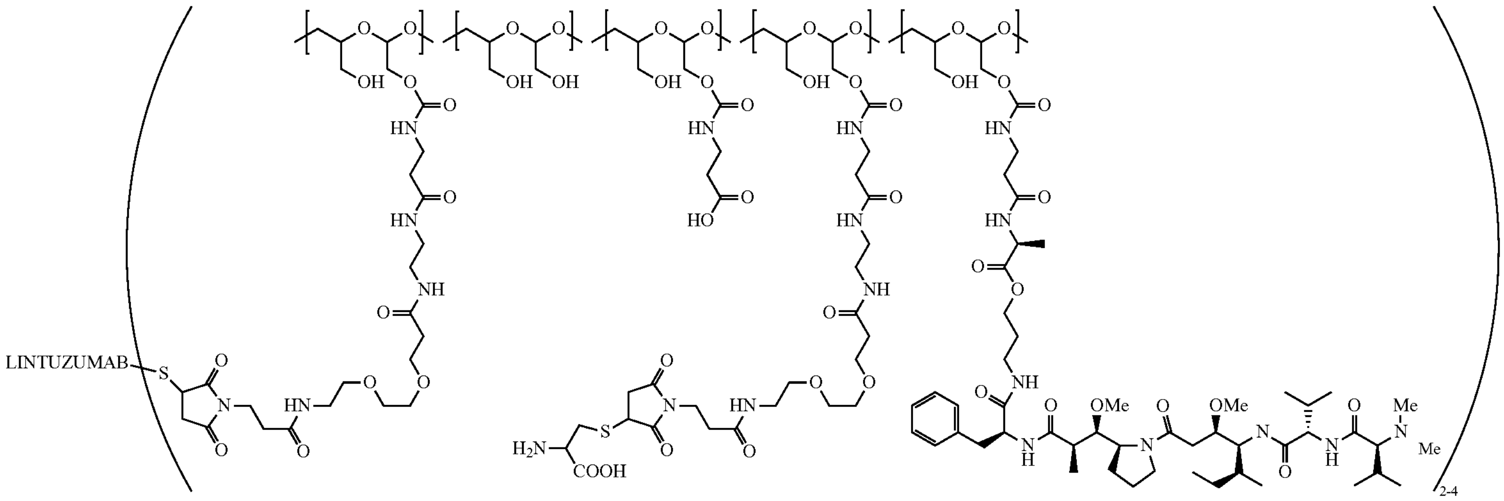 |
| Ex 9 | 13:1 to 18:1 | 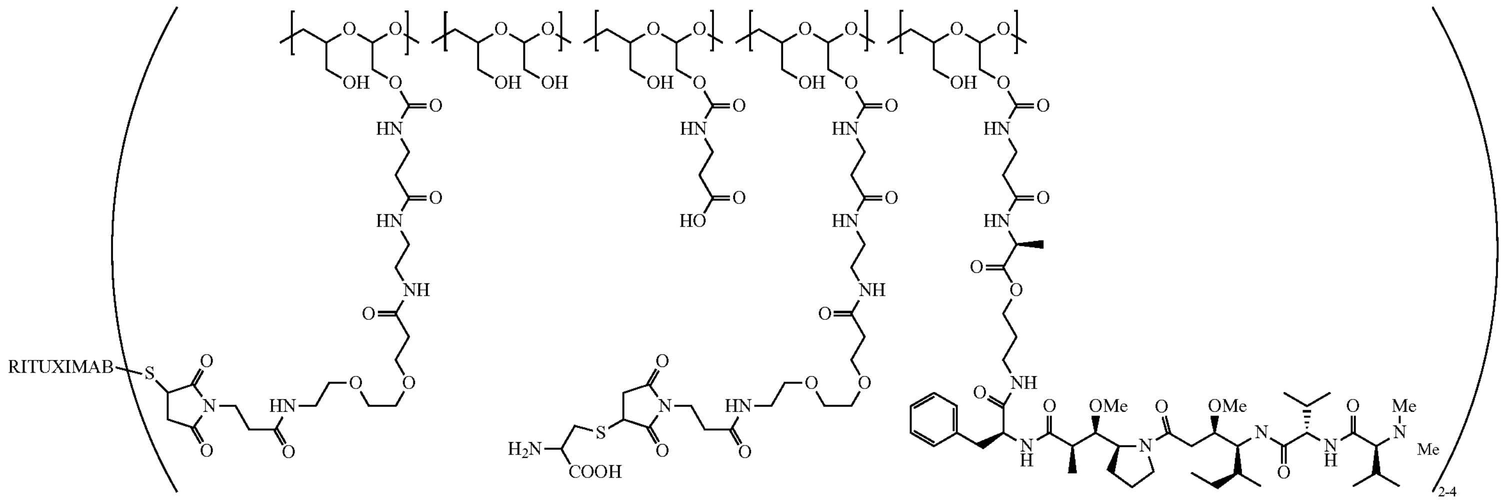 |

TABLE D-continued
| Ref # | Drug: PBRM Ratio | Structure |
|---|---|---|
| Ex 13 | 18:1 to 23:1 | 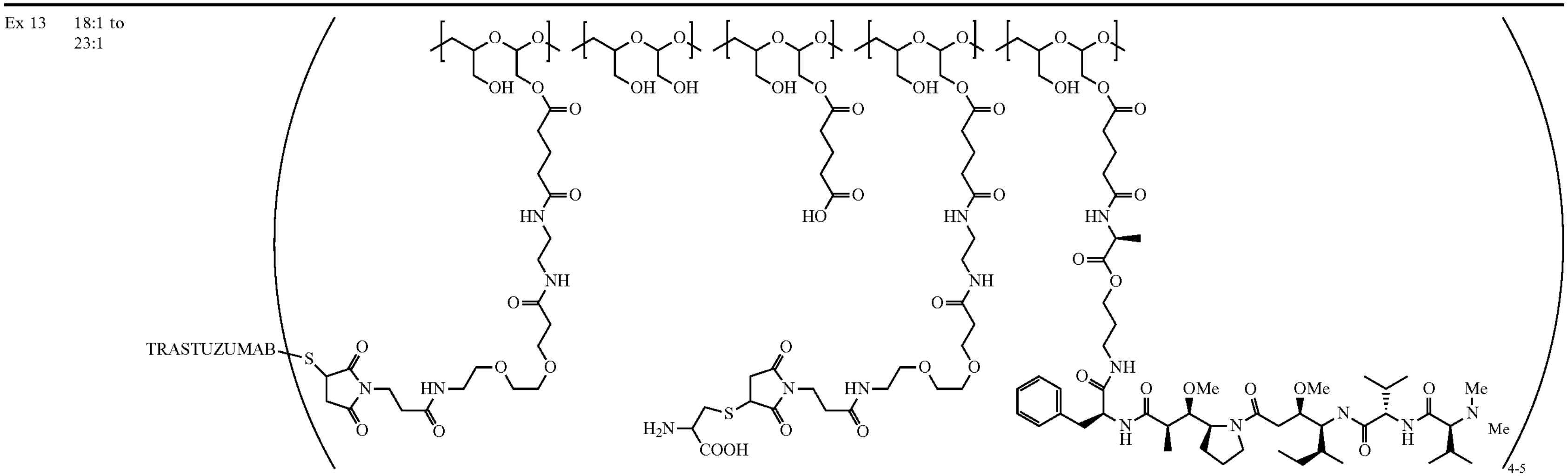 |

TABLE D-continued
| Ref # | Drug: PBRM Ratio | Structure |
| --- | --- | --- |
| | | 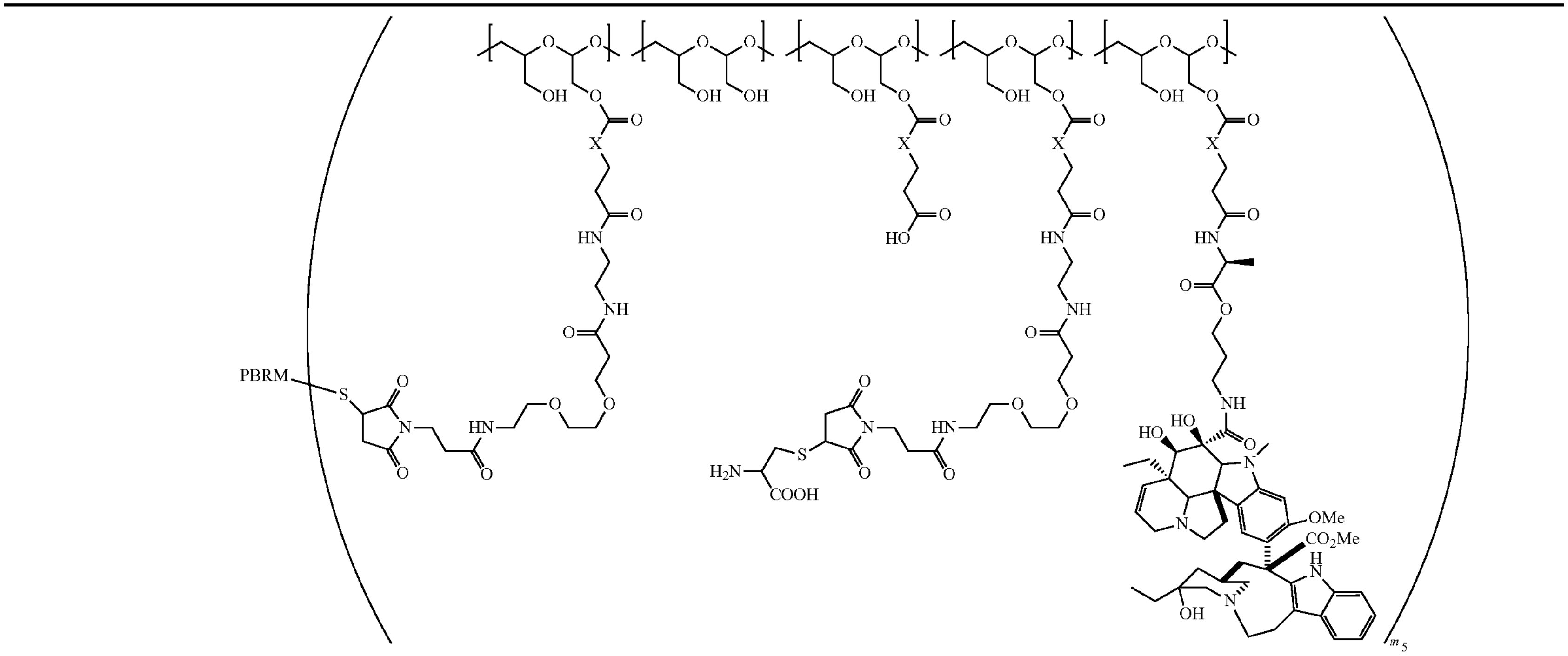 |

TABLE D-continued
| Ref # | Drug: PBRM Ratio | Structure |
|---|---|---|
| Ex 14 | 10:1 to 15:1 | 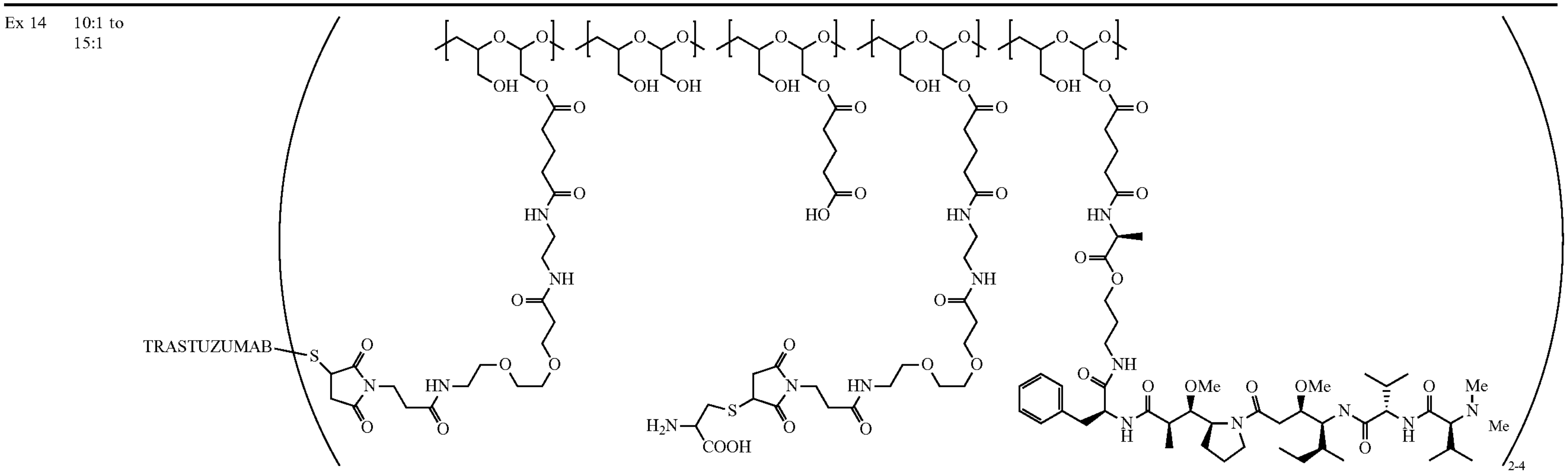 |
| Ex 10<br>Ex 15 | 11:1 to 16:1<br>11.1 to 16:1 | 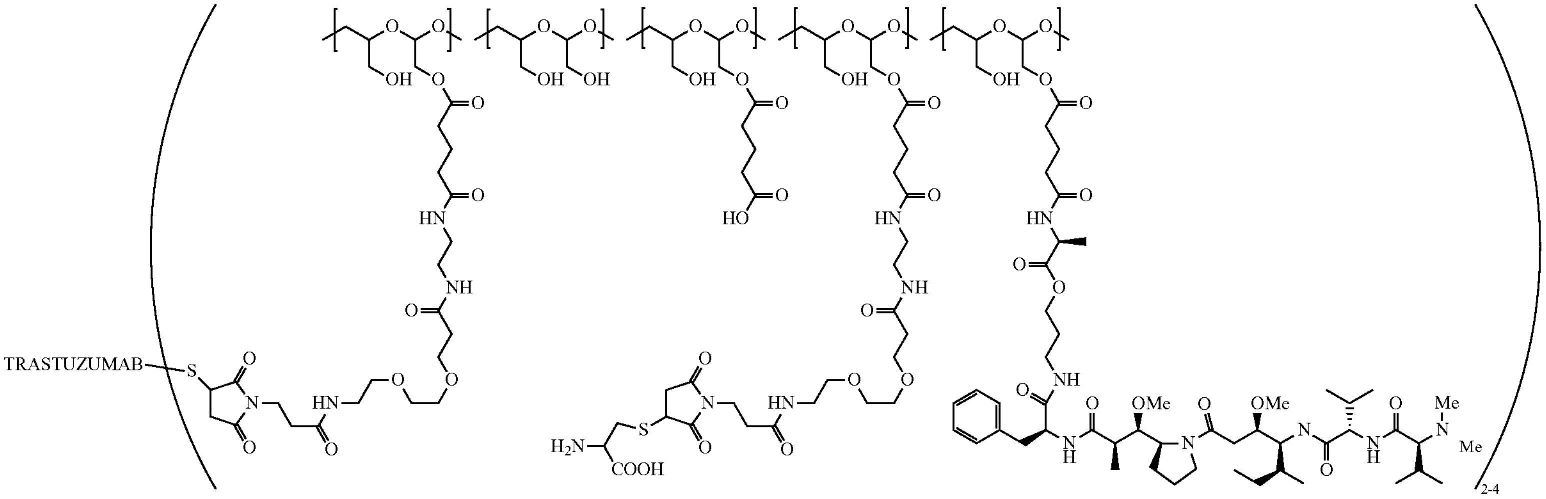 |

TABLE D-continued
| Ref # | Drug: PBRM Ratio | Structure |
|---|---|---|
| Ex 16 | 13:1 to 18:1 | 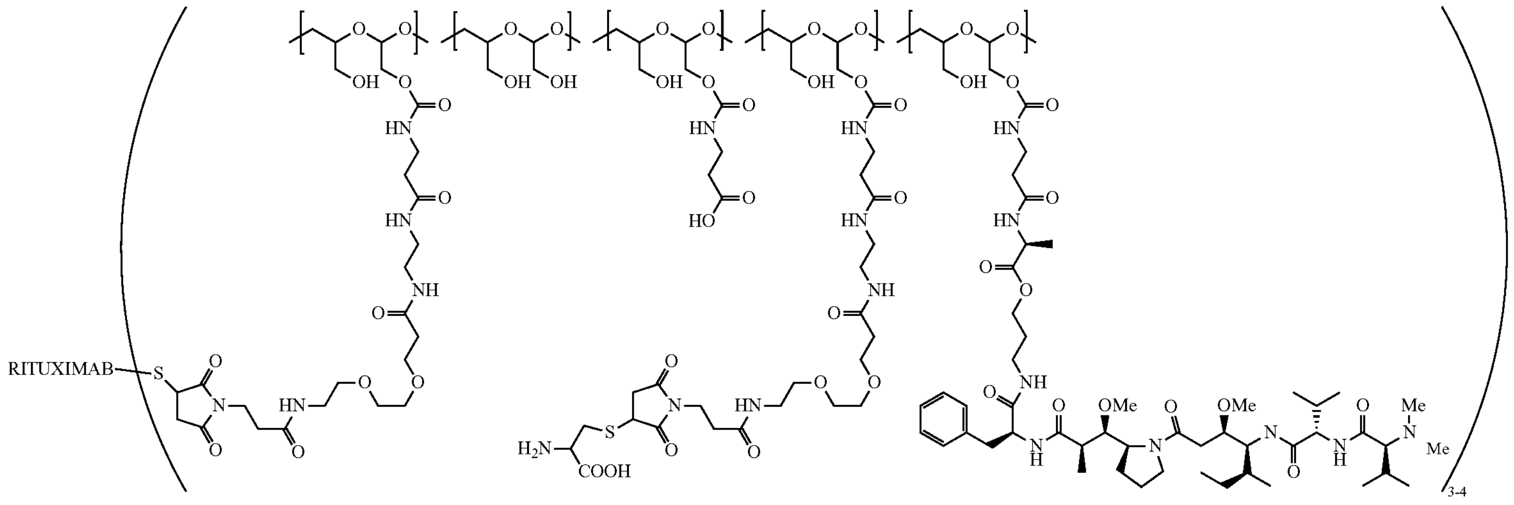 |
| Ex 17 | 5:1 to 10.1 | 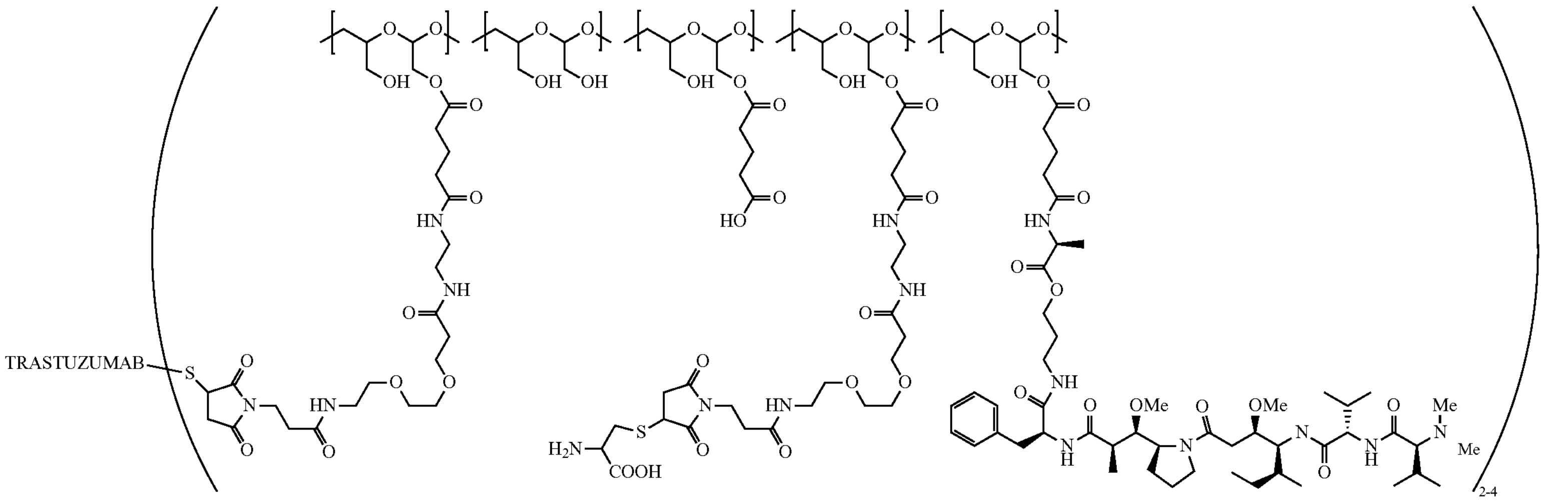 |

TABLE D-continued
| Ref # | Drug: PBRM Ratio | Structure |
|---|---|---|
| Ex 18A | 19:1 to 24:1 | 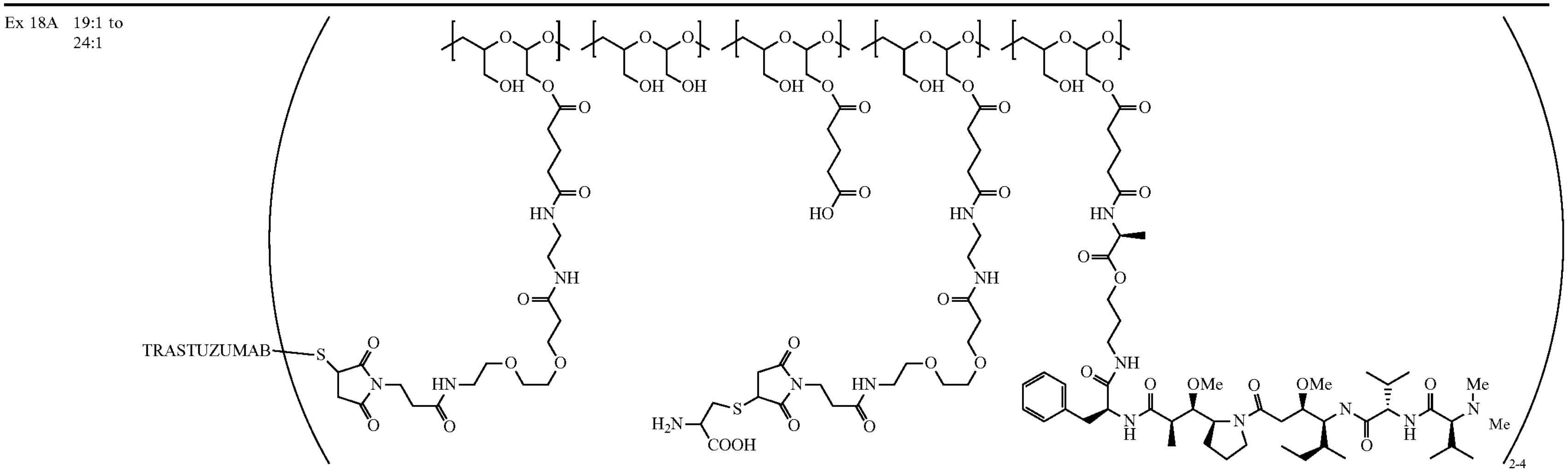 |
| Ex 18B | 20:1 to 25:1 | 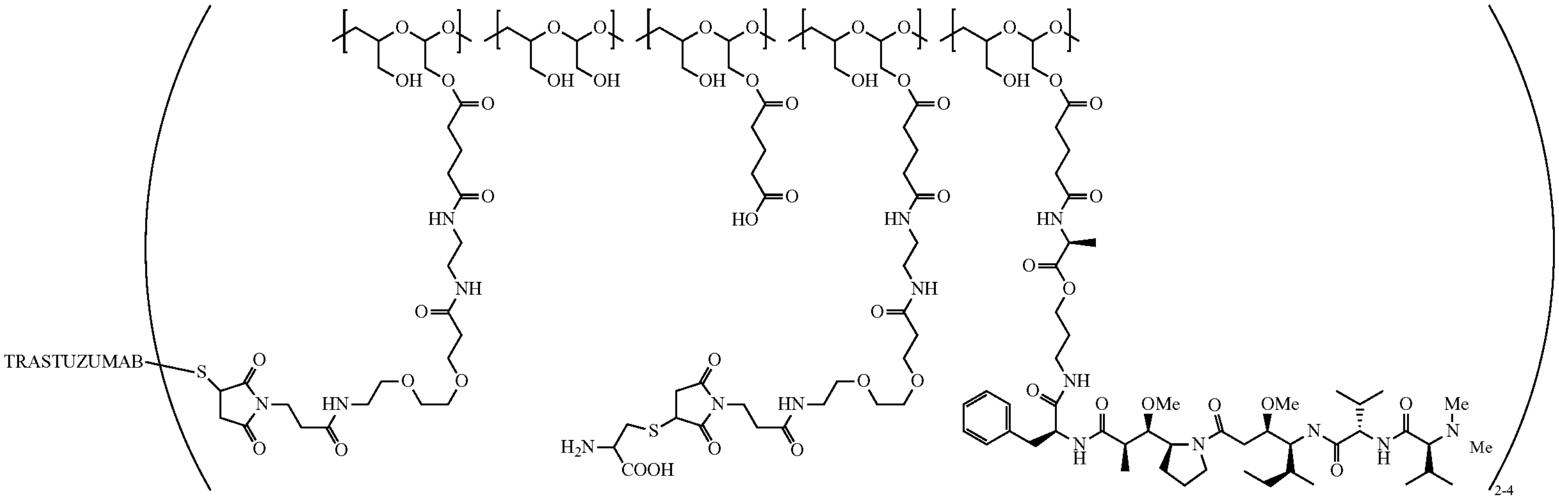 |

TABLE D-continued
| Ref # | Drug: PBRM Ratio | Structure |
|---|---|---|
| Ex 18C | 23:1 to 28:1 | 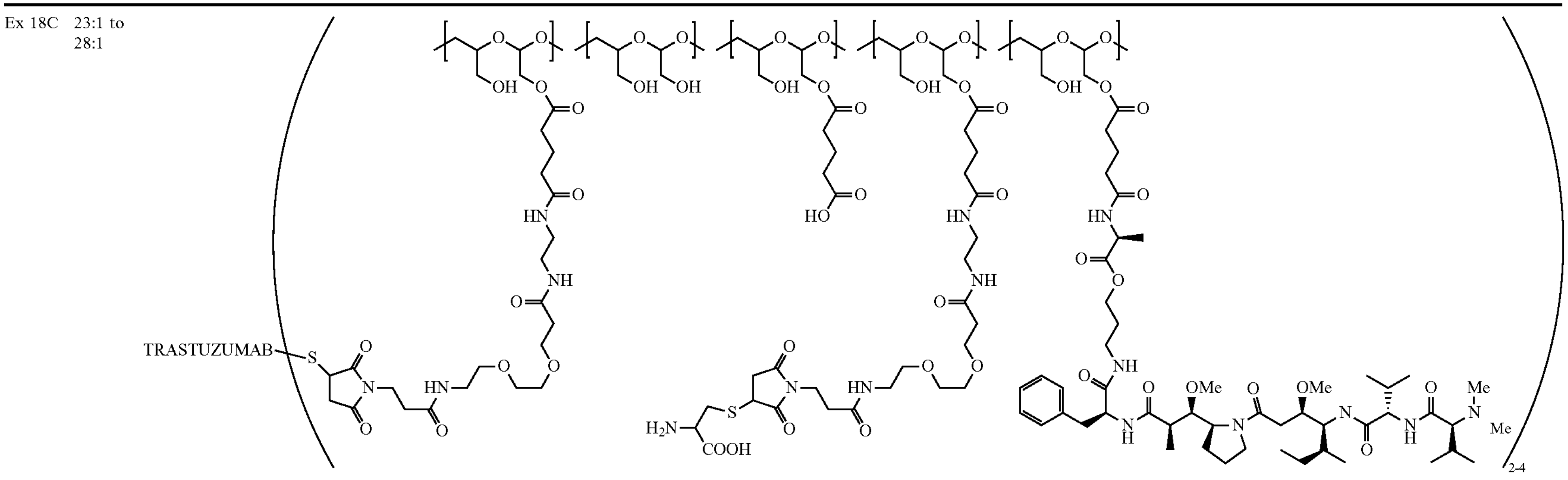 |

Synthetic Methods

According to the present invention, any available techniques can be used to make the inventive conjugates or compositions including them, and intermediates and components (e.g., carriers and modifiers) useful for making them. For example, semi-synthetic and fully synthetic methods may be used.

Carriers

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863,990; 5,958,398; 7,838,619; 7,790,150, 8,685,383, and 8,815,226, the contents of each of which are hereby incorporated by reference in their entireties. The skilled practitioner will know how to adapt these methods to make polymer carriers for use in the practice of the invention.

In one embodiment, a method for forming the biodegradable biocompatible polyal conjugates disclosed herein comprises a process by which a suitable polysaccharide is combined with an efficient amount of a glycol-specific oxidizing agent to form an aldehyde intermediate. The aldehyde intermediate, which is a polyal itself, may then be reduced to the corresponding polyol, succinylated, and coupled with one or more suitable modifiers to form a biodegradable biocompatible polyal conjugate comprising succinamide-containing linkages.

In another preferred embodiment, fully synthetic biodegradable biocompatible polyals for used in the present invention can be prepared by reacting a suitable initiator with a suitable precursor compound.

For example, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

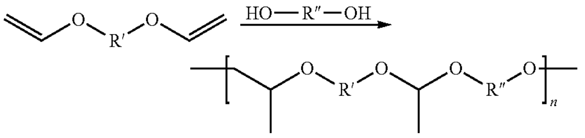

One of ordinary skill in the art will appreciate that solvent systems, catalysts and other factors may be optimized to obtain high molecular weight products.

In certain embodiments, the carrier is PHF.

In embodiments, the polymer carrier is PHF having a polydispersity index (PDI) of less than 1.5, e.g., <1.2.

Drugs and Drug Derivatives

In certain embodiments, the drug may be modified before conjugation to the polymeric carrier. Schemes 1 and 2 are illustrative methods for modifying a Vinca alkaloid. Scheme 3 shows a method for modifying a non-natural camptothecin derivative. Scheme 4 shows a method for modifying auristatin F. More modification methods are described in US 2010/0305149, which is hereby incorporated by reference.

Scheme 1

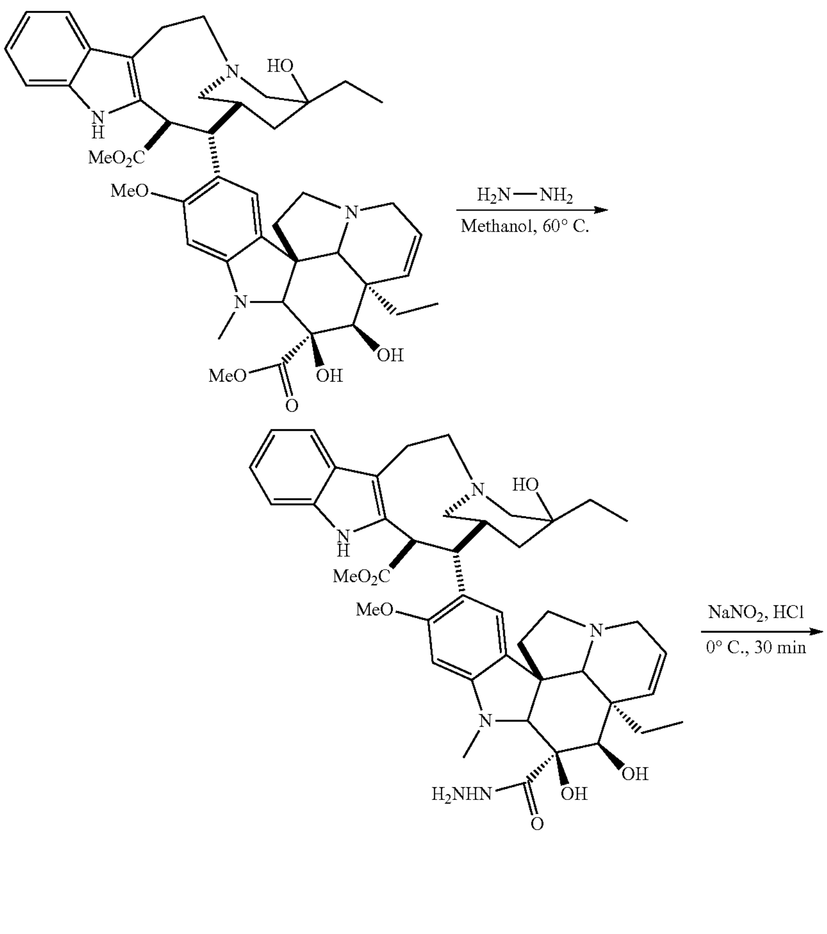

-continued

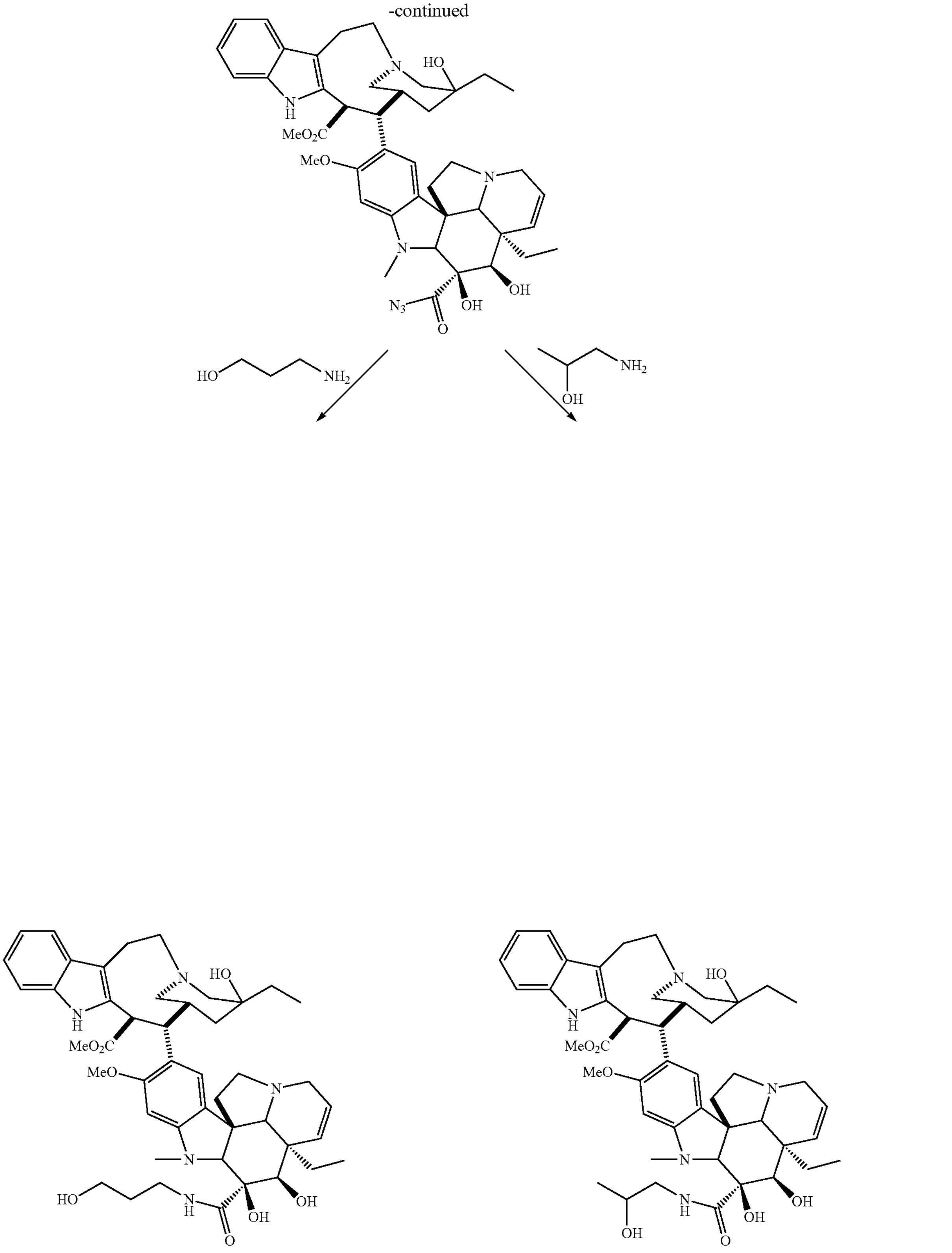

Reaction of the $C_{23}$ ester of a Vinca alkaloid with hydrazine followed by treatment with $NaNO_2$ results in an active azido ester. Reaction of the azido ester with an amino compound such as propanolamine or 1-aminopropan-2-ol results in a Vinca alkaloid derivative with a functionalized hydroxyl which can be further derivatized with amino containing compounds, such as, for example, alanine or methyl alanine derivatives, for conjugation with polymers (see Scheme 1).

Scheme 2

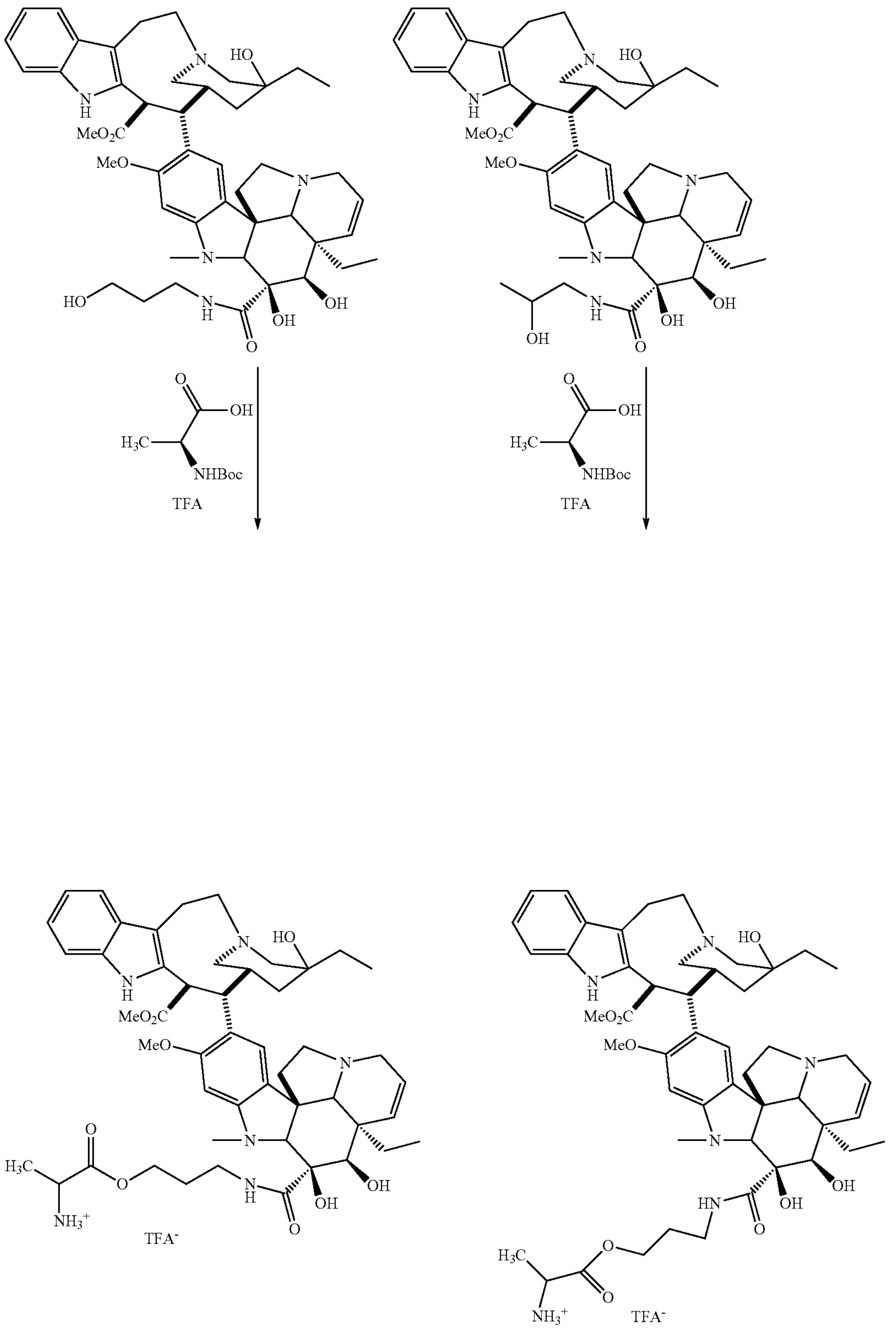

Treatment of the hydroxyl derivative of the Vinca alkaloid with a protected amino containing tether such as t-butoxy esterified amino acid followed by TFA hydrolysis of the ester gives the triflate salt of the vinca alkaloid. (Scheme 2)

Conjugation of the vinca alkaloid to functionalized polymers results in drug-polymer conjugates that can be further conjugated with a PBRM or its derivative to result in protein-polymer-drug conjugates.

Scheme 3

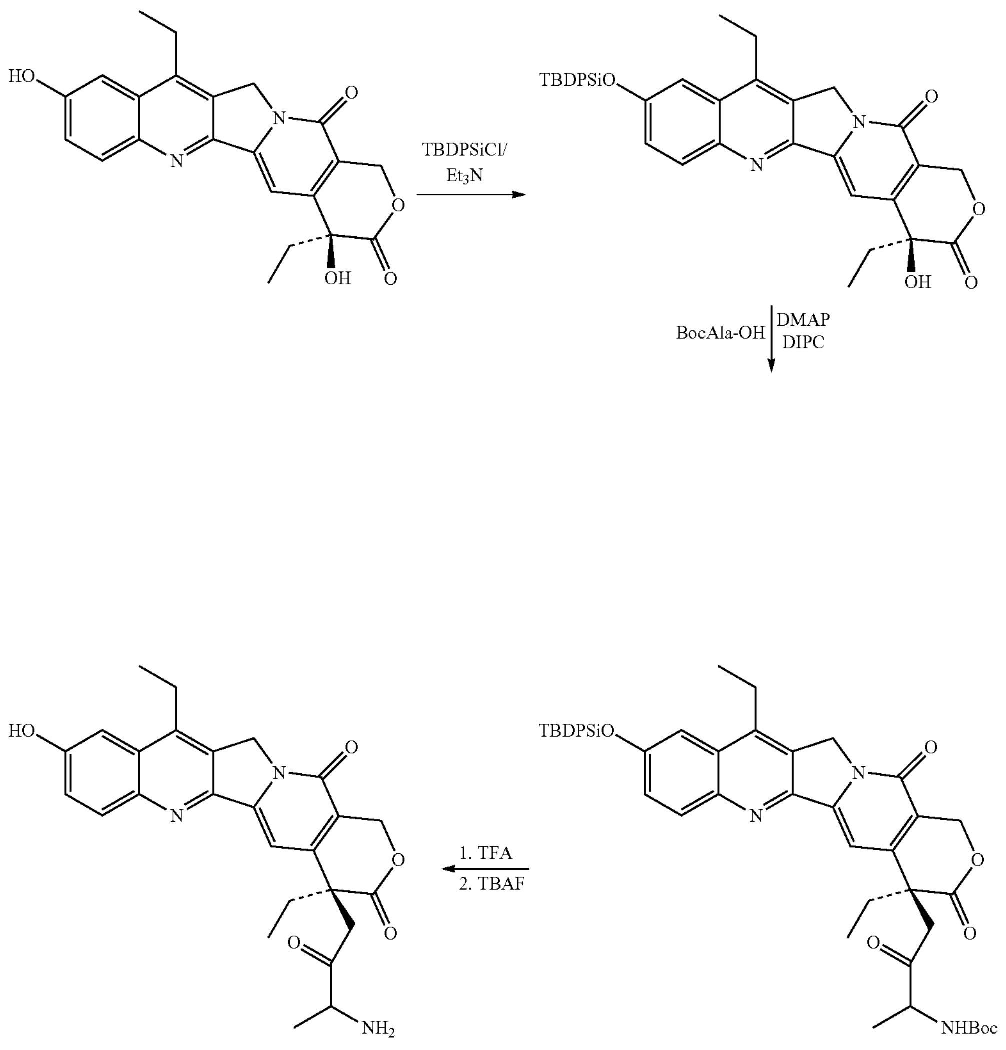

The 10-hydroxy group of non-natural camptothecin derivative, for example, SN38, is selectively protected by reacting the derivative with tert-butyldiphenylsilyl chloride (TBDPSiC1) in the presence of triethylamine. The 20-hydroxy group can be by reacted with t-butylcarbonyl-alanine to form the alanine derivative using the procedure described in Sapra, P. et al., Clin. Cancer Res., 14: 1888-1896 (2008). Alternatively, other amino acids can be employed, e.g., glycine. The primary amine is unmasked by removing the Boc protecting group by treatment with trifluoroacetic acid, followed by removing the TBDPS protecting group with tetrabutylammonium fluoride (see Scheme 3). The resulting amino derivatized SN38 compound can be conjugated with a functionalized polymer to form a drug-polymer conjugate.

Scheme 4

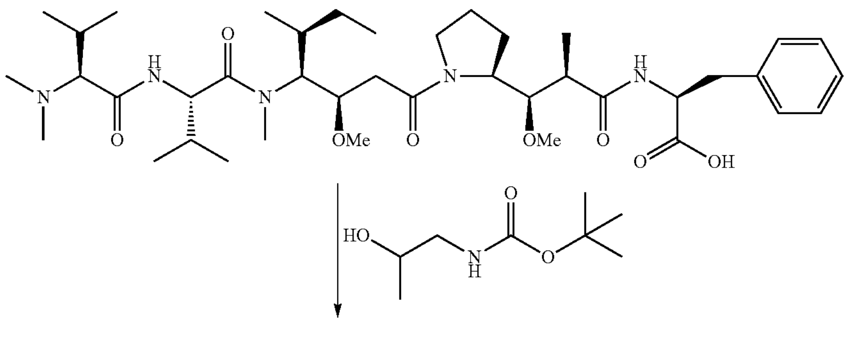

-continued

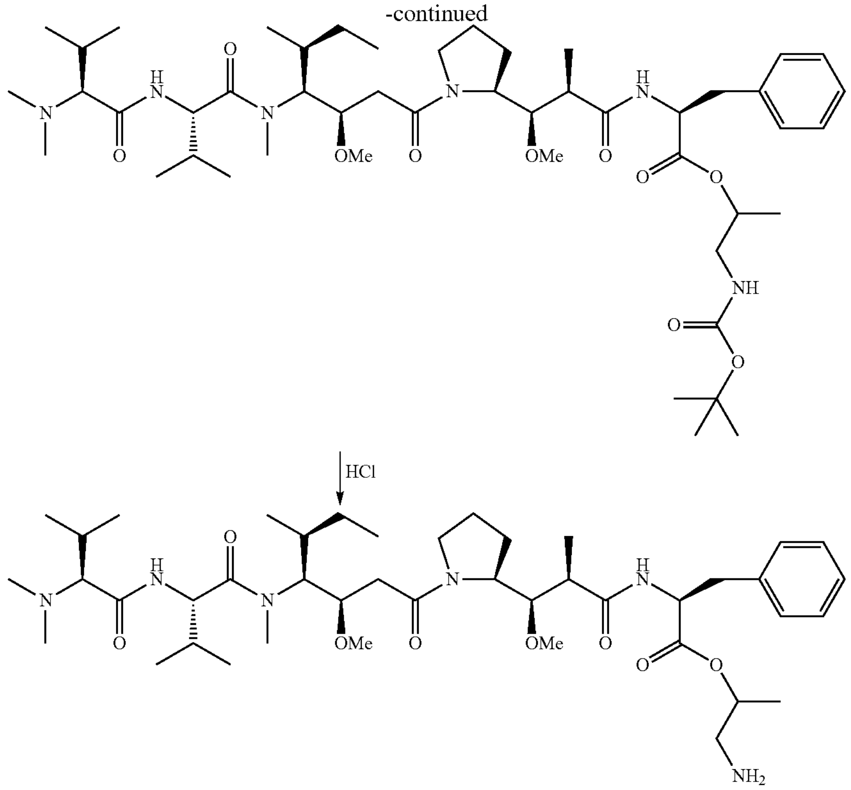

Treatment of auristatin F with a protected amino containing tether such as t-butoxy esterified 2-hydroxypropyl amine followed by HCl hydrolysis of the ester gives the 2-hydroxylpropyl amino derivative of auristatin F (see Scheme 4). Conjugation of the auristatin F derivative to functionalized polymers results in drug-polymer conjugates that can be further conjugated with a PBRM or its derivative to result in protein-polymer-drug conjugates.

Conjugates or Polymeric Scaffolds

Scheme 5 below shows a synthetic scheme of making the polymeric drug scaffolds disclosed herein. In one embodiment, the conjugates are formed in several steps: (1) the polymer, PHF is modified to contain a COOH moiety (e.g., —C(O)—X—$(CH_2)_2$—COOH); (2) the polymer is then further modified so that it contains a maleimido moiety (e.g., EG2-MI) that can react with a functional group of a PBRM; (3) the modified polymer, containing two different functional groups, is reacted with a functional group of a drug or its derivative (e.g., AF-HPA-Ala) to form a polymer-drug conjugate; (4) the disulfide bonds of a PBRM are reduced; (5) the reduced PBRM is then reacted with the polymer-drug conjugate to form the protein-polymer-drug conjugate; and (6) the remaining maleimido moieties are optionally reacted with a water-soluble maleimido blocking compound (e.g., cysteine).

In another embodiment the order of steps (2) and (3) can be reversed as depicted in the right side route in Scheme 5 below.

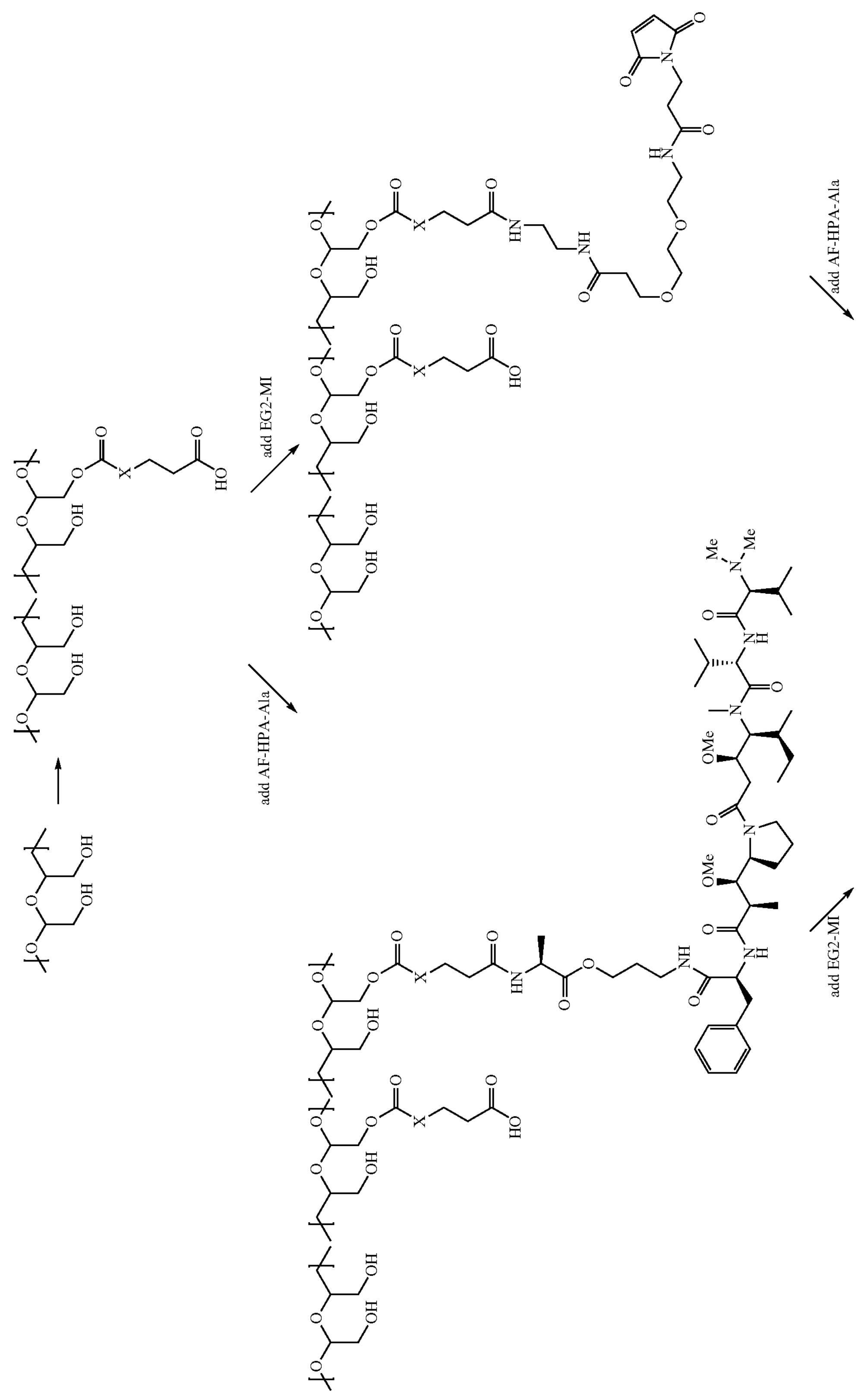
add EG2-MI
add AF-HPA-Ala
add AF-HPA-Ala
add EG2-MI

-continued
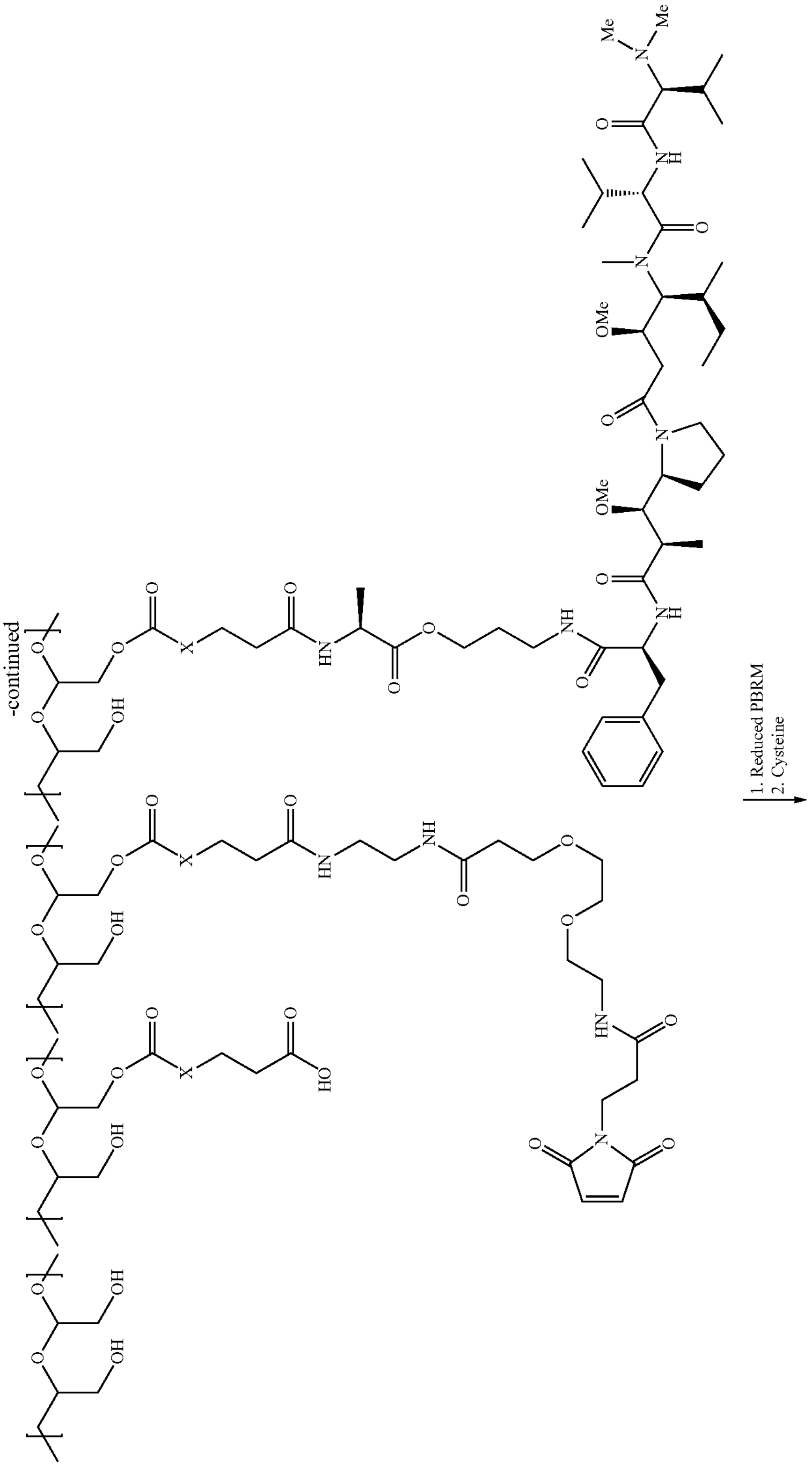

-continued
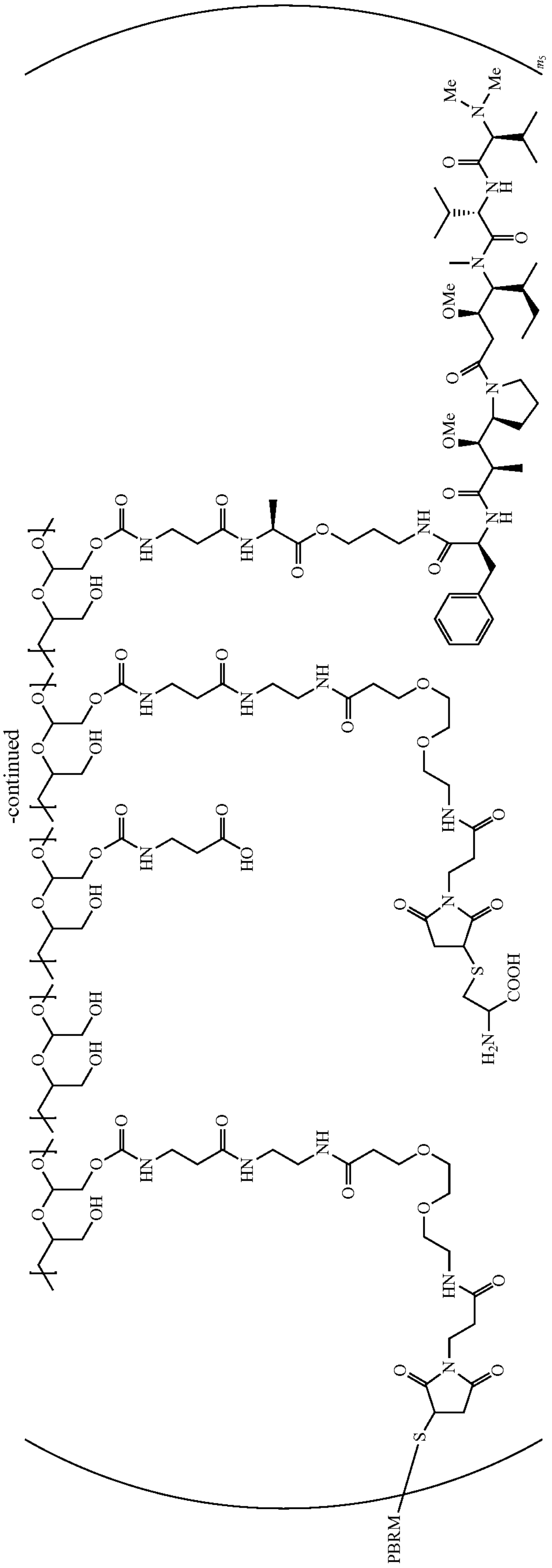

In yet another embodiment, steps (2) and (3) above are carried out simultaneously as depicted in Scheme 6 below.

Scheme 6
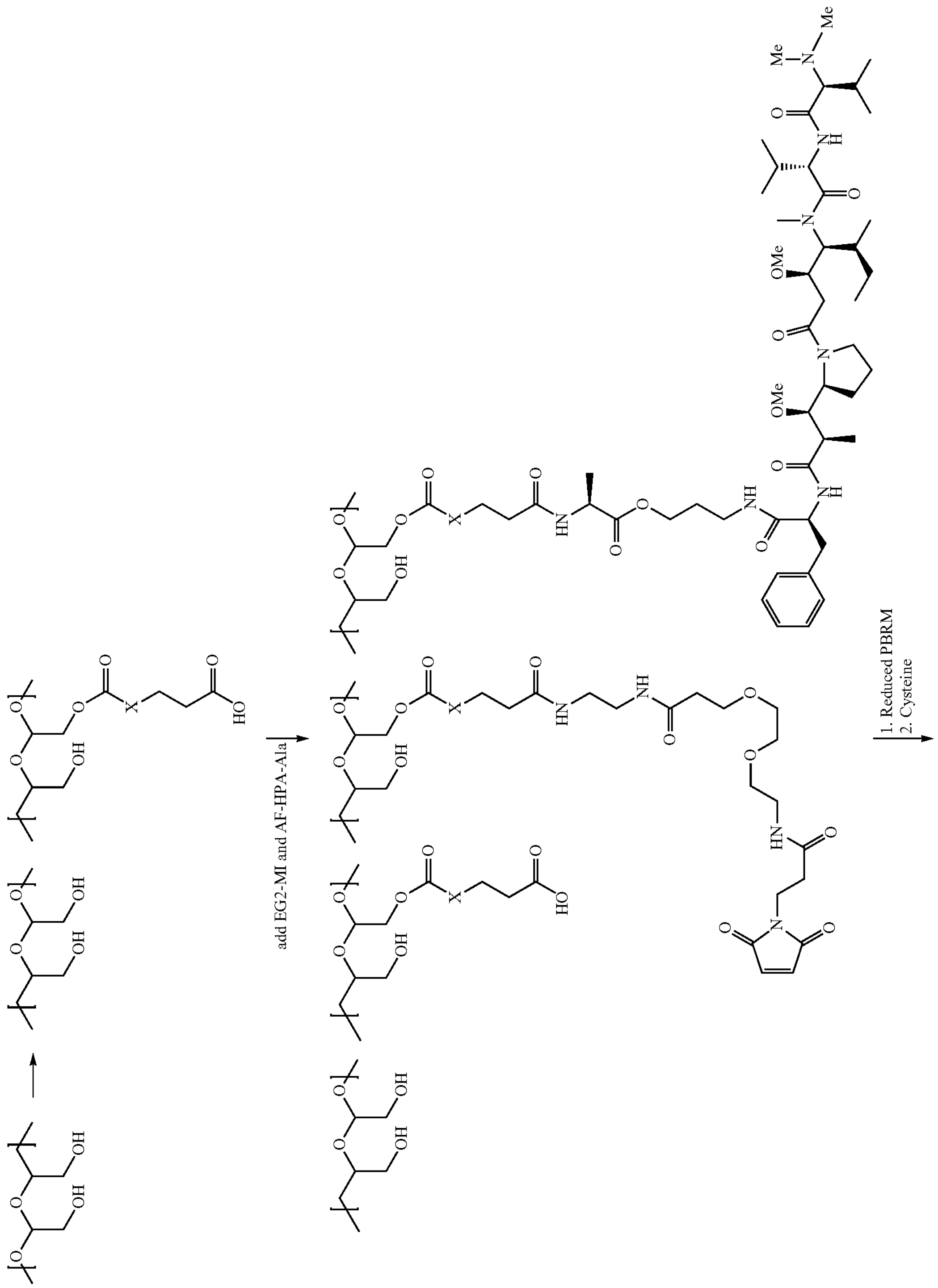

-continued
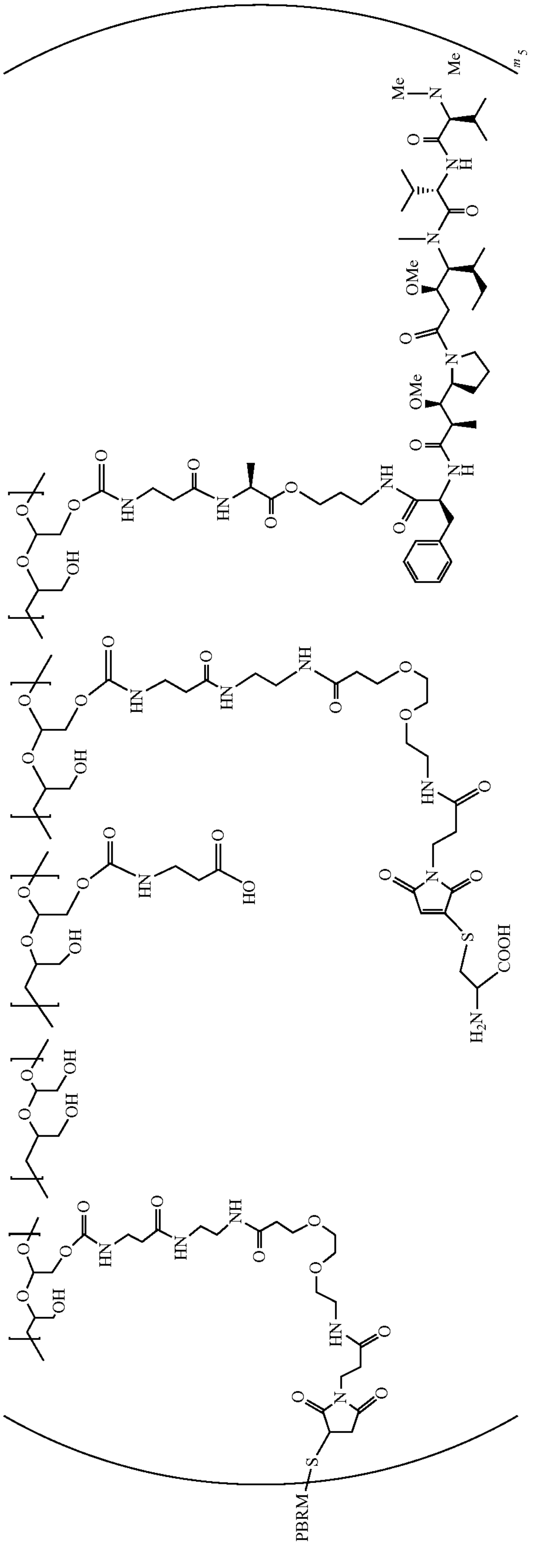

Pharmaceutical Compositions

Also included are pharmaceutical compositions comprising one or more protein-polymer-drug conjugates as disclosed herein in an acceptable carrier, such as a stabilizer, buffer, and the like. The conjugates can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the modified polymer in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the modified polymers to an accessible diseased tissue. The rate of entry of an active agent into the circulation has been shown to be a function of molecular weight or size. The use of a conjugate of this invention can localize the drug delivery in certain cells, such as cancer cells via the specificity of PBRMs.

A "pharmaceutically acceptable formulation" means a composition or formulation that allows for the effective distribution of the conjugates in the physical location most suitable for their desired activity. In one embodiment, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly (DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include a pharmaceutically effective amount of the desired conjugates in a pharmaceutically acceptable carrier or diluent. Acceptable carriers, diluents, and/or excipients for therapeutic use are well known in the pharmaceutical art. For example, buffers, preservatives, bulking agents, dispersants, stabilizers, dyes, can be provided. In addition, antioxidants and suspending agents can be used Examples of suitable carriers, diluents and/or excipients include, but are not limited to: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The term "pharmaceutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Pharmaceutically effective amounts for a given situation can be determined by routine experimentation that is within the skill and judgment of the clinician. In a preferred aspect, the disease or condition to can be treated via gene silencing.

For any conjugate, the pharmaceutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

For example, a drug or its derivatives, drug-polymer conjugates or PBRM-polymer-drug conjugates can be evaluated for their ability to inhibit tumor growth in several cell lines using Cell titer Glo. Dose response curves can be generated using SoftMax Pro software and $IC_{50}$ values can be determined from four-parameter curve fitting. Cell lines employed can include those which are the targets of the PBRM and a control cell line that is not the target of the PBRM contained in the test conjugates.

In one embodiment, the conjugates are formulated for parenteral administration by injection including using conventional catheterization techniques or infusion. Formulations for injection may be presented in unit dosage form, e.g., in ampules or in multi-dose containers, with an added preservative. The conjugates can be administered parenterally in a sterile medium. The conjugate, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. In addition, there is provided a pharmaceutical formulation comprising conjugates and a pharmaceutically acceptable carrier. One or more of the conjugates can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

The conjugates and compositions described herein may be administered in appropriate form, preferably parenterally, more preferably intravenously. For parenteral administration, the conjugates or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

Dosage levels of the order of from between about 0.001 mg and about 140 mg per kilogram of body weight, ranging from twice daily to once a month (e.g., once daily, once weekly; once every other week; once every 3 weeks or monthly) are useful in the treatment of the above-indicated conditions (between about 0.05 mg and about 7 g per subject, twice daily to once a month (e.g., once daily, once weekly; once every other week; once every 3 weeks or monthly)). In some embodiments, the dosage administered to a patient is between about 0.001 mg/kg to about 100 mg/kg of the subject's body weight. In some embodiments, the dosage administered to a patient is between about 0.01 mg/kg to about 20 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg). In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. The amount of conjugate that can be combined with the carrier materials to produce a single dosage form varies depending upon the host treated and the particular mode of administration. Dosage unit forms can generally contain from between about 0.001 mg and about 100 mg; between about 0.01 mg and about 75 mg; or between about 0.01 mg and about 50 mg; or between about 0.01 mg and about 25 mg; of a conjugate.

For intravenous administration, the dosage levels can comprise ranges described in the preceding paragraphs, or from about 0.01 to about 200 mg of a conjugate per kg of the animal's body weight. In one aspect, the composition can include from about 1 to about 100 mg of a conjugate per kg of the animal's body weight. In another aspect, the amount administered will be in the range from about 0.1 to about 25 mg/kg of body weight of a compound.

In some embodiments, the conjugates can be administered are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period.

In some embodiments about one to about four weeks after treatment, the patient can receive a second course of treatment. Specific clinical protocols with regard to route of administration, excipients, diluents, dosages, and times can be determined by the skilled artisan as the clinical situation warrants.

In other embodiments, the therapeutically effective amount may be provided on another regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the recommendations of the relevant regulatory bodies and judgment of a health-care practitioner. The therapeutically effective amounts described herein refer to total amounts administered for a given time period; that is, if more than one different conjugate described herein is administered, the therapeutically effective amounts correspond to the total amount administered. It is understood that the specific dose level for a particular subject depends upon a variety of factors including the activity of the specific conjugate, the age, body weight, general health, sex, diet, time of administration, route of administration, and rate of excretion, combination with other active agents, and the severity of the particular disease undergoing therapy.

For administration to non-human animals, the conjugates can also be added to the animal feed or drinking water. It can be convenient to formulate the animal feed and drinking water so that the animal takes in a therapeutically appropriate quantity of the conjugates along with its diet. It can also be convenient to present the conjugates as a premix for addition to the feed or drinking water.

The conjugates can also be administered to a subject in combination with other therapeutic compounds to increase the overall therapeutic effect. The use of multiple compounds to treat an indication can increase the beneficial effects while reducing the presence of side effects. In some embodiment the conjugates are used in combination with chemotherapeutic agents, such as those disclosed in U.S. Pat. No. 7,303,749. In other embodiments the chemotherapeutic agents, include, but are not limited to letrozole, oxaliplatin, docetaxel, 5-FU, lapatinib, capecitabine, leucovorin, erlotinib, pertuzumab, bevacizumab, and gemcitabine. The present invention also provides pharmaceutical kits comprising one or more containers filled with one or more of the conjugates and/or compositions disclosed herein, including, one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products. The compositions described herein can be packaged as a single dose or for continuous or periodic discontinuous administration. For continuous administration, a package or kit can include the conjugates in each dosage unit (e.g., solution or other unit described above or utilized in drug delivery), and optionally instructions for administering the doses daily, weekly, or monthly, for a predetermined length of time or as prescribed. If varying concentrations of a composition, of the components of the composition, or the relative ratios of the conjugates or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle. The packaging means of a kit may itself be geared for administration, such as a syringe, pipette, eye dropper, or other such apparatus, from which the formulation may be applied to an affected area of the body, injected into a subject, or even applied to and mixed with the other components of the kit.

Methods of Use

In certain preferred embodiments of the invention, the protein-polymer-drug conjugate disclosed herein are used in methods of treating animals (preferably mammals, most preferably humans and includes males, females, infants, children and adults). In one embodiment, the conjugates disclosed herein may be used in a method of treating animals which comprises administering to the animal a biodegradable biocompatible conjugate disclosed herein. For example, conjugates in accordance with the invention can be administered in the form of soluble linear polymers, copolymers, conjugates, colloids, particles, gels, solid items, fibers, films, etc. Biodegradable biocompatible conjugates of this invention can be used as drug carriers and drug carrier components, in systems of controlled drug release, preparations for low-invasive surgical procedures, etc. Pharmaceutical formulations can be injectable, implantable, etc.

In yet another aspect, the invention provides a method of treating a disease or disorder in a subject in need thereof, comprising administering to the subject an efficient amount of at least one conjugate disclosed herein; wherein said conjugate releases one or more therapeutic agents upon biodegradation.

In another embodiment the conjugates can be administered in vitro, in vivo and/or ex vivo to treat patients and/or to modulate the growth of selected cell populations including, for example, cancer. In some embodiments, the particular types of cancers that can be treated with the conjugates include, but are not limited to: (1) solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; (2) blood-borne cancers, including but not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma, acute and chronic leukemias, e.g., lymphoblastic myelogenous and lymphocytic myelocytic leukemias; and (3) lymphomas such as Hodgkin's disease, non-Hodgkin's Lymphoma, Multiple myeloma, Waldenstrom's macroglobulinemia, Heavy chain disease, and Polycythemia vera.

In another embodiment the conjugates can be administered in vitro, in vivo and/or ex vivo to treat autoimmune diseases, such as systemic lupus, rheumatoid arthritis, psoriasis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like.

In certain embodiments the conjugates can also be used for the manufacture of a medicament useful for treating or lessening the severity of disorders, such as, characterized by abnormal growth of cells (e.g., cancer).

In certain embodiments, the therapeutic agent is locally delivered to a specific target cell, tissue, or organ.

In certain embodiments, in practicing the method disclosed herein, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g., paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. Fluorescent labels can be used for photoimaging. In certain embodiments a modifier comprises a paramagnetic ion or group.

In another aspect, the invention provides a method of treating a disease or disorder in a subject, comprising preparing an aqueous formulation of at least one conjugate disclosed herein and parenterally injecting said formulation in the subject.

In another aspect, the invention provides a method of treating a disease or disorder in a subject, comprising preparing an implant comprising at least one conjugate disclosed herein, and implanting said implant into the subject. In certain exemplary embodiments, the implant is a biodegradable gel matrix.

In another aspect, the invention provides a method for treating of an animal in need thereof, comprising administering a conjugate according to the methods described above.

In another aspect, the invention provides a method for eliciting an immune response in an animal, comprising administering a conjugate as in the methods described above.

In another aspect, the invention provides a method of diagnosing a disease in an animal, comprising steps of:

administering a conjugate as in the methods described above, wherein said conjugate comprises a detectable molecule; and detecting the detectable molecule.

In certain exemplary embodiments, the step of detecting the detectable molecule is performed non-invasively. In certain exemplary embodiments, the step of detecting the detectable molecule is performed using suitable imaging equipment.

In one embodiment, a method for treating an animal comprises administering to the animal a biodegradable biocompatible conjugate disclosed herein as a packing for a surgical wound from which a tumor or growth has been removed. The biodegradable biocompatible conjugate packing will replace the tumor site during recovery and degrade and dissipate as the wound heals.

In certain embodiments, the conjugate is associated with a diagnostic label for in vivo monitoring.

The conjugates described above can be used for therapeutic, preventative, and analytical (diagnostic) treatment of animals. The conjugates are intended, generally, for parenteral administration, but in some cases may be administered by other routes.

In one embodiment, soluble or colloidal conjugates are administered intravenously. In another embodiment, soluble or colloidal conjugates are administered via local (e.g., subcutaneous, intramuscular) injection. In another embodiment, solid conjugates (e.g., particles, implants, drug delivery systems) are administered via implantation or injection.

In another embodiment, conjugates comprising a detectable label are administered to study the patterns and dynamics of label distribution in animal body.

In certain embodiments, any one or more of the conjugates disclosed herein may be used in practicing any of the methods described above. In certain exemplary embodiments, the conjugate is a Trastuzumab-PHF-, Rituximab-PHF-, or Lintuzumab-PHF-drug conjugate.

In one embodiment, trastuzumab-polymer-drug conjugates disclosed herein may be used as therapeutic agents. Such conjugates will generally be employed to diagnose, prognose, monitor, treat, alleviate, prevent, and/or delay the progression of a disease or pathology associated with aberrant HER2 activity and/or expression in a subject. A therapeutic regimen is carried out by identifying a subject, e.g., a human patient suffering from (or at risk of developing) a disease or disorder associated with aberrant HER2 activity and/or expression, e.g., a cancer, using standard methods. A trastuzumab-polymer-drug conjugate preparation is administered to the subject and will generally have an effect due to its binding with the HER2 target. Administration of the trastuzumab-polymer-drug conjugate may abrogate or inhibit or interfere with the signaling function of the HER2 target. Administration of the trastuzumab-polymer-drug conjugate may abrogate or inhibit or interfere with the binding of the HER2 target with an endogenous ligand to which it naturally binds.

Diseases or disorders related to aberrant HER2 activity and/or expression include but not limited to cancer. The target cancer can be anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, or gastric cancer.

In another aspect, diseases or disorders are cancer selected from the group consisting of breast cancer, gastric cancer, non-small cell lung cancer (NSCLC), and ovarian cancer.

Generally, alleviation or treatment of a disease or disorder involves the lessening of one or more symptoms or medical problems associated with the disease or disorder. For example, in the case of cancer, the therapeutically effective amount of the trastuzumab-polymer-drug conjugate can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this invention can be used to prevent the onset or reoccurrence of the disease or disorder in a subject.

A therapeutically effective amount of an trastuzumab-polymer-drug conjugate disclosed herein relates generally to the amount needed to achieve a therapeutic objective. The amount required to be administered will furthermore depend on the binding affinity of the antibody for its specific antigen, and will also depend on the rate at which an administered antibody is depleted from the free volume other subject to which it is administered. Common ranges for therapeutically effective dosing of the trastuzumab-polymer-drug conjugate disclosed herein may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular HER2-related disorder. Alleviation of one or more symptoms of the HER2-related disorder indicates that the conjugate confers a clinical benefit.

Methods for the screening of antibodies that possess the desired specificity include, but are not limited to, enzyme linked immunosorbent assay (ELISA) and other immunologically mediated techniques known within the art.

In another embodiment, antibodies directed against HER2 may be used in methods known within the art relating to the localization and/or quantitation of HER2 (e.g., for use in measuring levels of HER2 within appropriate physiological samples, for use in diagnostic methods, for use in imaging the protein, and the like). In a given embodiment, antibodies specific to HER2, or derivative, fragment, analog or homolog thereof, that contain the antibody derived antigen binding domain, are utilized as pharmacologically active compounds (referred to hereinafter as "Therapeutics").

In another embodiment, an antibody specific for HER2 be used to isolate a HER2 polypeptide, by standard techniques, such as immunoaffinity, chromatography or immunoprecipitation. Antibodies directed against HER2 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$. Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes disclosed herein can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Drug compounds used for the conjugates disclosed herein can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds disclosed herein.

Conjugates disclosed herein and the drug compounds included therein can be conveniently prepared by a variety of methods familiar to those skilled in the art. The conjugates or compounds of this invention with each of the formulae described herein may be prepared according to the following procedures from commercially available starting materials or starting materials which can be prepared using literature procedures. These procedures show the preparation of representative conjugates of this invention.

Conjugates designed, selected and/or optimized by methods described above, once produced, can be characterized using a variety of assays known to those skilled in the art to determine whether the conjugates have biological activity. For example, the conjugates can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following working examples are illustrative of the linkers, drug molecules and PBRM, and methods for preparing same. These are not intended to be limiting and it will be readily understood by one of skill in the art that other reagents or methods may be utilized.

Conjugates described herein can be prepared by the schemes generally outlined above and by methods described in the Examples below. The term "content" as used in certain examples below, unless otherwise specified, means the molar fraction or molar percentage of the polymer structural units that are substituted with the intended moiety, such as the linker, the drug molecule, or PBRM. Accordingly, the reported percentages for the various polymer units in the polymer-drug or PBRM-polymer-drug conjugates as used in the Examples below are molar percentages, unless otherwise specified.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

ACN Acetonitrile

AF-HPA Auristatin F-hydroxypropylamide

Ala Alanine

BA β-Alanine

BOC tert-Butyloxycarbonyl

DCM Dichloromethane

DMA Dimethylacetamide

DMF Dimethylformamide

DMSO Dimethylsulfoxide

EDC.HCl 1-Ethyl-3-[3-dimethylaminopropyl]carbodiimide hydrochloride

GA Glutaric acid

HIC-HPLC Hydrophobic interaction high pressure liquid chromatography

HPLC High pressure liquid chromatography

HPSEC High performance size exclusion chromatography

MWCO Molecular Weight Cut-Off

NHS 1-Hydroxypyrrolidine-2,5-dione (i.e., N-hydroxysuccinimide)

NMP N-methyl-2-pyrrolidone

PBS Phosphate buffered saline, 0.9% NaCl

EG Ethylene glycol

EG2 Diethylene glycol

MI Maleimide or maleimido

HPA-Ala Hydroxypropylamide-L-alanine

PHF poly(l-hydroxymethylethylene hydroxylmethylformal), or FLEXIMER®

RP-HPLC Reverse-phase high performance liquid chromatography

SEC Size exclusion chromatography

TCEP Tris[2-carboxyethyl]phosphine

TEA Triethylamine

TEAA Triethylammonium acetate

TFA Trifluoroacetic acid

WCX Weak cation exchange chromatography

General Information

Maleimido-EG2-NHS ester was purchased from Biomatrik, China.

Boc-diaminoethane HCl was purchased from Chem-Impex International Inc., Wood Dale, Ill.

Kadcyla® (ado-trastuzumab emtansine) for injection manufactured by Genentech was purchased.

HPLC purification was performed on a Phenomenex Gemini 5 μm 110 Å, 250×10 mm, 5 micron, semi-preparation column.

SEC was performed on a Tosoh Biosciences TSK gel G5000 column (7.8 mm×30 cm, 10 um) or Superose 12 column (GE Healthcare).

WCX was performed on ProPac WCX-10 (94 mm×250 mm) column (ThermoFisher).

Whenever possible the drug content of the conjugates was determined spectrophotometrically otherwise LC/MS was performed for quantitative determination of the drug content.

The protein content of the protein-polymer-drug conjugates was determined spectrophotometrically at 280 nm or by ELISA.

The molecular weights of the polymer conjugates (reported as the apparent weight average molecular weights or peak molecular weights) were determined by SEC with either polysaccharide or protein molecular weight standards. More specifically, for the polymer or polymer-drug conjugates, polysaccharide molecular weights standard were used, and for protein-drug-polymer conjugates, protein standards are used. Unless specifically indicated the reported polymer carrier molecular weight is the weight average molecular weight of PHF; and the polymer-drug conjugate molecular weight and the protein-polymer-drug conjugates is the peak molecular weight. The PBRM-polymer-drug conjugates have a peak molecular weight of about 160 kDa to about 260 kDa, e.g., about 170 kDa to about 230 kDa. The polymer and polymer conjugates synthesized/measured typically have a polydispersity ≤1.5.

PBRM-polymer-drug conjugates were isolated from residual unreacted drug-polymer conjugates by extensive diafiltration. If necessary, additional purification by size exclusion chromatography and/or WCX chromatography was conducted to remove any aggregated PBRM-polymer-drug conjugates. In general, the PBRM-polymer-drug conjugates typically contained <5% (w/w, e.g., <2% w/w) aggregated fraction as determined by SEC; <0.5% (w/w, e.g., <0.1% w/w) free (unconjugated) drug as determined by RP-HPLC or LC-MS/MS; <1% (w/w) of free polymer-drug conjugate as determined by SEC and/or RP-HPLC and <2% (w/w, e.g., <1% w/w) unconjugated PBRM as determined by HIC-HPLC and/or WCX HPLC. Reduced or partially reduced antibodies were prepared using procedures described in the literature, see, for example, Francisco et al., Blood 102 (4): 1458-1465 (2003). The total drug (conjugated and unconjugated) concentration was determined by LC-MS/MS;

To study the pharmacokinetic properties, i.e., time course of PBRM-polymer-drug conjugate absorption, distribution, metabolism, and excretion, assays were developed to measure the concentration of the PBRM-PHF-AF-HPA conjugate (i.e. conjugated AF-HPA) and concentration of the released, unconjugated AF-HPA and AF (free drug) in, e.g., plasma, tumor and tissue samples. To determine the concentration of the free drug in the sample, the acidified sample was treated with acetonitrile. The free drug was extracted from the supernatant and analyzed by LC-MS/MS. To determine the concentration of conjugated AF-HPA, the acidified plasma, tumor or tissue homogenate was subjected to basic hydrolysis followed by acidification and protein precipitation with acetonitrile. The acetonitrile supernatant containing the released AF-HPA and AF was analyzed by LC-MS/MS. The standard curves for the free drug and conjugated AF-HPA in plasma and tumor and tissue homogenates were linear over the concentration ranges of 0.3 to 3,000 ng/mL and 10 to 20,000 ng/mL, respectively. Total trastuzumab concentration was determined by ELISA.

In all the in vitro or in vivo experiments described herein, unless otherwise specified, the doses used were all based on the PBRM (e.g., antibody) of the PBRM-polymer-drug conjugates.

RP-HPLC, SDS-PAGE or capillary electrophorisis were used to characterize the specificity and distribution of the cysteine bioconjugation sites in the PBRM-polymer-drug conjugates. The results gave the positional distribution of the drug-polymer conjugates on the heavy (H) and light (L) chains of the PBRM and showed that conjugation to the PBRM occurred predominately at the heavy chain interchain cysteine hinge regions. Similar results were obtained with LC-MS PBRM peptide maps.

General Procedures

General Procedure A. Conjugation of Polymer with Linker or Drug

In general, the conjugation of the polymer (PHF-BA or PHF-GA) with an amine-containing linker, such as, for example, EG2-maleimide or an amine-containing linker drug, such as, for example, AF-HPA-Ala, HPA-Ala, is conducted in an aqueous or 10-90% organic/aqueous solvent mixture in the presence of an activating agent, such as, for example EDC.HCl. Typical organic solvents, include, but are not limited to, water miscible solvents, such as, for example, DMSO, DMF, DMA, NMP and ACN. To accelerate the coupling, a co-activator, such as, for example, NHS, is added. The polymer is first mixed with the amino-containing compound followed by addition of the co-activator (NHS) and then the addition of the activator (EDC.HCl). The reaction is conducted at 0-10° C., pH 4.5 to 7.5 for 1 h to 24 hours at ambient temperature. The resulting polymer conjugated product is purified by diafiltration or by SEC. The product is concentrated to 2-50 mg/mL, the pH is adjusted to 4.5 to 6.5 to insure drug-polymer linker stability and the conjugate is stored frozen at −20 to −80° C. until further use.

The conjugation of the polymer with the amine-containing linker or drug can conducted sequentially, in any order, or simultaneously.

General Procedure B. Partial Selective Reduction of Protein (PBRM)

The partial selective reduction of the inter-chain disulfide groups or unpaired disulfide in the relevant PBRM prior to conjugation with the polymer-drug conjugate is achieved by using a reducing agent, such as, for example, TCEP, DTT or β-mercaptoethanol. When the reduction is performed with an excess of the reducing agent, the reducing agent is removed prior to conjugation by SEC. The degree of conversion of the PBRM disulfide groups into reactive sulfhydryl groups depends on the stoichiometry of PBRM, reducing agent, pH, temperature and/or duration of the reaction. When some but not all of the disulfide groups in the PBRM are reduced, the reduced PBRM is a partially reduced PBRM.

General Procedure C. Conjugation of Partially Reduced PBRM with Polymer Drug Conjugate The conjugation of the partially reduced PBRM to the polymer-drug conjugate is conducted under neutral or slightly basic conditions (pH 6.5-8.5) at PBRM concentrations of 1-10 mg/mL and polymer-drug conjugate concentration of 0.5-10 mg/mL. The polymer-drug conjugate is typically used in 1-5.0 fold excess relative to the desired protein-polymer-drug conjugate stoichiometry. When the PBRM is conjugated to the maleimido group of the polymer-drug conjugate, the conjugation is optionally terminated by the addition of a water-soluble maleimido blocking compound, such as, for example, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol, and the like.

The resulting PBRM-polymer-drug conjugate is typically purified by diafiltration to remove any unconjugated polymer-drug conjugate, unconjugated drug and small molecule impurities. Alternatively or additionally, appropriate chromatographic separation procedures such as, for example, size-exclusion chromatography, hydrophobic interaction chromatography, ion chromatography such as, for example, WCX chromatography; reversed phase chromatography, hydroxyl apatite chromatography, affinity chromatography or combination thereof may be used to purify the PBRM-polymer-drug conjugate. The resulting purified PBRM-polymer-drug conjugate is typically formulated in a buffer at pH 5.0-6.5.

In general, the PBRM-polymer-drug conjugates had a peak molecular weight of about 170 kDa to about 230 kDa. The polymer and polymer conjugates synthesized/measured typically have a polydispersity <1.5. The polymer-drug conjugates (i.e., the drug-carrying polymer chain attached to antibody) contained about 27% mol to about 33% mol beta-alanine, about 6.4% mol to about 9.6% mol drug (e.g., AF-HPA-Ala) and about 1.5% mol to about 4% mol EG2-maleimide.

Example 1

Synthesis of EG2-maleimide: (O—[N-(3-maleimidopropionyl)aminoethyl]-O'-[3-(N-(2-aminoethyl)amino)-3-oxopropyl]ethylene glycol)

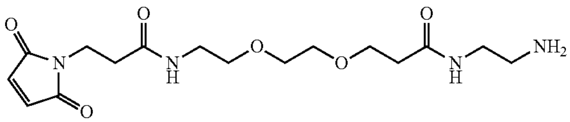

("EG2-maleimide" or "EG2-MI")

To an ice-cold suspension of maleimido-EG2-NHS ester (O—[N-(3-maleimidopropionyl)aminoethyl]-O'-[3-(N-succinimidyloxy)-3-oxopropyl]ethylene glycol, 1.2 g, 2.82 mmol) and Boc-diaminoethane hydrochloride (560 mg, 2.82 mmol) in ACN (15 mL) was added TEA (0.571 g, 5.64 mmol) dropwise while stirring. The resulting mixture was brought to room temperature and the stirring continued overnight at room temperature. Additional BOC-diaminoethane hydrochloride was added (110 mg) to drive the reaction to completion. The reaction mixture was concentrated under vacuum and the residue purified on reverse phase HPLC (0-100% ACN in water) to give Boc-diaminoethane-EG2-maleimide as a colorless solid (1.18 g, 89% yield). ESI MS: calculated $C_{21}H_{35}N_4O_8$ $[M+H]^+$ 471.3. found 471.2.

The Boc-diaminoethane-EG2-maleimide (1.18 g, 2.508 mmol) was dissolved in a 30% TFA solution in DCM (20 mL) at 0° C., the resulting solution was stirred for 2 hours at room temperature. The crude reaction mixture was concentrated under vacuum and then purified on reverse phase HPLC (0-10% ACN in water containing 0.1% TFA) to afford the title compound (EG2-maleimide) as a colorless oil (1.04 g, 86%).

$^1$H NMR (400 MHz, DMSO-$d_6$+$D_2O$): δ 6.95 (s, 2 H), 3.66-3.54 (m, 10 H), 3.34 (t, 2 H, J=5.6 Hz), 3.27 (t, 2 H, J=6.7 Hz), 3.18-3.10 (m, 2 H), 2.84 (t, 2 H, J=6.2 Hz), 2.33 (q, 4 H, J=6.7 Hz); ESI MS: calculated for $C_{16}H_{27}N_4O_6$ [M+H'] 371.2. found 371.2.

Example 2

Synthesis of 10K PHF-BA (30%)-EG2-MI (3%)

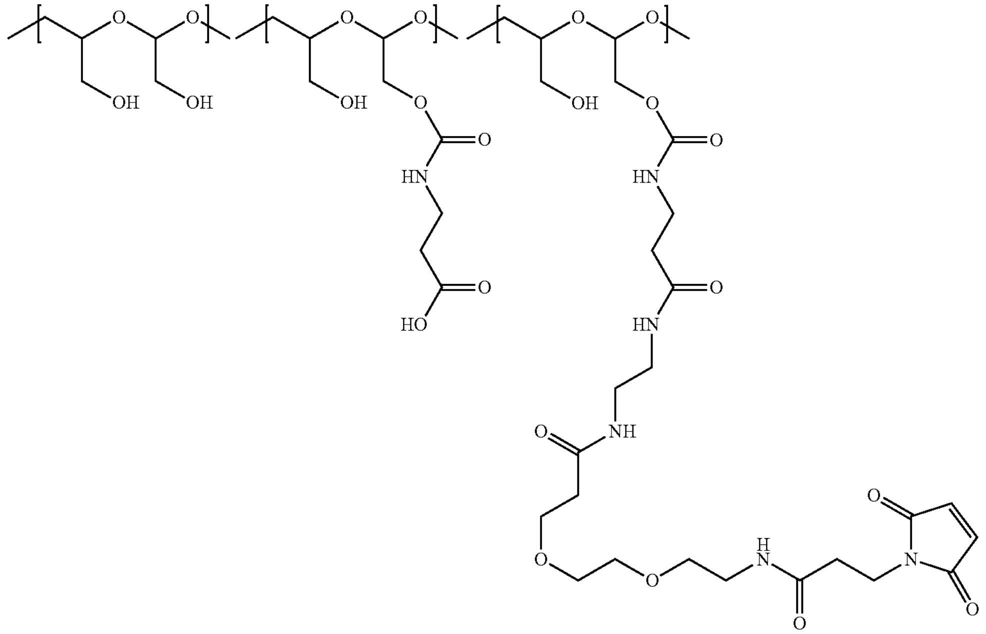

To a solution of 10K PHF-BA (30%) (588 mg, 3.46 mmol. prepared as described in U.S. Ser. No. 13/493,899, now U.S. Pat. No. 8,685,383, Example 1) in water (10 mL) was added a solution of EG2-maleimide (102 mg, 0.211 mmol, prepared as described in Example 1) in water (5 mL) followed by the addition of N-hydroxy-succinimide (NHS, 25 mg, 0.211 mmol). The resulting mixture was cooled to 5-10° C., and the pH was adjusted to 5.8 (from 5.3) using 0.1N NaOH solution. Then EDC.HCl (94 mg, 0.486 mmol) in water (2 mL) was added to the reaction mixture over 40 minutes. The reaction mixture was brought to room temperature and the stirring continued at room temperature for 18 hours. The resulting product was purified by diafiltration on 3K MWCO membrane and lyophilzied to give the title compound as an off-white solid product (0.460 g, 71% yield).

$^1$H-NMR (400 MHz, $D_2O$): 6.9 ppm (broad singlet, MI), 5.0-4.7 ppm (m, 1H, O—C<u>H</u>—O—, acetal-proton polymer), 4.3-3.6 ppm (m, O—$CH_2$— polymer back bone and linker protons), 3.4-3.3 ppm (m, C<u>H</u>$_2$—NH—, beta-alanine and linker protons), 2.7-2.4 ppm (m, C<u>H</u>$_2$—COOH—, beta-alanine and linker protons).

The EG2-MI linker loading (i.e., content of polymer units containing EG2-MI linker) determined by $^1$H-NMR was 3% mol of the polymer structural units.

Example 3

Synthesis of 10K PHF-BA (30%)-EG2-MI (3%)-AF-HPA-Ala (8%)

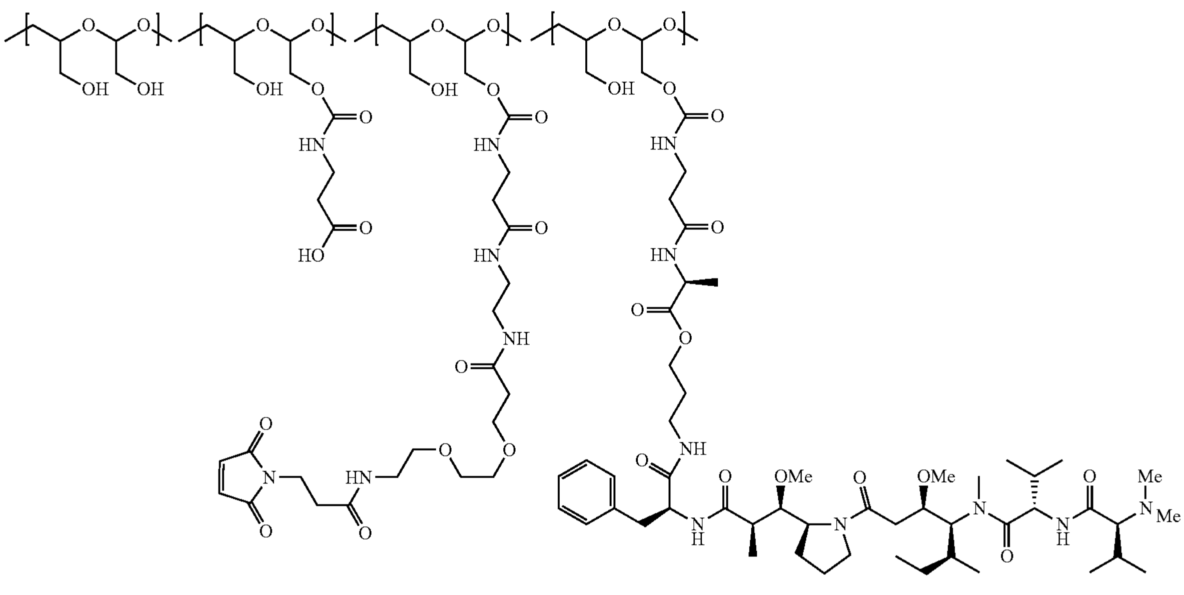

A homogeneous solution of 10K PHF-BA (30%) EG2-MI (3%) (144 mg, 11.08 μmol, prepared as described in Example 2) in water (4.2 g) was chilled to 5-10° C. The pH of the solution was adjusted to 5.8 using 1N HCl, followed by addition of Auristatin F-hydroxypropylamide-L-Alanine 2TFA (AF-HPA-Ala.2TFA) (85 mg, 77.52 μmol, prepared as described in U.S. Ser. No. 13/493,899, now U.S. Pat. No. 8,685,383, Example 50) dissolved in NMP (1.4 mL) and NHS (16 mg in 0.5 mL water). The mixture was stirred vigorously at 5-10° C. and the pH of the solution was adjusted to 5.8 with 0.1N NaOH. To the resulting mixture was added a freshly prepared aqueous solution of EDC.HCl (30 mg in 0.5 mL water). After 45 minutes additional EDC.HCl (30 mg in 0.5 mL water) was added and the resulting mixture was stirred for 18-24 hours while maintained the pH at 5.8. The RP HPLC analysis of the reaction mixture indicated >95% consumption of the starting material auristatin compound. The product was purified by diafiltration on 3K MWCO membrane, followed by purification by HPLC and lyophilzation to give the title compound (143 mg, 78% yield).

$^1$H-NMR (400 MHz, $D_2O$): 7.15 ppm (broad singlet, AF-HPA aromatic protons), 6.9 ppm (broad singlet, MI), 5.0-4.8 ppm (m, 1H, O—C<u>H</u>—O-acetal-proton polymer), 4.4-3.6 ppm (m, O—$CH_2$— polymer back bone and drug/linker protons), 3.4-2.8 ppm (m, C<u>H</u>$_2$—NH—, beta-alanine and drug/linker protons), 2.2-1.8 ppm (m, C<u>H</u>$_2$—COOH—, beta-alanine and drug/linker protons) and 1.6-0.9 ppm (m, drug/linker protons).

The drug loading of the conjugated product (i.e., content of polymer units containing the drug) determined by $^1$H-NMR was 8% mol of the polymer structural units (or on average about 6 AF-HPA molecules per polymer chain). The molecular weight of the title conjugate was about 17 kDa.

Example 4

Synthesis of Trastuzumab-((EG2-MI (3%))-(10 kDa PHF-BA (30%)-(AF-HPA-Ala (8%))

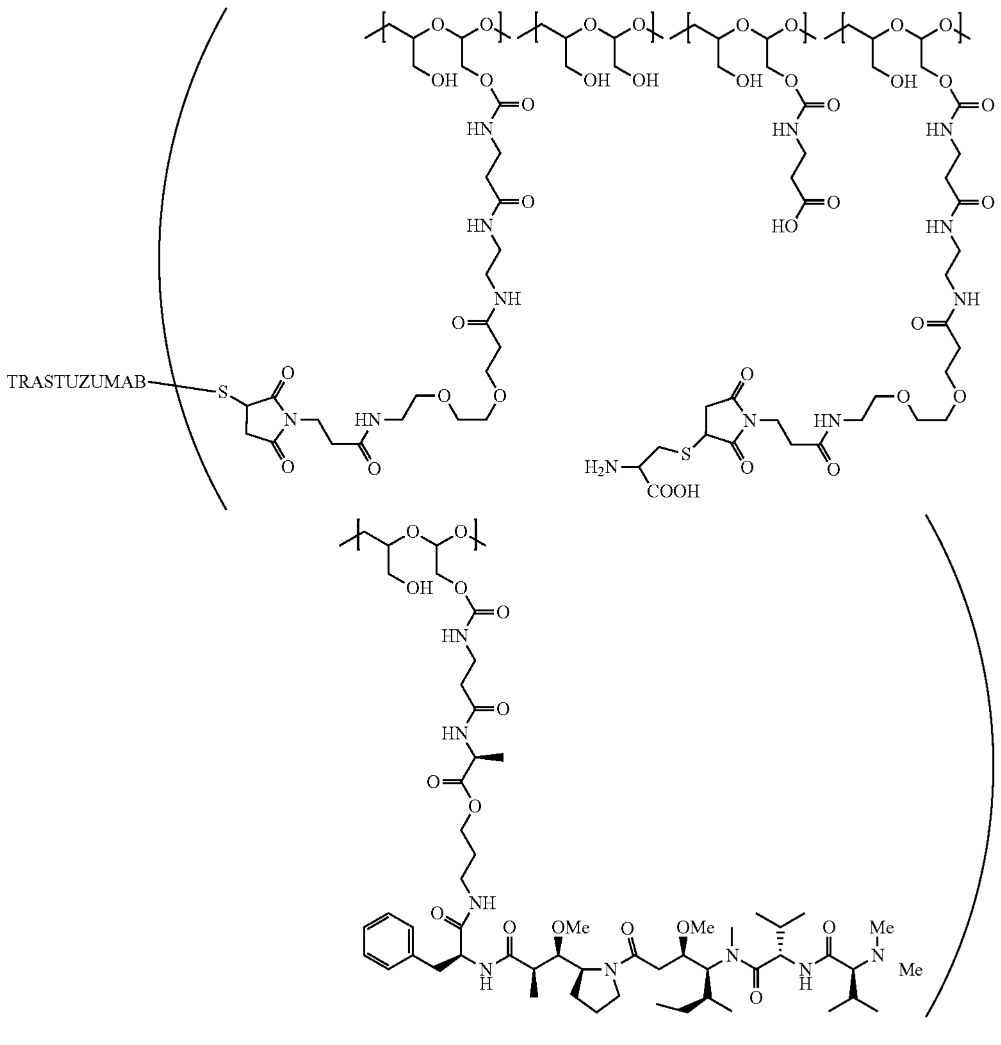

To a solution of trastuzumab (6.19 mL, 100 mg, 0.676 μmol) in TEAA buffer was added a solution of TCEP (0.6 mL, 2.36 μmol, 0.678 mg) while stirring. The mixture was incubated for 1 hour at 37° C., then cooled to ~0° C. The partially reduced trastuzumab was then added to a vigorously stirred solution of 10K PHF-BA (30%)-EG2-MI (3%)-AF-HPA-Ala (8%) (76 mg, prepared as described in Example 3) in TEAA buffer, pH 7.4 (26.5 mL) at 0° C. The stirring was continued for 30 min at 0° C. The reaction was quenched with an aqueous solution of cysteine hydrochloride (65 mg, 37 μmol, 1.9 mL). After stirring for 1 h at ambient temperature at pH 7.0, the reaction mixture was acidified to pH 5.0. The crude product was purified by chromatography followed by SEC purification to give the title compound (61 mg, 61% yield).

The AF-HPA to trastuzumab ratio was about 12:1 to about 17:1. The molecular weight of the title conjugate was 180 kDa, PDI 1.15. The average PHF-drug conjugate to trastuzumab ratio was about 2:1 to about 3:1 or about 3:1 to about 4:1.

PBRM-polymer-drug conjugate, trastuzumab-((PEG2-MI (3%))-(10 kDa PHF-BA (30%)-(AF-HPA-Ala (8%)) (2.5 μg, prepared as described above) was subjected to SDS-PAGE i.e., sodium dodecyl sulfate polyacrylamide gel electrophoresis) under non-reducing and reducing conditions and visualized with Odyssey IRDye® Blue Protein Stain Buffer. Under non-reducing conditions the conjugate was either heated at 70° C. for 10 minutes, or not heated prior to SDS-PAGE analysis.

The SGS-PAGE gels showed that the conjugate was stable and did not dissociate under non-reducing conditions, such as 70° C. for 10 minutes. Under reducing conditions the conjugate dissociated in to heavy and light chain fragments.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 5

Synthesis of 10K PHF-BA (30%)-AF-HPA-Ala (9%)

To a homogeneous solution of 10K PHF-BA (30%) (700 mg, prepared as described in U.S. Ser. No. 13/493,899, now U.S. Pat. No. 8,685,383, Example 1) in water (20 mL) was added auristatin F-hydroxypropylamide-L-alanine 2TFA (AF-HPA-Ala.2TFA) (460 mg, 417 μmol, prepared as described in U.S. Ser. No. 13/493,899, Example 50) dissolved in NMP (6.7 g). The resulting mixture was stirred vigorously while cooling to 5-10° C. The pH of the solution was adjusted to 5.8, followed by addition of NHS (129 mg in 1 mL water). To the resulting mixture was added a freshly prepared aqueous solution of EDC.HCl (223 mg in 1 mL water). After 30 minutes additional EDC.HCl (220 mg in 1 mL water) was added and the resulting mixture was stirred for 18 hours while maintained the pH at 5.8. The RP HPLC analysis of the indicated >95% consumption of the starting material auristatin compound. The product was purified by HPLC and lyophilzation to give the title compound (859 mg, 83% yield).

$^1$H-NMR (400 MHz, $D_2O$): 7.7-7.2 ppm (broad singlet, AF-HPA aromatic protons), 5.0-4.8 ppm (m, 1H, O—C<u>H</u>—O-acetal-proton polymer, partially buried under water signal), 4.4-3.6 ppm (m, O—$CH_2$— polymer back bone and drug/linker protons), 3.5-2.8 ppm (m, C$\underline{H}_2$—NH—, beta-alanine and drug/linker protons), 2.2-1.6 ppm (m, $CH_2$—COOH—, beta-alanine and drug/linker protons) and 1.6-0.8 ppm (m, drug/linker protons).

The drug loading of the conjugated product determined by $^1$H-NMR was 8.7% mol of the polymer structural units (or on average about 6 AF-HPA molecules per polymer chain).

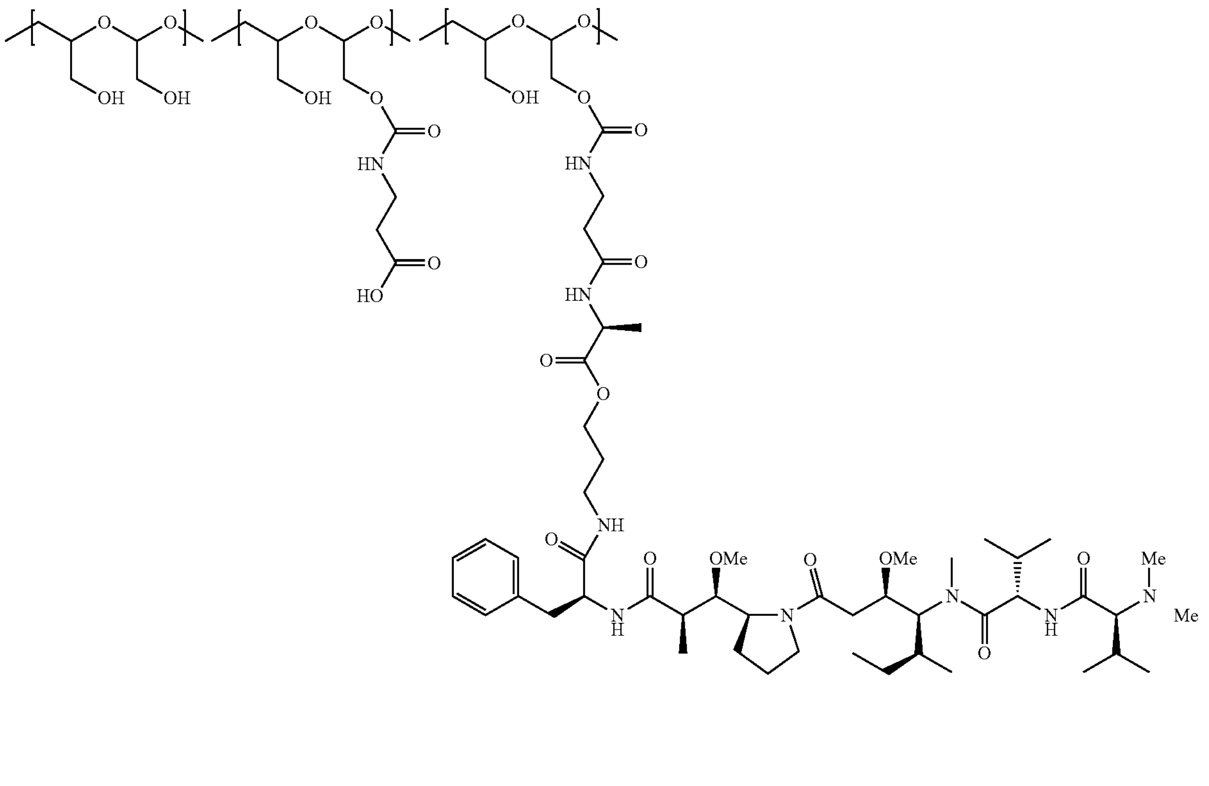

Example 6

Synthesis of 10K PHF-BA (30%)-EG2-MI (2%)-AF-HPA-Ala (9%)

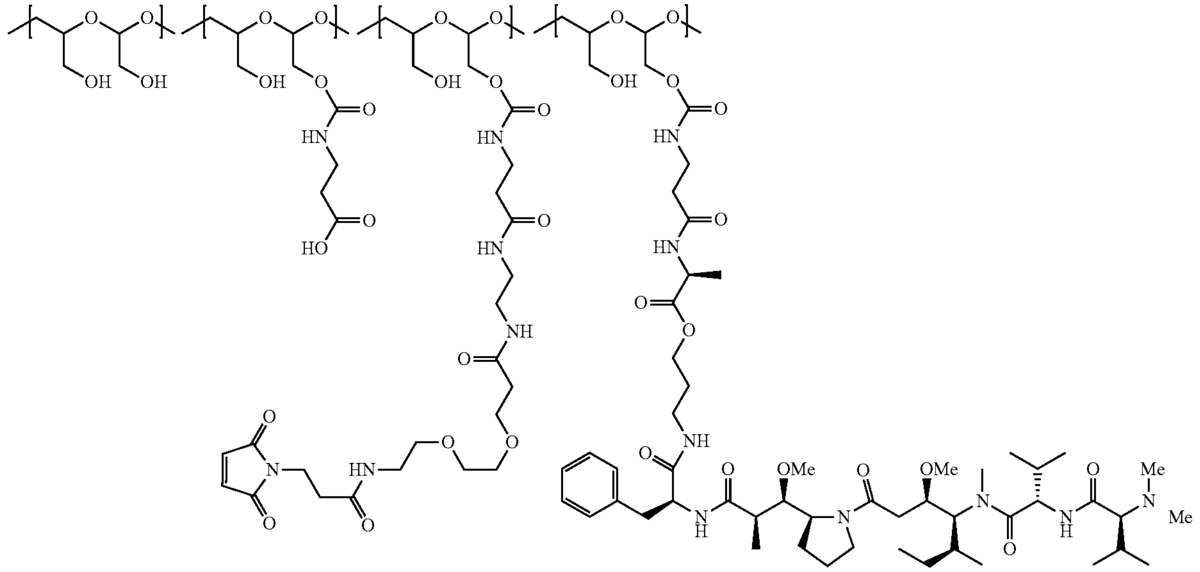

To a solution of 10K PHF-BA (30%)-AF-HPA-Ala (9%) (500 mg, 35 μmol. prepared as described in Example 5) in water (13.7 mL) was added a solution of EG2-maleimide (83 mg, 0.139 mmol, prepared as described in Example 1) followed N-hydroxy-succinimide (NHS, 40 mg, 0.348 mmol). The resulting mixture was cooled to 5-10° C., and the pH was adjusted to 5.8 (from 4.6) using 0.1N NaOH solution. Then EDC.HCl (174 mg, 0.91 mmol) in water (2 mL) was added to the reaction mixture over 40 minutes in two equal portions. The RP HPLC analysis of the reaction mixture indicated >95% consumption of the EG2-maleimide. The reaction mixture was brought to room temperature and the stirring continued at room temperature for 18 hours. The resulting product was purified by diafiltration on 3K MWCO membrane and lyophilzied to give the title compound as an off-white solid product (0.57 g, 100% yield).

$^1$H-NMR (400 MHz, $D_2O$): 7.4-7.2 ppm (broad singlet, AF-HPA aromatic protons), 6.9 ppm (broad singlet, MI), 5.0-4.8 ppm (m, 1H, O—CH—O-acetal-proton polymer, partially buried under water peak), 4.4-3.6 ppm (m, O—C$\underline{H}_2$— polymer back bone and drug/linker protons), 3.5-2.8 ppm (m, C$\underline{H}_2$—NH—, beta-alanine and drug/linker protons), 2.2-1.6 ppm (m, C$\underline{H}_2$—COOH—, beta-alanine and drug/linker protons) and 1.6-0.8 ppm (m, drug/linker protons).

The EG2-MI linker loading determined by $^1$H-NMR was ~2% mol of the polymer structural units. The molecular weight of the title compound was about 20 kDa. On average, there were 6 AF-HPA molecules per polymer chain.

Example 7

Synthesis of Trastuzumab-((EG2-MI (2%)-(10 kDa PHF-BA (30%)-(AF-HPA-Ala (9%))

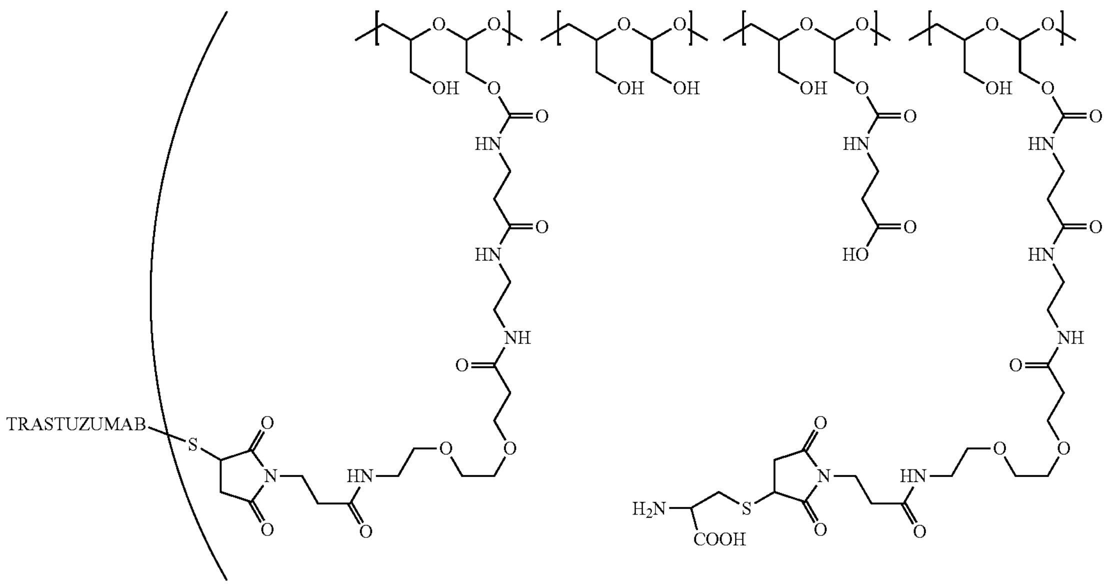

-continued

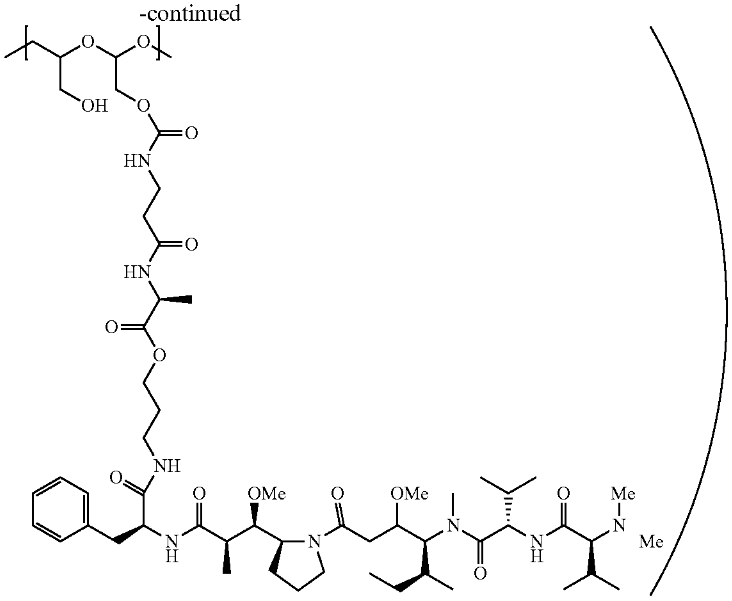

To a solution of trastuzumab (6.4 mL, 100 mg, 0.68 μmol) in TEAA buffer was added a solution of TCEP (0.993 mg) while stirring. The mixture was incubated for 1.5 h at room temperature. The partially reduced trastuzumab was then added to a vigorously stirred solution of 10K PHF-BA (30%)-EG2-MI (2%)-AF-HPA-Ala (9%) (86 mg, 4.7 μmol, prepared as described in Example 6) in TEAA buffer, pH 7.4 (26.5 mL) at 0° C. The stirring was continued for 45 minutes at room temperature. The reaction was quenched with an aqueous solution of cysteine in TEAA buffer, pH 6.8 (65 mg, 371 μmol, 1.9 mL). After stirring for 1 h at ambient temperature at pH 7.0, the reaction mixture was acidified to pH 5.8. The crude product was purified by SEC purification to give the title compound (35 mg, 35% yield).

The AF-HPA to trastuzumab ratio was about 16:1 to about 21:1. The molecular weight of the title conjugate was 210 kDa. The average PHF-drug conjugate to trastuzumab ratio was about 2:1 to about 3:1 or about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 8

Synthesis of Lintuzumab-((EG2-MI (2%)-(10 kDa PHF-BA (30%)-(AF-HPA-Ala (9%))

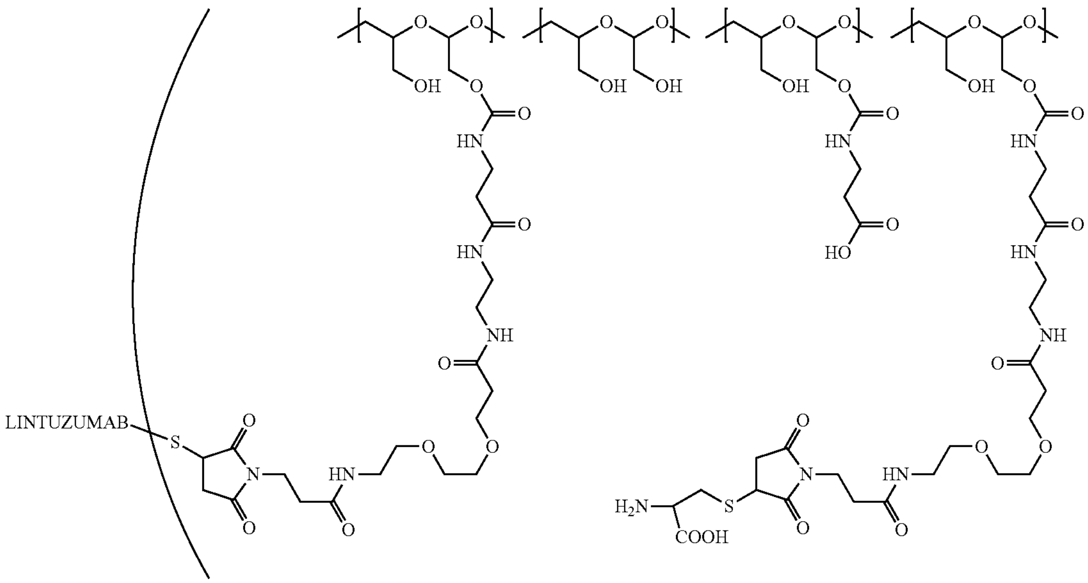

-continued

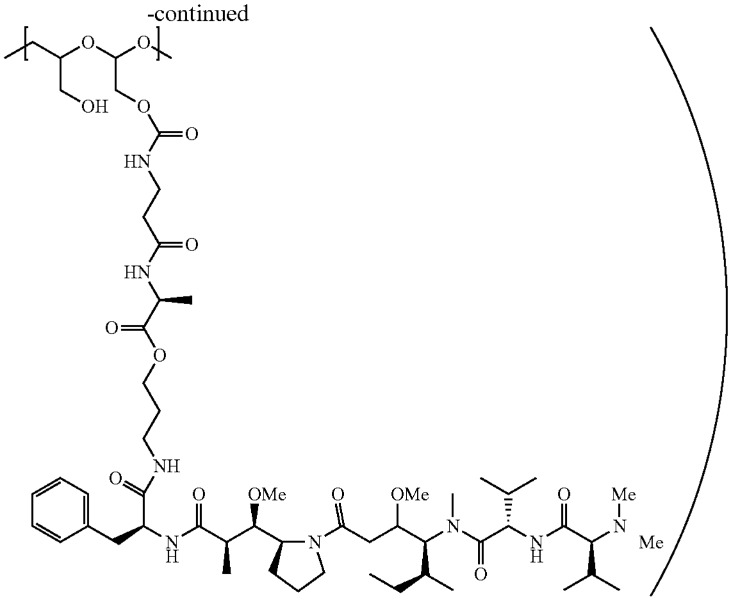

The title compound was prepared using the procedure described in Example 4 or Example 7 except 10K PHF-BA (30%)-EG2-MI (2%)-AF-HPA-Ala (9%) (prepared as described in Example 6) and lintuzumab were used.

The AF-HPA to lintuzumab ratio was about 10:1 to about 15:1. The molecular weight of the title conjugate was 184 kDa. The average PHF-drug conjugate to lintuzumab ratio was about 2:1 to about 3:1 or about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 9

Synthesis of Rituximab-((EG2-MI (3%)-(10 kDa PHF-BA (30%)-(AF-HPA-Ala (8%))

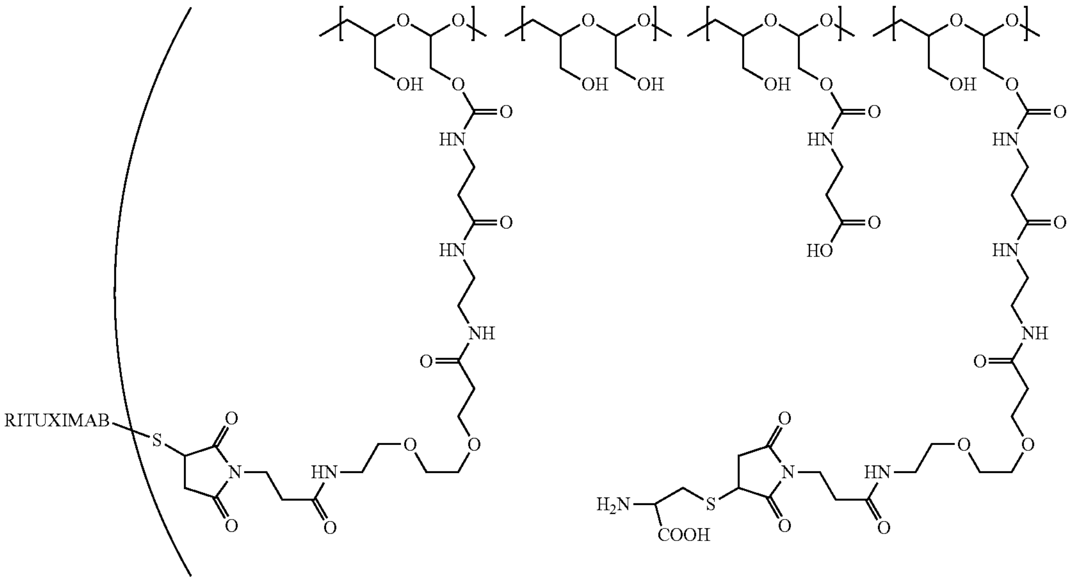

-continued

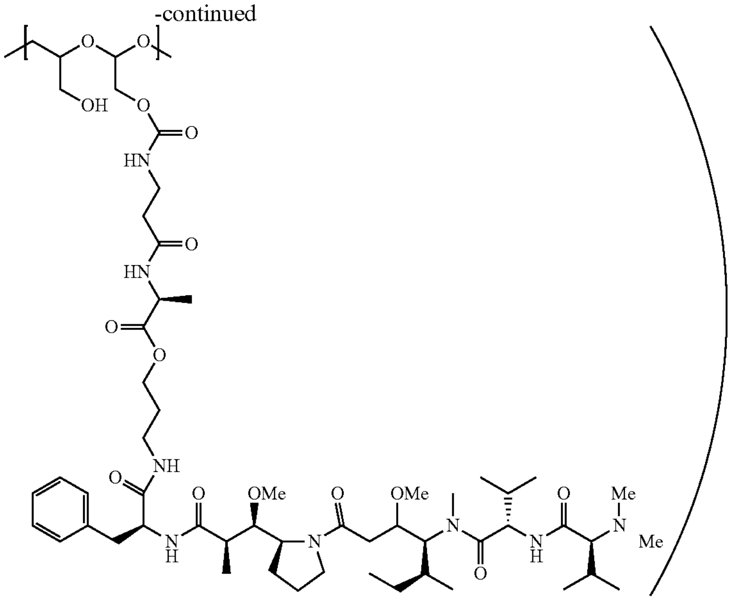

The title compound was prepared using the procedure described in Example 4 or Example 7 except 10K PHF-BA (30%)-EG2-MI (3%)-AF-HPA-Ala (8%) (prepared as described in Example 3) and rituximab were used.

The AF-HPA to rituximab ratio was about 13:1 to about 18:1. The molecular weight of the title conjugate was 163 kDa. The average PHF-drug conjugate to rituximab ratio was about 2:1 to about 3:1 or about 3:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 10

Synthesis of Trastuzumab-((EG2-MI (2.5%)-(10 kDa PHF-BA (28%)-(AF-HPA-Ala (8.4%)

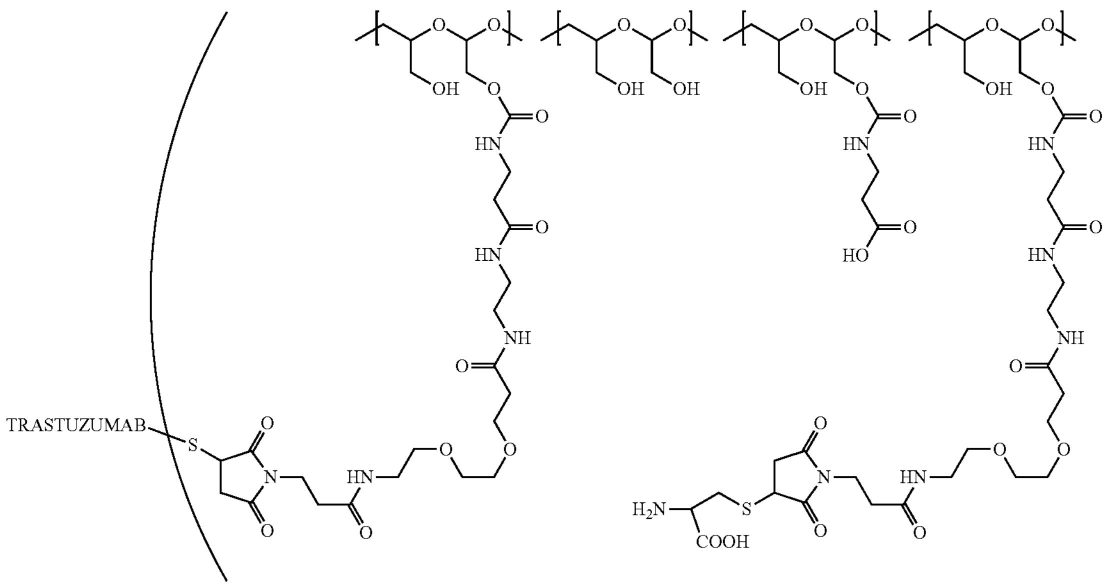

-continued

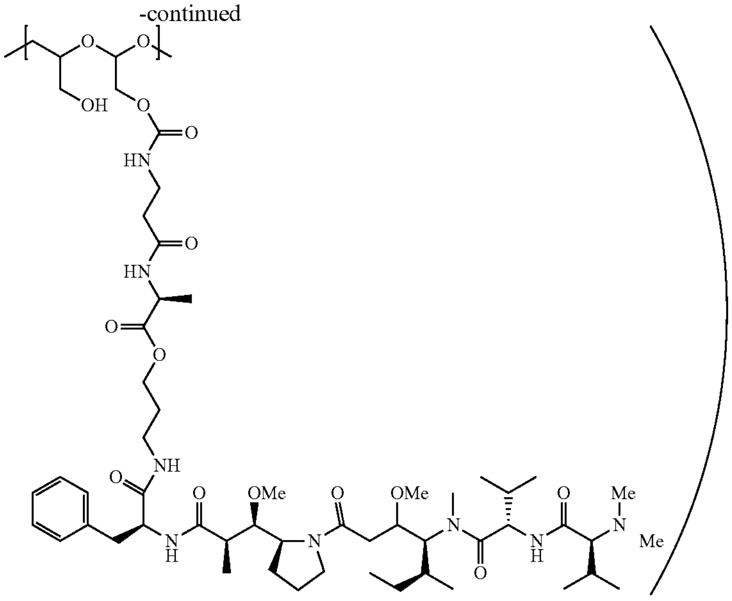

The title compound was prepared using the procedure described in Example 15 except that 10 kDa PHF-BA (28%)-EG2-MI (2.5%)-AF-HPA-Ala (8.4%) was used.

The AF-HPA to trastuzumab ratio was about 11:1 to about 16:1. The molecular weight of the title conjugate was 210 kDa. The average PHF-drug conjugate to trastuzumab ratio was about 2:1 to about 4:1.

PBRM are obtained by varying the number of PBRM sulfhydryl groups and drug-polymer conjugate drug load.

Example 11

Synthesis of 10K PHF-GA (29%)-EG2-MI (1%)

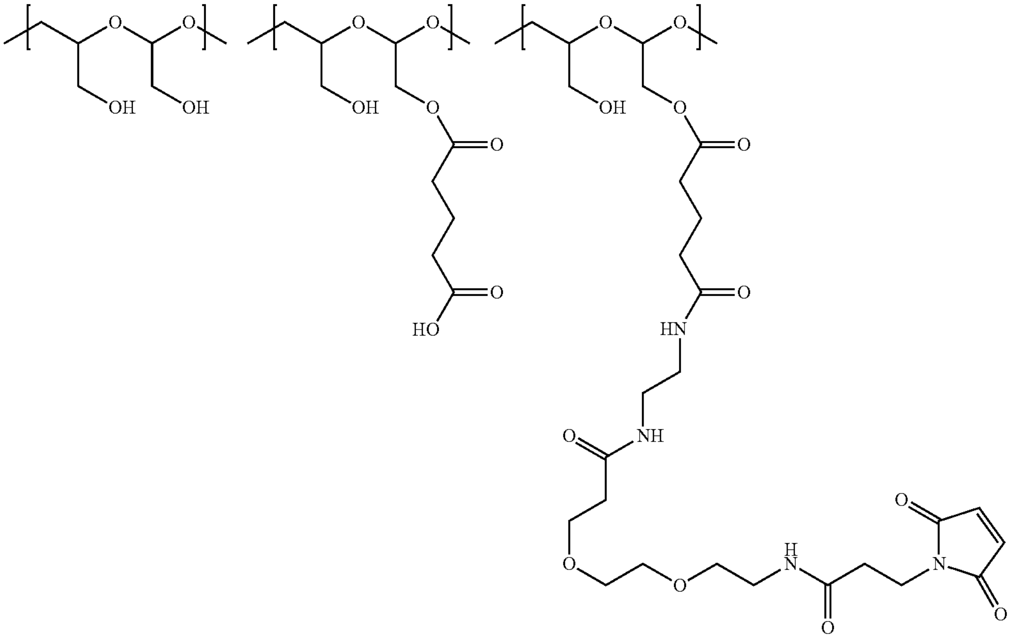

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to To a solution of 10K PHF-GA (29%) (1.7 g, 10.1 mmol, prepared as described in U.S. Ser. No. 13/493,899, now U.S. Pat. No. 8,685,383, Example 2) in water (35 mL) was added a solution of EG2-maleimide (204 mg, 0.42 mmol, prepared as described in Example 1) in DMA (3 mL) followed by the addition of N-hydroxy-succinimide (NHS, 70.3 mg, 0.611 mmol). The resulting mixture was cooled to 5-10° C. Then EDC.HCl (269 mg, 1.402 mmol) in water (2 mL) was added to the reaction mixture in two equal portions over 40 minutes. The reaction mixture was brought to room temperature and the stirring continued at room temperature for 18 hours. The resulting product was purified by diafiltration on 3K MWCO membrane and lyophilzied to give the title compound as an off-white solid product (1.7 g, 91% yield).

$^1$H-NMR (400 MHz, $D_2O$): 6.9 ppm (broad singlet, MI), 5.0-4.7 ppm (m, 1H, O—C<u>H</u>—O—, acetal-proton polymer, partially buried under water peak), 4.4-3.6 ppm (m, O—$CH_2$— polymer back bone and linker protons), 3.3-2.6 ppm (m, linker protons), 2.5 ppm (m, C<u>H</u>$_2$—CO—, glutaric protons), 2.3 ppm (broad singlet, C<u>H</u>$_2$—COO—, glutaric protons), 1.9 ppm (broad singlet, —$CH_2$—C<u>H</u>$_2$— $CH_2$—CO—, glutaric protons).

The EG2-MI linker loading determined by $^1$H-NMR was 1% mol of the polymer structural units.

Example 12

Synthesis of 10K PHF-GA (29%)-EG2-MI (1%)-AF-HPA-Ala (6%)

A homogeneous solution of 10K PHF-BA (29%)-EG2-MI (1%) (214 mg, 15 μmol, prepared as described in Example 11) in water (5.4 g) was added AF-HPA-Ala.2TFA) (98 mg, 90 μmol, prepared as described in U.S. Ser. No. 13/493,899, Example 50) dissolved in NMP (1.85 mL) and NHS (25 mg in 0.5 ml, water). The mixture was stirred vigorously at 5-10° C. To the resulting mixture was added a freshly prepared aqueous solution of EDC.HCl (40 mg in 0.8 mL water). After 30 minutes additional EDC.HCl (44 mg in 0.8 mL water) was added and the resulting mixture was stirred for 18-24 hours while maintained the pH at 5.8. The RP HPLC analysis of the indicated >95% consumption of the starting material auristatin compound. The product was purified by diafiltration on 3K MWCO membrane and concentrated to 10 mL to give the title compound (177 mg, 63% yield).

$^1$H-NMR (400 MHz, $D_2O$): 7.4-7.2 ppm (broad singlet, AF-HPA aromatic protons), 6.9 ppm (broad singlet, MI), 5.0-4.8 ppm (m, 1H, O—CH—O—, acetal-proton polymer), 4.4-3.6 ppm (m, O—$CH_2$— polymer back bone and linker protons), 3.4-2.9 ppm (m, drug linker protons), 2.5 ppm (broad triplet, CO— $CH_2$—, glutaric protons), 24-2.2 ppm (m, C<u>H</u>$_2$—COO—, glutaric protons and drug/linker protons), 2.0-1.8 ppm (m, —$CH_2$—C<u>H</u>$_2$—$CH_2$—CO—, glutaric protons), 1.5-0.8 (m, drug/linker protons).

The conjugated product drug loading determined by $^1$H-NMR was 5.9% mol of the polymer structural units (or on average about 4.5 AF-HPA molecules per polymer chain). The molecular weight of the title conjugate was about 17 kDa.

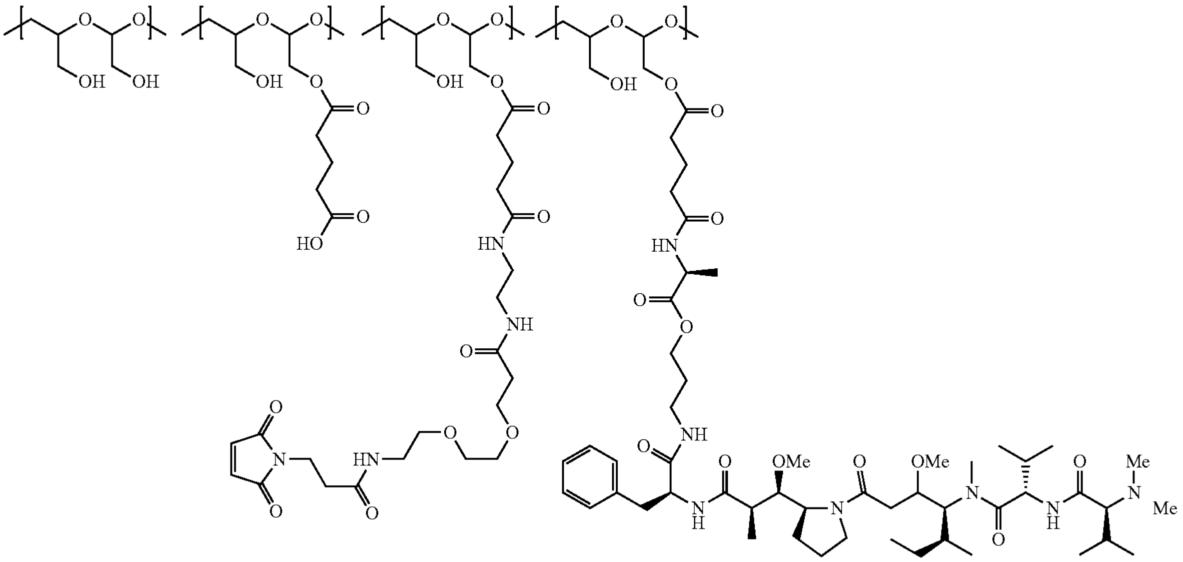

Example 13

Synthesis of Trastuzumab-((EG2-MI (1%))-(10 kDa PHF-GA (29%)-(AF-HPA-Ala (6%))

Other PBRM-polymer-drug conjugates are synthesized with methods similar to the procedure described above, involving other PBRM derivatives, such as, for example, partially reduced form of cetuximab, rituximab, bevaci as described in Example 12) and trastuzumab (25 mg) were used.

The AF-HPA to trastuzumab ratio was about 18:1 to about 23:1. The molecular weight of the title conjugate was 200 kDa. The average PHF-drug conjugate to trastuzumab ratio was about 4:1 to about 5:1.zumab, nimotuzumab, gemtuzumab, alemtuzumab, lintuzumab, anti-5T4 or anti-mesothelin antibodies. Also PBRM-polymer-drug conjugates

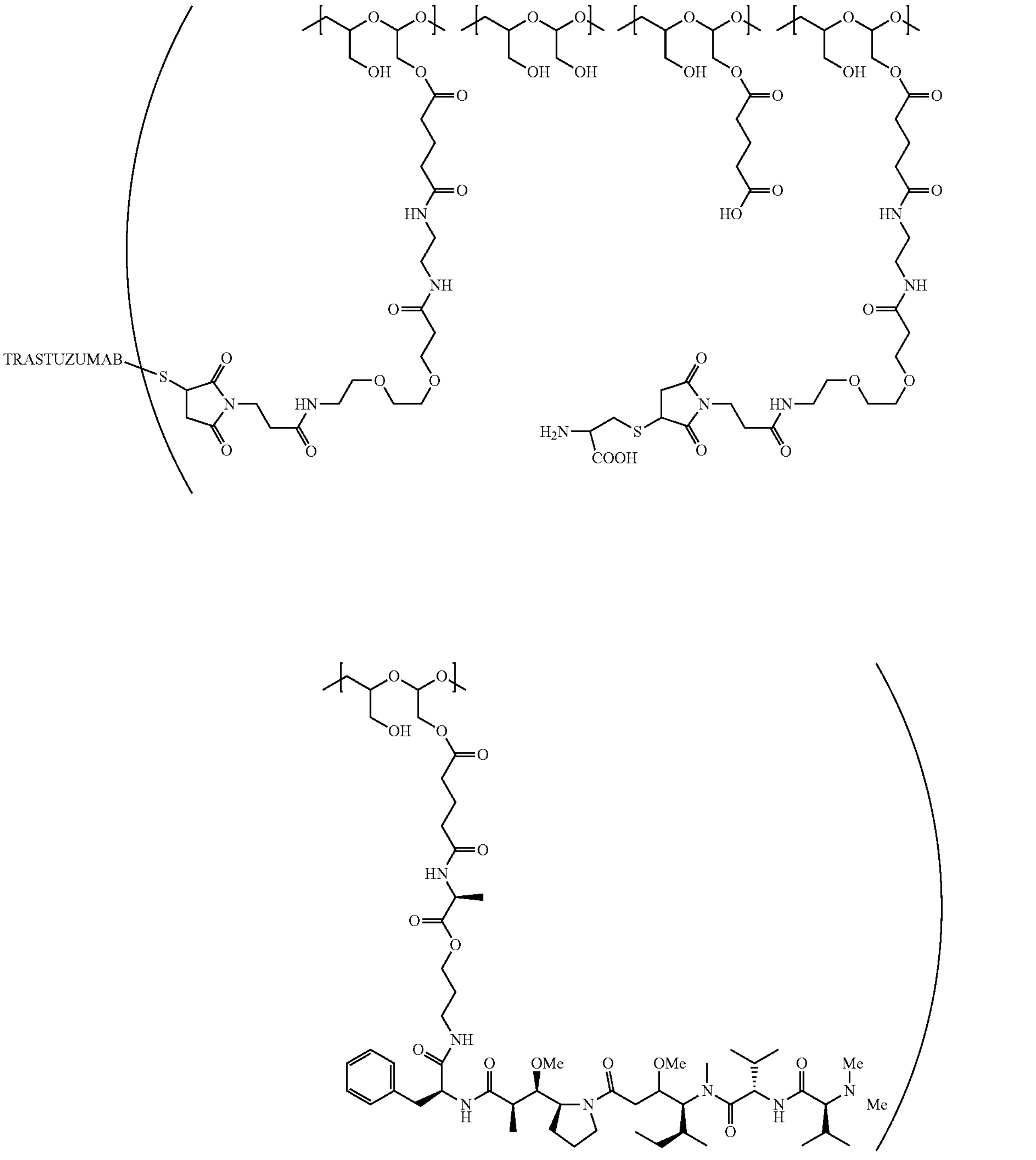

The title compound was prepared using the procedure described in Example 4 or Example 7 except 10K PHF-GA (29%)-EG2-MI (1%)-AF-HPA-Ala (6%) (78 mg, prepared with varying ratios of drug to PBRM are obtained by varying the number of PBRM sulfhydryl groups and drug-polymer conjugate drug load.

Example 14

Synthesis of Trastuzumab-((EG2-MI (2%)-(10 kDa PHF-BA (28%)-(AF-HPA-Ala (9%)

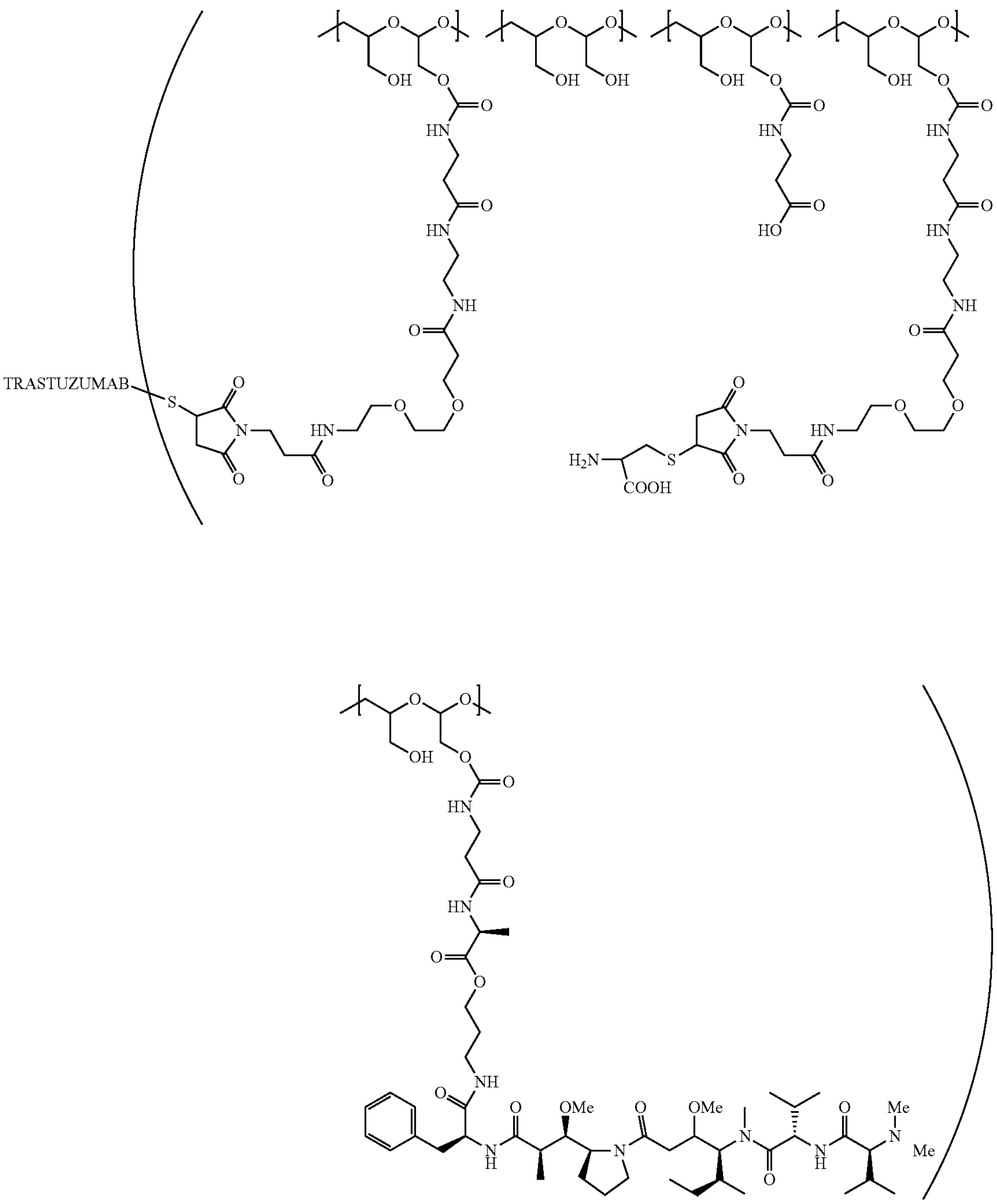

The title compound was prepared using the procedure described in Example 4 or Example 7 except 10K PHF-BA (28%)-EG2-MI (2%)-AF-HPA-Ala (9%) (11 mg, prepared using the procedure described in Example 6) and trastuzumab (620 mg) were used.

The AF-HPA to trastuzumab ratio was about 10:1 to about 15:1. The molecular weight of the title conjugate was 183 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 15

Synthesis of Trastuzumab-((EG2-MI (2%)-(10 kDa PHF-BA (28%)-(AF-HPA-Ala (9%)

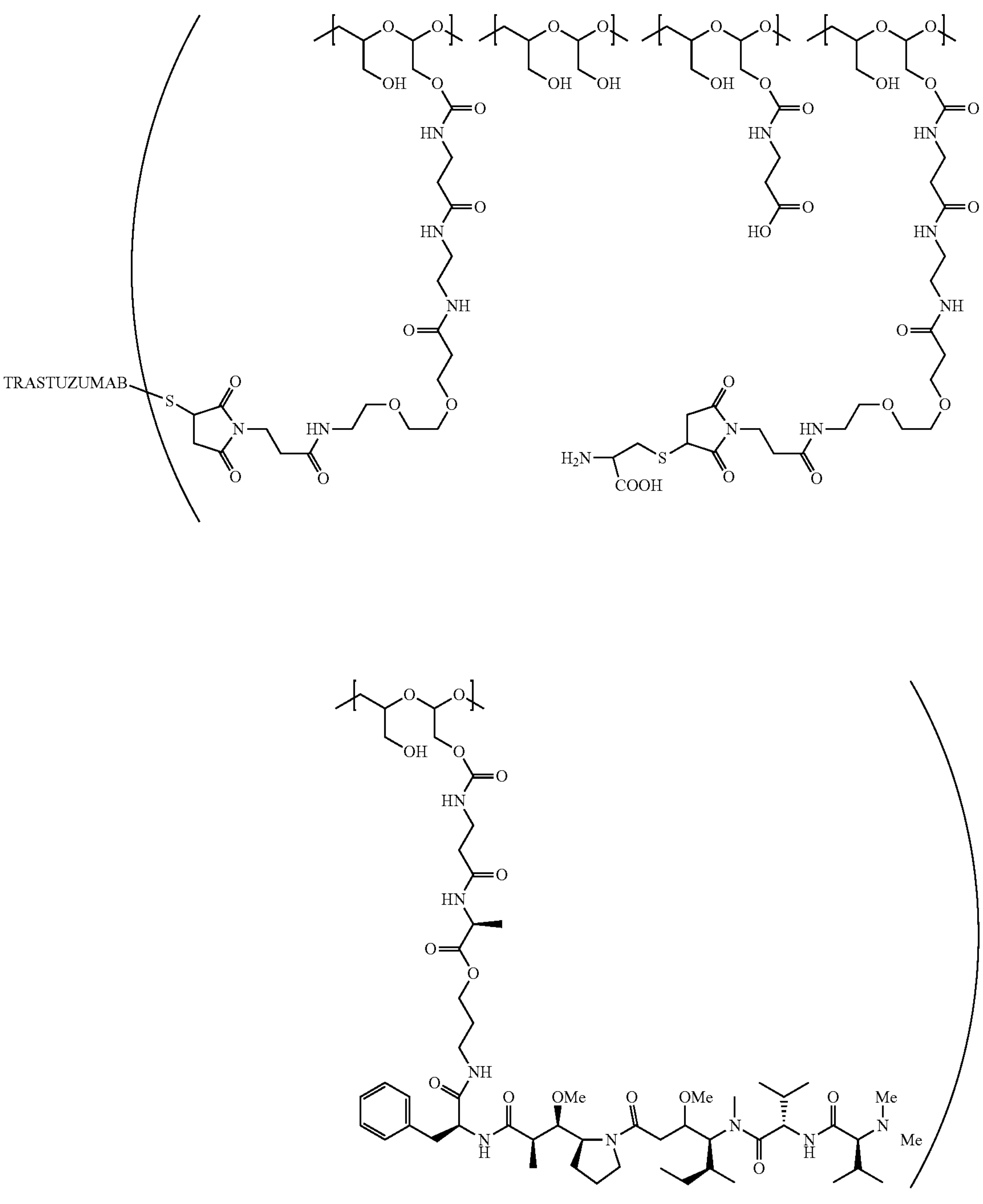

The title compound was prepared using the procedure described in Example 4 or Example 7 except 10K PHF-BA (28%)-EG2-MI (2%)-AF-HPA-Ala (9%) (243 mg, prepared using the procedure described in Example 6) and trastuzumab (435 mg) were used.

The AF-HPA to trastuzumab ratio was about 11:1 to about 16:1. The molecular weight of the title conjugate was 197 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 16

Synthesis of Rituximab-((EG2-MI (2%)-(10 kDa PHF-BA (28%)-(AF-HPA-Ala (9%))

kDa. The average PHF-drug conjugate to rituximab ratio was about 3:1 to about 4:1.

Other PBRM-polymer-drug conjugates are synthesized with methods similar to the procedure described above, involving other PBRM derivatives, such as, for example,

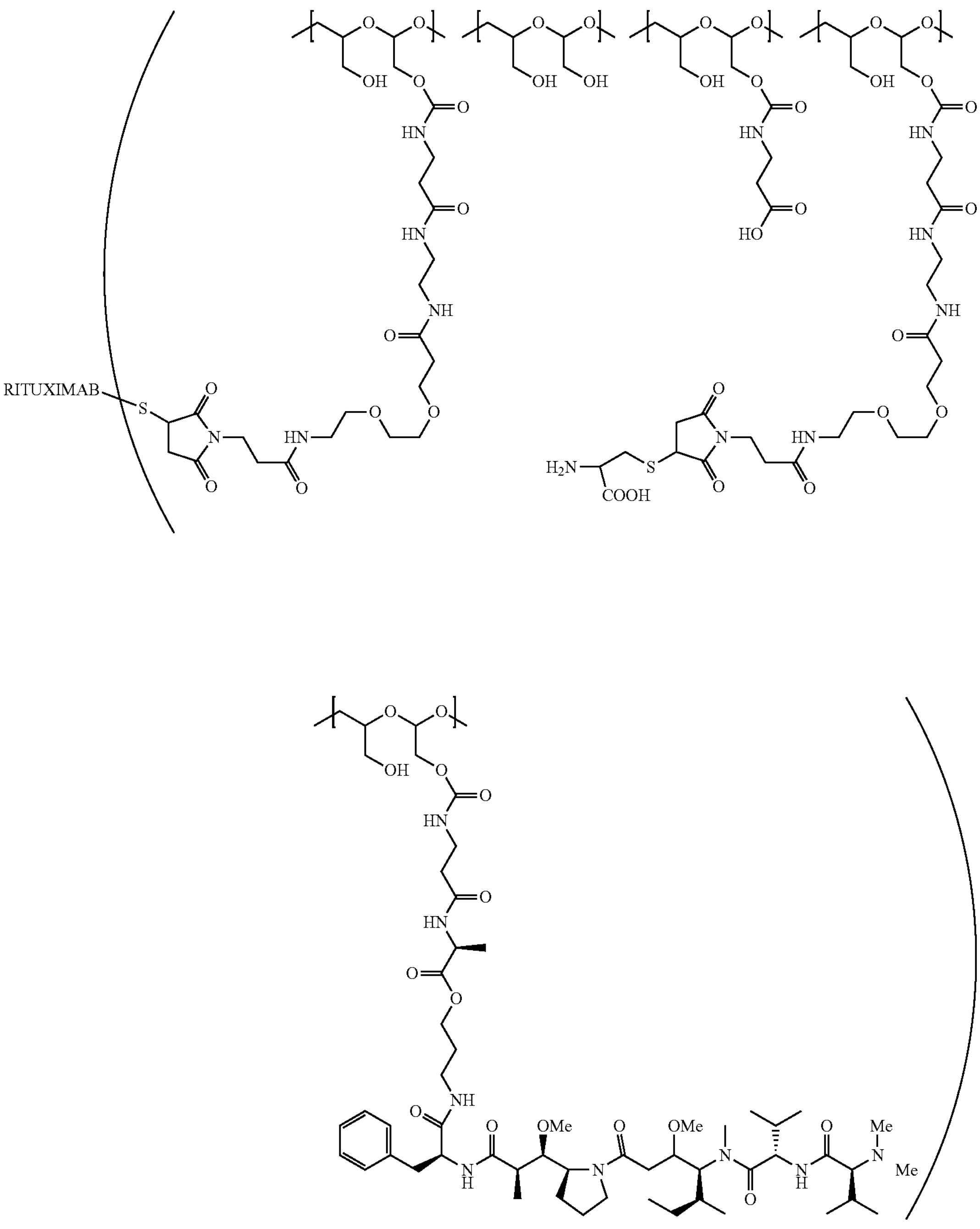

The title compound was prepared using the procedure described in Example 4 or Example 7 except 10K PHF-BA (28%)-EG2-MI (2%)-AF-HPA-Ala (9%) (170 mg, prepared using the procedure described in Example 6) and 300 mg rituximab were used.

The AF-HPA to rituximab ratio was about 13:1 to about 18:1. The molecular weight of the title conjugate was 180 partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 17

Synthesis of Trastuzumab-((EG2-MI (2%)-(10 kDa PHF-BA (28%)-(AF-HPA-Ala (9%)

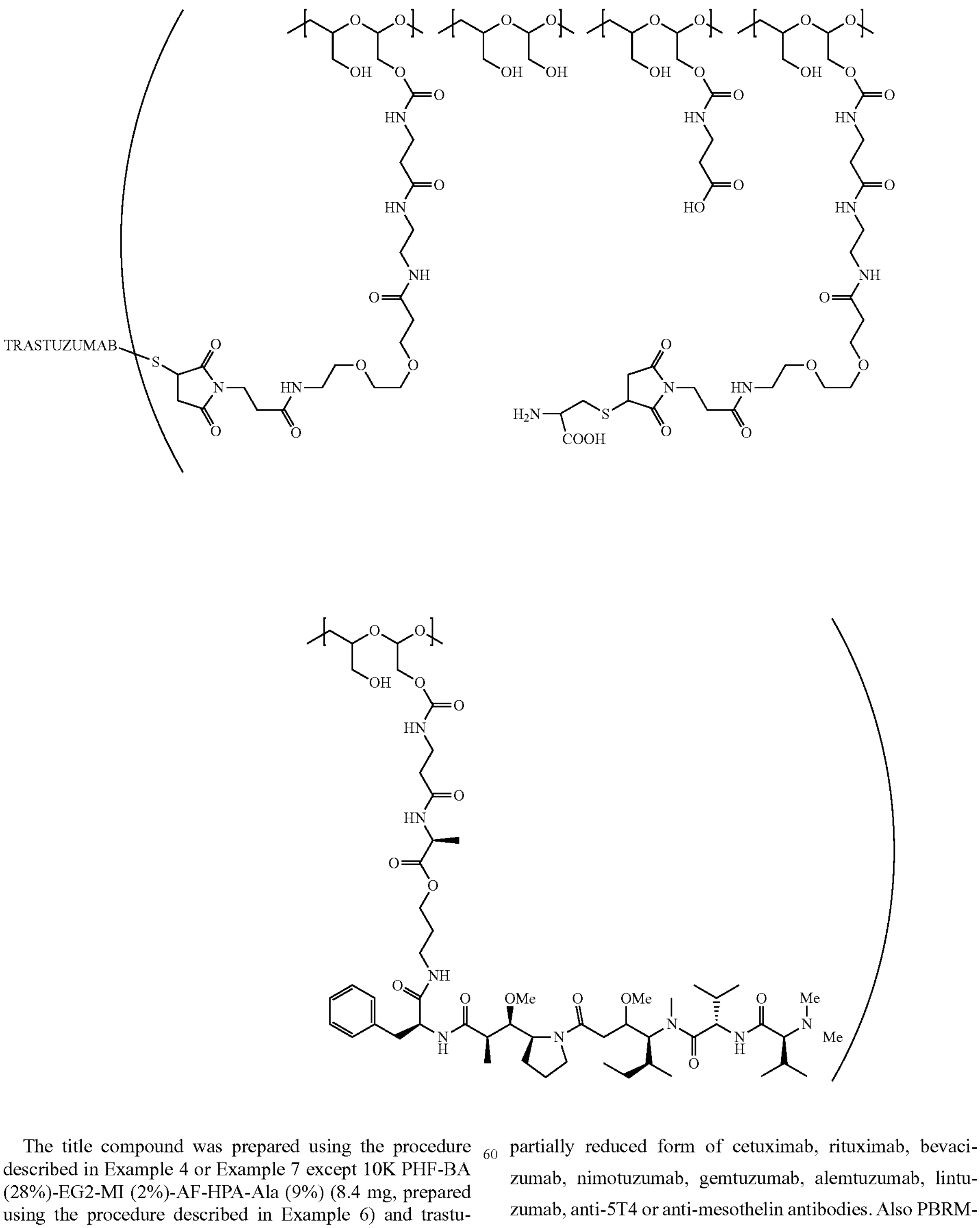

The title compound was prepared using the procedure described in Example 4 or Example 7 except 10K PHF-BA (28%)-EG2-MI (2%)-AF-HPA-Ala (9%) (8.4 mg, prepared using the procedure described in Example 6) and trastuzumab (15 mg) were used.

The AF-HPA to trastuzumab ratio was about 5:1 to about 10:1. The molecular weight of the title conjugate was 183 kDa. The average PHF-drug conjugate to trastuzumab ratio was about 2:1 to about 4:1.

Other PBRM-polymer-drug conjugates are synthesized with methods similar to the procedure described above, involving other PBRM derivatives, such as, for example, partially reduced form of cetuximab, rituximab, bevacizumab, nimotuzumab, gemtuzumab, alemtuzumab, lintuzumab, anti-5T4 or anti-mesothelin antibodies. Also PBRM-polymer-drug conjugates with varying ratios of drug to PBRM are obtained by varying the number of PBRM sulfhydryl groups and drug-polymer conjugate drug load.

Example 18

Synthesis of Trastuzumab-((EG2-MI (2%)-(10 kDa PHF-BA (28%)-(AF-HPA-Ala (9%))

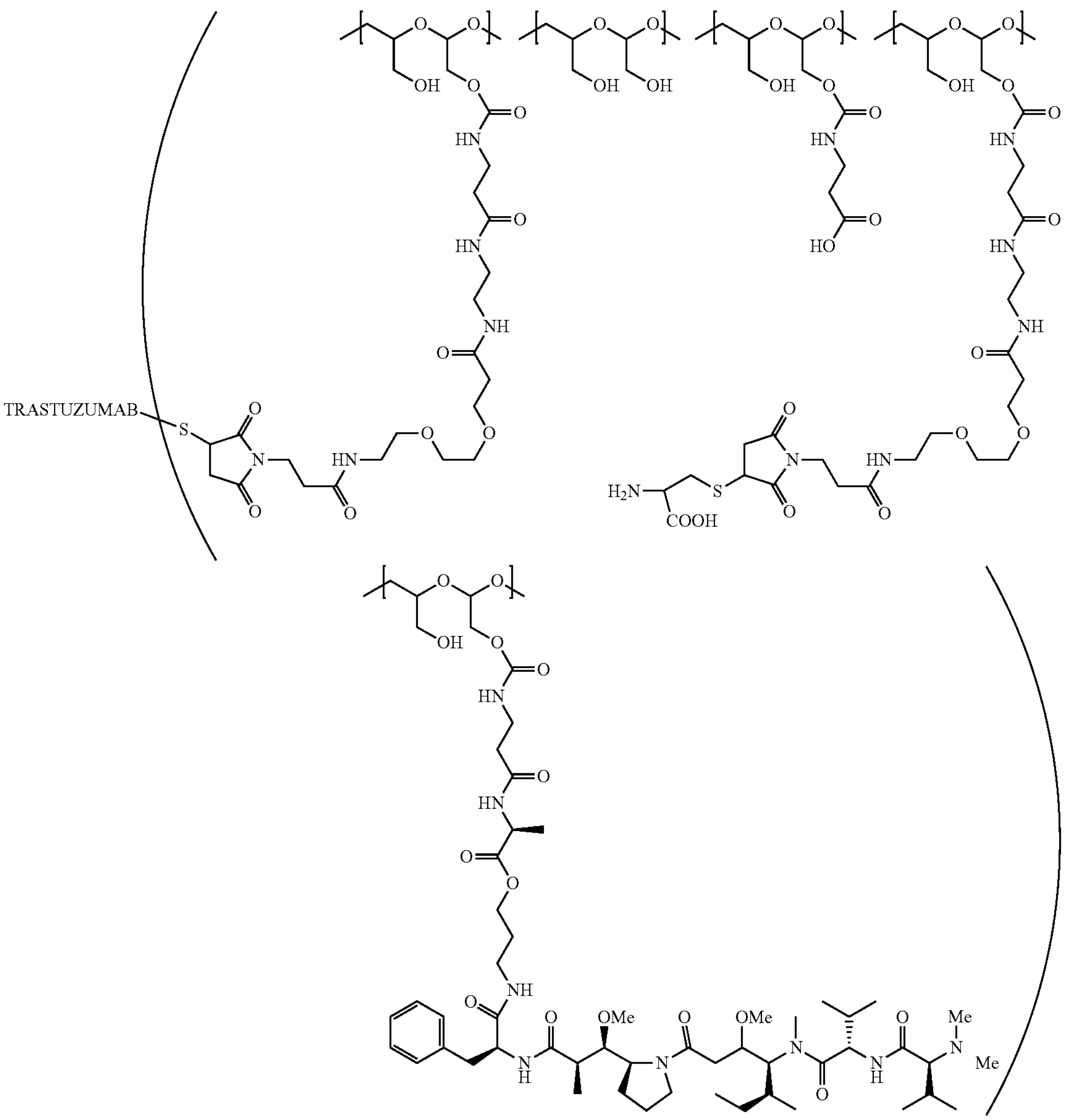

The title compound was prepared using the procedure described in Example 4 or Example 7.

Conjugate A—The AF-HPA to trastuzumab ratio was about 19:1 to about 24:1. The molecular weight of the title conjugate was 201 kDa. The average PHF-drug conjugate to trastuzumab ratio was about 2:1 to about 4:1.

Conjugate B—The AF-HPA to trastuzumab ratio was about 20:1 to about 25:1. The molecular weight of the title conjugate was 224 kDa. The average PHF-drug conjugate to trastuzumab ratio was about 2:1 to about 4:1.

Conjugate C—The AF-HPA to trastuzumab ratio was about 23:1 to about 28:1. The molecular weight of the title conjugate was 259 kDa. The average PHF-drug conjugate to trastuzumab ratio was about 2:1 to about 4:1.

Example 19

Cell Viability Assay for PBRM-Polymer-Drug Conjugates

PBRM-polymer-drug conjugates were evaluated for their antiproliferation properties in tumor cell lines in vitro using Cell Titer-Glo (Promega Corp). Cells were plated in black walled 96-well plate and allowed to adhere overnight at 37° C. in a humidified atmosphere of 5% $CO_2$. SKBR3, BT474, NCI-N87 cells (HER2 expressing cells), MCF7 cells (HER2 low expressing levels cells) and JIMT1 cells (HER2 medium expression level cells) were plated at a density of 5,000 cells per well. The next day the medium was replaced with 50 μL fresh medium and 50 μL of 2× stocks of PBRM-polymerdrug conjugate, drug polymer conjugate or drug were added to appropriate wells, mixed and incubated for 72 h. Cell Titer-Glo reagent was added to the wells at room temperature and the luminescent signal was measured after 10 min using a SpectraMax M5 plate reader (Molecular Devices). Dose response curves were generated using SoftMax Pro software. $IC_{50}$ values were determined from four-parameter curve fitting.

CD33 expressing cells HL-60 were passed at a density of 5,000 cells per well and treated with PBRM-polymer-drug conjugate on the same day. After 72 h or 6 days incubation, the cells were analyzed using the same procedure described above.

OVCAR-3, TF-1α and HCT-15 expression cells were plated and analyzed using the same procedure described above.

Tables I and II are illustrative results for the antiproliferation properties of the PBRM-polymer-drug conjugate in either HER2 expressing cells (Tables I), or CD33 expressing cells (Table II).

Table IV are illustrative results for the antiproliferation properties of the drug, AF-HPA in OVCAR-3 and TF-1α cell lines.

Table I lists the results for PBRM-polymer-drug conjugate Trastuzumab-((EG2-MI (3%))-(10 kDa PHF-BA (30%)-(AF-HPA-Ala (8%)), (AF-HPA:trastuzumab about 12:1 to 17:1), Example 4 Trastuzumab-((EG2-MI (2%)-(10 kDa PHF-BA (30%)-(AF-HPA-Ala (9%)), (AF-HPA:trastuzumab about 16:1 to about 21:1), Example 7; Trastuzumab-((EG2-MI (1%))-(10 kDa PHF-GA (29%)-(AF-HPA-Ala (6%)), (AF-HPA:trastuzumab about 18:1 to about 23:1), Example 13; Trastuzumab-((EG2-MI (2%))-(10 kDa PHF-BA (28%)-(AF-HPA-Ala (9%)), (AF-HPA:trastuzumab about 10:1 to about 15:1), Example 14; Trastuzumab-((EG2-MI (2%))-(10 kDa PHF-BA (28%)-(AF-HPA-Ala (9%)), (AF-HPA:trastuzumab about 11:1 to about 16:1), Example 15; and Rituximab-((EG2-MI (2%))-(10 kDa PHF-BA (28%)-(AF-HPA-Ala (9%)), (AF-HPA:trastuzumab about 13:1 to about 18:1), Example 16; Trastuzumab-((EG2-MI (2%)-(10 kDa PHF-BA (28%)-(AF-HPA-Ala (9%), (AF-HPA:trastuzumab about 5:1 to about 10:1), Example 17; Trastuzumab-((EG2-MI (2%)-(10 kDa PHF-BA (28%)-(AF-HPA-Ala (9%), (AF-HPA:trastuzumab about 19:1 to about 24:1), Example 18A; (AF-HPA:trastuzumab about 20:1 to about 25:1), Example 18B; (AF-HPA:trastuzumab about 23:1 to about 28:1), Example 18C; free drug (AF-HPA); and Kadcyla.

TABLE I

| | BT474 $IC_{50}$ (nmol/L) | SKBR3 $IC_{50}$ (nmol/L) | N87 $IC_{50}$ (nmol/L) | MCF7 $IC_{50}$ (nmol/L) | JIMT1 $IC_{50}$ (nmol/L) |
|---|---|---|---|---|---|
| Example 4 | 0.05 | 0.02 | 0.03 | 40 | 0.14 |
| Example 7 | 0.03 | 0.01 | 0.05 | 3.6 | 0.11 |
| Example 13 | 0.12 | 0.03 | 0.05 | 7.7 | 0.28 |
| Example 14 | 0.07 | 0.02 | 0.11 | 28.9 | 0.13 |
| Example 15 | 0.05 | 0.01 | 0.11 | 23.5 | 0.12 |
| Example 16 | 3.04 | 1.44 | 5.23 | 27.9 | 1.88 |
| Example 17 | 0.03 | 0.03 | 0.43 | 28.8 | 0.06 |
| Example 18A | 0.04 | 0.02 | 0.06 | 9.6 | 0.16 |
| Example 18B | 0.05 | 0.01 | 0.04 | 33 | 0.12 |
| Example 18C | 0.03 | 0.02 | 0.06 | 3.8 | 0.18 |
| AF-HPA (toxin equivalents) | 1.01 | 0.40 | 0.42 | 4.4 | 0.86 |
| Kadcyla | 2.40 | 0.23 | 0.09 | 38.6 | 18.0 |

The results in Table I show that, for the HER2 expressing cell lines SKBR3, BT474, N87 and JIMT1, the PBRM-polymer-drug conjugates (Example 4, Example 7, Examples 13 to 15, Example 17 and Examples 18A to 18C) exhibited higher antiproliferative activity as compared to the low HER2 expressing cell line MCF7 and as compared to the control PBRM-polymer-drug conjugate (Example 16) or Kadcyla.

Table II lists the results for Lintuzumab-((EG2-MI (2%)-(10 kDa PHF-BA (30%)-(AF-HPA-Ala (9%)), (AF-HPA: lintuzumab about 10:1 to about 15:1), Example 8; and Rituximab-((EG2-MI (3%)-(10 kDa PHF-BA (30%)-(AF-HPA-Ala (8%)) (AF-HPA:rituximab about 13:1 to about 18:1), Example 9; and free drug (AF-HPA).

TABLE II

| | HL-60 $IC_{50}$ (nmol/L) |
|---|---|
| Example 8 | 0.77 |
| Example 9 | 6.74 |
| AF-HPA | 4.8 |

The results in Table II show that, for the CD33 expressing cell line HL-60 the PBRM-polymer-drug conjugate (Examples 8) exhibited higher antiproliferative activity compared to control PBRM-polymer-drug conjugate (Example 9).

Table IV lists the results for free drug (AF-HPA).

TABLE IV

| | OVCAR3 $IC_{50}$ (nmol/L) | TF-1a $IC_{50}$ (nmol/L) |
|---|---|---|
| AF-HPA | 0.8 | 13.8 |

Example 19A

Cytotoxicity Assays for Trastuzumab-((EG2-MI-(10 kDa PHF-BA-(AF-HPA-Ala) Conjugates Trastuzumab-((EG2-MI-(10 kDa PHF-BA-(AF-HPA-Ala) conjugate (Example 7) was evaluated for their antiproliferation properties in tumor cell lines in vitro using Cell Titer-Glo (Promega Corp). JIMT-1(HER2 medium expressing cells, DSMZ, Braunschweig, Germany, Cat.# ACC589), MDA-MB-361 (HER2 medium expressing human breast cancer cells, ATCC, Cat.# HTB-27), MDA-MB-453 cells (triple negative breast cancer cell line, ATCC, Cat.# HTB-131), were cultured in DMEM media (ATCC, Manassas, Va., Cat.#30-2002) with 10% FBS (Gibco®, Life Technologies, Grand Island, N.Y., Cat.#16140-071). NCI-H522 (non-small cell lung carcinoma cell line, not amplified, ATCC, Cat.# CRL-5810), and NCI-H2170 (non-small cell lung carcinoma cell line, ATCC, Cat.# CRL-5928) cells were cultured in RPMI-1640 medium (ATCC, Cat#30-2001). NCI-H1581 (non-small cell lung carcinoma medium expressing cell line, not amplified, ATCC, Cat.# CRL-5878) cells were cultured in DMEM:F12 medium (ATCC, Cat#30-2006). SNU5 (gastric carcinoma, not amplified, ATCC, Cat# CRL-5973) was cultured in Iscove's Modified Dulbecco's Medium (Invitrogen Life Technologies, Cat#12440053) with 20% FBS. OVCAR3 (ovarian adenocarcinoma, not amplified, ATCC, Cat# HTB-161) was cultured in RPMI medium with 20% FBS. MDA-MB-175-VII (human breast cancer cell line, not amplified, ATCC, Cat.# HTB-25), was cultured in Leibovitz's L-15 Medium with 20% FBS. CAMA-1 (human breast cancer cell line, not amplified, ATCC, Cat.# HTB-21), was cultured in 90% ATCC-formulated Eagle's Minimum Essential Medium. ZR75-1 (human breast cancer cell line, not amplified, ATCC, Cat.# CRL-1500), was cultured in RPMI-1640 Medium. HCC1187 (human breast cancer cell line, not amplified, ATCC, Cat.# CRL-2322), was cultured in RPMI-1640 Medium. HCC38 (human breast cancer cell line, not amplified, ATCC, Cat.# CRL-2314), was cultured in RPMI-1640 Medium. T47D (human breast cancer cell line, not amplified, ATCC, Cat.# HTB-133), was cultured in RPMI-1640 Medium. MDA-MB-231 (human breast cancer cell line, not amplified, ATCC, Cat.# HTB-26), was cultured in DMEM Medium. CALU3 (human lung adenocarcinoma cell line, ATCC, Cat# HTB-55) was cultured in ATCC-formulated Eagle's Minimum Essential Medium. A549 (human lung carcinoma cell line, not amplified, ATCC, Cat# CCL-185) was cultured in F12K Medium. NCI-H2122 (human lung adenocarcinoma cell line, not amplified, ATCC, Cat# CRL-5985) was cultured in RPMI-1640 Medium, (ATCC, Cat#30-2001). NCI-H460 (human lung carcinoma cell line, not amplified, ATCC, Cat.# HTB-177) was cultured in RPMI-1640 Medium, (ATCC, Cat.#30-2001). SHP-77 (human small cell lung cancer cell line, not amplified, ATCC, Cat.# CRL-2195) was cultured in RPMI-1640 Medium, (ATCC, Cat#30-2001). KATO III (human gastric carcinoma cell line, not amplified, ATCC, Cat.# HTB-103) was cultured in Iscove's Modified Dulbecco's Medium with 20% FBS. MKN-45 III (human gastric adenocarcinoma cell line, not amplified, DSMZ, Braunschweig, Germany, Cat.# ACC409) was cultured in RPMI-1640 Medium, (ATCC, Cat#30-2001). SKOV3 (human ovary adenocarcinoma cell line ATCC, Cat.# HTB-77), was cultured in McCoy's 5a Medium. TOV-21G (human ovarian adenocarcinoma cell line, not amplified, ATCC, Cat.# CRL-11730 was cultured in 1:1 mixture of MCDB 105 medium containing a final concentration of 1.5 g/L sodium bicarbonate and Medium 199 containing a final concentration of 2.2 g/L sodium bicarbonate. BT474 (HER2 high expressing human breast cancer cells, ATCC, Cat.# HTB-20) was cultured in DMEM Medium with 10% FBS. NCI-N87 (high HER2 expressing gastric cancer cell line, ATCC, Cat.# CRL-5822), was grown in RPMI-1640 Medium 10% FBS.

For the cytotoxicity assay, cells were seeded at a density of 3000 cells per well in 96 well plates and allowed to attach during overnight incubation at 37° C. in the presence of 5% $CO_2$. The media was then replaced with fresh media containing a range of Trastuzumab-((EG2-MI-(10 kDa PHF-BA-(AF-HPA-Ala) conjugates (100 nM to 0.1 pM), or Kadcyla (Genentech) and the cells were incubated for 72 hours or 6 days at 37° C. in the presence of 5% $CO_2$. Cell survival was measured using CellTiter-Glo® Luminescent Cell Viability Assay (Promega, Madison, Wis.) as described in the kit instructions. Cell viability was normalized to untreated control and expressed as a percentage. The values were plotted and $IC_{50}$ values calculated with Graphpad Prism software (San Diego, Calif.) using 4 parameter, variable slope, dose response curve fitting algorithm. Table III below gives illustrative results for the cytotoxicity of the Trastuzumab-((EG2-MI-(10 kDa PHF-BA-(AF-HPA-Ala) conjugates and Kadcyla.

TABLE III

| Cell Line | HER2 molecules per cell | Her2 expression | $IC_{50}$ (nM) Example 7 | Kadcyla |
|---|---|---|---|---|
| JIMT-1 | 80,000 | 2+ | $0.3^b$ | 17.5 |
| MDA-MB-453 | 125,000 | 2+ | 0.08/0.04 | ~100 |
| MDA-MB-361 | 135,000 | 2+ | 0.001/0.005 | 0.27/0.33 |
| MDA-MB-175VII | 51,000 | 1+ | 0.1 | 1.2 |
| CAMA-1 | 50,000 | 1+ | 0.02 | 7.8 |
| ZR75-1 | 40,000 | 1+ | 1.1 | >100 |
| HCC1187 | 38,000 | 2+ | 0.8 | 30 |
| HCC38 | 36,000 | 2+ | 0.8 | >100 |
| T47D | 20,000 | 1+ | 4.3 | 82.3 |
| MDA-MB-231 | 5400 | 1+ | 11 | 27 |
| NCI-H522 | 25,000 | 1+ | 0.18 | ~100 |
| NCI-H1581 | 13,000 | 1+ | 2.3 | ~100 |
| NCI-H2170 | 660,000 | 3+ | 0.07 | 0.4 |
| CALU3 | 330,000 | 3+ | 0.25 | >100 |
| NCI-H2122 | 12,000 | 1+ | 0.5 | 19 |
| A549 | 6,000 | 1+ | 20 | >100 |
| NCI-H460 | 4,000 | 1+ | 16 | 68 |
| SHP-77 | 0 | | 67 | >100 |
| SNU5 | 22,000 | 1+ | 2.9 | ~100 |
| KATOIII | 19,000 | 1+ | 19 | >100 |
| MKN45 | 16,000 | 1+ | ~80 | >100 |
| OVCAR3 | 7,200 | 1+ | 1.6 | ~85 |
| SKOV3 | 220,000 | 3+ | 0.19 | 5.6 |
| TOV21G | 12,000 | 1+ | 0.04 | >100 |
| BT474 | 860,000 | 3+ | 0.1 | 1.3 |
| NCI-N87 | 700,000 | 3+ | 0.03 | 0.3 |

$^b$= Example 17 was used in the assay instead of Example 7.

As shown in Table III, the trastuzumab-antibody-polymer-drug conjugates are more potent than Kadcyla in all the tested cell lines.

Example 20

Ligand Binding Studies by BIAcore Surface Plasmon Resonance (SPR)

The kinetic binding of the PBRM-polymer-drug conjugate to an immobilized receptor is determined by BIAcore SPR. The binding constants for the PBRM in the PBRM-polymer-drug conjugate and PBRM alone can be determined using standard BIAcore procedures.

Using standard amine coupling chemistry, hErbB2 is immobilized in three flow channels to the surface Plasmon resonance sensor chip surface at three similar densities. trastuzumab readily bound to the immobilized hErbB2 thereby demonstrating that both binding partners were active. The binding parameters $k_a$ (association or affinity rate constant) and $K_D$ (dissociation constant) are measured at 25° C. for the PBRM-polymer-drug conjugate and PBRM using a BioRad ProteOn XPR36 optical biosensor equipped with a GLC sensor chip and equilibrated with running buffer.

The results show that the PBRM in the PBRM-polymer-drug conjugate is recognized by the PBRM receptor and that the binding of the PBRM in the PBRM-polymer-drug conjugate is not significantly affected relative to the unconjugated PBRM.

Example 21

FACS Binding Assay

Cell surface binding of the PBRM-polymer-drug conjugate Trastuzumab-((EG2-MI (3%))-(10 kDa PHF-BA (30%)-(AF-HPA-Ala (8%)), (AF-HPA:trastuzumab about 12:1 to 17:1), Example 4 or Trastuzumab-((EG2-MI (2.5%)-

(10 kDa PHF-BA (28%)-(AF-HPA-Ala (8.4%), (AF-HPA:trastuzumab about 11:1 to 16:1) Example 10, were evaluated using the MACSQuant® Analyzer 10 digital bench top flow cytometer in different human cancer cell lines. 100,000 cells were incubated in 6% goat serum on ice. PBRM polymer drug conjugate or unconjugated PBRM was added to the cells and incubated on ice for three hours, then cells were washed with ice cold PBS and incubated with the secondary fluorescently labeled antibodies in ice for one hour. Upon completion cells were washed with PBS, fixed with 1% paraformaldehyde and analyzed by flow cytometer. The cell surface binding of the PBRM polymer drug conjugate was determined by titration and compared to that of non-conjugated PBRM.

Table Va gives the dissociation constant ($K_d$) of PBRM-polymer-drug conjugate Trastuzumab-((EG2-MI (3%))-(10 kDa PHF-BA (30%)-(AF-HPA-Ala (8%)), (AF-HPA:trastuzumab about 12:1 to 17:1), Example 4, and trastuzumab alone to JIMT-1 cells.

TABLE Va

| | $K_d$ (nM) |
|---|---|
| Example 4 | 2.16 |
| Trastuzumab | 0.92 |

Table Vb gives the dissociation (KO of PBRM-polymer-drug conjugate Trastuzumab-((EG2-MI (2.5%)-(10 kDa PHF-BA (28%)-(AF-HPA-Ala (8.4%), (AF-HPA:trastuzumab about 11:1 to 16:1) Example 10 and trastuzumab alone to JIMT-1 cells.

TABLE Vb

| | $K_d$ (nM) |
|---|---|
| Example 10 | 5.37 |
| Trastuzumab | 3.53 |

The results show that the cell surface binding of the PBRM in the PBRM-polymer-drug conjugate was comparable to that of unconjugated PBRM.

The cell surface binding of the PBRM in other PBRM-polymer-drug conjugates to other human cancer cells can be determined and should be comparable to that of the unconjugated PBRM.

Example 22

Ligand Binding Studies by BIAcore Surface Plasmon Resonance (SPR)

The kinetic binding of the PBRM-polymer-drug conjugate to an immobilized receptor was determined by BIAcore SPR. The binding constants for the PBRM in the PBRM-polymer-drug conjugates such as Trastuzumab-((EG2-MI (3%))-(10 kDa PHF-BA (30%)-(AF-HPA-Ala (8%)), (AF-HPA:trastuzumab about 12:1 to 17:1), Example 4; Trastuzumab-((EG2-MI (2%)-(10 kDa PHF-BA (30%)-(AF-HPA-Ala (9%)), (AF-HPA:trastuzumab about 16:1 to about 21:1), Example 7, Trastuzumab-((EG2-MI (2%)-(10 kDa PHF-BA (28%)-(AF-HPA-Ala (9%), (AF-HPA:trastuzumab about 5:1 to 10:1), Example 17; and Trastuzumab-((EG2-MI (2%)-(10 kDa PHF-BA (28%)-(AF-HPA-Ala (9%), (AF-HPA:trastuzumab about 19:1 to 24:1), Example 18A; (AF-HPA:trastuzumab about 20:1 to 25:1), Example 18B; (AF-HPA:trastuzumab about 23:1 to 28:1), Example 18C PBRM in PBRM-drug conjugate (i.e., Kadcyla) and PBRM (i.e., trastuzumab) alone were determined using standard BIAcore procedures.

Using standard amine coupling chemistry, hErbB2 was immobilized in three flow channels to the surface Plasmon resonance sensor chip surface at three similar densities. trastuzumab readily bound to the immobilized hErbB2 thereby demonstrating that both binding partners were active. Table VI provides the binding parameters $k_a$ (association or affinity rate constant), $k_d$ (dissociation rate constant), and $K_D$ (dissociation constant) measured at 25° C. for the conjugates of Example 4 and Example 7 and trastuzumab using a BioRad ProteOn XPR36 optical biosensor equipped with a GLC sensor chip and equilibrated with running buffer.

TABLE VI

| | $k_a$ ($M^{-1}s^{-1}$) | $k_d$ ($s^{-1}$) | $K_D$ (pM) |
|---|---|---|---|
| Trastuzumab | $9.90 \pm 0.1 \times 10^5$ | $2.60 \pm 0.1 \times 10^{-5}$ | $26.2 \pm 0.1$ |
| Kadcyla | $4.61 \pm 0.2 \times 10^5$ | $3.17 \pm 0.9 \times 10^{-5}$ | $68.7 \pm 0.3$ |
| Example 4 | $4.61 \pm 0.3 \times 10^5$ | $2.60 \pm 0.9 \times 10^{-5}$ | $56.3 \pm 0.3$ |
| Example 7 | $5.3 \pm 0.3 \times 10^5$ | $2.43 \pm 0.1 \times 10^{-5}$ | $45.9 \pm 0.3$ |
| Example 14 | $3.91 \pm 0.3 \times 10^5$ | $2.56 \pm 0.1 \times 10^{-5}$ | $65.5 \pm 0.5$ |
| Example 17 | $8.30 \pm 0.2 \times 10^5$ | $2.32 \pm 0.2 \times 10^{-5}$ | $28.0 \pm 0.1$ |
| Example 18A | $4.67 \pm 0.7 \times 10^5$ | $2.07 \pm 0.2 \times 10^{-5}$ | $44.4 \pm 0.6$ |
| Example 18B | $3.05 \pm 0.2 \times 10^5$ | $2.46 \pm 0.1 \times 10^{-5}$ | $80.7 \pm 0.6$ |
| Example 18C | $4.25 \pm 0.5 \times 10^5$ | $2.03 \pm 0.1 \times 10^{-5}$ | $47.7 \pm 0.5$ |

The results show that the PBRM in the PBRM-polymer-drug conjugate was recognized by the PBRM receptor.

Example 23

In Vivo Efficacy, Pharmacokinetic and Biodistribution Studies

In order to evaluate the efficacy and pharmacokinetics of the protein drug conjugate mouse and rat subcutaneous and orthotopic xenograft models are used.

Test articles, along with appropriate controls are administered intravenously (IV) via tail-vein injection or intraperitoneally. To assess circulating levels of test article blood sample is collected at designated times via terminal cardiac-puncture. Samples are kept at room temperature for 30 min to coagulate, then centrifuged for 10 min at 1,000×g at 4° C. and immediately frozen at −80° C. Total PBRM concentrations in serum samples are measured using ELISA. Circulating drug concentration (conjugated and free) is determined by LC/MS/MS methods.

To assess efficacy of the PBRM-polymer-drug conjugates the tumor size are measured using digital calipers. Tumor volume is calculated and used to determine the delay in tumor growth.

For the determination of drug biodistribution, tumor, and major organs such as, for example, liver, kidney, spleen, lung, heart, muscles, and brain are harvested, immediately frozen in liquid nitrogen, stored at −80° C. PBRM and/or drug levels are determined in tissue homogenates by standard methods, such as, for example, ELISA or LC/MS/MS methods respectively.

Example 24

Mouse Tissue Distribution after Administration of PBRM-Polymer-Drug Conjugates

Female CB-17 SCID mice were inoculated subcutaneously with BT474 tumor fragments (n=4 for each group).

Vehicle or PBRM-polymer-drug conjugates: Trastuzumab-((EG2-MI (3%))-(10 kDa PHF-BA (30%)-(AF-HPA-Ala (8%)), (AF-HPA:trastuzumab about 12:1 to about 17:1), Example 4, at 5 mg/kg; and Trastuzumab-((EG2-MI (1%))-(10 kDa PHF-GA (29%)-(AF-HPA-Ala (6%)), (AF-HPA: trastuzumab about 18:1 to about 23:1), Example 13, at 5 mg/kg were dosed IV as a single dose on day 1.

At 48 hours post administration, the mice were sacrificed and the blood was collected by terminal cardiac. The organs: kidney left, liver, lung, skeletal muscle, spleen and tumor were harvested, immediately frozen in liquid nitrogen and stored at −80° C. until analysis for conjugated, free AF-HPA and AF.

Tables VII, VIII and VIIIA give the concentration of the conjugated drug (conjugated AF-HPA, i.e., PBRM-PHF-AF-HPA); unconjugated (free) drug (i.e., AF-HPA and AF); free AF-HPA and free AF in different tissues. The concentrations are reported as ng AF-HPA (and/or AF) equivalent/g tissue as mean value±standard deviation.

TABLE VII

| Conjugated AF-HPA concentration | | |
|---|---|---|
| Tissue | Example 4 | Example 13 |
| Tumor | 476 ± 52 | 371 ± 16 |
| Liver | 200 ± 57 | 100 ± 17 |
| Spleen | 127 ± 97 | 77 ± 18 |
| Kidney | 190 ± 15 | 137 ± 4 |
| Muscle | 39 ± 22 | 16 ± 86 |
| Plasma | 2218 ± 182 | 1720 ± 501 |

TABLE VIII

| Total concentrations of unconjugated AF-HPA and AF | | |
|---|---|---|
| Tissue | Example 4 | Example 13 |
| Tumor | 93.6 ± 25.5 | 82.9 ± 23.9 |
| Liver | 11.0 ± 2.3 | 3.4 ± 1.1 |
| Spleen | 9.9 ± 2.2 | 6.6 ± 1.3 |
| Kidney | 9.0 ± 2.1 | 0.7 ± 0.0 |
| Muscle | 0.2 ± 0.0 | ND |
| Plasma | 0.4 ± 0.02 | 0.3 ± 0.02 |

TABLE VIIIA

| Unconjugated AF-HPA and unconjugated AF concentrations | | | | |
|---|---|---|---|---|
| | Example 4 | | Example 13 | |
| Tissue | AF | AF-HPA | AF | AF-HPA |
| Tumor | 67.3 ± 17.5 | 21.6 ± 6.8 | 56.3 ± 16.2 | 22.3 ± 6.8 |
| Liver | 8.4 ± 1.5 | 2.0 ± 0.7 | 5.0 ± 1.3 | 1.6 ± 1.2 |
| Lung | 2.4 ± 0.7 | 1.2 ± 0.1 | 1.5 ± 0.4 | 0.9 ± 0.2 |
| Spleen | 7.9 ± 1.9 | 1.4 ± 0.2 | 5.5 ± 1.0 | 0.9 ± 0.1 |
| Kidney | 7.9 ± 1.9 | 0.5 ± 0.1 | 0.7 ± 0.0 | ND |
| Muscle | 0.5 ± 0.1 | 0.1 ± 0.03 | ND | ND |
| Plasma | ND | 0.4 ± 0.02 | ND | 0.3 ± 0.02 |

ND = not determined

The results show that in tissue the released unconjugated AF-HPA is further metabolized to AF whereas in plasma the unconjugated AF-HPA is not converted to AF.

Example 25

Tumor Growth Response to Administration of PBRM-Polymer-Drug Conjugates

Female CB-17 SCID mice were inoculated subcutaneously with BT474 tumor fragments (n=10 for each group) or JIMT-1 cells (n=10 for each group) or NCI-N87 cells (n=10 for each group). Female NCr nu/nu mice were inoculated subcutaneously with HL-60 cells (n=10 for each group). Test compounds or vehicle were dosed IV as a single dose on day 1. Tumor size was measured at the times indicated in FIGS. 1 to 6 using digital calipers. Tumor volume was calculated and was used to determine the delay in tumor growth. Mice were sacrificed when tumors reached a size of 800 to 1500 $mm^3$. Tumor volumes are reported as the mean±SEM ("standard error of mean") for each group.

FIG. 1 provides the results for the tumor response in mice inoculated subcutaneously with BT474 tumor fragments (n=10 for each group) after IV administration of vehicle; PBRM (trastuzumab) at 10 mg/kg; PBRM-polymer-drug conjugates Trastuzumab-((EG2-MI (3%))-(10 kDa PHF-BA (30%)-(AF-HPA-Ala (8%)), (AF-HPA:trastuzumab about 12:1 to about 17:1), Example 4, at 2.5 mg/kg and 5 mg/kg; and Trastuzumab-((EG2-MI (1%))-(10 kDa PHF-GA (29%)-(AF-HPA-Ala (6%)), (AF-HPA:trastuzumab about 18:1 to about 23:1), Example 13, at 2.5 mg/kg and 5 mg/kg. The results show reduction of tumor volume for Examples 4 and 13 with 100% regressions at 5 mg/kg dose and 100% and 80% tumor free survival respectively. The vehicle and trastuzumab alone, showed an increase of tumor volume. The conjugation of a PBRM specific for HER2 (trastuzumab) to a drug polymer conjugate was necessary for the reduction of tumor volume as the PBRM alone did not show reduction in tumor volume).

Figure 2:
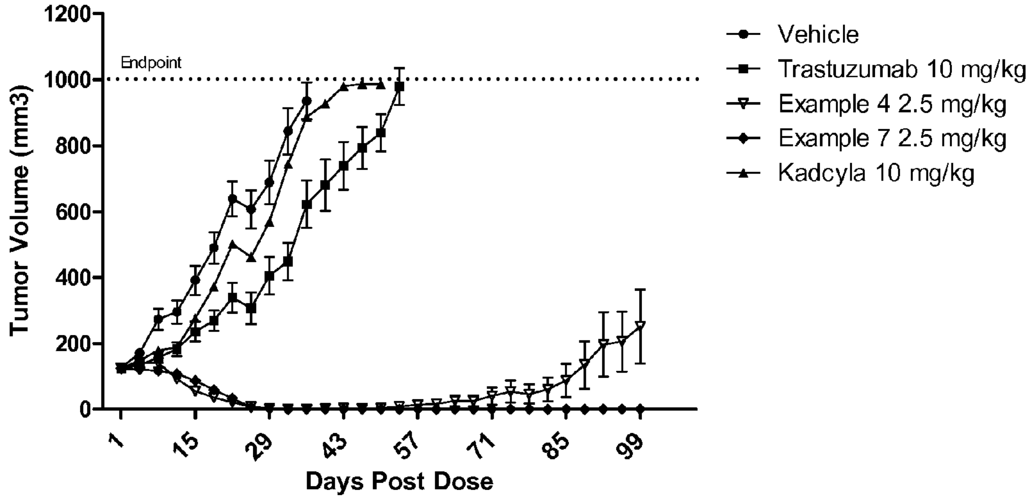
FIG. 2 shows the tumor response in mice inoculated subcutaneously with JIMT-1 (n=10 for each group) after IV administration as a single dose on day 1 of vehicle; PBRM (trastuzumab) at 10 mg/kg; PBRM-polymer-drug conjugates described in Example 4 and Example 7, at 2.5 mg/kg or Kadcyla at 10 mg/kg.

FIG. 2 provides the results for the tumor response in mice inoculated subcutaneously with JIMT-1 cells (n=10 for each group) after IV administration of vehicle; PBRM (trastuzumab) at 10 mg/kg; PBRM-polymer-drug conjugates Trastuzumab-((EG2-MI (3%))-(10 kDa PHF-BA (30%)-(AF-HPA-Ala (8%)), (AF-HPA:trastuzumab about 12:1 to about 17:1), Example 4, at 2.5 mg/kg; and Trastuzumab-((EG2-MI (2%)-(10 kDa PHF-BA (30%)-(AF-HPA-Ala (9%)), (AF-HPA:trastuzumab about 16:1 to about 21:1), Example 7, at 2.5 mg/kg or Kadcyla at 10 mg/kg. The results show reduction of tumor volume for both Examples 4 and 7. Specifically, in the tested group administered with the conjugate described in Example 4, there were 100% regressions at 2.5 dose consisting of nine complete regressions (one animal died due to non-treatment-related death) and three tumor free survivors. In the tested group administered with the conjugate described in Example 7, there were 100% regressions, consisting of complete regressions, all remained tumor free (two animals died tumor free at the end of the study due to non-treatment-related death). The vehicle, Kadcyla and trastuzumab alone, showed an increase of tumor volume. The conjugation of a PBRM specific for HER2 (trastuzumab) to a drug polymer conjugate was necessary for the reduction of tumor volume as the PBRM alone did not show reduction in tumor volume).

Female NCr nu/nu mice were inoculated subcutaneously with HL-60 cells (n=10 for each group). Test compounds or vehicle were dosed IV as a single dose on day 1. Tumor size was measured at the times indicated in FIG. 3 using digital calipers. Tumor volume was calculated and was used to determine the delay in tumor growth. Mice were sacrificed when tumors reached a size of 2000 $mm^3$. Tumor volumes are reported as the mean±SEM for each group.

Figure 3:
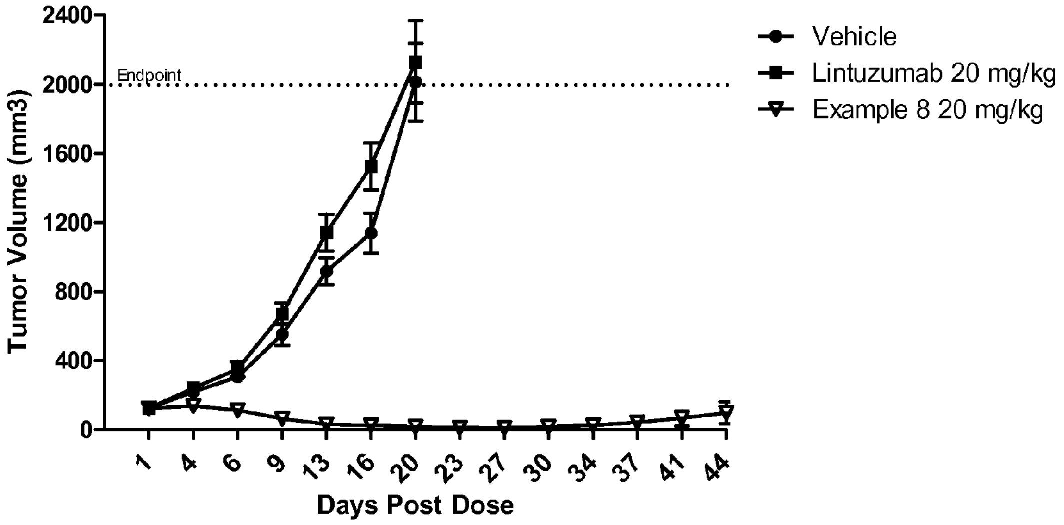
FIG. 3 shows the tumor response in mice inoculated subcutaneously with HL-60 (n=10 for each group) after IV administration as a single dose on day 1 of vehicle; PBRM (lintuzumab) at 20 mg/kg; PBRM-polymer-drug conjugates described in Example 8 at 20 mg/kg.

FIG. 3 provides the results for the tumor response in mice inoculated subcutaneously with HL-60 cells (n=10 for each group) after IV administration of vehicle; PBRM (lintuzumab) at 20 mg/kg; PBRM-polymer-drug conjugates Lintuzumab-((EG2-MI (2%))-(10 kDa PHF-BA (30%)-(AF-HPA-Ala (9%)), (AF-HPA:lintuzumab about 10:1 to about 15:1), Example 8, 20 mg/kg. The results show reduction of tumor volume for Example 8 with 100% regressions and 70% tumor free survival on day 44. The vehicle, and lintuzumab alone, showed an increase of tumor volume. The conjugation of a PBRM specific for CD33 (lintuzumab) to a drug polymer conjugate was necessary for the reduction of tumor volume as the PBRM alone did not show reduction in tumor volume.

Figure 4A:
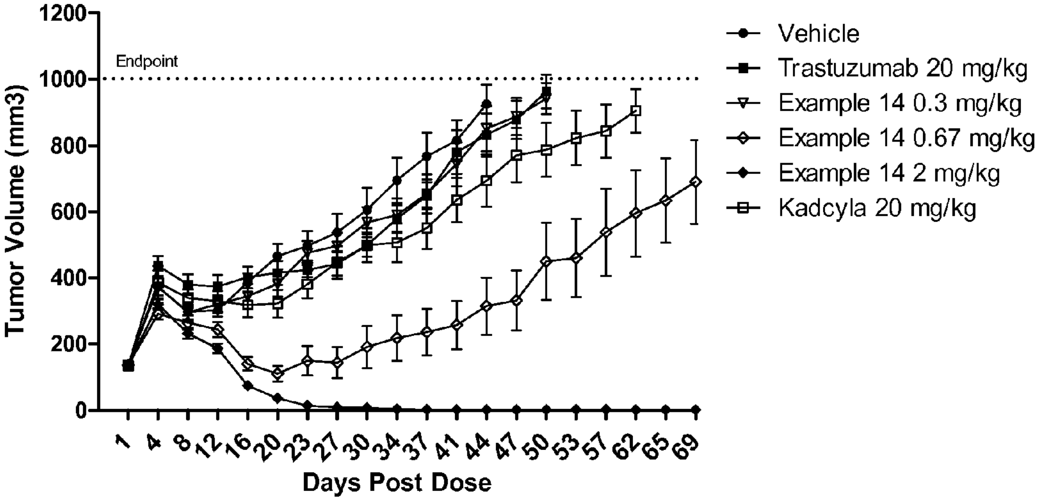
FIG. 4A shows the tumor response in mice inoculated subcutaneously with JIMT-1 (n=10 for each group) after IV administration as a single dose on day 1 of vehicle; PBRM (trastuzumab) at 20 mg/kg; Kadcyla at 20 m/kg; PBRM-polymer-drug conjugate described in Example 14, at 2 mg/kg, 0.67 mg/kg and 0.3 mg/kg.

FIG. 4A provides the results for the tumor response in mice inoculated subcutaneously with JIMT-1 cells (n=10 for each group) after IV administration of vehicle; PBRM (trastuzumab) at 20 mg/kg; Kadcyla (PBRM-drug conjugate) at 20 mg/kg; PBRM-polymer-drug conjugate Trastuzumab-((EG2-MI (2%))-(10 kDa PHF-BA (28%)-(AF-HPA-Ala (9%)), (AF-HPA:trastuzumab about 10:1 to about 15:1), Example 14, at 2 mg/kg, 0.67 mg/kg and 0.3 mg/kg. The results show reduction of tumor volume for Example 14 with 100% regressions at 2.0 mg/kg dose and 100% tumor free survival. The vehicle, Kadcyla and trastuzumab alone, showed an increase of tumor volume. The conjugation of a PBRM specific for HER2 (trastuzumab) to a drug polymer conjugate was necessary for the reduction of tumor volume as the PBRM alone did not show reduction in tumor volume.

Figure 4B:
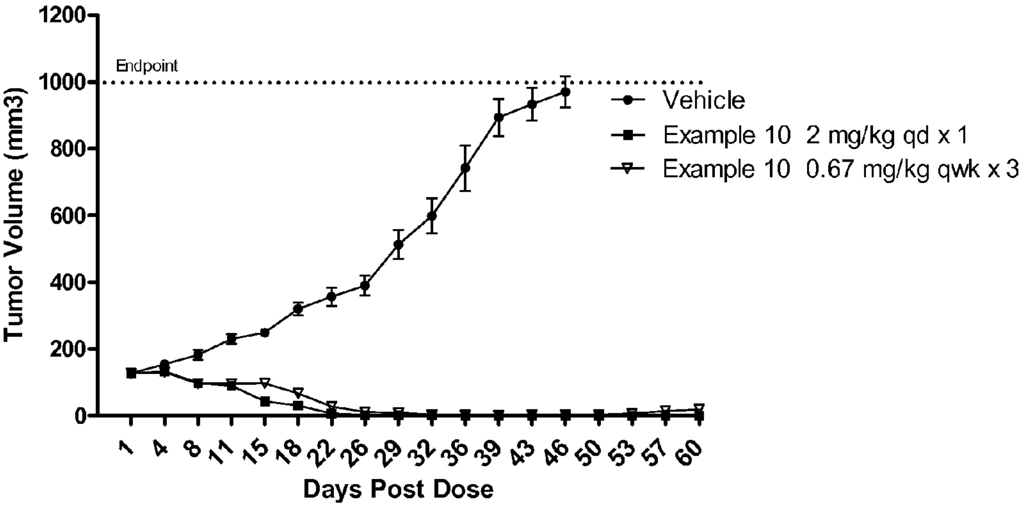
FIG. 4B shows the tumor response in mice inoculated subcutaneously with JIMT-1 (n=10 for each group) after IV administration as a single dose on day 1 of vehicle or PBRM-polymer-drug conjugate described in Example 10 at 2 mg/kg as a single dose or at 0.67 mg/kg dosed weekly for 3 weeks.

FIG. 4B provides the results for the tumor response in mice inoculated subcutaneously with JIMT-1 cells (n=10 for each group) after IV administration of vehicle; Example 10, at 2 mg/kg, as a single dose or at 0.67 mg/kg dosed weekly for 3 weeks. The results show reduction of tumor volume for Example 10 with 100% regressions at 2.0 mg/kg, all of which remained tumor free survival at the end of the study. At 0.67 mg/kg dose, there were 90% regressions consisting of one partial response and eight complete responses, six of which remained tumor free survivors at the end of the study. The vehicle showed an increase of tumor volume.

Figure 5:
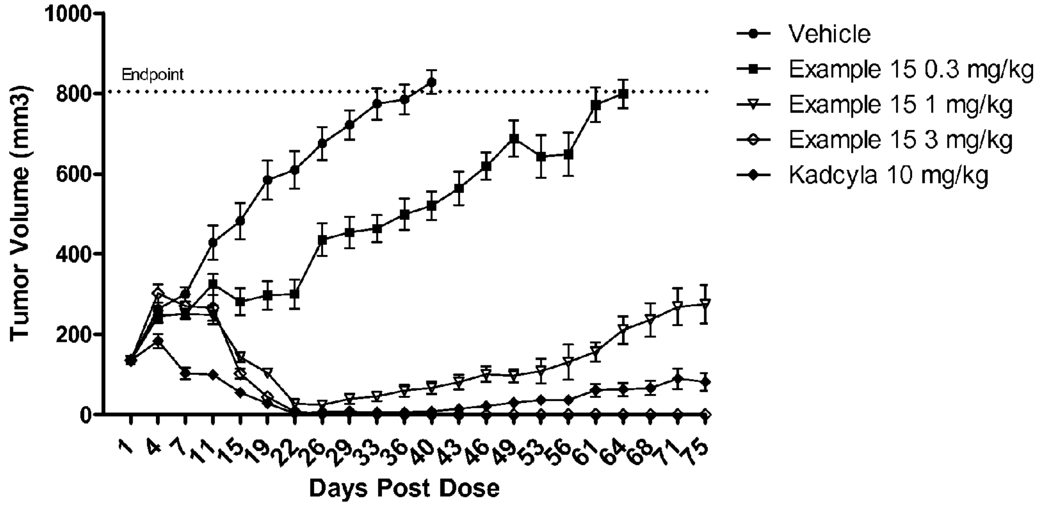
FIG. 5 shows the tumor response in mice inoculated subcutaneously with NCI-N87 cells (n=10 for each group) after IV administration as a single dose on day 1 of vehicle, PBRM-polymer-drug conjugate described in Example 15, at 3 mg/kg, 1 mg/kg and 0.3 mg/kg; or Kadcyla at 10 mg/kg.

FIG. 5 provides the results for the tumor response in mice inoculated subcutaneously with NCI-N87 cells (n=10 for each group) after IV administration of vehicle, PBRM-polymer-drug conjugate Trastuzumab-((EG2-MI (2%))-(10 kDa PHF-BA (28%)-(AF-HPA-Ala (9%)), (AF-HPA:trastuzumab about 11:1 to about 16:1), Example 15, at 3 mg/kg, 1 mg/kg and 0.3 mg/kg; or Kadcyla at 10 mg/kg. The results show a dose response for PBRM-polymer-drug conjugate (Example 15) with the highest dose of 3 mg/kg showing complete regression of tumor volume with 100 complete responses. At the middle dose 1 mg/kg there were 7 partial and 1 complete regression out of 10 animals.

Figure 6:
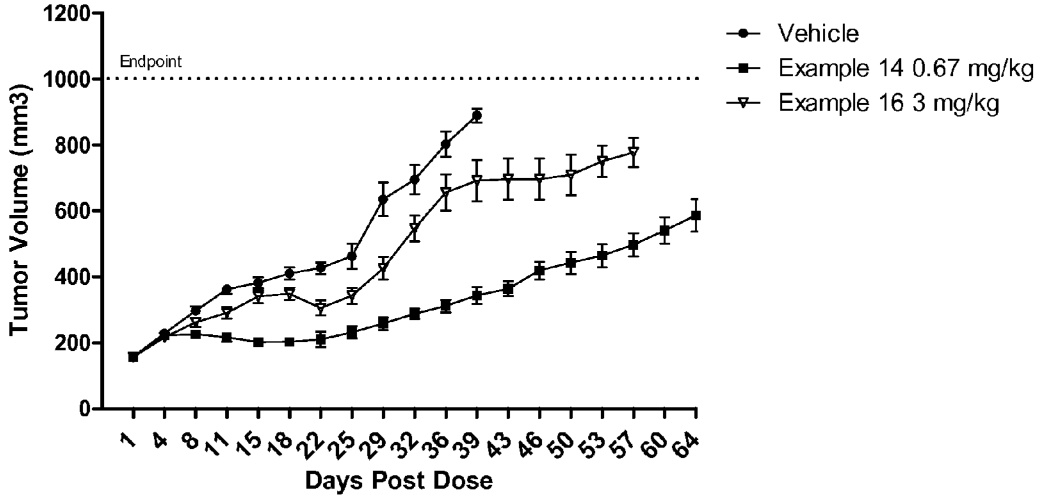
FIG. 6 shows the tumor response in mice inoculated subcutaneously with NCI-N87 cells (n=10 for each group) after IV administration as a single dose on day 1 of vehicle, PBRM-polymer-drug conjugates described is Example 14, at 0.67 mg/kg and Example 16, at 3 mg/kg.

FIG. 6 provides the results for the tumor response in mice inoculated subcutaneously with NCI-N87 cells (n=10 for each group) after IV administration of vehicle, PBRM-polymer-drug conjugates Trastuzumab-((EG2-MI (2%))-(10 kDa PHF-BA (28%)-(AF-HPA-Ala (9%)), (AF-HPA:trastuzumab about 11:1 to about 16:1), Example 14, at 0.67 mg/kg and Rituximab-((EG2-MI (2%))-(10 kDa PHF-BA (28%)-(AF-HPA-Ala (9%)), (AF-HPA:trastuzumab about 13.7 to about 18.7), Example 16, at 3 mg/kg. The results show a tumor growth delay response for PBRM-polymer-drug conjugate (Example 14). The vehicle, Rituximab-drug polymer conjugate (Example 16) at the dose of 3 mg/kg has no effect on tumor growth.

Example 26

Mouse Plasma PK after Administration of PBRM-Polymer-Drug Conjugates

Female CD-1 mice were allowed to acclimate for at least 4 days prior to initial dosing. All mice were given regular chow and water ad libitum and were not fasted prior to compound administration. Test compounds or vehicle were dosed IV as a single dose on day 1.

The mice were injected intravenously with vehicle (n=3) or with PBRM-polymer-drug conjugate, Trastuzumab-((EG2-MI (3%))-(10 kDa PHF-BA (30%)-(AF-HPA-Ala (8%)), (AF-HPA:trastuzumab about 12:1 to about 17:1), Example 4, at 5 mg/kg, n=3 for each group). Plasma was collected at 5 min, 1 h, 3 h, 6 h, 24 h, 48 h, 72 h, day 7 and day 14 post dosing. Body weight was measured prior to dosing on day 1 and on days 1, 7 and 14. All animals were observed throughout the fourteen day period for mortality or morbidity.

The conjugated AF-HPA and unconjugated (free) drug (such as AF-HPA and AF) concentrations were determined by LC/MS analysis. Total trastuzumab concentration was determined by ELISA.

Figure 7:
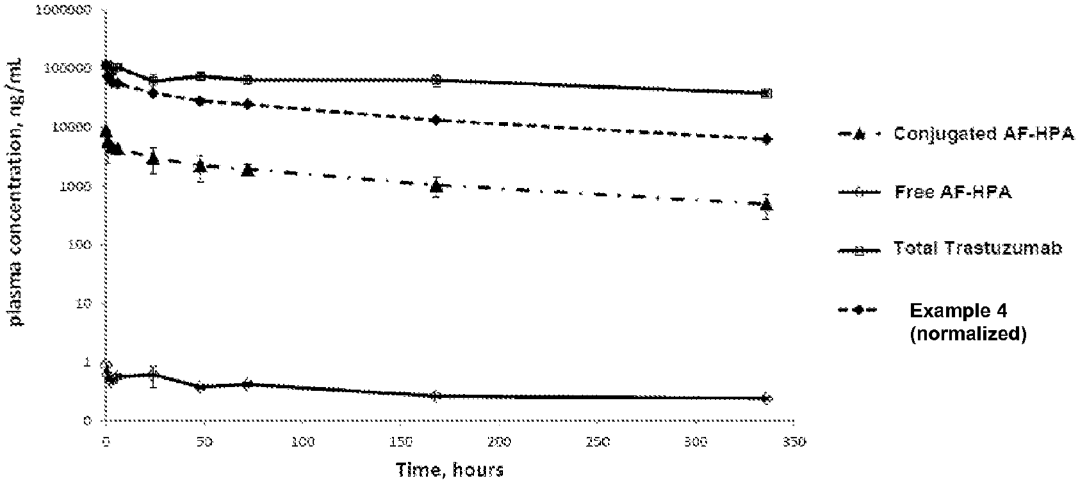
FIG. 7 shows the plasma PK for the conjugated AF HPA (total), unconjugated AF HPA and AF (denoted as "Free AF-HPA"), and trastuzumab in mice inoculated subcutaneously with BT474 tumor fragments after IV bolus administration of PBRM-polymer-drug conjugate described in Example 4, at 5 mg/kg, 3 animals/time point.

The results in FIG. 7 showed that the trastuzumab had a plasma concentration of ~100 μg/mL and a half-life of ~12 days whereas unconjugated AF-HPA and AF had a total plasma concentration of <1 ng/mL. The PBRM-polymer-drug conjugate had a half-life of >5 days with an $AUC_{0\ to\ inf}$ of ~300 ug·day/mL.

Example 27

Mouse Plasma PK after Administration of PBRM-Polymer-Drug Conjugates

Female CD-1 mice were allowed to acclimate for at least 4 days prior to initial dosing. All mice were given regular chow and water ad libitum and were not fasted prior to compound administration. Test compounds or vehicle were dosed IV as a single dose on day 1.

The mice were injected intravenously with vehicle (n=3) or with PBRM-polymer-drug conjugates, as described in Examples 4, 7, 18A, 18B and 18C. Plasma was collected at 5 min, 1 h, 3 h, 6 h, 24 h, 48 h, 72 h, day 7 and day 14 post dosing. Body weight was measured prior to dosing on day 1 and on days 1, 7 and 14. All animals were observed throughout the fourteen day period for mortality or morbidity.

The total AF-HPA (conjugated AF-HPA and unconjugated (free) drug (such as AF-HPA and AF) concentrations were determined by LC-MS/MS analysis.

TABLE IX

| Plasma PK | | | |
|---|---|---|---|
| Test Sample | AF-HPA to trastuzumab ratio | $T_{1/2}$ (hr) | $AUC_{0\ to\ 336}$ (μg · hr/mL) |
| Example 4 | about 12:1 to about 17:1 | 125 | 20.1 |
| Example 7 | about 16:1 to about 21:1 | 136 | 22.9 |
| Example 18A | about 19:1 to about 24:1. | 154 | 19.4 |
| Example 18B | about 20:1 to about 25:1. | 139 | 22.7 |
| Example 18C | about 23:1 to about 28:1 | 119 | 25.1 |

The results in Table IX showed that the PBRM-polymer-drug conjugates had a half-life of ~120-154 hours (~5-6.4 days) with an $AUC_{0\ to\ 336}$ of ~19 to 25 μg·hr/mL and were independent of the AF-HPA to trastuzumab ratio of the PBRM-polymer-drug conjugates.

Example 28

Tolerability of the PBRM-Polymer Drug Conjugate (MTD Study)

Tolerability of the PBRM-polymer drug conjugate was estimated in CD-1 female mice. The PBRM-polymer-drug conjugate, Example 4, was administered as a single IV dose at a dose of 20 mg/kg, 40 mg/kg, 60 mg/kg (n=6 for each group). The vehicle control group received physiological saline. Animals were monitored for clinical signs over a twenty-one day period. Individual body weights of all study animals were recorded on day zero (baseline), every day for the first five days and approximately every other day thereafter. The results are summarized in Table X.

TABLE X

| Group | Dose (mg/kg) | % Change vs its Own Baseline on Day 7 | % Change vs its Own Baseline on Day 21 | Mortality or morbidity |
|---|---|---|---|---|
| 1 | Vehicle | −1% | +7.3% | None |
| 2 | 20 | +3.7% | +14.8% | None |
| 3 | 40 | −20% | +10.8% | 1 animal died on day 7 at 12% body weight loss |
| 4 | 60 | −28% | NA | 4 animals were moribund and sacrificed on Day 9 |

The 20 mg/kg dose was tolerated well, no body weight loss was observed in any of the mice in this group. At the 40 mg/kg dose the maximum body weight loss of −20% was observe red on Day 7. One animal in this group was found dead on day 7 and had ~12% body weight loss on the previous day. By the end of the study (Day 21) all surviving animals (5 out of 6) in this study group gained weight relative to the control group. The 60 mg/kg dose clearly exceeded the maximum tolerated dose as all the animals in this group had significant body weight loss on Day 7 and were moribund and were sacrificed on Day 9.

The result show that the maximum tolerated dose for the mouse was between 20 and 40 mg/kg.

Example 29

Tolerability of the Auristatin F-Hydroxypropylamide-L-Alanine 2TFA (MTD Study)

Tolerability of the Auristatin F-hydroxypropylamide-L-Alanine 2TFA (AF-HPA-Ala.2THF) was estimated in CD-1 female mice. The AF-HPA-Ala.2THF, (prepared as described in U.S. Ser. No. 13/493,899, now U.S. Pat. No. 8,685,383, Example 50), was administered as a single IV dose at a dose of 1.6 mg/kg, 3.2 mg/kg, 4.7 mg/kg (n=6 for each group). The vehicle control group received physiological saline. Animals were monitored for clinical signs over a twenty-one day period. Individual body weights of all study animals were recorded on day zero (baseline), every day for the first five days and approximately every other day thereafter. The results are summarized in Table XI.

TABLE XI

| Group | Dose (mg/kg) | % Change vs its Own Baseline on Day 7 | % Change vs its Own Baseline on Day 21 | Mortality or morbidity |
|---|---|---|---|---|
| 1 | Vehicle | −1% | +7.3% | None |
| 2 | 1.6 | 11.6% | +5.5% | None |
| 3 | 3.2 | −20% | +10.8% | 1 animal died on day 7, 3 animals were moribund and sacrificed on Day 7. Two survivors |
| 4 | 4.7 | −28% | NA | 1 animal died on Day 3, 1 was moribund and sacrificed on Day 3, 3 animals were moribund and sacrificed on Day 4 and 1 animal on day 5. No survivors |

The 1.6 mg/kg dose was acceptably tolerated, with 11.6% body weight loss observed on Day 7. Animals fully recovered by Day 21 with 5.5% body weight increase relative to its group baseline. At the 3.2 mg/kg dose, 1 animal died on Day 7, 3 animals were moribund and sacrificed on Day 7. By the end of the study (Day 21) 2 out of 6 animals survived. The 4.7 mg/kg dose clearly exceeded the maximum tolerated dose as all the animals in this group either died, or were moribund and sacrificed.

All publications, including, e.g., non-patent literature, patent applications, and patents, cited in this specification are incorporated herein by reference for all purposes. The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of alleviating a symptom of a cancer in a subject in need thereof, wherein the subject is identified as having low HER2 expression, comprising administering a conjugate to the subject in an amount sufficient to alleviate the symptom of the cancer, wherein the conjugate is of Formula (Ie), comprising a polymeric scaffold comprising a poly(1-hydroxymethylethylene hydroxymethyl-formal) (PHF):

(Ie)

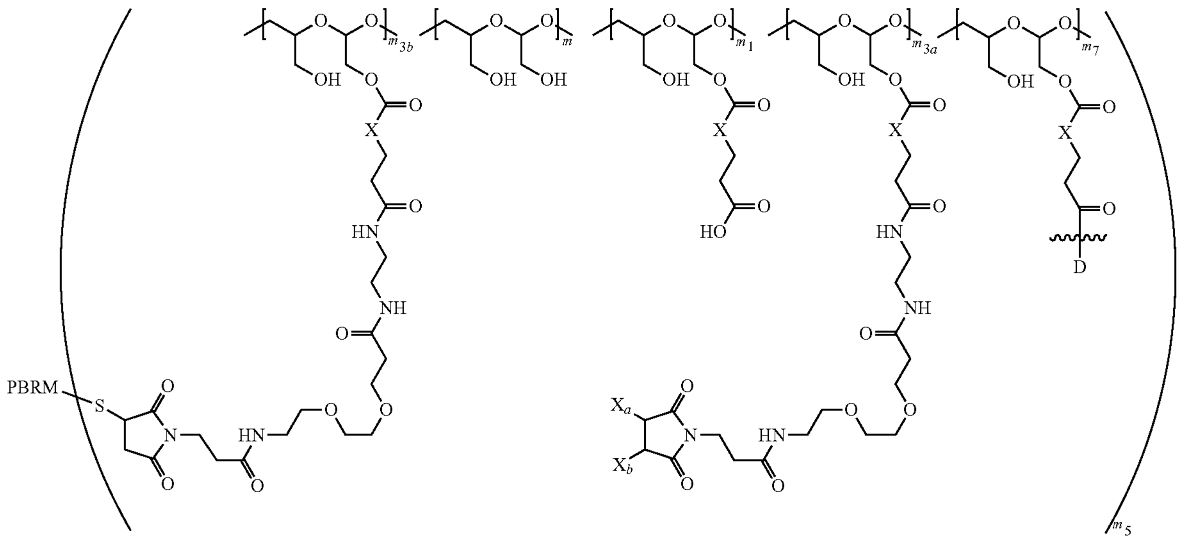

, , wherein:

the PHF has a molecular weight ranging from about 2 kDa to about 40 kDa;

PBRM is trastuzumab or a biosimilar thereof;

each occurrence of D independently is a therapeutic agent having a molecular weight of ≤5kDa, and the

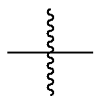

the between D and the carbonyl group denotes direct or indirect attachment of D to the carbonyl group, X is $CH_2$, O, or NH;

one of $X_a$ and $X_b$ is H and the other is a water-soluble maleimido blocking moiety, or $X_a$and $X_b$, together with the carbon atoms to which they are attached for a carbon-carbon double bond, $m_1$ is an integer from 1 to about 140, $m_7$ is an integer from 1 to about 40, wherein the sum of $m_1$ and $m_7$ is about 2 to about 180, m is an integer from 1 to about 300, $m_{3a}$ is an integer from 0 to about 17, $m_{3b}$ is an integer from 1 to about 8, wherein the sum of $m_{3a}$ and $m_{3b}$ is an integer between 1 and about 18, the sum of m, $m_1$, $m_7$, $m_{3a}$, and $m_{3b}$ ranges from about 15 to about 300, and $m_5$is an integer from 1 to about 10.

2. The method of claim 1, wherein the PHF has a molecular weight ranging from about 2 kDa to about 20 kDa, the sum of m, $m_1$, $m_7$, $m_{3a}$and $m_{3b}$ ranges from about 15 to about 150, $m_1$ is an integer from 1 to about 70, $m_7$is an integer from 1 to about 20, $m_{3a}$ is an integer from 0 to about 9, $m_{3b}$ is an integer from 1 to about 8 and $m_5$is an integer from 2 to about 8.

3. The method of claim 1, wherein the PHF has a molecular weight ranging from about 3 kDa to about 15 kDa, the sum of m, $m_1$, $m_7$, $m_{3a}$and $m_{3b}$ ranges from about 20 to about 110, $m_1$ is an integer from 2 to about 50, $m_7$is an integer from 2 to about 15, $m_{3a}$ is an integer from 0 to about 7, $m_{3b}$ is an integer from 1 to about 8 and $m_5$ is an integer from 2 to about 8.

4. The method of claim 1, wherein the PHF has a molecular weight ranging from about 5 kDa to about 10 kDa, the sum of m, $m_1$, $m_7$, $m_{3a}$ and $m_{3b}$ ranges from about 40 to about 75, $m_1$ is an integer from about 2 to about 35, $M_7$ is an integer from about 2 to about 10, $m_{3a}$ is an integer from 0 to about 4, $m_{3b}$ is an integer from 1 to about 5 and $m_5$ is an integer from 2 to about 8.

5. The method of claim 1, wherein the conjugate is of Formula (B):

(B)

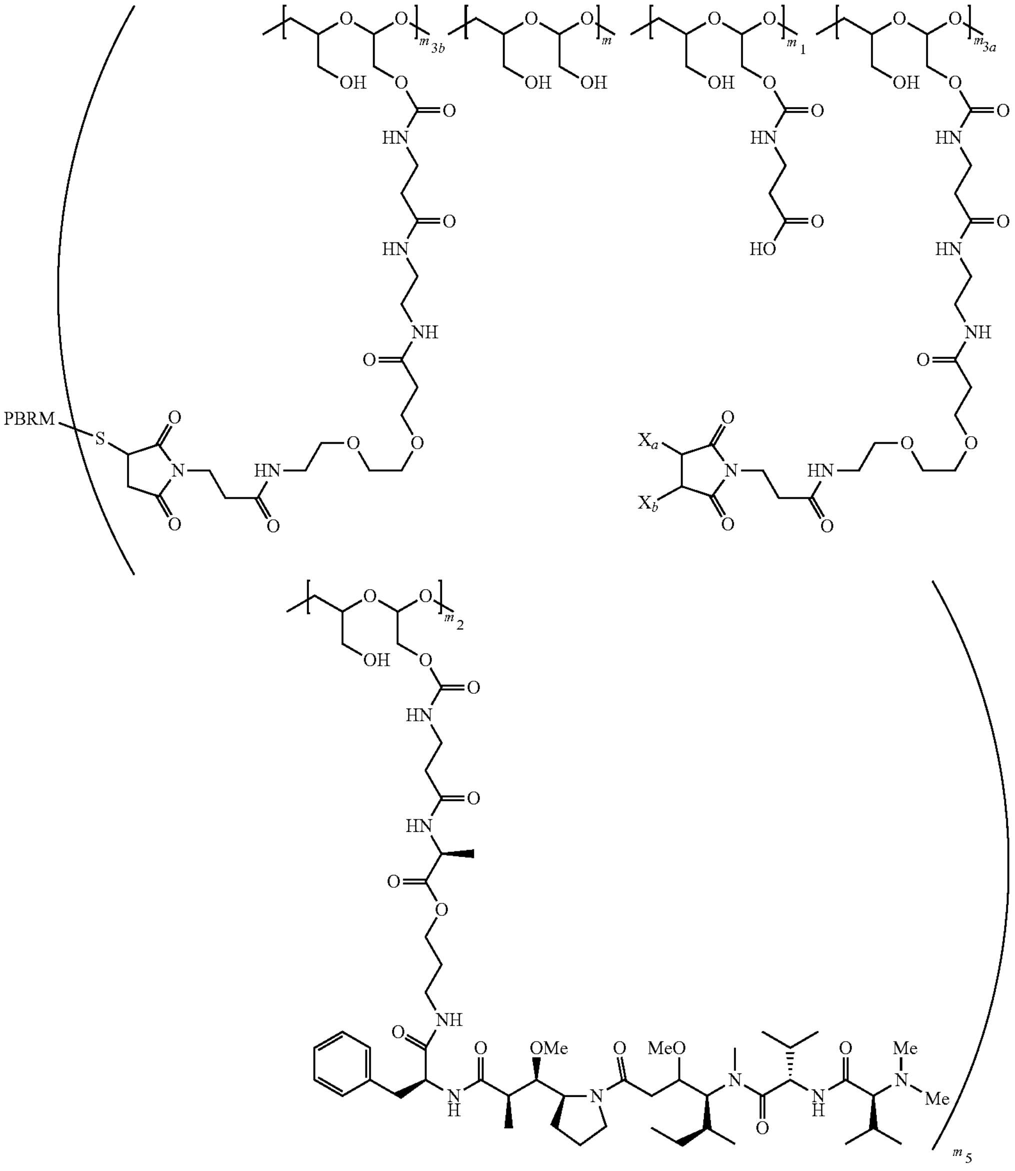

wherein:

the PHF has a molecular weight ranging from about 5 kDa to about 10 kDa;

m is an integer from 1 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of m, $m_1$, $m_2$, $m_{3a}$, and $m_{3b}$ ranges from about 40 to about 75, and $m_5$ is an integer from 2 to about 4.

6. The method of claim 1, wherein the total number of sulfide bonds formed between the PBRM and the PHF is 10 or less.

7. The method of claim 6, wherein the total number of sulfide bonds formed between the PBRM and the PHF is 4 or less.

8. The method of claim 1, wherein the subject is human.

9. The method of claim 1, wherein the cancer is selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian, prostate cancer, lung cancer, non-small cell lung cancer (NSCLC), colon cancer, pancreatic cancer, renal cancer, and gastric cancer.

10. The method of claim 9, wherein the cancer is selected from the group consisting of breast cancer, gastric cancer, non-small cell lung cancer (NSCLC), and ovarian cancer.

11. The method of claim 1, further comprising administering a second agent to the subject.

12. The method of claim 11, wherein the second agent is at least a second antibody or antigen binding fragment thereof that specifically binds HER2.

13. The method of claim 12, wherein the second antibody or antigen binding fragment thereof is a HER2 antibody, a HER2 dimerization inhibitor antibody, or a combination of a HER2 antibody and a HER2 dimerization inhibitor antibody.

14. The method of claim 13, wherein the HER2 antibody, the HER2dimerization inhibitor antibody or the combination of a HER2 antibody and a HER2dimerization inhibitor antibody comprises trastuzumab or pertuzumab or a combination thereof.

15. The method of claim 12, wherein the second antibody or antigen binding fragment thereof is pertuzumab.

16. The method of claim 1, wherein the subject is identified as having a scoring of 1+or 2+for HER2 expression as detected by immunohistochemistry (IHC) analysis performed on a test cell population, and wherein the HER2 gene is not amplified in the test cell population.

17. The method of claim 1, wherein the subject is refractory to chemotherapy.

18. The method of claim 1, wherein the subject is resistant to treatment with ado-trastuzumab emtansine.

19. The method of claim 1, wherein the subject is not resistant to treatment with ado-trastuzumab emtansine.

20. The method of claim 1, wherein the subject is identified as having a scoring of 2+or 3+for HER2 expression as detected by immunohistochemistry (IHC) analysis performed on a test cell population, and wherein the HER2 gene is amplified or mutated in the test cell population.

* * * * *

UNITED STATES PATENT AND TRADEMARK OFFICE

CERTIFICATE OF CORRECTION

PATENT NO. : 9,808,528 B2
APPLICATION NO. : 14/742936
DATED : November 7, 2017
INVENTOR(S) : Natalya D. Bodyak et al.

It is certified that error appears in the above-identified patent and that said Letters Patent is hereby corrected as shown below:

In the Claims

At Column 243, Line 51, in Claim 1:
"the between D and the carbonyl group denotes direct or"
Should read:
-- between D and the carbonyl group denotes direct or --

At Columns 245-246, Lines 1-48, in Claim 5:

"
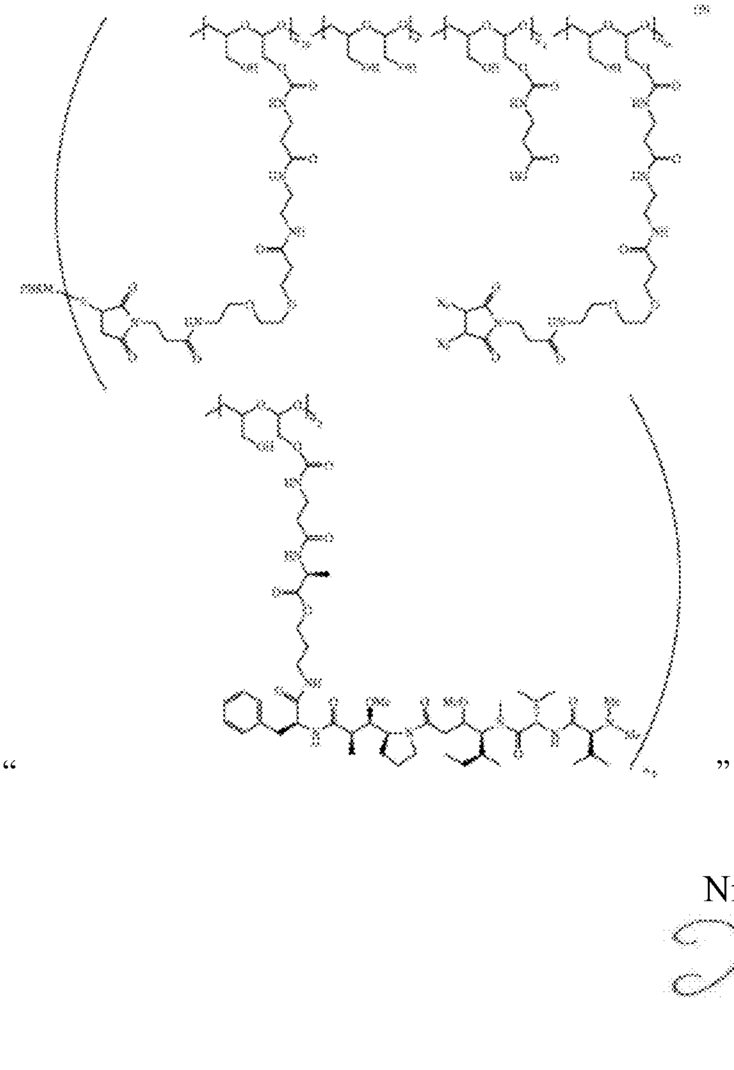
"

Signed and Sealed this
Nineteenth Day of December, 2017

Joseph Matal

*Performing the Functions and Duties of the Under Secretary of Commerce for Intellectual Property and Director of the United States Patent and Trademark Office*

Should read:

-- 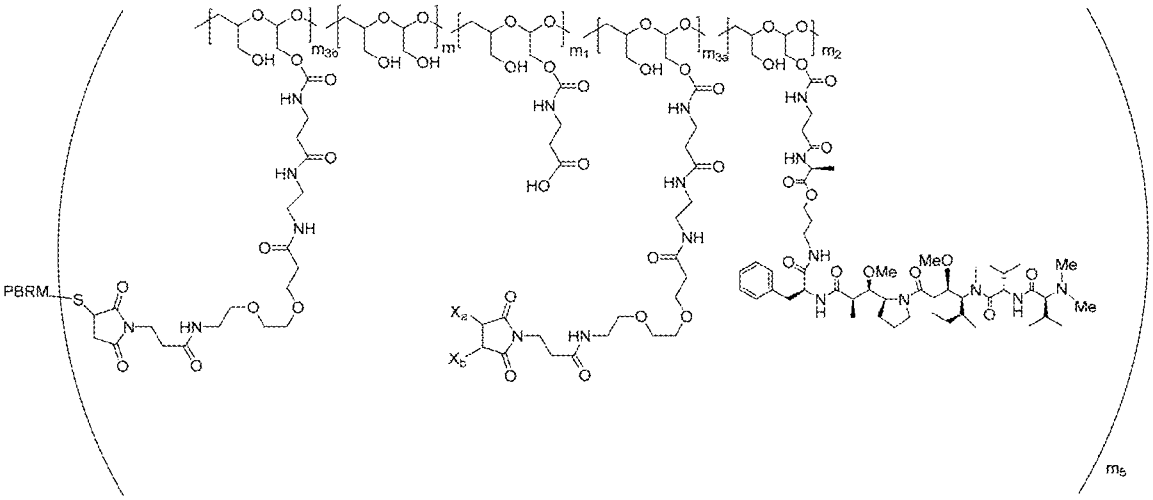 --

At Column 247, Line 7, in Claim 14:
"the HER2dimerization inhibitor antibody or the combination"
Should read:
-- the HER2 dimerization inhibitor antibody or the combination --

At Column 247, Line 8, in Claim 14:
"of a HER2 antibody and a HER2dimerization inhibitor"
Should read:
-- of a HER2 antibody and a HER2 dimerization inhibitor --

At Column 247, Line 14, in Claim 16:
"tified as having a scoring of 1+or 2+for HER2 expression as"
Should read:
-- tified as having a scoring of 1+ or 2+ for HER2 expression as --

At Column 247, Line 25, in Claim 20:
"tified as having a scoring of 2+or 3+for HER2 expression as"
Should read:
-- tified as having a scoring of 2+ or 3+ for HER2 expression as --